US011142835B2

(12) United States Patent
Grapperhaus et al.

(10) Patent No.: US 11,142,835 B2
(45) Date of Patent: Oct. 12, 2021

(54) COMPOUNDS, THEIR PREPARATION, RELATED COMPOSITIONS, CATALYSTS, ELECTROCHEMICAL CELLS, FUEL CELLS, AND USES THEREOF

(71) Applicant: UNIVERSITY OF LOUISVILLE RESEARCH FOUNDATION, INC., Louisville, KY (US)

(72) Inventors: Craig A. Grapperhaus, Jeffersonville, IN (US); Robert M. Buchanan, Louisville, KY (US); Andrew Z. Haddad, Berkeley, CA (US); Caleb Aaron Calvary, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 248 days.

(21) Appl. No.: 16/214,088

(22) Filed: Dec. 9, 2018

(65) Prior Publication Data
US 2019/0106385 A1    Apr. 11, 2019

Related U.S. Application Data

(63) Continuation-in-part of application No. PCT/US2017/036815, filed on Jun. 9, 2017.
(Continued)

(51) Int. Cl.
*C25B 11/04* (2021.01)
*C07C 337/06* (2006.01)
(Continued)

(52) U.S. Cl.
CPC ............ *C25B 11/04* (2013.01); *C07C 337/06* (2013.01); *C07D 323/00* (2013.01); *C07F 1/005* (2013.01);
(Continued)

(58) Field of Classification Search
CPC ...... C25B 1/04; C25B 11/0489; C07C 337/06; C07C 337/08
See application file for complete search history.

(56) References Cited

U.S. PATENT DOCUMENTS

2019/0106385 A1    4/2019  Grapperhaus et al.

FOREIGN PATENT DOCUMENTS

WO    2008/061306 A1    5/2008
WO    2010/066010 A1    6/2010
(Continued)

OTHER PUBLICATIONS

Marinescu et al. (2012) "Molecular Mechanisms of Cobalt-Catalyzed Hydrogen Evolution" Proc. Natl. Acad. Sci. USA, vol. 109, pp. 15127-15131.
(Continued)

*Primary Examiner* — Nicholas A Smith
(74) *Attorney, Agent, or Firm* — ALGM LLP; Harry J. Guttman

(57) ABSTRACT

In some embodiments, this application relates to inventive compounds (e.g., Formula (I), Formula (II), thiosemicarbazones and/or thiosemicarbazones and their metal (e.g., zinc, cobalt, nickel, or copper) complexes, and extended structures thereof), methods for preparation of the inventive compounds, compositions comprising the inventive compounds (e.g., anode, cathodes, catalysts (e.g., electrocatalysts), glassy carbon electrodes, carbon paste electrodes, covalently modified carbon (e.g., modified graphene)), electrochemical cells comprising compositions that comprise one or more inventive compounds, fuel cells comprising compositions that comprise one or more inventive compounds, uses of one or more inventive compounds to produce $H_2$ (e.g., via an electrochemical cell), and uses of one or more inventive compounds to create energy from $H_2$ (e.g.,
(Continued)

via a fuel cell). Additional embodiments of the invention are also discussed herein.

29 Claims, 81 Drawing Sheets
(81 of 81 Drawing Sheet(s) Filed in Color)

Related U.S. Application Data

(60) Provisional application No. 62/348,420, filed on Jun. 10, 2016, provisional application No. 62/436,490, filed on Dec. 20, 2016, provisional application No. 62/719,972, filed on Aug. 20, 2018.

(51) Int. Cl.
| | |
|---|---|
| *C07F 3/06* | (2006.01) |
| *C07F 1/08* | (2006.01) |
| *C07F 15/04* | (2006.01) |
| *C25B 1/04* | (2021.01) |
| *C07F 15/06* | (2006.01) |
| *C07D 323/00* | (2006.01) |
| *C07F 3/00* | (2006.01) |
| *C07F 1/00* | (2006.01) |
| *C25B 11/075* | (2021.01) |
| *C25B 11/095* | (2021.01) |

(52) U.S. Cl.
CPC ............... *C07F 1/08* (2013.01); *C07F 3/003* (2013.01); *C07F 3/06* (2013.01); *C07F 15/045* (2013.01); *C07F 15/065* (2013.01); *C25B 1/04* (2013.01); *C25B 11/075* (2021.01); *C25B 11/095* (2021.01)

(56) References Cited

FOREIGN PATENT DOCUMENTS

| WO | 2015/070177 A2 | 5/2015 |
|---|---|---|
| WO | 2017/214546 A1 | 12/2017 |
| WO | 2018/204564 A1 | 11/2018 |

OTHER PUBLICATIONS

Maroney et al., (1984) "Coordination chemistry of copper macrocyclic complexes: synthesis and characterization of copper complexes of TIM" Inorg. Chem., vol. 23, pp. 2252-2261.
McCrory et al., (2015) "Benchmarking Hydrogen Evolving Reaction and Oxygen Evolving Reaction Electrocatalysts for Solar Water Splitting Devices" J. Am. Chem. Soc., vol. 137, pp. 4347-4357.
McKone et al., (2014) "Earth-abundant hydrogen evolution electrocatalysts" Chemical Science, vol. 5, pp. 865-878.
McNamara et al., (2011) "A Cobalt-Dithiolene Complex for the Photocatalytic and Electrocatalytic Reduction of Protons" J. Am. Chem. Soc., vol. 133, pp. 15368-15371.
McNamara et al., (2012) "Cobalt-dithiolene complexes for the photocatalytic and electrocatalytic reduction of protons in aqueous solutions" Proc. Natl. Acad. Sci. USA, vol. 109, No. 39, pp. 15594-15599.
McQueen et al., (2009) "Electrochemical Analysis of Single-Walled Carbon Nanotubes Functionalized with Pyrene-Pendant Transition Metal Complexes" J. Am. Chem. Soc., vol. 131, pp. 17554-17556.
Merki et al., (2011) "Amorphous molybdenum sulfide films as catalysts for electrochemical hydrogen production in water" Chem Sci, vol. 2, pp. 1262-1267.
Merki et al., (2012) "Fe, Co, and Ni ions promote the catalytic activity of amorphous molybdenum sulfide films for hydrogen evolution" Chem Sci, vol. 3, pp. 2515-2525.
Mondal et al., (2013) "Cobalt Corrole Catalyst for Efficient Hydrogen Evolution Reaction from H2O under Ambient Conditions: Reactivity, Spectroscopy, and Density Functional Theory Calculations" Inorganic Chemistry, vol. 52, pp. 3381-3387.
Navaee et al., (2015) "Efficient amine functionalization of graphene oxide through the Bucherer reaction: an extraordinary metal-free electrocatalyst for the oxygen reduction reaction" RSC Adv. , vol. 5, pp. 59874-59880.
Osmanbaş et al., (2008) "Electrocatalytic activity of phthalocyanines bearing thiophenes for hydrogen production from water" Int. J. Hydrogen Energy, vol. 33, pp. 3281-3288.
Pantani et al., (2007) "Electroactivity of cobalt and nickel glyoximes with regard to the electro-reduction of protons into molecular hydrogen in acidic media" Electrochem. Commun., vol. 9, pp. 54-58.
Park et al., (2006) "Hydrothermal Synthesis and Structural Characterization of Novel Zn-Triazole-Benzenedicarboxylate Frameworks" Chem. Mater., vol. 18, pp. 525-531.
Paterson et al., (2010) "Versatile New Bis(thiosemicarbazone) Bifunctional Chelators: Synthesis, Conjugation to Bombesin(7-14)-NH2, and Copper-64 Radiolabeling" Inorg. Chem., vol. 49, pp. 1884-1893.
Popczun et al., (2013) "Nanostructured Nickel Phosphide as an Electrocatalyst for the Hydrogen Evolution Reaction" J. Am. Chem. Soc., vol. 135, pp. 9267-9270.
Popczun et al., (2014) "Highly Active Electrocatalysis of the Hydrogen Evolution Reaction by Cobalt Phosphide Nanoparticles" Angew. Chem. Int. Ed., vol. 53, pp. 5427-5430.
Reath et al., (2017) "Redox Potential and Electronic Structure Effects of Proximal Nonredox Active Cations in Cobalt Schiff Base Complexes" Inorg. Chem., vol. 56, p. 3713-3718.
Remita et al., (2006) "Activity evaluation of carbon paste electrodes loaded with pt nanoparticles prepared in different radiolytic conditions" J. Solid State Electrochem., vol. 10, pp. 506-511.
Rijnberg et al., (1998) "A Homologous Series of Homoleptic Zinc Bis(1,4-di-tert-butyl-1,4-diaza-1,3-butadiene) Complexes: K-[Zn(t-BuNCHCHN-t-Bu)2], Zn(t-BuNCHCHN-t-Bu)2, and [Zn(t-BuNCHCHN-t-Bu)2](OTf)x (x=1, 2)" Inorg. Chem., vol. 37, pp. 56-63.
Ringenberg et al., (2008) "Redox-switched oxidation of dihydrogen using a non-innocent ligand" J. Am. Chem. Soc., vol. 130, pp. 788-789.
Ringenberg et al., (2010) "Oxidation of Dihydrogen by Iridium Complexes of Redox-Active Ligands" Organometallics, vol. 29, pp. 1956-1965.
Rosenkoetter et al., (2016) "A Heterobimetallic W-Ni Complex Containing a Redox-Active W[SNS](2) Metalloligand" Inorg. Chem., vol. 55, pp. 6794-6798.
Rüfenacht, (1972) "120. Arbeiten über phosphorsäure- und thiophosphorsäureester mit einem heterocyclischen substituenten. Thiadiazol-ringschluss und eine dabei auftretende methylübertragung." Helv. Chim. Acta, vol. 55, pp. 1178-1187.
Saha et al., (2002) "Synthesis and structural characterisation of new iron(III) complexes with biologically relevant pyrazolyl thiosemicarbazones" Inorg. Chim. Acta, vol. 339, pp. 348-354.
Saha et al., (2003a) "Synthesis and spectroscopic identification of new iron(III) complexes with 5-methyl-3-formylpyrazole-3-piperidinylthiosemicarbazone (HMPz3Pi): X-ray structure of [Fe(MPz3Pi)2]ClO4-2H2O" Polyhedron, vol. 22, pp. 375-381.
Saha et al., (2003b) "Synthesis and spectroscopic characterisation of cobalt(III) and nickel(II) complexes with 5-methyl-3-formylpyrazole-N(4)-dibutylthiosemicarbazone (HMPzNBu2): X-ray crystallography of [Co(MPzNBu2)2] NO3—H2O (I) and [Ni(HMPzNBu2)2](ClO4)2 (II)" Polyhedron, vol. 22, pp. 383-390.
Saha et al., (2005) "Synthesis, spectroscopy and cyclic voltammetry of new iron(III) complexes with 5-methyl-3-formyl pyrazole 3-hexamethyleneiminyl thiosemicarbazone (HMPz3Hex): X-ray crystallographic identification of [Fe (MPz3Hex)2]ClO4—2H2O with an indication for unusual rotation about the azomethine double bond on complexation with iron(III)" Transition Met. Chem., vol. 30, pp. 532-540.
Bau et al., (2004) "Synthesis and spectroscopic characterization of new cobalt(III) complexes with 5-methyl-3-formyl pyrazole 3-hexamethyleneiminyl thiosemicarbazone (HMPz3Hex): X-ray crystallographic identification of HMPz3Hex and [Co(MPz3Hex)2]Br—

(56) References Cited

OTHER PUBLICATIONS

H2O with evidence for unusual rotation about the azomethine double bond of the ligand on complexation with cobalt(III)" Polyhedron, vol. 23, pp. 5-14.
Saveant et al., (1984) "Homogeneous Redox Catalysis of Electrochemical Reaction, Part VI. Zone Diagram Representation of the Kinetic Regimes" Journal of Electroanalytical Chemistry, vol. 171, pp. 341-349.
Shima et al., (2008) "The crystal structure of Fe-hydrogenase reveals the geometry of the active site" Science, vol. 321, pp. 572-575.
Shu et al., (1976) "Rotating-Ring-Disk Enzyme Electrode for Surface Catalysis Studies" Anal. Chem., vol. 48, No. 12, pp. 1679-1686.
Smith et al., (2012) "Reversible Electrocatalytic Production and Oxidation of Hydrogen at Low Overpotentials by a Functional Hydrogenase Mimic" Angew. Chem. Int. Ed., vol. 51, pp. 3152-3155.
Solis et al., (2016) "Nickel phlorin intermediate formed by proton-coupled electron transfer in hydrogen evolution mechanism" Proc. Natl. Acad. Sci. USA, vol. 113, pp. 485-492.
Sosna et al., (2010) "Monolayer anthracene and anthraquinone modified electrodes as platforms for Trametes hirsuta laccase immobilisation" Phys. Chem. Chem. Phys., vol. 12, pp. 10018-10026.
Stefani et al., (2015) "Identification of differential anti-neoplastic activity of copper bis(thiosemicarbazones) that is mediated by intracellular reactive oxygen species generation and lysosomal membrane permeabilization" Journal of Inorganic Biochemistry, vol. 152, pp. 20-37.
Straistarit et al., (2017) "A thiosemicarbazone-Nickel(II) complex as efficient electrocatalyst for hydrogen evolution" Chemcatchem vol. 9, pp. 2262-2268.
Sun et al., (2010) "Synthesis, Crystal Structures and Fluorescence Properties of Ni (II) and Cu (II) Complexes with 1-(Furan-2-ylmethylene)-4-phenylthiosemicarbazone" J. Chem. Crystallogr., vol. 40, pp. 4-9.
Tan et al., (2009) , K. W.; Ng, C. H.; Maah, M. J.; Ng, S. W. "Bis(acetone 4-phenylthiosemicarbazonato-kappa2N1,S) zinc(II)" Acta Crystallogr. Sect. Sect. E: Struct. Rep. Online, vol. E65, m969 plus supplementary materials. (7 pages).
Thompson et al., (2015) "Electrocatalytic Hydrogen Production by an Aluminum(III) Complex: Ligand-Based Proton and Electron Transfer" Angewandte Chemie, vol. 127, pp. 11808-11812.
Thorn et al., (2008) "Structures of [(n-C4H9)2NH2]2Cd9Cl20—2H2O and [Cu(C14H24N4)]2Cu13Cl30(H2O)2-xH2O: Perforated Layer Structures Based on the CdCl2 Layer Network" Inorg. Chem., vol. 47, No. 13, pp. 5775-5779.
Todd et al., (1998) "Electrochemically induced metalation of polymeric phthalocyanines" J. Am. Chem. Soc., vol. 120, pp. 4887-4888.
Tran et al., (2011) "Noncovalent Modification of Carbon Nanotubes with Pyrene-Functionalized Nickel Complexes: Carbon Monoxide Tolerant Catalysts for Hydrogen Evolution and Uptake" Angew. Chem. Int. Ed., vol. 50, pp. 1371-1374.
Tributsch et al., (1977) "Electrochemistry and photochemistry of MoS2 layer crystals. I" Journal of Electroanalytical Chemistry, vol. 81, pp. 97-111.
Turner, (2004) "Sustainable hydrogen production" Science, vol. 305, pp. 972-974.
PCT/US2017/036815, ISR dated Aug. 14, 2017, 6 pages.
PCT/US2017/036815, Written Opinion dated Aug. 14, 2017, 8 pages.
Abbaspour et al., (2012) "Electrocatalytic behavior of carbon paste electrode modified with metal phthalocyanines nanoparticles toward the hydrogen evolution" Electrochim. Acta, vol. 76, pp. 404-409.
Abbaspour et al., (2013) "Electrocatalytic hydrogen evolution reaction on carbon paste electrode modified with Ni ferrite nanoparticles" Fuel, vol. 104, pp. 575-582.

Abe et al. (1998) "Highly active electrocatalysis by cobalt tetraphenylporphyrin incorporated in a nafion membrane for proton reduction" Polym. Adv. Technol., vol. 9, pp. 559-562.
Andrieux et al., (1980) "Homogeneous Redox Catalysis of Electrochemical Reactions" Journal of Electroanalytical Chemistry, vol. 113, pp. 19-40.
Appel et al., (2005) "Molybdenum-Sulfur Dimers as Electrocatalysts for the Production of Hydrogen at Low Overpotentials" Journal of the American Chemical Society, vol. 127, pp. 12717-12726.
Appel et al., (2014) "Determining the Overpotential for a Molecular Electrocatalyst" ACS Catal., vol. 4, pp. 630-633.
Bard et al., Electrochemical Methods: Fundamentals and Applications; 2nd ed.; Wiley: Somerset, New Jersey, 2001. (850 pages).
Barton et al., (2004) "Enzymatic Biofuel Cells for Implantable and Microscale Devices" Chem Rev, vol. 104, pp. 4867-4886.
Barton et al., (2008) "Selective Solar-Driven Reduction of CO2 to Methanol Using a Catalyzed p-GaP Based Photoelectrochemical Cell" Journal of the American Chemical Society, vol. 130, pp. 6342-6344.
Barton et al., (2010) "Artificial hydrogenases" Current Opinion in Biotechnology, vol. 21, pp. 292-297.
Berben et al., (2010) "Hydrogen evolution by cobalt tetraimine catalysts adsorbed on electrode surfaces" Chem. Commun., vol. 46, pp. 398-400.
Betts et al., (2008) "Controlled Axial Coordination: Solid-Phase Synthesis and Purification of Metallo-Radiopharmaceuticals" Angew. Chem. Int. Ed., vol. 47, pp. 8416-8419.
Blower et al., (2003) "Structural trends in copper(II) bis(thiosemicarbazone) radiopharmaceuticals" Dalton Trans., pp. 4416-4425.
Bocokic et al., (2012) "Bis-(thiosemicarbazonato) Zn(II) complexes as building blocks for construction of supramolecular catalysts" Dalton Trans., vol. 41, pp. 3740-3750.
Calatayud et al., (2012) "Complexes of group 12 metals containing a hybrid thiosemicarbazone-pyridylhydrazone ligand" Inorganica Chimica Acta, vol. 381, pp. 150-161.
Calatayud et al., (2013) "A fluorescent dissymmetric thiosemicarbazone ligand containing a hydrazone quinoline arm and its complexes with cadmium and mercury" European Journal of Inorganic Chemistry, pp. 80-90.
Cao et al., (2014) "First mononuclear copper(II) electrocatalyst for catalyzing hydrogen evolution from acetic acid and water" International Journal of Hydrogen Energy, vol. 39, pp. 13972-13978.
Carta et al., (2013) "Xanthates and Trithiocarbonates Strongly Inhibit Carbonic Anhydrases and Show Antiglaucoma Effects in Vivo" J. Med. Chem., vol. 56, pp. 4691-4700.
Castiñeiras et al., (2002) "Structural study of a zinc(II) complex with acetone 3-hexamethyleneiminylthiosemicarbazone" J. Mol. Struct., vol. 604, pp. 113-118.
Chakraborty et al., (2016) "High yield synthesis of amine functionalized graphene oxide and its surface properties" RSC Adv., vol. 6, pp. 67916-67924.
Chebotareva et al., (1997) "First-Row Transition Metal Phthalocyanines as Catalysts for Water Electrolysis: A Comparative Study" Electrochim. Acta, vol. 42, pp. 3519-3524.
Chen et al., (2011) "Core-shell MoO3—MoS2 Nanowires for Hydrogen Evolution: A Functional Design for Electrocatalytic Materials" Nano Lett., vol. 11, pp. 4168-4175.
Christlieb et al., (2007a) "The exocyclic functionalisation of bis(thiosemicarbazonate) complexes of zinc and copper: the synthesis of monomeric and dimeric species" Dalton Trans., pp. 5043-5054.
Christlieb et al., (2007b) "New bimetallic compounds based on the bis(thiosemicarbazonato) motif" Dalton Trans., pp. 2007, pp. 327-331.
Compton et al., (2010) "Electrically Conductive 'Alkylated' Graphene Paper via Chemical Reduction of Amine-Functionalized Graphene Oxide Paper" Adv. Mater., vol. 22, pp. 892-896.
Cook et al., (2010) "Solar Energy Supply and Storage for the Legacy and Nonlegacy Worlds" Chem. Rev., vol. 110, pp. 6474-6502.
Costentin et al., (2012) "Turnover Numbers, Turnover Frequencies, and Overpotential in Molecular Catalysis of Electrochemical Reac-

(56) References Cited

OTHER PUBLICATIONS tions. Cyclic Voltammetry and Preparative-Scale Electrolysis" J. Am. Chem. Soc., vol. 134, pp. 11235-11242.
Cowley et al., (2002) "An Unusual Dimeric Structure of a Cu(I) Bis(thiosemicarbazone) Complex: Implications for the Mechanism of Hypoxic Selectivity of the Cu(Ii) Derivatives" J. Am. Chem. Soc., vol. 124, pp. 5270-5271.
Cowley et al., (2006) "Copper Complexes of Thiosemicarbazone-Pyridylhydrazine (THYNIC) Hybrid Ligands: A New Versatile Potential Bifunctional Chelator for Copper Radiopharmaceuticals" Inorganic Chemistry, vol. 45, No. 2, pp. 496-498.
Cowley et al., (2007) "Bifunctional chelators for copper radiopharmaceuticals: the synthesis of [Cu(ATSM)-amino acid] and [Cu(ATSM)-octreotide] conjugates" Dalton Trans., pp. 209-217.
Cracknell et al., (2008) "Enzymes as working or inspirational electrocatalysts for fuel cells and electrolysis" Chem. Rev., vol. 108, pp. 2439-2461.
Darensbourg et al., (2003) "The organometallic active site of Fe hydrogenase: Models and entatic states" Proc. Natl. Acad. Sci. USA, vol. 100, pp. 3683-3688.
Darmon et al., (2014) "Iron Complexes for the Electrocatalytic Oxidation of Hydrogen: Tuning Primary and Secondary Coordination Spheres" ACS Catalysis, vol. 4, pp. 1246-1260.
Das et al., (2015) "Nickel Complexes for Robust Light-Driven and Electrocatalytic Hydrogen Production from Water" ACS Catal., vol. 5, pp. 1397-1406.
Dubois et al., (2009) "Development of Molecular Electrocatalysts for CO2 Reduction and H2 Production/Oxidation" Acc. Chem. Res., vol. 42, No. 12, 1974-1982.
Fontecilla-Camps et al., (2007) "Structure/function relationships of NiFe- and FeFe-hydrogenases" Chem. Rev., vol. 107, pp. 4273-4303.
Foster et al., (2000) "Bis[N,N'-bis(2,4,6-trimethylphenyl)-1,2-ethanediylidenediamine]copper(I) tetrafluoroborate" Acta Crystallogr. Sect. C: Cryst. Struct. Commun., vol. C56, pp. 319-320 (plus suppoorting information). (9 pages).
Fourmond et al., (2010) "H2 Evolution and Molecular Electrocatalysts: Determination of Overpotentials and Effect of Homoconjugation" Inorganic Chemistry, vol. 49, pp. 10338-10347.
Gallucci (1982) "Reactions of Substituted Hydrazines with Glyoxal" J. Chem. Eng. Data, vol. 27, pp. 217-219.
Gardiner et al., (1994) "Paramagnetic Bis(1,4-di-tert-butyl-1,4-diazabutadiene) Adducts of Lithium, Magnesium, and Zinc" Inorg. Chem., vol. 33, pp. 2456-2461.
Ghaffarinejad et al, (2013) "Hydrogen Generation by Shimalite Ni Catalyst" Anal. Bioanal. Electrochem., vol. 5, No. 3, pp. 316-324.
Ghiamaty (2016) "Synthesis of palladium-carbon nanotube-metal organic framework composite and its application as electrocatalyst for hydrogen production" Journal of Nanostructure in Chemistry, vol. 6, pp. 299-308.
Goff et al., (2010) "Facile and tunable functionalization of carbon nanotube electrodes with ferrocene by covalent coupling and π-stacking interactions and their relevance to glucose bio-sensing" J. Electroanal. Chem., vol. 641, pp. 57-63.
Grass (1997) "Electrochemical generation of rhodium porphyrin hydrides. Catalysis of hydrogen evolution" J. Am. Chem. Soc., vol. 119, pp. 7526-7532.
Gray, (2009) "Powering the Planet with Solar Fuel" Nat. Chem., vol. 1, p. 7.
Haddad et al., (2015) "Proposed Ligand-Centered Electrocatalytic Hydrogen Evolution and Hydrogen Oxidation at a Noninnocent Mononuclear Metal-Thiolate" J. Am. Chem. Soc., vol. 137, pp. 9238-9241.
Haddad et al., (2016) "Beyond Metal-Hydrides: Non-Transition-Metal and Metal-Free Ligand-Centered Electrocatalytic Hydrogen Evolution and Hydrogen Oxidation" J. Am. Chem. Soc., vol. 138, pp. 7844-7847.
Haddad, (2017) Ph.D Thesis "Homogeneous Ligand-Centered Hydrogen Evolution and Hydrogen Oxidation: Exploiting Redox Non-Innocence to Drive Catalysis" (266 pages).
Haddleton et al., (1998) "Copper diimine complexes: the synthesis and crystal structures of [Cu(C10H14N2)2(MeOH)] [BF4], [Cu(C10H2ON2)2]Br, [{(C10H14N2)CuBr(☐-OMe)}2(MeOH)] and [{(C10H2ON2)CuBr(☐-OMe)}2]" J. Chem. Soc., Dalton Trans., pp. 381-385.
Halbert et al., (1985) "Electrocatalytic and Analytical Response of Cobalt Phthalocyanine Containing Carbon Paste Electrodes toward Sulfhydryl Compounds" Anal. Chem., vol. 57, pp. 591-595.
Harnisch et al., (2009) "Tungsten carbide as electrocatalyst for the hydrogen evolution reaction in pH neutral electrolyte solutions" Appl Catal B—Environ, vol. 89, pp. 455-458.
Hess et al., (2010) "Influence of the Redox Active Ligand on the Reactivity and Electronic Structure of a Series of Fe (TIM) Complexes" Inorg. Chem., vol. 49, pp. 5686-5700.
Heyduk et al., (2011) "Designing Catalysts for Nitrene Transfer Using Early Transition Metals and Redox-Active Ligands" Inorg. Chem., vol. 50, pp. 9849-9863.
Hinnemann (2005) "Biomimetic hydrogen evolution: MoS2 nanoparticles as catalyst for hydrogen evolution" J. Am. Chem. Soc., vol. 127, pp. 5308-5309.
Holland et al., (2007) "Functionalized Bis(thiosemicarbazonato) Complexes of Zinc and Copper: Synthetic Platforms Toward Site-Specific Radiopharmaceuticals" Inorg. Chem., vol. 46, 465-485.
Holzinger et al., (2012) "Carbon nanotube/enzyme biofuel cells" Electrochim. Acta, vol. 82, pp. 179-190.
Hu et al., (2007) "Electrocatalytic hydrogen evolution at low overpotentials by cobalt macrocyclic glyoxime and tetraimine complexes" J. Am. Chem. Soc., vol. 129, pp. 8988-8998.
Hueting et al., (2010) "Bis(thiosemicarbazones) as bifunctional chelators for the room temperature 64-copper labeling of peptides" Dalton Transactions, vol. 39, pp. 3620-3632.
Ibrahim et al., (2007) "Electropolymeric materials incorporating subsite structures related to iron-only hydrogenase: active ester functionalised poly(pyrroles) for covalent binding of {2Fe3S}-carbonylicyanide assemblies" Chem. Commun., pp. 1535-1537.
Jaegermann et al., (1988) "Interfacial properties of semiconducting transition metal chalcogenides" Prog. Surf. Sci., vol. 29, pp. 1-167.
Jain et al., (2016) "Copper catalysed aerobic oxidation of benzylic alcohols in an imidazole containing N4 ligand framework" Dalton Trans., vol. 45, pp. 18356-18364.
Jaramillo et al., (2007) "Identification of active edge sites for electrochemical H-2 evolution from MoS2 nanocatalysts" Science, vol. 317, pp. 100-102.
Jiang (2014) "A Cost-Effective 3D Hydrogen Evolution Cathode with High Catalytic Activity: FeP Nanowire Array as the Active Phase" Angew. Chem. Int. Ed., vol. 53, pp. 12855-12859.
Jing et al., (2015) "Light-driven hydrogen evolution with a nickel thiosemicarbazone redox catalyst featuring Ni H interactions under basic conditions" New Journal of Chemistry, vol. 39, pp. 1051-1059.
Jones et al., (1970) "Complexes of Transition Metals with Schiff Bases and the Factors Influencing their Redox Properties. Part I. Nickel and Copper Complexes of Some Diketone Bisthiosemicarbazones" J. Chem. Soc. A, pp. 2829-2836.
Jouad et al., (2005) "Structural and spectral studies of nickel(II), copper(II) and cadmium(II) complexes of 3-furaldehyde thiosemicarbazone" Polyhedron, vol. 24, pp. 327-332.
Kaeffer et al., (2015) "Hydrogen Evolution Catalyzed by Cobalt Diimine Dioxime Complexes" Acc. Chem. Res., vol. 48, No. 5, pp. 1286-1295.
Kaeffer et al., (2016) "The Dark Side of Molecular Catalysis: Diimine-Dioxime Cobalt Complexes Are Not the Actual Hydrogen Evolution Electrocatalyst in Acidic Aqueous Solutions" ACS Catal. vol. 6, pp. 3727-3737.
Kamin et al., (1980) "Rotating-Ring-Disk Enzyme Electrode for Biocatalysis Kinetic-Studies and Characterization of the Immobilized Enzyme Layer" Anal. Chem., vol. 52, pp. 1198-1205.
Kellett et al., (1985) "Cobalt porphyrin electrode films as hydrogen catalysts" Inorg. Chem., vol. 24, pp. 2378-2382.
Koca et al., (2009) "Voltammetric, in-situ spectroelectrochemical and in-situ electrocolorimetric characterization of phthalocyanines" Electrochimica Acta, vol. 54, pp. 2684-2692.

(56) References Cited

OTHER PUBLICATIONS

Koca et al., (2010) "Electrochemical, In Situ Spectroelectrochemical, In Situ Electrocolorimetric and Electrocatalytic Characterization of Metallophthalocyanines Bearing Four Dioctylaminocarbonyl Biphenyloxy Substituents" Electroanalysis, vol. 22, No. 3, pp. 310-319.

Koca et al., (2011) "Electrocatalytic oxygen reduction and hydrogen evolution reactions on phthalocyanine modified electrodes: Electrochemical, in situ spectroelectrochemical, and in situ electrocolorimetric monitoring" Electrochim. Acta, vol. 56, pp. 5513-5525.

Koca, (2009a) "Copper phthalocyanine complex as electrocatalyst for hydrogen evolution reaction" Electrochem. Commun., vol. 11, pp. 838-841.

Koca, (2009b) "Hydrogen evolution reaction on glassy carbon electrode modified with titanyl phthalocyanines" Int. J. Hydrogen Energy, vol. 34, pp. 2107-2112.

Kotani et al., (2011) "Size- and Shape-Dependent Activity of Metal Nanoparticles as Hydrogen-Evolution Catalysts: Mechanistic Insights into Photocatalytic Hydrogen Evolution" Chemistry—A European Journal, vol. 17, pp. 2777-2785.

Lalaoui et al., (2016a) "Direct Electron Transfer between a Site-Specific Pyrene-Modified Laccase and Carbon Nanotube/Gold Nanoparticle Supramolecular Assemblies for Bioelectrocatalytic Dioxygen Reduction" ACS Catal., vol. 6, pp. 1894-1900.

Lalaoui et al., (2016b) "Diazonium Functionalisation of Carbon Nanotubes for Specific Orientation of Multicopper Oxidases: Controlling Electron Entry Points and Oxygen Diffusion to the Enzyme" Chem.-Eur. J., vol. 22, pp. 10494-10500.

Laursen et al., (2013) "A high-porosity carbon molybdenum sulphide composite with enhanced electrochemical hydrogen evolution and stability" Chem. Commun., vol. 49, pp. 4965-4967.

Lawrence et al., (2015) "Electrochemical—Frustrated Lewis Pair Approach to Hydrogen Activation: Surface Catalytic ffects at Platinum Electrodes" Chem. Eur. J., vol. 21, pp. 900-906.

Le Gac et al., (2006) "Efficient synthesis and host-guest properties of a new class of calix[6]azacryptands" J. Org. Chem., vol. 71, pp. 9233-9236.

Le Goff et al., (2009) "From Hydrogenases to Noble Metal-Free Catalytic Nanomaterials for H-2 Production and Uptake" Science, vol. 326, pp. 1384-1387.

Lee at al., (2017) "Identification of an Electrode-Adsorbed Intermediate in the Catalytic Hydrogen Evolution Mechanism of a Cobalt Dithiolene Complex" Inorg. Chem., vol. 56, pp. 1988-1998.

Lei et al., (2014) "Electrochemical, spectroscopic and theoretical studies of a simple bifunctional cobalt corrole catalyst for oxygen evolution and hydrogen production" PCCP, vol. 16, pp. 1883-1893.

Lei et al., (2016)"Noncovalent Immobilization of a Pyrene-Modified Cobalt Corrole on Carbon Supports for Enhanced Electrocatalytic Oxygen Reduction and Oxygen Evolution in Aqueous Solutions" ACS Catal., vol. 6, pp. 6429-6437.

Lewis et al., (2006) "Powering the planet: Chemical challenges in solar energy utilization" Proc. Natl. Acad. Sci. USA, vol. 103, pp. 15729-15735.

Li et al., (2011) "MoS2 Nanoparticles Grown on Graphene: An Advanced Catalyst for the Hydrogen Evolution Reaction" J. Am. Chem. Soc., vol. 133, pp. 7296-7299.

López-Torres et al., (2009) "Reactivity of Thiosemicarbazides with Redox Active Metal Ions: Controlled Formation of Coordination Complexes versus Heterocyclic Compounds" Chem. Eur. J., vol. 15, pp. 3012-3023.

Löw et al., (2013) "Reactions of Copper(II) Chloride in Solution: Facile Formation of Tetranuclear Copper Clusters and Other Complexes That Are Relevant in Catalytic Redox Processes" Chem. Eur. J., vol. 19, pp. 5342-5351.

Venkatraman et al (2015) "bis(N-Phenyl-N'-(1-(1,3-thiazol-2-yl)ethylidene)carbamohydrazonothioato)-zinc N,N-dimethylformamide solvate" Deposit No. 1059843, deposit date Apr. 15, 2015. (1 page).

Vijaikanth et al., (2005) "Chemically modified electrode based on an organometallic model of the [FeFe] hydrogenase active center" Electrochem. Commun., vol. 7, pp. 427-430.

Vijayan et al., (2016) "Toward a new avenue in ruthenium-sulphur chemistry of binuclear[mu]-sulphido bridged ([mu]-S)2complexes having Ru2S2core: Targeted synthesis, crystal structure, biomolecules interaction and thier in vitro anticancer activities" Inorganica Chimica Acta, vol. 453, pp. 596-617.

Viñuelas-Zahínos et al., (2011) "Co(III), Ni(II), Zn(II) and Cd(II) complexes with 2-acetyl-2-thiazoline thiosemicarbazone: Synthesis, characterization, X-ray structures and antibacterial activity" Eur. J. Med. Chem., vol. 46, pp. 150-159.

Voiry et al., (2013) "Enhanced catalytic activity in strained chemically exfoliated WS2 nanosheets for hydrogen evolution" Nat Mater, vol. 12, pp. 850-855.

Vuilleumier et al., (2012) "Hopping along hydrogen bonds" Nature Chemistry, vol. 4, pp. 432-433.

Walgama et al., (2014) "Tuning the Electrocatalytic Efficiency of Heme-Protein Films by Controlled Immobilization on Pyrene-Functionalized Nanostructure Electrodes" J. Electrochem. Soc., vol. 161, No. 1, pp. H47-H52.

Wan et al., (2014) "Multiple Phases of Molybdenum Carbide as Electrocatalysts for the Hydrogen Evolution Reaction" Angew. Chem. 2014, vol. 126, pp. 6525-6528.

Wang et al., (2009) "Synthesis, characterization and spectra studies on Zn(II) and Cu(II) complexes with thiocarbamide ligand containing Schiff base group" Struct. Chem., vol. 20, pp. 995-1003.

West et al., (1993) "Thiosemicarbazone complexes of copper(II): structural and biological studies" Coordination Chemistry Reviews, vol. 123, pp. 49-71.

Wiese et al., (2012) "[Ni(PMe2NPh2)2](BF4)2 as an Electrocatalyst for H2 Production" ACS Catal., vol. 2, pp. 720-727.

Willner et al., (2009) "Integrated Enzyme-Based Biofuel Cells—A Review" Fuel Cells, vol. 9, No. 1, pp. 7-24.

Wilson et al., (2006) "Hydrogen Oxidation and Production Using Nickel-Based Molecular Catalysts with Positioned Proton Relays" Journal of the American Chemical Society, vol. 128, pp. 358-366.

Winkelmann et al., (1977) "Anticoccidial activity of dithiosemicarbazones", Arzneimittel Forschung. Drug Research, vol. 27, No. 5, pp. 950-967.

Xie et al., (2016) "Exploiting Copper Redox for 19F Magnetic Resonance-Based Detection of Cellular Hypoxia" J. Am. Chem. Soc., vol. 138, pp. 2937-2940.

Yaghi et al., (1995) "Hydrothermal Synthesis of a Metal-Organic Framework Containing Large Rectangular Channels" J. Am. Chem. Soc., vol. 117, pp. 10401-10402.

Yan et al., (2014) "Recent Development of Molybdenum Sulfides as Advanced Electrocatalysts for Hydrogen Evolution Reaction" ACS Catal., vol. 4, pp. 1693-1705.

Yang et al., (2010) "Hydrogen oxidation catalysis by a nickel diphosphine complex with pendant tert-butyl amines" Chemical Communications, vol. 46, pp. 8618-8620.

Zarkadoulas et al., (2012) "A perspective on solar energy conversion and water photosplitting by dithiolene complexes" Coord. Chem. Rev., vol. 256, pp. 2424-2434.

Zarkadoulas et al., (2016) "Experimental and Theoretical Insight into Electrocatalytic Hydrogen Evolution with Nickel Bis(aryldithiolene) Complexes as Catalysts" Inorg. Chem., vol. 55, pp. 432-444.

Zhang et al., (2016) "Reversible Methanol Addition to Copper Schiff Base Complexes: A Kinetic, Structural, and Spectroscopic Study of Reactions at Azomethine C=N Bonds" Dalton Trans., vol. 45, No. 40., pp. 15791-15799.

Zhang et al., (2017) "Translation of Ligand-Centered HER Activity and Mechanism of a Rhenium-Thiolate from Solution to Modified Electrodes: A Combined Experimental and Density Functional Theory Study." Dalton Trans., vol. 56, pp. 2177-2187.

Zhao et al., (1999) "Electrocatalytic proton reduction by phthalocyanine cobalt derivatives incorporated in poly(4-vinylpyridine-co-styrene) film" J. Mol. Catal. A: Chem., vol. 145, pp. 245-256.

Zhao et al., (2008) "In situ hydrothermal synthesis of tetrazole coordination polymers with interesting physical properties" Chem. Soc. Rev., vol. 37, pp. 84-100.

(56) References Cited

OTHER PUBLICATIONS

Zhao et al., (2010) "Synthesis, structures, and property studies on Zn(II), Ni(II), and Cu(II) complexes with a Schiff base ligand containing thiocarbamide group" Struct. Chem., vol. 21, pp. 977-987.

Zheng et al., (2014) "Hydrogen Evolution by a Metal-Free Electrocatalyst" Nat. Commun., vol. 5, Article 3783. (8 pages).

International Search Report from PCT/US2018/030765, dated Jul. 24, 2018, 4 pages.

Written Opinion from PCT/US2018/030765, dated Jul. 24, 2018, 6 pages.

Alsop et al. (2005) "Investigations into some aryl substituted bis(thiosemicarbazones) and their copper complexes" Inorganica Chimica Acta, vol. 358, pp. 2770-2780.

Bates et al. (1999) "Antiproliferative Activity of G-rich Oligonucleotides Correlates with Protein Binding" J. Biol. Chem., vol. 274, No. 37, pp. 26369-26377.

Boodram et al. (2016) "Breast Cancer Stem Cell Potent Copper (II)—Non-Steroidal Anti-Inflammatory Drug Complexes." Angewandte Chemie, vol. 128, No. 8, pp. 2895-2900.

Cater et al. (2013) "Increasing Intracellular Bioavailable Copper Selectively Targets Prostate Cancer Cells" ACS Chem. Biol., vol. 8, pp. 1621-1631.

Dearling et al. (2002) "Copper bis(thiosemicarbazone) complexes as hypoxia imaging agents: structure-activity relationships" J. Biol. Inorg. Chem., vol. 7, pp. 249-259.

Fujibayashi et al. (1997) "Copper-62-ATSM: A New Hypoxia Imaging Agent with High Membrane Permeability and Low Redox Potential" J. Nucl. Med., vol. 38, pp. 1155-1160.

Gao et al. (2009) "Cytotoxic Activities, Cellular Uptake, Gene Regulation, and Optical Imaging of Novel Platinum(II) Complexes" Chem. Res. Toxicol., vol. 22, pp. 1705-1712.

Haddad et al. (2017) "Metal-Assisted Ligand-Centered Electrocatalytic Hydrogen Evolution upon Reduction of a Bis(thiosemicarbazonato)Cu(II) Complex" Inorg. Chem., vol. 56, pp. 11254-11265.

Huuskonen et al. (2017) "The Copper bis(thiosemicarbazone) Complex CuII(atsm) Is Protective Against Cerebral Ischemia Through Modulation of the Inflammatory Milieu" Neurotherapeutics, vol. 14, pp. 519-532.

Liskova et al. (2012) "Cellular Response to Antitumor cis-Dichlorido Platinum(II) Complexes of CDK Inhibitor Bohemine and Its Analogues" Chem. Res. Toxicol., vol. 25, pp. 500-509.

Marshall et al. (2017) "Small non-coding RNA transcriptome of the NCI-60 cell line panel" Sci Data, vol. 4, Article 170157 (8 pages).

Marzano et al. (2009) "Copper complexes as anticancer agents." Anti-Cancer Agents in Medicinal Chemistry (Formerly Current Medicinal Chemistry—Anti-Cancer Agents), vol. 9, No. 2, pp. 185-211.

Morgan (1998) "Tetrazolium (MTT) Assay for Cellular Viability and Activity" Methods Mol. Biol., vol. 79, pp. 179-183.

Palanimuthu et al. (2013) "In Vitro and in Vivo Anticancer Activity of Copper Bis(thiosemicarbazone) Complexes" J. Med. Chem., vol. 56, pp. 722-734.

Reüfenacht (1972) "Arbetien über Phosphosäure- und Thiophosphorsäureester mit einem Heterocyclischen Substituenten Thiadiazol-Ringschluss und eine Dabei Auftretende Methylübertragung" Helv. Chim. Acta, vol. 55, Issue 1, pp. 1178-1187.

Salipur et al., (2014) "A Novel Small Molecule That Induces Oxidative Stress and Selectively Kills Malignant Cells" Free Radical Biology and Medicine, vol. 68, pp. 110-121.

Vishnosky et al. (2017) "Syntheses, structures, and electrochemical studies of N,N'bis(alkylthiocarbamate)butane-2,3-diimine Cu(II) complexes as pendent alkoxy derivatives of Cu(ATSM)" Inorg. Chim. Acta, vol. 461, pp. 45-51.

Wehbe et al. (2017) "A Perspective—can copper complexes be developed as a novel class of therapeutics?" Dalton Trans., vol. 46, pp. 10758-10773.

U.S. Appl. No. 16/672,481 Restriction Requirement dated Oct. 16, 2020 (8 pages).

U.S. Appl. No. 16/672,481 Response to Restriction Requirement dated Dec. 15, 2020 (5 pages).

U.S. Appl. No. 16/672,481 nonfinal Office action dated Jan. 7, 2021 (15 pages).

*Ligand Non-Innocence in Catalysis*

Ligand-Assisted Metal-Centered Reactivity

*ligand is electron reservoir for metal-centered reaction*

Ligand-Centered Reactivity

*ligand serves as redox-active reaction center*

Metal-Assisted Ligand-Centered Reactivity

*metal is electron reservoir for ligand-centered reaction*

COMPOUNDS, THEIR PREPARATION, RELATED COMPOSITIONS, CATALYSTS, ELECTROCHEMICAL CELLS, FUEL CELLS, AND USES THEREOF

CROSS-REFERENCE TO RELATED APPLICATIONS

This application is a Continuation-In-Part of International Application No. PCT/US2017/036815 filed Jun. 9, 2017, entitled "COMPOUNDS, RELATED COMPOSITIONS, CATALYSTS, ELECTROCHEMICAL CELLS, FUEL CELLS, THEIR PREPARATION AND THEIR USES" which is herein incorporated by reference in its entirety, and which claims the benefit of (1) U.S. Provisional Application No. 62/348,420, filed Jun. 10, 2016, entitled "COMPOUNDS, THEIR PREPARATION, RELATED COMPOSITIONS, CATALYSTS, ELECTROCHEMICAL CELLS, FUEL CELLS, AND USES THEREOF" which is herein incorporated by reference in its entirety and (2) U.S. Provisional Application No. 62/436,490, filed Dec. 20, 2016, entitled "COMPOUNDS, THEIR PREPARATION, RELATED COMPOSITIONS, CATALYSTS, ELECTROCHEMICAL CELLS, FUEL CELLS, AND USES THEREOF" which is herein incorporated by reference in its entirety.

This application claims the benefit of U.S. Provisional Application No. 62/719,972, filed Aug. 20, 2018, entitled "COMPOUNDS, THEIR PREPARATION, RELATED COMPOSITIONS, CATALYSTS, ELECTROCHEMICAL CELLS, FUEL CELLS, AND USES THEREOF, which is herein incorporated by reference in its entirety.

GOVERNMENT RIGHTS

This invention was made with government support under CHE-1361728 and CHE-1800245, both awarded by the National Science Foundation. The U.S. Government has certain rights in the invention.

BACKGROUND

Rising energy demands, coupled with growing concerns of repercussion from global climate change, have ignited considerable interest in the development of carbon neutral energy systems. Hydrogen is a promising component of these systems representing a light weight, energy dense energy carrier. Hydrogen evolution reactions (HERs), which involve a two-electron reduction of protons, can be used to store energy in $H_2$, with subsequent energy release through hydrogen oxidation reactions (HORs). Platinum is a catalyst for HER and HOR, yet its scarcity and high costs limit practical large scale application.

In addition, there remains a broader need for catalysts, related compounds, related compositions, and related electrochemical cells that have more desirable properties compared than currently exist, such as but not limited to: better efficiency (e.g., lower overpotential and higher turnover frequency), less expensive to produce, more easily synthesized, and more robust.

Certain embodiments of the invention can address one or more of the deficiencies discussed above.

In some embodiments, this application relates to inventive compounds (e.g., Formula (I), Formula (II), thiosemicarbazones and/or thiosemicarbazones and their metal (e.g., zinc, cobalt, or copper) complexes, and extended structures thereof), methods for preparation of the inventive compounds, compositions comprising the inventive compounds (e.g., anode, cathodes, catalysts (e.g., electrocatalysts), glassy carbon electrodes, carbon paste electrodes, covalently modified carbon (e.g., modified graphene)), electrochemical cells comprising compositions that comprise one or more inventive compounds, fuel cells comprising compositions that comprise one or more inventive compounds, uses of one or more inventive compounds to produce $H_2$ (e.g., via an electrochemical cell), and uses of one or more inventive compounds to create energy from $H_2$ (e.g., via a fuel cell). Additional embodiments of the invention are also discussed herein.

SUMMARY

Some embodiments of the present invention include a compound selected from Formula (I),

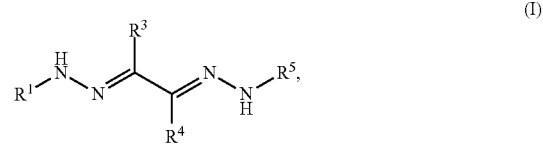

and salts, optical isomers, geometric isomers, salts of isomers, and derivatives thereof.

Some embodiments of the present invention include a compound selected from Formula (II), M.L (II) and salts, optical isomers, geometric isomers, salts of isomers, and derivatives thereof.

Yet other embodiments include a catalyst (e.g., an electrocatalyst) comprising a composition comprising a compound of Formula (I), a compound of Formula (II), or both. Some embodiments encompass an anode comprising a composition comprising a compound of Formula (I), a compound of Formula (II), or both. Other embodiments include a cathode comprising a composition comprising a compound of Formula (I), a compound of Formula (II), or both.

Still other embodiments of the invention include an electrochemical cell comprising a composition comprising a compound of Formula (I), a compound of Formula (II), or both. Additional embodiments include a fuel cell comprising a composition comprising a compound of Formula (I), a compound of Formula (II), or both.

Some embodiments of the invention include a method for producing $H_2$ comprising contacting, in an electrochemical cell, a first composition comprising a compound of Formula (I), a compound of Formula (II), or both with a second composition comprising water. Additional embodiments include a method for producing electricity comprising contacting, in a fuel cell, a first composition comprising a compound of Formula (I), a compound of Formula (II), or both with a second composition comprising $H_2$.

Further embodiments encompass a method for preparing a compound of Formula (I) comprising any suitable method, such as those disclosed herein, or a method for preparing a compound of Formula (II) comprising any suitable method, such as those disclosed herein. Additional embodiments encompass a method for preparing a catalyst (e.g., an electrocatalyst) comprising a composition comprising a compound of Formula (I), a compound of Formula (II), or both, comprising any suitable method, such as those disclosed herein. Still other embodiments include a method for preparing an anode comprising a composition comprising a compound of Formula (I), a compound of Formula (II), or both, comprising any suitable method, including those disclosed herein. Still further embodiments include a method for preparing a cathode comprising a composition comprising a compound of Formula (I), a compound of Formula (II), or both, comprising any suitable method, such as those disclosed herein.

Other embodiments of the invention are also disclosed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

The patent or application file contains at least one drawing executed in color. Copies of this patent or patent application publication with color drawing(s) will be provided by the Office upon request and payment of the necessary fee.

DETAILED DESCRIPTION

Figure 1:
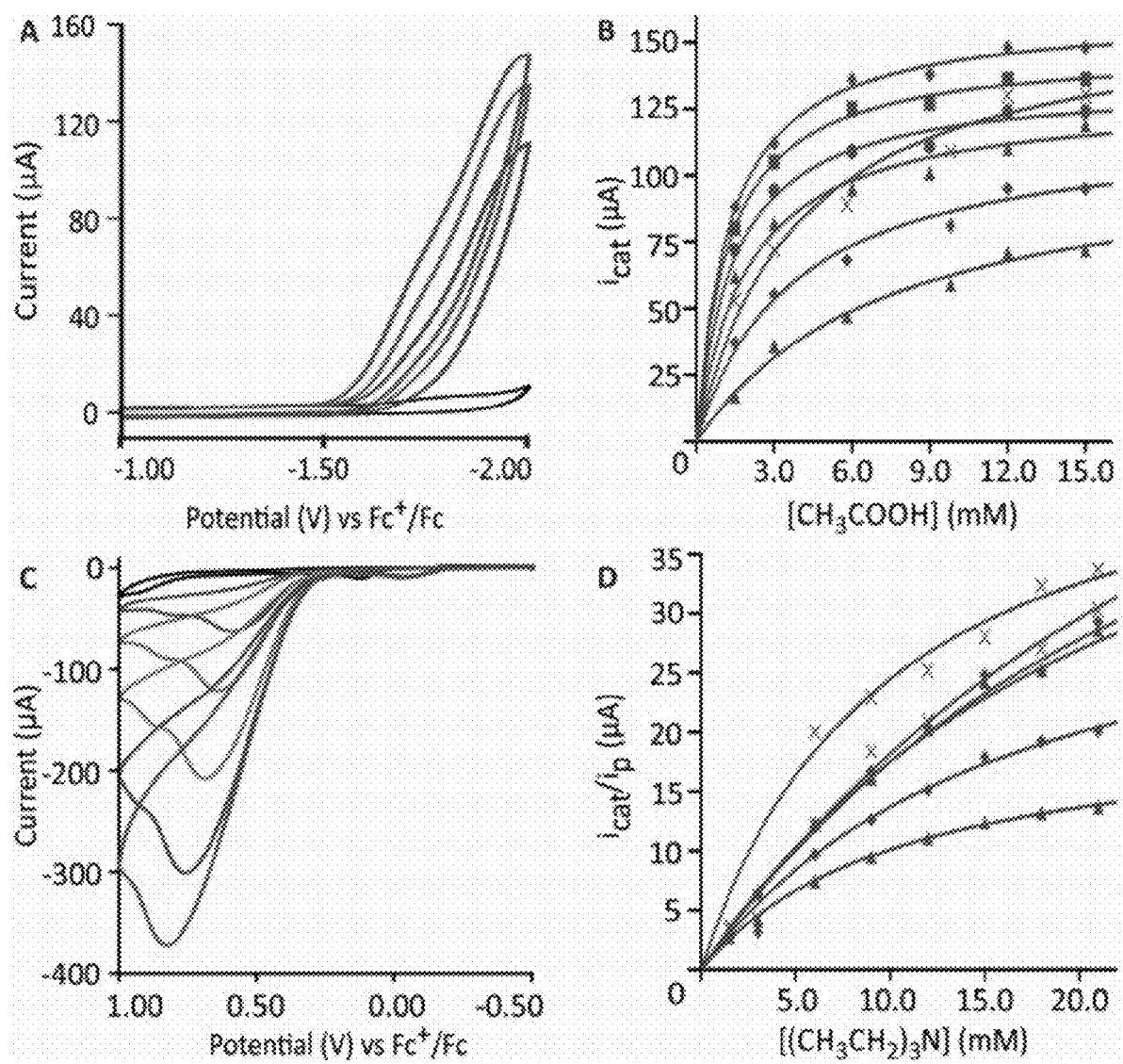
FIG. 1. Electrocatalytic $H_2$ evolution and $H_2$ oxidation. (A) Cyclic voltammograms of 3 mM ZnL in methanol with (from bottom to top) no added acid, 6 mM $CH_3COOH$, 9 mM $CH_3COOH$, and 12 mM $CH_3COOH$. Data collected at a scan rate of 0.5 V/s in the presence of 0.1 M $Bu_4NPF_6$ as supporting electrolyte. (B) Plot of $i_{cat}$ versus $[CH_3COOH]$ for 3 mM ZnL (upper lines at 3 mM $CH_3COOH$) at scan rates of 0.2 (Δ), 0.3 (○), 0.4 (□), and 0.5 (◇) V/s and 3 mM $H_2L$ (lower lines at 3 mM $CH_3COOH$) at scan rates of 0.2(Δ), 0.5 (◇), and 1.0 (×) V/s. (C) Cyclic voltammograms of 0.3 mM ZnL in methanol under 1 atm. $H_2$ (from top to bottom at 1.00 V) with no added base, 3 mM $(CH_3CH_2)_3N$, 6 mM $(CH_3CH_2)_3N$, 12 mM $(CH_3CH_2)_3N$, 21 mM $(CH_3CH_2)_3N$, and 30 mM $(CH_3CH_2)_3N$. Data collected at a scan rate of 0.5 V/s in the presence of 0.1 M $Bu_4NPF_6$ as supporting electrolyte. (D) Plot of $i_{cat}/i_p$ versus $[(CH_3CH_2N)_3]$ for 0.3 mM ZnL under 1 atm. $H_2$ (clustered lines second from the top) and 3 mM $H_2L$ under 1 atm. $H_2$ (top line and bottom two lines) at scan rates of 0.2(Δ), 0.5 (◇), and 1.0 (×) V/s.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

In some embodiments, this application relates to inventive compounds (e.g., Formula (I), Formula (II), thiosemicarbazones and/or thiosemicarbazones and their metal (e.g., zinc, cobalt, or copper) complexes, and extended structures thereof), methods for preparation of the inventive compounds, compositions comprising the inventive compounds (e.g., anode, cathodes, catalysts (e.g., electrocatalysts), glassy carbon electrodes, carbon paste electrodes, covalently modified carbon (e.g., modified graphene)), electrochemical cells comprising compositions that comprise one or more inventive compounds, fuel cells comprising compositions that comprise one or more inventive compounds, uses of one or more inventive compounds to produce H$_2$ (e.g., via an electrochemical cell), and uses of one or more inventive compounds to create energy from H$_2$ (e.g., via a fuel cell). Additional embodiments of the invention are also discussed herein.

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, 12, 13, 14, 15, 16, 17, 18, 19, or 20 member aromatic hydrocarbon group which, when unsubstituted. Examples of aryl groups include, but are not limited to, phenyl, naphthyl, pyrene, tolyl, and xylyl. For an aryl that is bicyclic, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, 12, 13, 14, 15, 16, 17, 18, 19, or 20 membered, hydrocarbon group, where 1, 2, 3, 4, 5, 6, 7, 8, or 9 carbon atoms are replaced by a hetero atom independently selected from nitrogen, oxygen, or sulfur atom, and the monocyclic or bicyclic ring system is aromatic.

Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, 1-methyl-imidazolyl, triazolyl, tetrazolyl, 1H-pyrazol-4-yl, 1-Me-pyrazol-4-yl, pyridin-3-yl, pyridin-4-yl, 3,5-dimethylisoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl, one or both rings can be substituted. An N-heteroaryl means a heteroaryl that comprises one or more N (e.g., 1, 2, 3, 4, 5, 6, 7, or 8); an N-heteroaryl may also comprise other hetero atoms.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl,). For a bicyclic heterocyclyl, if one ring is aromatic (e.g., monocyclic aryl or heteroaryl), then the other ring is not aromatic (e.g., a benzo crown ether). For a bicyclic heterocyclyl, one or both rings can have one or more hetero atoms. For a bicyclic heterocyclyl, one or both rings can be substituted. An N-heterocyclyl means a heterocyclyl that comprises one or more N (e.g., 1, 2, 3, 4, 5, or 6); an N-heterocyclyl may also comprise other hetero atoms.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein a "benzo crown ether" is benzene ring fused to a crown ether, such as but not limited to

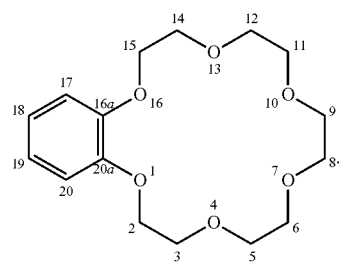

"Benzo crown ether" is defined to encompass one, two, three, four, five, or six benzene rings fused to a crown ether. Any suitable crown ether can be used, such as but not limited to 12-crown-4, 15-crown-5, or 18-crown-6.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention encompass any optically active, racemate, stereoisomer form, polymorphism, or mixtures thereof. If a chiral center does not provide an indication of its configuration (i.e., R or S) in a chemical structure, it should be considered to represent R, S or a racemate.

Some embodiments of the invention include compounds of Formula (I),

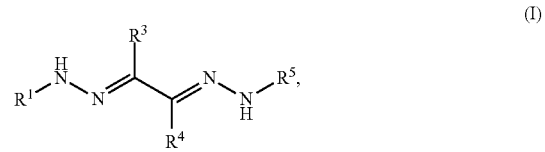

and salts, optical isomers, geometric isomers, salts of isomers, and derivatives thereof, wherein
—$R^1$ is

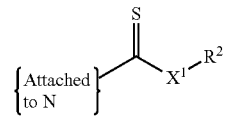

or is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$X^1$ is bivalent —(NH)—, —O—, —($CH_2$)—, or —S—, which —(NH)— or —($CH_2$)— can optionally be substituted with one or more (e.g., 0, 1, or 2) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$R^2$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), amine (—$NH_2$), —$NR_aR_b$, —$N^{(+)}R_aR_bR_c$, methanoly (—COH), carboxy (—$CO_2H$), nitro (—$NO_2$), cyano (—CN), ethynyl (—CCH), sulfo (—$SO_3H$), methyl, or ethyl;

—$R^3$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$R^4$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$R^5$ is

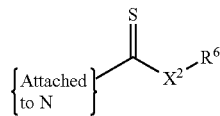

or is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$X^2$ is bivalent —(NH)—, —O—, —($CH_2$)—, or —S—, which —(NH)— or —($CH_2$)— can optionally be substituted with one or more (e.g., 0, 1, or 2) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$R^6$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), amine (—$NH_2$), —$NR_aR_b$, —$N^{(+)}R_aR_bR_c$, methanoly (—COH), carboxy (—$CO_2H$), nitro (—$NO_2$), cyano (—CN), ethynyl (—CCH), sulfo (—$SO_3H$), methyl, or ethyl; and $R_a$, $R_b$, and $R_c$ are each independently selected from $C_1$-$C_5$ alkyl (e.g., $C_1$, $C_2$, $C_3$, $C_4$, or $C_5$ alkyl). If there are more than one of any of $R_a$, $R_b$, or $R_c$ on the same compound (for example, if $R^2$ comprises an $R_a$ and $R^6$ also comprises an $R_a$), then each is chosen independently.

In some embodiments, one or both of $R^2$ or $R^6$ is (a) $C_1$-$C_7$ alkyl (e.g., $C_1$, $C_2$, $C_3$, $C_4$, $C_5$, $C_6$, or $C_7$ alkyl) substituted with —$NR_aR_b$, (b) $C_1$-$C_7$ alkyl (e.g., $C_1$, $C_2$, $C_3$, $C_4$, $C_5$, $C_6$, or $C_7$ alkyl) substituted with —$N^{(+)}R_aR_bR_c$, (c) substituted or unsubstituted benzo crown ether (e.g., mono benzo 18-crown-6 ether), (d) phenyl substituted with a carboxy (e.g., para, meta, or ortho substituted), (e) substituted or unsubstituted pyrrolyl (e.g., 2-amine or 5-amine substituted pyrrolyl), (f) substituted or unsubstituted pyridyl, or (g) substituted or unsubstituted imidazolyl.

In some embodiments, the compound of Formula (I) comprises one or more of the following:
(a) $R^3$ is the same as $R^4$;
(b) $R^3$ is the same as $R^4$ and $R^1$ is the same as $R^5$;
(c) $R^3$ is the same as $R^4$, $X^1$ is —(NH)—, $X^2$ is —(NH)—, and $R^2$ is the same as $R^6$;

(d) $R^3$ is the same as $R^4$, $R^3$ is methyl, $R^1$ is the same as $R^5$, $R^1$ is

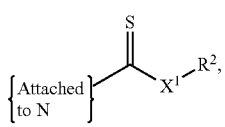

$X^1$ is —(NH)—, and $R^2$ is —$CH_3$;

(e) $R^3$ is the same as $R^4$, $R^3$ is methyl, $R^1$ is the same as $R^5$, $R^1$ is

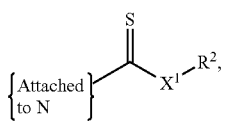

$X^1$ is —(NH)—, and $R^2$ is —$C_5H_6$;

(f) $R^3$ is the same as $R^4$, $R^3$ is methyl, $R^1$ is the same as $R^5$, $R^1$ is

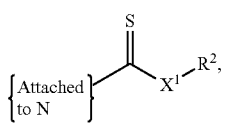

$X^1$ is —(NH)—, and $R^2$ is —$CH_2F_3$;

(g) $R^3$ is the same as $R^4$, $R^3$ is methyl, $R^1$ is the same as $R^5$, $R^1$ is

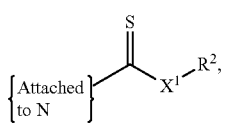

$X^1$ is —($NCH_3$)—, and $R^2$ is —$CH_3$;

(h) $R^3$ is the same as $R^4$, $R^3$ is methyl, $R^1$ is the same as $R^5$, $R^1$ is

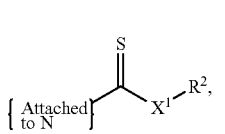

$X^1$ is —O—, and $R^2$ is —$CH_3$;

(i) $R^3$ is the same as $R^4$ and $R^3$ is methyl;
(j) $R^3$ is the same as $R^4$ and $R^3$ is ethyl;
(k) $R^3$ is methyl and $R^4$ is phenyl;
(l) $R^1$ is

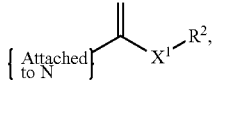

$X^1$ is —(NH)—, $R^2$ is —$CH_3$, $R^5$ is

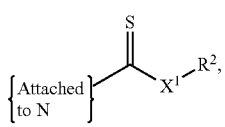

$X^2$ is —(N—$CH(CH_3)_2$)—, and $R^6$ is —$CH(CH_3)_2$;

(m) $R^1$ is

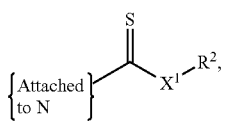

$X^1$ is —(NH)—, $R^2$ is —$CH_3$, $R^5$ is

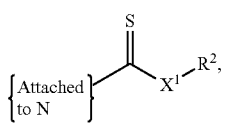

$X^2$ is —(NH)—, and $R^6$ is —$C_5H_6$;

(n) $R^1$ is

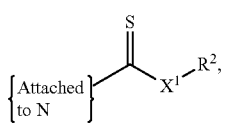

$X^1$ is —(NH)—, $R^2$ is —$CH_3$, $R^5$ is

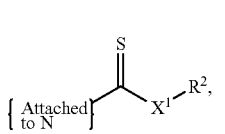

$X^2$ is —(NH)—, and $R^6$ is —$CH_2CF_3$;

(o) $R^1$ is

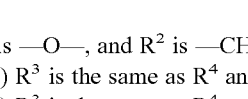

$X^1$ is —(NH)—, $R^2$ is —$CH_3$, $R^5$ is

$X^2$ is —O—, and $R^6$ is —$CH_3$;

(p) $R^1$ is

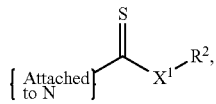

$X^1$ is —(NH)—, $R^2$ is —$CH_3$, $R^5$ is

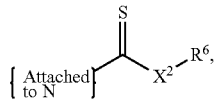

$X^2$ is —O—, and $R^6$ is —$CH_2CH_3$;

(q) (1) the limitations of (l) and (2) the limitations of (i), (j), or (k);

(r) (1) the limitations of (m) and (2) the limitations of (i), (j), or (k);

(s) (1) the limitations of (n) and (2) the limitations of (i), (j), or (k);

(t) (1) the limitations of (o) and (2) the limitations of (i), (j), or (k); or (u) (1) the limitations of (p) and (2) the limitations of (i), (j), or (k).

In some embodiments, Formula (I) further comprises a solvent molecule coordinated with Formula (I). In other embodiments, the solvent molecule can be any suitable solvent. In some embodiments, the solvent molecule is selected from water, methanol, ethanol, propanol, acetonitrile, dimethylformamide, and acetone.

In certain embodiments, the compound of Formula (I) is

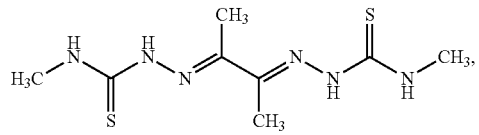

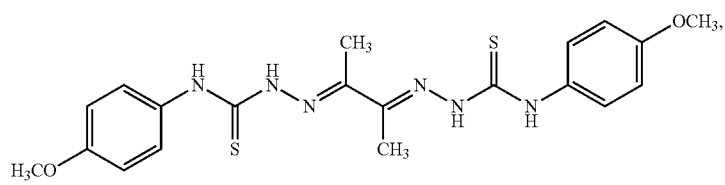

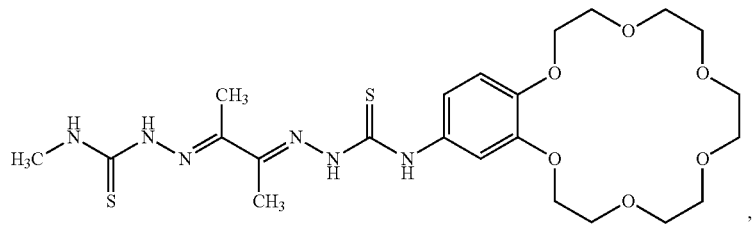

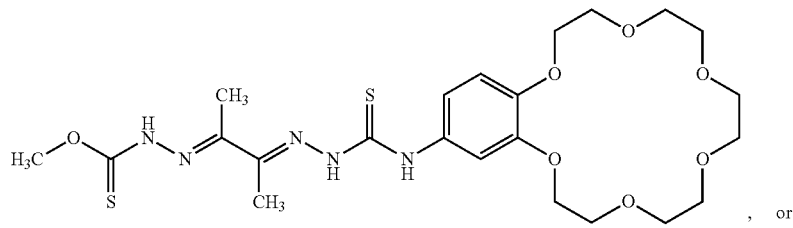

, or

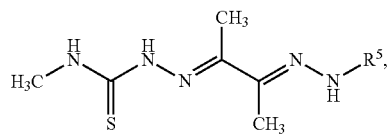

where $R^5$ is pyridinyl, 1-methyl-imidazolyl, an N-containing heterocyclyl, or an N-containing heteroaryl.

In some embodiments, Formula (I) is one of the molecules described in Example Sets A, B, C, D, or E. In other embodiments, Formula (I) can be symmetric or asymmetric.

In certain embodiments of Formula (I) (a) $X^1$ is not —(NH)—, (b) $R^2$ is not methoxyphenyl or p-methoxyphenyl, or (c) both (a) and (b). In other embodiments of Formula (I) (a) $X^2$ is not —(NH)—, (b) $R^6$ is not methoxyphenyl or p-methoxyphenyl, or (c) both (a) and (b). In yet other embodiments, (a) $R^3$ is not methyl, (b) $R^4$ is not methyl, or (c) both (a) and (b). In still other embodiments, Formula (I) is not

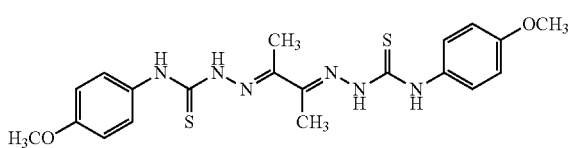 [SMILES: COc1ccc(NC(=S)N/N=C(C)/C(C)=N/NC(=S)Nc2ccc(OC)cc2)cc1]

In some embodiments, Formula (I) is part of a homogenous solution, a homogenous aqueous solution, a heterogeneous solution, a heterogeneous aqueous solution, or a glassy carbon electrode. In other embodiments, a homogenous solution, a homogenous aqueous solution, a heterogeneous solution, or a heterogeneous aqueous solution, can each comprise a compound of Formula (I). In certain embodiments, a glassy carbon electrode, a carbon paste (e.g., embedded with one or more of polynuclear catalysts, coordinated polymers, or metal-organic frameworks), covalent modified carbon (e.g., graphene), or non-covalent modified carbon (e.g., graphene), can each comprise or reacted with the compound of Formula (I).

Some embodiments of the invention include a compound selected from Formula (II), M.L (II) and salts, optical isomers, geometric isomers, salts of isomers, and derivatives thereof, wherein -M is Ni, Pd, Pt, Cu, Ag, Au, Zn, Cd, Hg, Co, Rh, Ti, V, Cr, Mn, or Fe; or M is $Cu^{2+}$, $Cu^+$, $Zn^{2+}$, $Co^{2+}$, $Ni^{2+}$, $Cd^{2+}$, $Mn^{2+}$, $Ru^{2+}$, or $Fe^{2+}$; or M is $Cu^{2+}$, Cut, $Zn^{2+}$, $Co^{2+}$, $Cd^{2+}$, $Mn^{2+}$, $Ru^{2+}$, or $Fe^{2+}$; or M is $Cu^{2+}$, $Zn^{2+}$, $Co^{2+}$, $Cd^{2+}$, $Mn^{2+}$, or $Fe^{2+}$; or M is $Cu^{2+}$, $Zn^{2+}$, $Ni^{2+}$, or $Co^{2+}$; or M is $Cu^{2+}$, $Zn^{2+}$, or $Co^{2+}$; or M is $Cu^{2+}$, $Zn^{2+}$, or $Ni^{2+}$; or M is $Cu^{2+}$ or $Zn^{2+}$; and -L is selected from a compound of Formula (I). In some embodiments, M includes one or more transition metals. In other embodiments, M does not include a transition metal. In certain embodiments, M includes non-transition metals.

In some embodiments, Formula (II) is a compound of Formula (II-A)

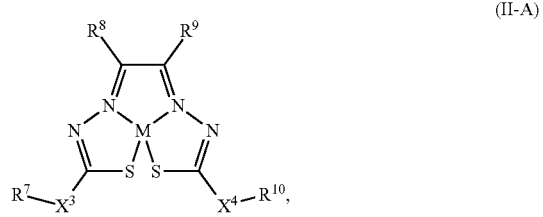

(II-A)

wherein
—$R^7$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), amine (—$NH_2$), —$NR_aR_b$, —$N^{(+)}R_aR_bR_c$, methanoly (—COH), carboxy (—$CO_2H$), nitro (—$NO_2$), cyano (—CN), ethynyl (—CCH), sulfo (—$SO_3H$), methyl, or ethyl;

—$X^3$ is bivalent —(NH)—, —(N—CH($CH_3$)$_2$)—, —(N—$CH_2CH_3$)—, —(N—$CH_3$)—, or —O—, which —(NH)—, —(N—CH($CH_3$)$_2$)—, —(N—$CH_2CH_3$)—, or —(N—$CH_3$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

—$R^8$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$R^9$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$X^4$ is bivalent —(NH)—, —(N—CH($CH_3$)$_2$)—, —(N—$CH_2CH_3$)—, —(N—$CH_3$)—, or —O—, which —(NH)—, —(N—CH(CH$_3$)$_2$)—, —(N—CH$_2$CH$_3$)—, or —(N—CH$_3$)— can optionally be substituted with one or more of halogen, hydroxy (—OH), C$_1$-C$_5$ alkyl, C$_1$-C$_4$ alkoxy, methanoly (—COH), carboxy (—CO$_2$H), nitro (—NO$_2$), cyano (—CN), ethynyl (—CCH), sulfo (—SO$_3$H), methyl, or ethyl;

—R$^{10}$ is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), C$_1$-C$_7$ alkyl (e.g., C$_1$, C$_2$, C$_3$, C$_4$, C$_5$, C$_6$, or C$_7$ alkyl), C$_2$-C$_7$ alkenyl (e.g., C$_2$, C$_3$, C$_4$, C$_5$, C$_6$, or C$_7$ alkenyl), C$_2$-C$_7$ alkynyl (e.g., C$_2$, C$_3$, C$_4$, C$_5$, C$_6$, or C$_7$ alkynyl), or C$_1$-C$_6$ alkoxy (C$_1$, C$_2$, C$_3$, C$_4$, C$_5$, or C$_6$ alkoxy), which aryl (e.g., benzene or pyrene), cycloalkyl, heterocyclyl (e.g., benzo crown ether or pyrrolyl), heteroaryl (e.g., pyridinyl, imidazolyl, or 1-methyl imidazolyl), C$_1$-C$_7$ alkyl, C$_2$-C$_7$ alkenyl, C$_2$-C$_7$ alkynyl, or C$_1$-C$_6$ alkoxy can optionally be substituted with one or more (e.g., 0, 1, 2, 3, 4, 5, or 6) of halogen (e.g., F, Cl, Br, or I), hydroxy (—OH), C$_1$-C$_5$ alkyl (e.g., C$_1$, C$_2$, C$_3$, C$_4$, or C$_5$ alkyl), C$_1$-C$_4$ alkoxy (C$_1$, C$_2$, C$_3$, or C$_4$ alkoxy), amine (—NH$_2$), —NR$_a$R$_b$, —N$^{(+)}$R$_a$R$_b$R$_c$, methanoly (—COH), carboxy (—CO$_2$H), nitro (—NO$_2$), cyano (—CN), ethynyl (—CCH), sulfo (—SO$_3$H), methyl, or ethyl; and -M is Ni, Pd, Pt, Cu, Ag, Au, Zn, Cd, Hg, Co, Rh, Ti, V, Cr, Mn, or Fe; or M is Cu$^{2+}$, Cu$^+$, Zn$^{2+}$, Co$^{2+}$, Ni$^{2+}$, Cd$^{2+}$, Mn$^{2+}$, Ru$^{2+}$, or Fe$^{2+}$; or M is Cu$^{2+}$, Cu$^+$, Zn$^{2+}$, Co$^{2+}$, Cd$^{2+}$, Mn$^{2+}$, Ru$^{2+}$, or Fe$^{2+}$; or M is Cu$^{2+}$, Zn$^{2+}$, Co$^{2+}$, Cd$^{2+}$, Mn$^{2+}$, or Fe$^{2+}$; or M is Cu$^{2+}$, Zn$^{2+}$, Ni$^{2+}$, or Co$^{2+}$; or M is Cu$^{2+}$, Zn$^{2+}$, or Co$^{2+}$; or M is Cu$^{2+}$, Zn$^{2+}$, or Ni$^{2+}$; or M is Cu$^{2+}$ or Zn$^{2+}$.

In certain embodiments, M is Cu$^{2+}$, Zn$^{2+}$, Ni$^{2+}$, or Co$^{2+}$; or M is Cu$^{2+}$, Zn$^{2+}$, or Co$^{2+}$; or M is Cu$^{2+}$, Zn$^{2+}$, or Ni$^{2+}$; or M is Cu$^{2+}$ or Zn$^{2+}$. In some embodiments, M includes one or more transition metals. In other embodiments, M does not include a transition metal. In certain embodiments, M includes non-transition metals.

R$_a$, R$_b$, and R$_c$ are each independently selected from C$_1$-C$_5$ alkyl (e.g., C$_1$, C$_2$, C$_3$, C$_4$, or C$_5$ alkyl). If there are more than one of any of R$_a$, R$_b$, or R$_c$ on the same compound (for example, if R$^7$ comprises an R$_a$ and R$^6$ also comprises an R$_a$), then each is chosen independently.

In some embodiments, one or both of R$^7$ or R$^{10}$ is (a) C$_1$-C$_7$ alkyl (e.g., C$_1$, C$_2$, C$_3$, C$_4$, C$_5$, C$_6$, or C$_7$ alkyl) substituted with —NR$_a$R$_b$, (b) C$_1$-C$_7$ alkyl (e.g., C$_1$, C$_2$, C$_3$, C$_4$, C$_5$, C$_6$, or C$_7$ alkyl) substituted with —N$^{(+)}$R$_a$R$_b$R$_c$, (c) substituted or unsubstituted benzo crown ether (e.g., mono benzo 18-crown-6 ether), (d) phenyl substituted with a carboxy (e.g., para, meta, or ortho substituted), (e) substituted or unsubstituted pyrrolyl (e.g., 2-amine or 5-amine substituted pyrrolyl), (f) substituted or unsubstituted pyridyl, or (g) substituted or unsubstituted imidazolyl.

In some embodiments of Formula (II),
(a) R$^3$ is the same as R$^4$;
(b) R$^3$ is the same as R$^4$ and R$^1$ is the same as R$^5$;
(c) R$^3$ is the same as R$^4$, X$^1$ is —(NH)—, X$^2$ is —(NH)—, and R$^2$ is the same as R$^6$;
(d) R$^3$ is the same as R$^4$, R$^3$ is methyl, R$^1$ is the same as R$^5$, R$^1$ is

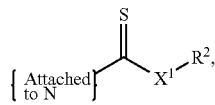

X$^1$ is —(NH)—, and R$^2$ is —CH$_3$;
(e) R$^3$ is the same as R$^4$, R$^3$ is methyl, R$^1$ is the same as R$^5$, R$^1$ is

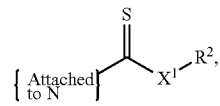

X$^1$ is —(NH)—, and R$^2$ is —C$_5$H$_6$;
(f) R$^3$ is the same as R$^4$, R$^3$ is methyl, R$^1$ is the same as R$^5$, R$^1$ is

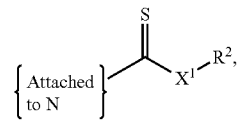

X$^1$ is —(NH)—, and R$^2$ is —CH$_2$F$_3$;
(g) R$^3$ is the same as R$^4$, R$^3$ is methyl, R$^1$ is the same as R$^5$, R$^1$ is

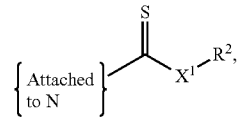

X$^1$ is —(NCH$_3$)—, and R$^2$ is —CH$_3$;
(h) R$^3$ is the same as R$^4$, R$^3$ is methyl, R$^1$ is the same as R$^5$, R$^1$ is

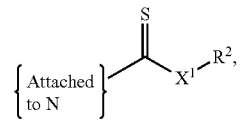

X$^1$ is —O—, and R$^2$ is —CH$_3$;
(i) R$^3$ is the same as R$^4$ and R$^3$ is methyl;
(j) R$^3$ is the same as R$^4$ and R$^3$ is ethyl;
(k) R$^3$ is methyl and R$^4$ is phenyl;
(l) R$^1$ is

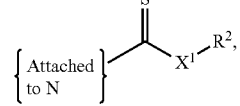

X$^1$ is —(NH)—, R$^2$ is —CH$_3$, R$^5$ is

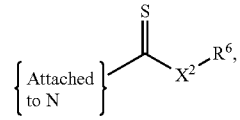

$X^2$ is —(N—CH(CH$_3$)$_2$)—, and R$^6$ is —CH(CH$_3$)$_2$;
  (m) R$^1$ is

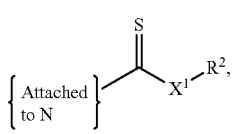

$X^1$ is —(NH)—, R$^2$ is —CH$_3$, R$^5$ is

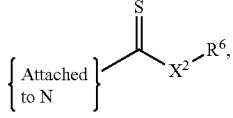

$X^2$ is —(NH)—, and R$^6$ is —C$_5$H$_6$;
  (n) R$^1$ is

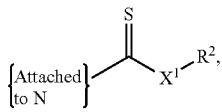

$X^1$ is —(NH)—, R$^2$ is —CH$_3$, R$^5$ is

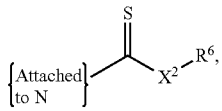

$X^2$ is —(NH)—, and R$^6$ is —CH$_2$CF$_3$;
  (o) R$^1$ is

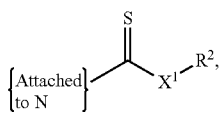

$X^1$ is —(NH)—, R$^2$ is —CH$_3$, R$^5$ is

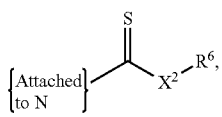

$X^2$ is —O—, and R$^6$ is —CH$_3$;
  (p) R$^1$ is

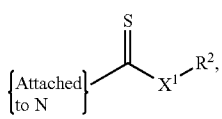

$X^1$ is —(NH)—, R$^2$ is —CH$_3$, R$^5$ is

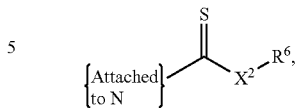

$X^2$ is —O—, and R$^6$ is —CH$_2$CH$_3$;
  (q) (1) the limitations of (l) and (2) the limitations of (i), (j), or (k);
  (r) (1) the limitations of (m) and (2) the limitations of (i), (j), or (k);
  (s) (1) the limitations of (n) and (2) the limitations of (i), (j), or (k);
  (t) (1) the limitations of (o) and (2) the limitations of (i), (j), or (k); or
  (u) (1) the limitations of (p) and (2) the limitations of (i), (j), or (k).

In some embodiments of Formula (II),
  (a) R$^8$ is the same as R$^9$;
  (b) R$^8$ is the same as R$^9$ and X$^3$—R$^7$ is the same as X$^4$—R$^{10}$;
  (c) R$^8$ is the same as R$^9$, X$^3$ is —(NH)—, X$^4$ is —(NH)—, and R$^7$ is the same as R$^{10}$;
  (d) R$^8$ is the same as R$^9$, R$^8$ is methyl, X$^3$—R$^7$ is the same as X$^4$—R$^{10}$, X$^3$ is —(NH)—, and R$^7$ is —CH$_3$;
  (e) R$^8$ is the same as R$^9$, R$^8$ is methyl, X$^3$—R$^7$ is the same as X$^4$—R$^{10}$, X$^3$ is —(NH)—, and R$^7$ is —C$_5$H$_6$;
  (f) R$^8$ is the same as R$^9$, R$^8$ is methyl, X$^3$—R$^7$ is the same as X$^4$—R$^{10}$, X$^3$ is —(NH)—, and R$^7$ is —CH$_2$F$_3$;
  (g) R$^8$ is the same as R$^9$, R$^8$ is methyl, X$^3$—R$^7$ is the same as X$^4$—R$^{10}$, X$^3$ is —(NCH$_3$)—, and R$^7$ is —CH$_3$;
  (h) R$^8$ is the same as R$^9$, R$^8$ is methyl, X$^3$—R$^7$ is the same as X$^4$—R$^{10}$ X$^3$ is —O—, and R$^7$ is —CH$_3$;
  (i) R$^8$ is the same as R$^9$ and R$^8$ is methyl;
  (j) R$^8$ is the same as R$^9$ and R$^8$ is ethyl;
  (k) R$^8$ is methyl and R$^9$ is phenyl;
  (l) X$^3$ is —(NH)—, R$^7$ is —CH$_3$, X$^4$ is —(N—CH(CH$_3$)$_2$)—, and R$^{10}$ is —CH(CH$_3$)$_2$;
  (m) X$^3$ is —(NH)—, R$^7$ is —CH$_3$, X$^4$ is —(NH)—, and R$^{10}$ is —C$_5$H$_6$;
  (n) X$^3$ is —(NH)—, R$^7$ is —CH$_3$, X$^4$ is —(NH)—, and R$^{10}$ is —CH$_2$CF$_3$;
  (o) X$^3$ is —(NH)—, R$^7$ is —CH$_3$, X$^4$ is —O—, and R$^{10}$ is —CH$_3$;
  (p) X$^3$ is —(NH)—, R$^7$ is —CH$_3$, X$^4$ is —O—, and R$^{10}$ is —CH$_2$CH$_3$;
  (q) (1) the limitations of (l) and (2) the limitations of (i), (j), or (k);
  (r) (1) the limitations of (m) and (2) the limitations of (i), (j), or (k);
  (s) (1) the limitations of (n) and (2) the limitations of (i), (j), or (k);
  (t) (1) the limitations of (o) and (2) the limitations of (i), (j), or (k); or
  (u) (1) the limitations of (p) and (2) the limitations of (i), (j), or (k).

In some embodiments of Formula (II), M is Zn$^{2+}$, Co$^{2+}$, Ni$^{2+}$ or Cu$^{2+}$, (e.g., M is Zn$^{2+}$, Ni$^{2+}$ or Cu$^{2+}$; or M is Zn$^{2+}$, Co$^{2+}$ or Cu$^{2+}$; or M is Zn$^{2+}$ or Cu$^{2+}$).

In other embodiments, Formula (II) further comprises a solvent molecule coordinated with Formula (II). In other embodiments, the solvent molecule can be any suitable solvent molecule. In certain embodiments, the solvent molecule is selected from water, ethanol, propanol, acetonitrile, dimethylformamide, and acetone.

In some embodiments, Formula (II) is

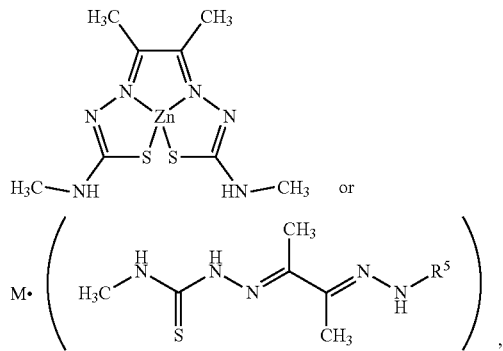

or where M is Zn, Co, Ni, or Cu (e.g., M is Zn, Ni, or Cu; or M is Zn, Co, or Cu; or M is Zn or Cu) and $R^5$ is pyridinyl, 1-methyl-imidazolyl, an N-containing heterocyclyl, or an N-containing heteroaryl.

In certain embodiments, Formula (II) is symmetric or is asymmetric.

In other embodiments, (a) $X^1$ is not —(NH)—, (b) $R^2$ is not methoxyphenyl or p-methoxyphenyl, or (c) both (a) and (b). In yet other embodiments, (a) $X^2$ is not —(NH)—, (b) $R^6$ is not methoxyphenyl or p-methoxyphenyl, or (c) both (a) and (b). In certain embodiments, (a) $R^3$ is not methyl, (b) $R^4$ is not methyl, or (c) both (a) and (b).

In some embodiments, Formula (II) is not

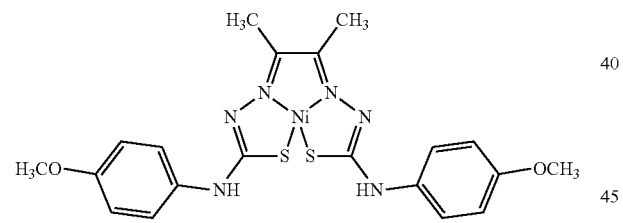

In some embodiments, Formula (II) is

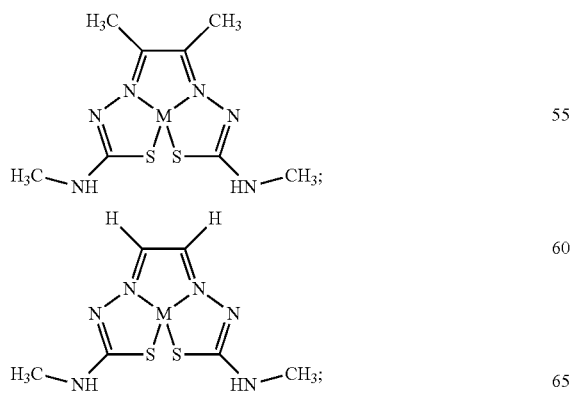

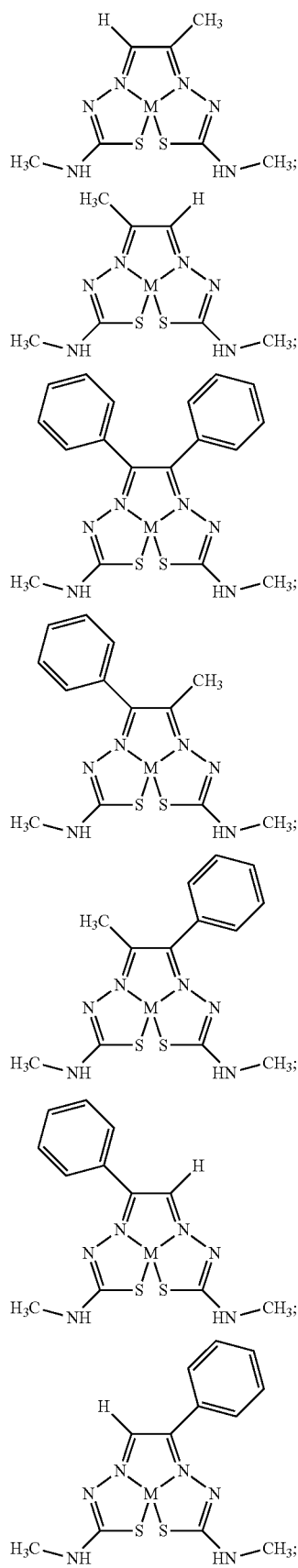

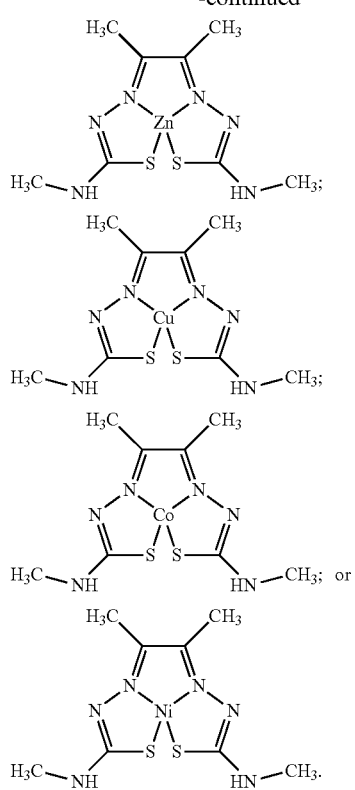
In other embodiments, Formula (II) is
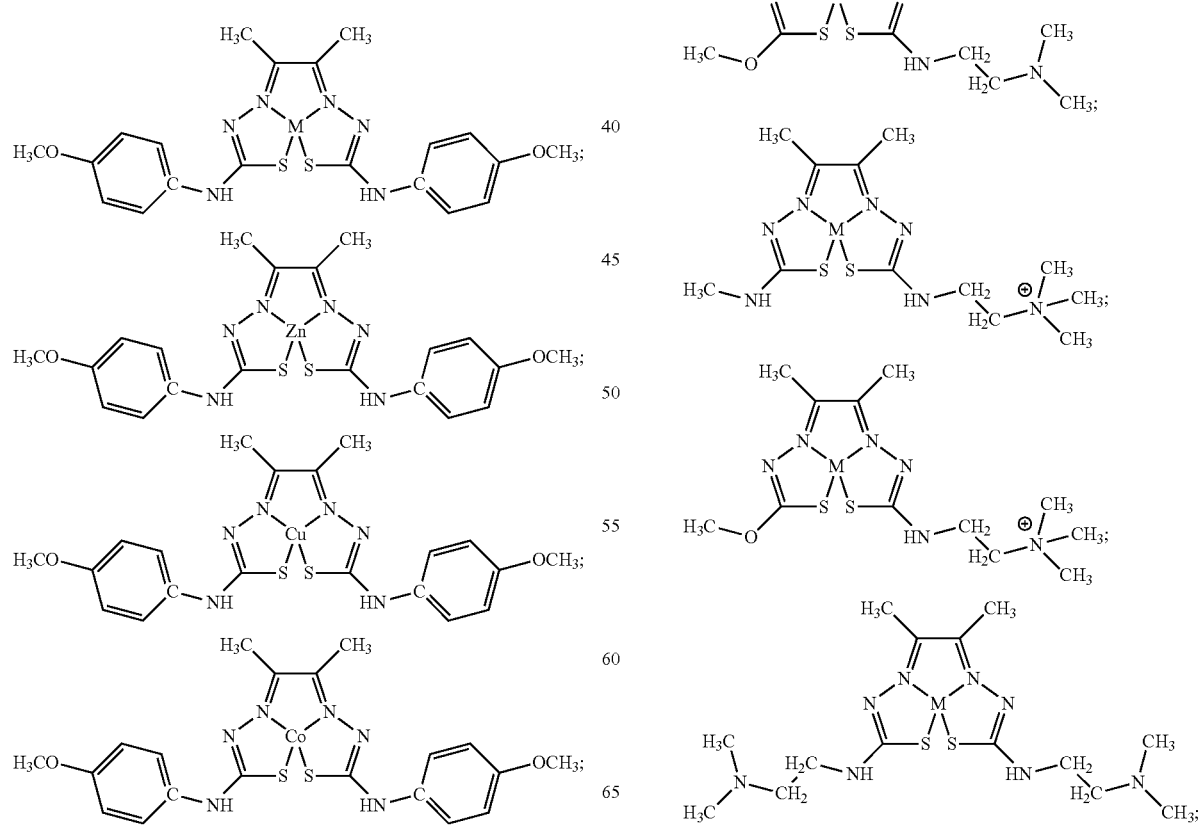

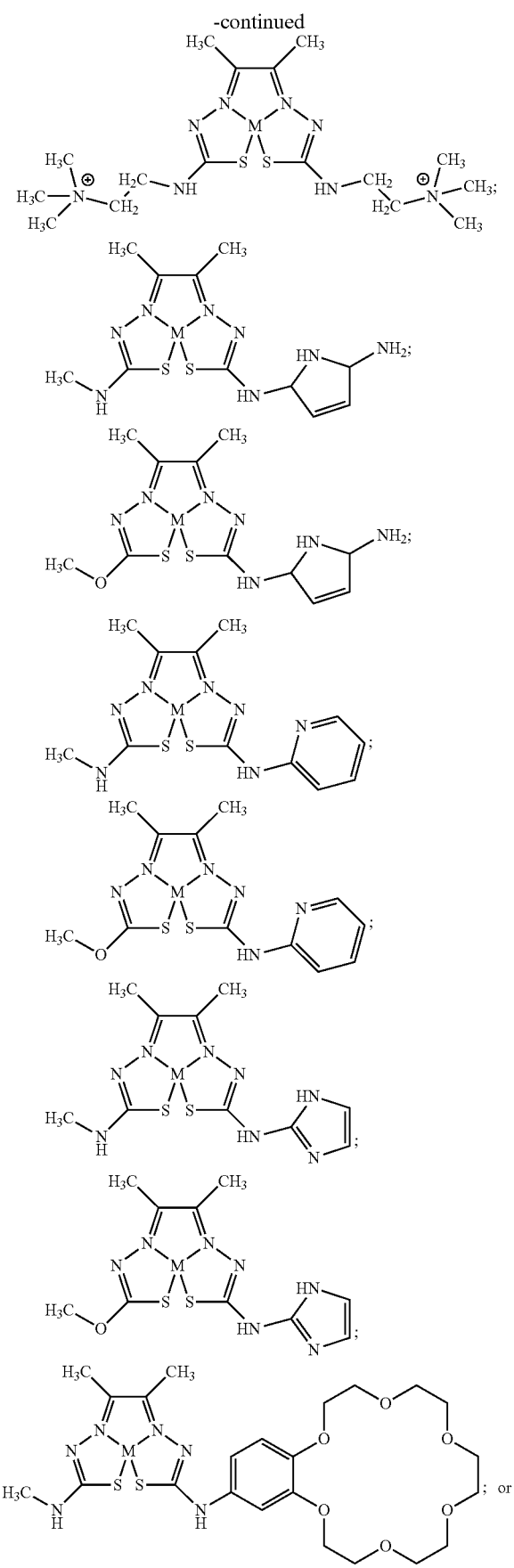

In some embodiments, Formula (II) is one of the molecules described in Example Sets A, B, C, D, E, F, G, or H.

In some embodiments, a compound of Formula (II) is part of a homogenous solution, a homogenous aqueous solution, a heterogeneous solution, or a heterogeneous aqueous solution. In other embodiments, a homogenous solution, a homogenous aqueous solution, a heterogeneous solution, or a heterogeneous aqueous solution, each comprise a compound of Formula (II).

Figure 81:
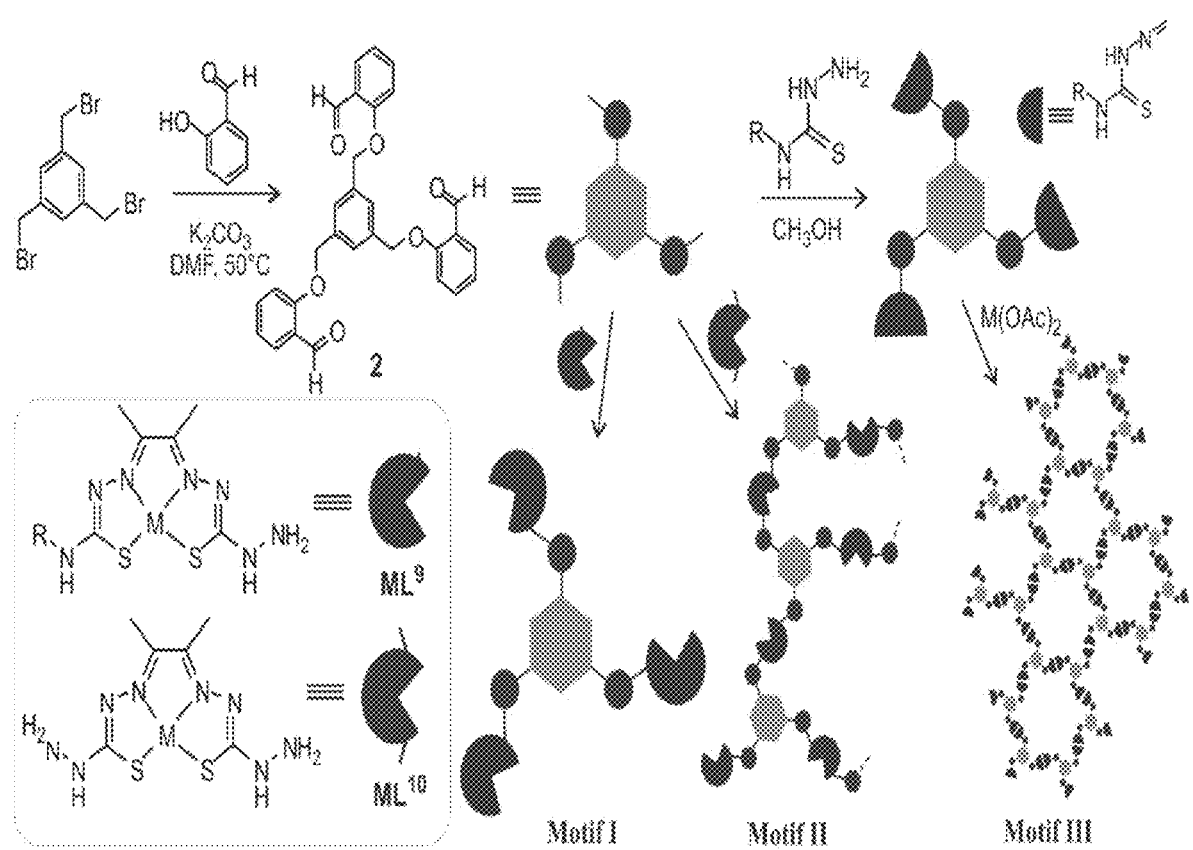
FIG. 81 Embodiments of an extended structure motif.

In other embodiments, a glassy carbon electrode, a carbon paste (e.g., embedded with one or more of polynuclear catalysts, coordinated polymers, or metal-organic frameworks), covalent modified carbon (e.g., graphene), or non-covalent modified carbon (e.g., graphene), each comprises or is reacted with a compound of Formula (II). In certain embodiments, the carbon paste comprises an extended structure motif (e.g., motif I, motif II, or motif III of the scheme shown in FIG. 81).

Certain embodiments of the invention include glassy carbon electrodes (GCE) comprising Formula (I), Formula (II), or both. Glassy carbon electrodes can be used for any suitable purpose including but not limited to use in heterogeneous aqueous solutions. Glassy carbon electrodes can be made using any suitable method including but not limited to dropcast or spray coating. In some instances, contributions to adhesion to the electrode can include but are not limited to π-π interactions, the water-insolubility of Formula (I) or Formula (II), or both. In some instances, asymmetric structures of Formula (I), Formula (II) or both can be used, in that the asymmetric structure is capable (e.g., designed) of linking to the GCE. In other instances, symmetric molecules of Formula (I), Formula (II) or both can be used to make GCEs.

Other embodiments of the invention include carbon paste electrodes (CPE) embedded with compositions comprising Formula (I), Formula (II), or both. The embedded compositions can be any suitable composition including but not limited to molecular catalysts or related extended structures (e.g., polynuclear catalysts, coordination polymers, metal-organic frameworks, or extended structures as described herein). Extended structures can be made using any suitable technique, including but not limited to those exemplified in the Examples or the scheme above; that technique can be applied to any suitable Formula (I) or Formula (II) and is not limited to the specific molecules used. In some instances, asymmetric structures of Formula (I), Formula (II) or both can be used, in that the asymmetric structure can be capable (e.g., designed) of forming desired extended networks. In other instances, symmetric molecules of Formula (I), Formula (II) or both can be used to make extended structures.

Still other embodiments of the invention include attachment of Formula (I), Formula (II), or both, to carbon surfaces (e.g., graphene, glassy carbon, graphite, carbon nanotubes, carbon nanospheres, or multiwalled carbon ananotubes). Attachment can include any suitable attachment including but not limited to covalent or enhanced non-covalent attachment (e.g., π-π interactions, insolubility of Formula (I) or Formula (II), or combinations thereof). In certain instances, the carbon surface (e.g., carbon electrode) can be modified with any suitable linker, such as being modified with diazonium compounds, amination chemistry, amide, coupling amines, carboxylic acids, epoxides or any suitable linker so that Formula (I), Formula (II), or an extended structure thereof can be linked to the carbon surface. Linker length, in some embodiments, is chosen to allow catalyst to adopt one or more confirmations that occur during catalysis (e.g., the linker can be used to force drive a desired catalytic mechanism, such as ligand centered reactivity). In yet other embodiments, the linker length is not so long as to diminish electron transfer between catalyst and carbon surface. In certain embodiments, Formula (I), Formula (II) or both can comprise a carboxylic acid or carboxaldehyde to attach to a carbon surface (e.g., modified with amines). In some instances, asymmetric structures of Formula (I), Formula (II) or both can be used, in that the asymmetric structure is capable (e.g., designed) of linking to the modified or unmodified carbon surface. In other instances, symmetric molecules of Formula (I), Formula (II) or both can be used (e.g., designed) to linking to the modified or unmodified carbon surface. In certain embodiments, related extended structures (e.g., polynuclear catalysts, coordination polymers, metal-organic frameworks, or extended structures as described herein) can be attached to the modified or unmodified carbon surface.

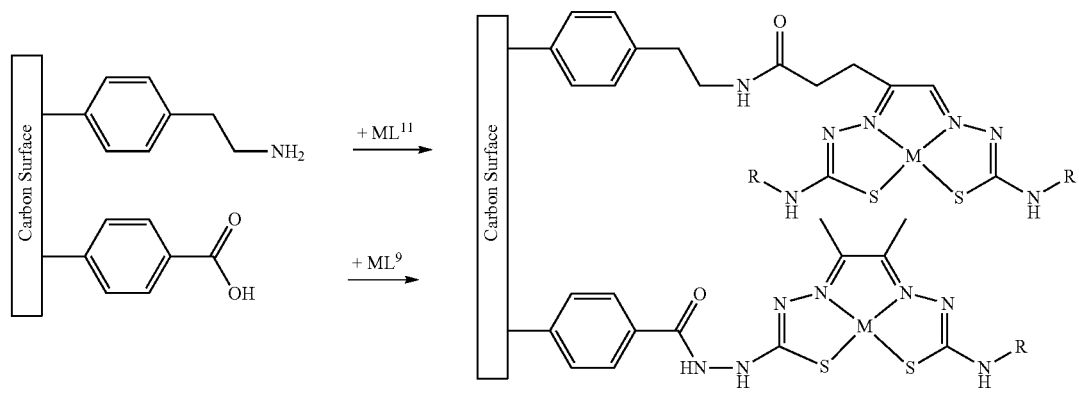

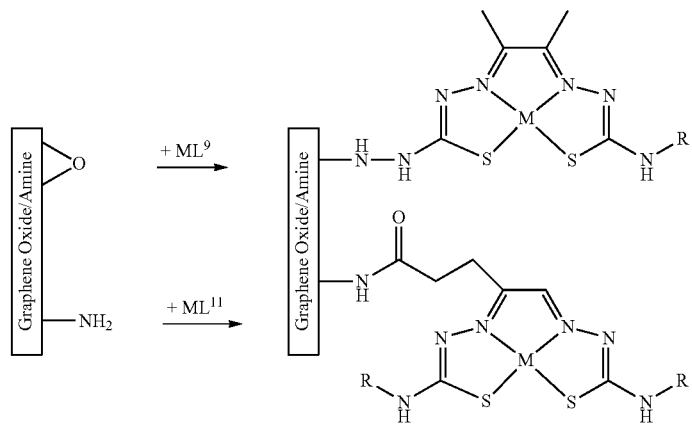

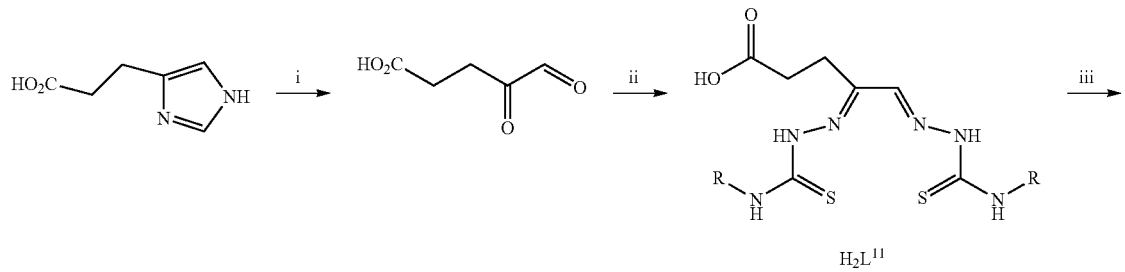

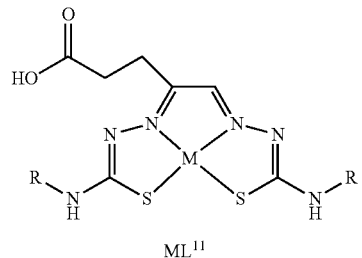

ML<sup>11</sup> i) N-bromosuccinimide, MeCN, H₂O; ii) H₂NNHC(S)NHR, MeOH;
iii) M(OAc)₂, MeOH

Covalent modification of carbon surfaces can be accomplished using any suitable technique, including but not limited to those exemplified in the scheme above; that technique can be applied to any suitable Formula (I) or Formula (II) and is not limited to the specific molecules used.

In some embodiments, the inventive compounds (e.g., Formula (I) or Formula (II), or their embodiments in any of the above GCEs, CPEs, or carbon surfaces) can be used in one or more of the following applications: catalysts (e.g., electrocatalysts) for activation of small molecules (e.g., alcohols, such as, but not limited to, methanol, ethanol, propanol, butanol, and all their isomers), integration into PEM fuel cells; hydrogen evolution for solar energy storage; sustainable hydrogen resource for fertilizer production; solid electrolytes for small battery development; hydrogenation/dehydrogenation catalysts; electrocatalytic $CO_2$ reduction catalyst; selective olefin binding and functionalization; ethylene and small molecule detection; desulfurization; incorporation into electroactive films or thin films; incorporation into conductive polymers; electroactive, tunable metal-organic-frameworks; water purification; and water desalination.

In some embodiments, the inventive compounds (e.g., Formula (I) or Formula (II) and their metal (e.g., zinc or copper) complexes) can have one or more of the following uses or properties: use as a substitution for metal-hydride intermediates; capable of being engineered with different functional groups to match a desired application; air and water stable; no special precautions in preparation, storage, or handling; low molecular weights; capable of reducing the mass of catalyst in a particular application; capable of being prepared in high yield (e.g., in 4-7 steps from commercially available bulk reagents) and/or inexpensively; does not utilize precious or semi-precious metals for catalysts; catalysts can be prepared in alcohol solution; and catalysis can be conducted in alcohol or water.

In certain embodiments, the inventive (e.g., Formula (I) or Formula (II) and their metal (e.g., zinc or copper) complexes) comprise proton relay groups (e.g., as part of the ligand structure). In certain embodiments, the inventive compounds comprise structure(s) or modification(s) that are capable of attaching to an electrode surface, a solid support, or both. In certain instances, light driven evolution of $H_2$ with the inventive compounds can be accomplished using various photosensitizers and sacrificial redox mediators. In other embodiments, the inventive compounds (e.g., where M is Cu) can be used as a catalyst for the oxidation alcohols to aldehydes using air.

Some embodiments of the invention include a catalyst (e.g., an electrocatalyst) comprising a composition comprising a compound of Formula (I), a compound of Formula (II), or both. Other embodiments include an anode comprising a composition comprising a compound of Formula (I), a compound of Formula (II), or both. Other embodiments include a cathode comprising a composition comprising a compound of Formula (I), a compound of Formula (II), or both.

Other embodiments include an electrochemical cell comprising a composition comprising a compound of Formula (I), a compound of Formula (II), or both. In some instances, the cathode of the electrochemical cell comprises the composition, the anode of the electrochemical cell comprises the composition, or both.

Still other embodiments of the invention include a fuel cell comprising a composition comprising a compound of Formula (I), a compound of Formula (II), or both. In some instances, the cathode of the fuel cell comprises the composition, the anode of the fuel cell comprises the composition, or both.

Additional embodiments of the invention include a method for producing $H_2$ comprising contacting, in an electrochemical cell, a first composition comprising a compound of Formula (I), a compound of Formula (II), or both with a second composition comprising water. In some instances, the cathode of the electrochemical cell comprises the first composition. In certain embodiments, the Turn Over Frequency (TOF) is from about 20 $s^{-1}$ to about 100,000 $s^{-1}$, about 100 $s^{-1}$ to about 100,000 $s^{-1}$, from about 500 $s^{-1}$ to about 100,000 $s^{-1}$, from about 500 $s^{-1}$ to about 50,000 $s^{-1}$, from about 500 $s^{-1}$ to about 20,000 $s^{-1}$, about 20 $s^{-1}$, about 100 $s^{-1}$, about 500 $s^{-1}$, about 1000 $s^{-1}$, about 5000 $s^{-1}$, about 10000 $s^{-1}$, about 12000 $s^{-1}$, about 16000 $s^{-1}$, about 20000 $s^{-1}$, about 50000 $s^{-1}$, or about 100,000 $s^{-1}$. In some embodiments, the overpotential is greater than about 0 V, not less than about 0.1 V, not more than about 0.1 V, not more than 0.5 V, not more than 1 V, not more than 10 V, not more than 100 V, from about 0 V to about 2000 V, from about 0 V to about 1000 V, from about 0 V to about 750 V, from about 0 V to about 300 V, from about 0 V to about 350 V, from about 0 V to about 200 V, from about 0 V to about 100 V, from about 0 V to about 20 V, from about 0 V to about 10 V, from about 0 V to about 5 V, from about 0 V to about 2 V, from about 0 V to about 1 V, from about 0.1 V to about 2000 V, from about 0.1 V to about 1000 V, from about 0.1 V to about 750 V, from about 0.1 V to about 300 V, from about 0.1 V to about 350 V, from about 0.1 V to about 200 V, from about 0.1 V to about 100 V, from about 0.1 V to about 20 V, from about 0.1 V to about 10 V, from about 0.1 V to about 5 V, from about 0.1 V to about 2 V, from about 0.1 V to about 1 V, about 0.1 V, about 0.5 V, about 1 V, about 5 V, about 10 V, about 100 V, about 250 V, about 350 V, about 400 V, about 500 V, or about 1000 V.

Other instances of the invention include a method for oxidizing an aldehyde, an alcohol, acetonitrile, or water comprising contacting, in an electrochemical cell, a composition comprising a compound of Formula (I), a compound of Formula (II), or both. In some embodiments, the overpotential is greater than about 0 V, not less than about 0.1 V, not more than about 0.1 V, not more than 0.5 V, not more than 1 V, not more than 10 V, not more than 100 V, from about 0 V to about 2000 V, from about 0 V to about 1000 V, from about 0 V to about 750 V, from about 0 V to about 300 V, from about 0 V to about 350 V, from about 0 V to about 200 V, from about 0 V to about 100 V, from about 0 V to about 20 V, from about 0 V to about 10 V, from about 0 V to about 5 V, from about 0 V to about 2 V, from about 0 V to about 1 V, from about 0.1 V to about 2000 V, from about 0.1 V to about 1000 V, from about 0.1 V to about 750 V, from about 0.1 V to about 300 V, from about 0.1 V to about 350 V, from about 0.1 V to about 200 V, from about 0.1 V to about 100 V, from about 0.1 V to about 20 V, from about 0.1 V to about 10 V, from about 0.1 V to about 5 V, from about 0.1 V to about 2 V, from about 0.1 V to about 1 V, about 0.1 V, about 0.5 V, about 1 V, about 5 V, about 10 V, about 100 V, about 250 V, about 350 V, about 400 V, about 500 V, or about 1000 V.

Some embodiments of the invention include a method for producing electricity comprising contacting, in a fuel cell, a first composition comprising a compound of Formula (I), a compound of Formula (II), or both with a second composition comprising $H_2$. In some embodiments of this method, the anode of the fuel cell comprises the first composition. In some embodiments of this method, the cathode of the fuel cell comprises the first composition. In certain instances, the TOF is from about 1 $s^{-1}$ to about 1000 $s^{-1}$, from about 5 $s^{-1}$ to about 1000 $s^{-1}$, from about 5 $s^{-1}$ to about 500 $s^{-1}$, from about 5 $s^{-1}$ to about 200 $s^{-1}$, about 1 $s^{-1}$, about 5 $s^{-1}$, about 10 $s^{-1}$, about 32 $s^{-1}$, about 50 $s^{-1}$, about 76 $s^{-1}$, about 100 $s^{-1}$, about 120 $s^{-1}$, about 200 $s^{-1}$, about 300 $s^{-1}$, about 500 $s^{-1}$, or about 1000 $s^{-1}$. In yet additional embodiments, the overpotential is greater than about 0 V, not less than about 0.1 V, not more than about 0.1 V, not more than 0.5 V, not more than 1 V, not more than 10 V, not more than 100 V, from about 0 V to about 2000 V, from about 0 V to about 1000 V, from about 0 V to about 750 V, from about 0 V to about 300 V, from about 0 V to about 0 V to about 350 V, from about 0 V to about 200 V, from about 0 V to about 100 V, from about 0 V to about 20 V, from about 0 V to about 10 V, from about 0 V to about 5 V, from about 0 V to about 2 V, from about 0 V to about 1 V, from about 0.1 V to about 2000 V, from about 0.1 V to about 1000 V, from about 0.1 V to about 750 V, from about 0.1 V to about 300 V, from about 0.1 V to about 350 V, from about 0.1 V to about 200 V, from about 0.1 V to about 100 V, from about 0.1 V to about 20 V, from about 0.1 V to about 10 V, from about 0.1 V to about 5 V, from about 0.1 V to about 2 V, from about 0.1 V to about 1 V, about 0.1 V, about 0.5 V, about 1 V, about 5 V, about 10 V, about 100 V, about 250 V, about 350 V, about 400 V, about 500 V, or about 1000 V.

Other embodiments of the invention include a method for preparing a compound of Formula (I) comprising any suitable method, such as those disclosed herein. In some instances, the compound of Formula (I) is prepared comprising (a) reacting a compound of Formula (III)

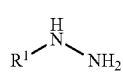

(III)

with a compound of Formula (IV)

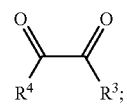

(IV)

(b) reacting a compound of Formula (V)

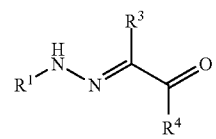

(V)

with a compound of Formula (VI)

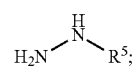

(VI)

and (c) recovering the compound of Formula (I), wherein $R^1$, $R^3$, $R^4$, and $R^5$ are defined herein. Recovery can occur using any suitable method including but not limited to HPLC (e.g., reverse phase), LC, precipitation, centrifugation, column chromatography (e.g., size exclusion chromatography or ion exchange chromatography), use of silica gel, or combinations thereof.

Other embodiments of the invention include a method for preparing a compound of Formula (II) comprising any suitable method, such as those disclosed herein. In certain instances, the compound of Formula (II) is prepared comprising (a) reacting a compound of Formula (I) with M (e.g., Zn, Co, or Cu) or salt thereof; and (b) recovering the compound of Formula (II), wherein M is defined herein. Recovery can occur using any suitable method including but not limited to HPLC (e.g., reverse phase), LC, precipitation, centrifugation, column chromatography (e.g., size exclusion chromatography or ion exchange chromatography), use of silica gel, or combinations thereof.

Additional embodiments include a method for preparing a catalyst (e.g., an electrocatalyst) comprising a composition comprising a compound of Formula (I), a compound of Formula (II), or both, comprising any suitable method, including those described herein. Additional embodiments include a method for preparing an anode comprising a composition comprising a compound of Formula (I), a compound of Formula (II), or both, comprising any suitable method, including those described herein. Further embodiments include a method for preparing a cathode comprising a composition comprising a compound of Formula (I), a compound of Formula (II), or both, comprising any suitable method, including those described herein.

The presently-disclosed subject matter is further illustrated by the following specific but non-limiting examples. The following examples may include compilations of data that are representative of data gathered at various times during the course of development and experimentation related to the present invention.

EXAMPLES

Example Set A: HER and HOR of Zn and Metal-Free Complexes

The compounds discussed in Example Set A include $H_2L$ and ZnL.

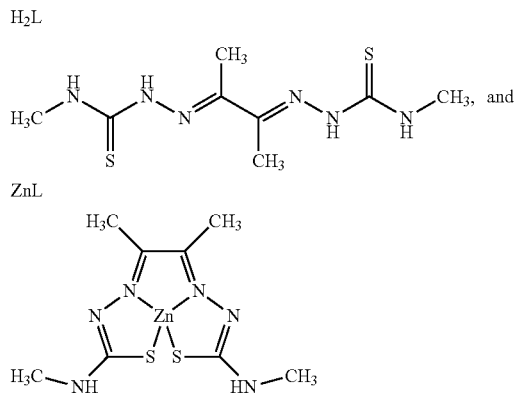

$H_2L$

ZnL

Materials and Methods for Example Set A

All solvents were purified with an MBraun solvent purification system prior to use.

Electrochemical Methods

All cyclic voltammetry (CV) and controlled potential coulometry (CPC) measurements were recorded using a Gamry Interface potentiostat/galvanostat, which was connected to a glassy carbon working electrode (6.5 mm diameter, surface area=0.07 cm$^2$), a platinum wire counter electrode, and Ag/AgCl reference electrode. Before use, the working electrode was polished using aqueous alumina slurry. Working and counter electrodes were cleaned before use by washing with water, ethanol, acetone, isopropanol and methanol, and then sonicated in methanol. CV measurements were conducted using a three-neck electrochemical cell that was washed and dried in oven over night before use. All electrochemical experiments were conducted under a $N_2$ atmosphere, aside from HOR experiments. All CPC measurements were conducted using a custom built gas tight Parr-electrolysis reactor with a volume of 30 mL washed and dried night before use. The working compartment was fitted with a platinum working electrode (surface area=0.07 cm$^2$) and an Ag/AgCl reference electrode. The auxiliary compartment was fitted with a Pt wire counter electrode. The working compartment contained 12 mM acetic acid added to a 0.1 M $Bu_4NPF_6$ methanol solution, while the auxiliary compartment was filled with 0.1 M $Bu_4NPF_6$ methanol solution. Both compartments were purged for 15 min with $N_2$ and kept under a constant $N_2$ flow. A control (blank) CPC study was conducted and subtracted from experimental results. Electrolysis was then measured with the addition of the 0.1 mM ZnL. Electrolysis was conducted for 2.5 hours and the samples were subjected to gas chromatographic analysis every 30 minutes. A Gow-Mac series 400 GC-TCD with molecular sieve column was used for product detection. The column was heated to 130° C. under $N_2$ gas flow with 250 µL injection samples injected onto the column. The integrated area of the $H_2$ peak was then compared to the pre-made $H_2$ calibration curve in order to calculate the volume and moles of $H_2$ generated.

Statistical Analysis

Overpotential Determination: Overpotential can be defined as the difference between the thermodynamic and equilibrium potentials for a given reaction and the potential at which the reaction occurs under a set of specific conditions. Using this method of Appel and Helm (ACS Catal., 2014, Vol. 4, pp. 630-633; DOI: 10.1021/cs401013v), the overpotential ($\eta$) for proton reduction or $H_2$ oxidation by ZnL or $H_2L$ under specific experimental conditions can be estimated as:

$$\eta = |(E_{OCP} - E_{cat/2})|$$

$E_{OCP}$ is the measured open circuit potential measured under catalytic conditions specific for each reaction, and $E_{cat/2}$ is the potential at one-half the maximum of the catalytic current measured for the catalyzed reduction of protons or oxidation of $H_2$ by ZnL or $H_2L$.

Overpotential calculation; ZnL HER:

$$\eta = \text{Overpotential} = |(E_{BH+(OCP)}) - (E_{cat/2})|$$

$$\eta = |[-0.924 - (-1.68V)]|$$

$$\eta = 0.756 \ V \text{ vs } Fc^+/Fc^0$$

Overpotential calculation; ZnL HOR:

$$\eta = \text{Overpotential} = |(E_{BH+(OCP)}) - (E_{cat/2})|$$

$$\eta = |(0.190 - 0.505)|$$

$$\eta = 0.315 \ V \text{ vs } Fc^+/Fc^0$$

Overpotential calculation; $H_2L$ HER:

$$\eta = \text{Overpotential} = |(E_{BH+(OCP)}) - (E_{cat/2})|$$

$$\eta = |[-0.37 - (-1.80)]|$$

$$\eta = 1.43 \ V \text{ vs } Fc^+/Fc^0$$

Overpotential calculation; $H_2L$ HOR:

$$\eta = \text{Overpotential} = |(E_{BH+(OCP)}) - (E_{cat/2})|$$

$$\eta = |(0.177 - 0.505)|$$

$$\eta = 0.328 \ V \text{ vs } Fc^+/Fc^0$$

Determination of ZnL Diffusion Coefficient ($D_0$):

Using the Randles-Sevcik equation (Eq. A2), and plotting peak current vs the square root of the scan rate allows for accurate calculation of the diffusion coefficient, $D_0$.

Slope (FIGS. 10-11)=$1.94E-5 = 0.4463FA[cat][(FD_0/RT)]^{0.5}$

A=0.071 cm$^2$
[cat]=3E-6 moles/cm$^3$
F=96485 C/mole e$^-$
R=ideal gas constant
T=298 K
$D_0$=1.15E-7 cm$^2$/s in MeOH Sample Calculations Electrolysis:

Theoretical Moles of Hydrogen Made via Total Charge:

19.8 C×(1 mol e$^-$/96485 C)×(1 mol $H_2$/2 mol e$^-$)=moles $H_2$ theoretical

Moles $H_2$ theoretical=0.00011 moles $H_2$ based on charge from electrolysis

Faradaic Efficiency Calculations:

Faradaic Efficiency=(Moles $H_2$ Quantified/Moles of $H_2$ Theoretical)×100%

Faradaic Efficiency=(0.000093 moles)/(0.00011 moles)×100%

Faradaic Efficiency=85%

TON Calculations:

TON=Moles of $H_2$ Produced/Moles of ZnL Used

TON=(0.00011 moles $H_2$ produced)/(0.000003 moles ZnL used)

TON=36.7

HER Equations for TOF Calculation:

Equation A1 details the relationship between the catalytic current $i_{cat}$, the catalyst concentration [cat], and the acid concentration [H$^+$] for a catalytic reaction that is first-order in acid and first-order in catalyst under scan rate independent conditions. The terms n, F, A, and D are the normal electrochemical terms related to the number of electrons transferred, Faraday's constant, area of the electrode, and diffusion constant, respectively.

$$i_{cat} = nFA[cat]\sqrt{Dk[H^+]} \quad (A1)$$

Equation A2 (Randle-Sevcik equation) provides the relationship between the peak current $i_p$, catalyst concentration, and scan rate (v) in the absence of acid. The factor of 0.4463 is related to the diffusion equations, R is the gas constant, and T is temperature in K. The other terms are the same as in equation A1.

$$i_p = 0.4463 FA[cat]\sqrt{\frac{FvD}{RT}} \quad (A2)$$

Thus, the ratio of $i_{cat}/i_p$ (equation A3) is obtained from equations A1 and A2

$$\frac{i_{cat}}{i_p} = \frac{n}{0.4463}\sqrt{\frac{RTk[H^+]}{Fv}} \quad (A3)$$

Under pseudo first-order conditions where $k_{obs}=k[H^+]$, equation A3 simplifies to A4.

$$\frac{i_{cat}}{i_p} = \frac{n}{0.4463}\sqrt{\frac{RTk_{obs}}{Fv}} \quad (A4)$$

Equation A4 can further be simplified to equation A5, when n=1 for bimolecular processes.

$$k_{obs} = v \times \left[\frac{\frac{i_{cat}}{i_p}}{0.35}\right]^2 \quad (A5)$$

Since no peak current for ZnL was observed in the absence of substrate in methanol, the experimentally determined diffusion coefficient, 1.15E-7, was used to calculate the value for $i_p$. This gave an $i_p$ of 43 μA when run at 5 V/s (the scan rate in which catalytic current becomes independent of scan rate). Furthermore, the value of $i_p$ was confirmed through simulations using DigiElch, which agree with the calculated $i_p$ values. Using equation A5, the TOF or $k_{obs}$ can be calculated using the experimentally determined $i_p$ value as well as the $i_{cat}$ observed at 5 V/s, 230 μA. This results in a TOF of 1170 s$^{-1}$.

We then calculated the TOF using Eq. A6, which is Eq. A1 under pseudo first-order conditions, in order to compare both calculated values, which are in agreement with each other.

$$i_{cat} = nFA[cat]\sqrt{Dk_{obs}} \quad (A6)$$

Sample Calculations ZnL TOF/$k_{obs}$:

Using Eq. A5:

$i_{cat}$=230 μA; $i_p$=43 μA; bv=5.0 V/s

=$k_{obs}$/TOF=1170 s$^{-1}$

Using Eq. A6:

$i_{cat}$=230 μA; n=1 mole e$^-$/mole of ZnL; F=96485 C/mole$^-$; A=0.071 cm$^2$; [cat]=3E-6 moles/cm$^3$; $D_{cat}$=1.15E-7 cm$^2$/s.

=$k_{obs}$/TOF=1100 s$^{-1}$

ZnL HER Kinetic Isotope Effect: Acetic Acid vs d-Acetic Acid:

| Scan Rate | $k_H$ | $k_D$ | $k_H/k_D$ |
|---|---|---|---|
| 5 V/s | 1170 | 975 | 1.2 |

HOR TOF ZnL and $H_2L$ Sample Calculation when v=1.0 V/s:

ZnL: TOF = $k_{obs}$ =

$v * 1.94(i_{cat}/i_p)^2$ when $i_{cat} = -712$ μA and $i_p = -117$ μA at 1.0 V/s TOF = 72 s$^{-1}$ $H_2L$: TOF = $k_{obs}$ =

$v * 1.94(i_{cat}/i_p)^2$ when $i_{cat} = -475$ μA and $i_p = -117$ μA at 1.0 V/s TOF = 32 s$^{-1}$ Computational Methods All calculations were performed in the gas phase using density functional theory (DFT) employing the B97-D exchange correlation functional, and the 6-311G(d) basis set for all atoms as implemented in the Gaussian09 suite of programs for electronic structure and ChemCraft was used for graphics visualization. Transition states were determined locally using the Berny algorithm with GEDIIS, and verified by IRC calculations with forward and reverse step sizes of 40. All optimizations were performed under tight constraints, with no symmetry imposed. Several dimeric TS structures in various protonation states were initially investigated by DFT using the berny algorithm for local TS optimization in the gas phase. These structures were constructed manually based on optimized reactants and products, or by modifying previously published semicarbazide dimers. Dimers without ruptured Zn—S and Zn—N bonds were also considered, but precluded based on energetic grounds.

Supplementary Text

Blank and control experiments were performed for ZnL and $H_2L$ HER CV studies. Blank runs consisted of 0.1 M $Bu_4NPF_6$ methanol or acetonitrile, depending on experiment, which had been purged with $N_2$ gas for 10 minutes. Control CVs run in 0.1 M $Bu_4NPF_6$ methanol or acetonitrile with 12 mM acetic acid showed minimal currents when compared to currents observed after addition of either ZnL or $H_2L$ electrocatalysts.

Blank and control experiments were performed for ZnL and $H_2L$ HOR CV studies. Blank runs consisted of 0.1 M $Bu_4NPF_6$ methanol solutions, which had been purged with $N_2$ gas for 10 minutes. Control CVs in the absence of ZnL or $H_2L$ were performed. CVs were run under an $H_2$ atmosphere in solutions of 0.1 M $Bu_4NPF_6$ methanol with increasing concentrations of triethylamine, added until a concentration of 30 mM. The current observed was significantly lower when compared to the current observed after the addition of the ZnL or $H_2L$ electrocatalysts. Additionally, control experiments were performed with ZnL or $H_2L$ in 0.1 M $Bu_4NPF_6$ methanol solutions under an $N_2$ atmosphere. Application of an $N_2$ atmosphere resulted in no catalytic currents. After introduction of an $H_2$ atmosphere and purging the solution with $H_2$ for 15 minutes, catalytic current was observed.

To quantify $H_2$ production, the output gas was sampled, 250 μL, every 30 minutes and analyzed by the GC-TCD described in electrochemical methods section. After sampling, the chromatographic peak area of hydrogen is obtained. The GC-TCD calibration curve was prepared by sampling known hydrogen concentrations, made with known volumes of hydrogen, from the working compartment, with a constant known $N_2$ flow rate, and then measured by the same procedure described above. A linear relationship between the chromatographic peak areas of the hydrogen sampled and the specific amounts of hydrogen used was established, defined by y=mx+b, where y is the peak area and x is the amount of hydrogen. Using this linear relationship, the amount of hydrogen produced during experimental electrolysis can be calculated from the integrated peak areas obtained.

Digital simulations of voltammetric data were performed using commercially available DigiElch Pro software package (v.7). Models were fit using an experimentally determined ZnL diffusion coefficient and an experimentally determined value of α and $k_s$. The consistency of the mechanism over a broad set reaction conditions was confirmed through models employing multiple scan rates and acid concentrations, all which agree with experimental results Examination of the change in bond lengths and bond angles amongst ZnL, [Zn(HL)]$^+$, Zn(HL.), and [Zn($H_2$L.)]$^+$ (Tables A4-A6) assist to explain structural and electronic changes over the course of the ZnL catalyzed HER mechanism. Initial protonation of ZnL to give [Zn(HL$^+$)] results in a slight puckering of the ligand framework around the Zn center shown by the lengthening of the Zn—S1, Zn—N2, Zn—N3 bonds and a decrease in the Zn—S2 bond as well as an increase in the S1-Zn—S2, N3-Zn—S2 bond angles and decrease of the S1-Zn—N2, N2-Zn—N3 bond angles. Subsequent reduction to the neutral radical species, Zn(HL.), is accompanied by significant contraction of the Zn—N2 and Zn—N3 bonds, 2.118 Å and 2.125 Å to 2.059 Å and 2.045 Å, respectively. Furthermore, moving across the mechanism from protonation to reduction, the C2-C3 bond length always decreases in length moving from an initial length of 1.478 Å to 1.470 Å after protonation, and then decreasing further to 1.427 Å after reduction, in agreement with the spin-density map of Zn(HL.).

Results and Discussion for Example Set A

Figure 4:
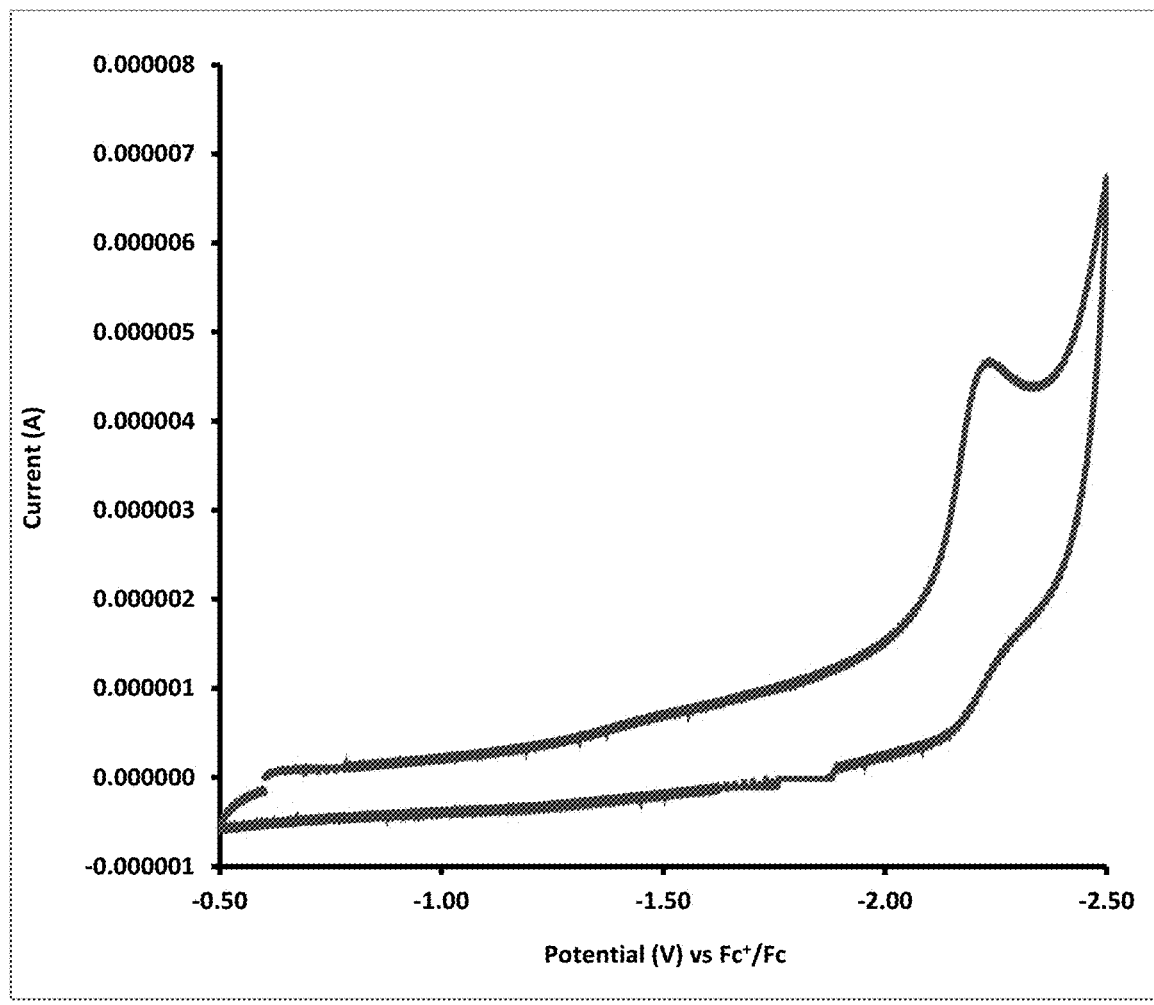
FIG. 4. ZnL in acetonitrile CV, v=0.2 V/s—0.1 M $Bu_4NPF_6$ acetonitrile solution with 3 mM ZnL vs $Fc^+/Fc^0$.
Figure 5:
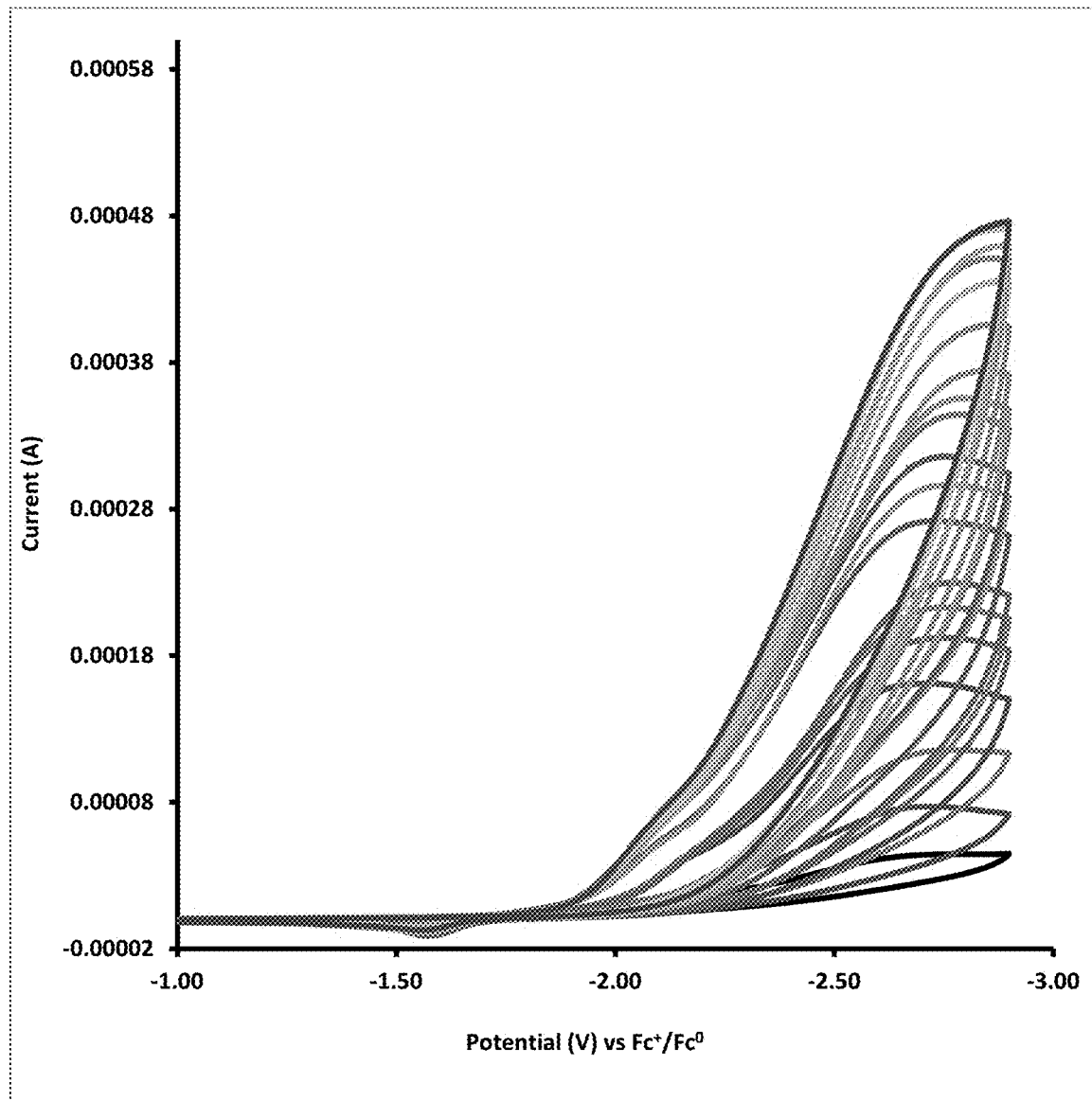
FIG. 5. ZnL HER acid concentration dependent CVs, v=0.2 V/s—0.1 M $Bu_4NPF_6$ acetonitrile solution with increasing concentrations of acid; vs $Fc^+/Fc^0$.

Solutions of ZnL in methanol or acetonitrile display catalytic hydrogen evolution upon reduction in the presence of acetic acid. In methanol, the cathodic current at −1.7 V increases with increasing acid concentration indicative of an electrocatalytic process (FIG. 1A). The current plateaus at 12.0 mM acetic acid indicating acid-saturation (FIG. 1B) with a maximum turnover frequency (TOF) of 1170 s$^{-1}$ at overpotential of 756 mV. No reduction wave for ZnL is observed within the potential limits of methanol in the absence of acid, signifying that HER might require protonation prior to reduction. In acetonitrile, addition of acetic acid results in catalytic current at −2.3 V, which is near the irreversible ligand-centered reduction of $H_2L$ in the absence of acid (FIGS. 4-5) and within the range of reduction potentials previously reported for thiosemicarbizides. Catalytic current becomes independent of acid concentration at 23 mM, yielding a higher TOF of 11700 s$^{-1}$, but with a larger overpotential of 1074 mV. The lower overpotential in methanol appears consistent with outer-coordination sphere proton shuttling, which facilitates ligand protonation prior to electrochemical reduction. The HER TOF of ZnL is substantially higher than other proposed ligand-centered catalysts suggesting $H_2L$ itself may also demonstrate catalytic activity.

Figure 6:
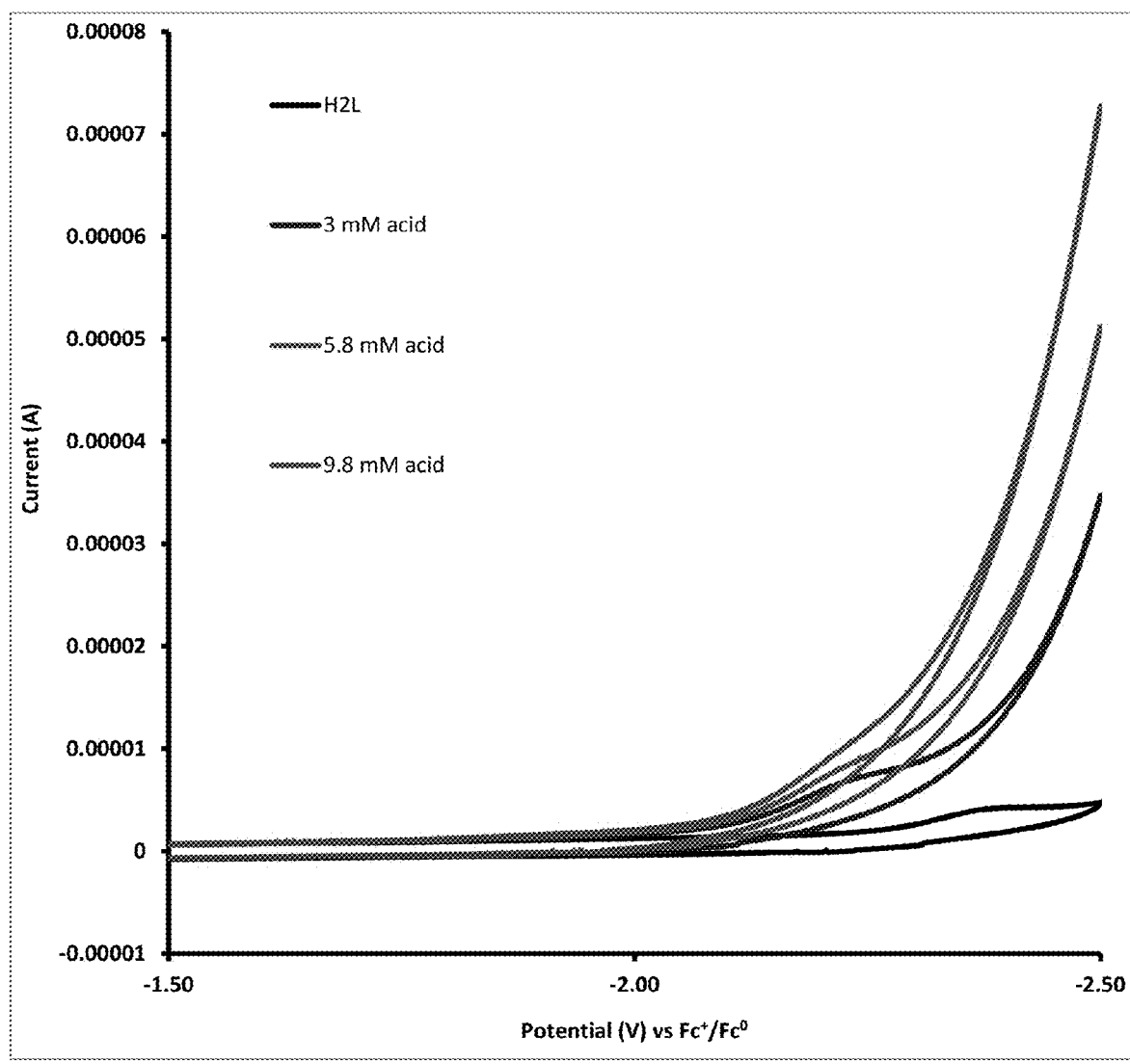
FIG. 6. $H_2L$ HER acid dependent CVs, v=0.5 V/s—0.1 M $Bu_4NPF_6$ methanol solution with increasing concentrations of acid; vs $Fc^+/Fc$ (lowest concentration at bottom).

The metal-free $H_2L$ ligand was subsequently evaluated as a proton reduction catalyst. $H_2L$ displays an irreversible reduction at −2.1 V and an irreversible oxidation at +0.5 V in methanol versus Fc$^+$/Fc. Upon addition of acetic acid, the cathodic current at −2.1 V increases steadily (FIG. 6) reaching a maximum at concentrations of 9.8 mM (FIG. 1B). Under acid-saturated conditions, $H_2L$ displays a TOF of 1320 s$^{-1}$ with an overpotential of 1430 mV. To our knowledge, this is the only reported metal-free, homogeneous electrocatalyst for HER.

Figure 7:
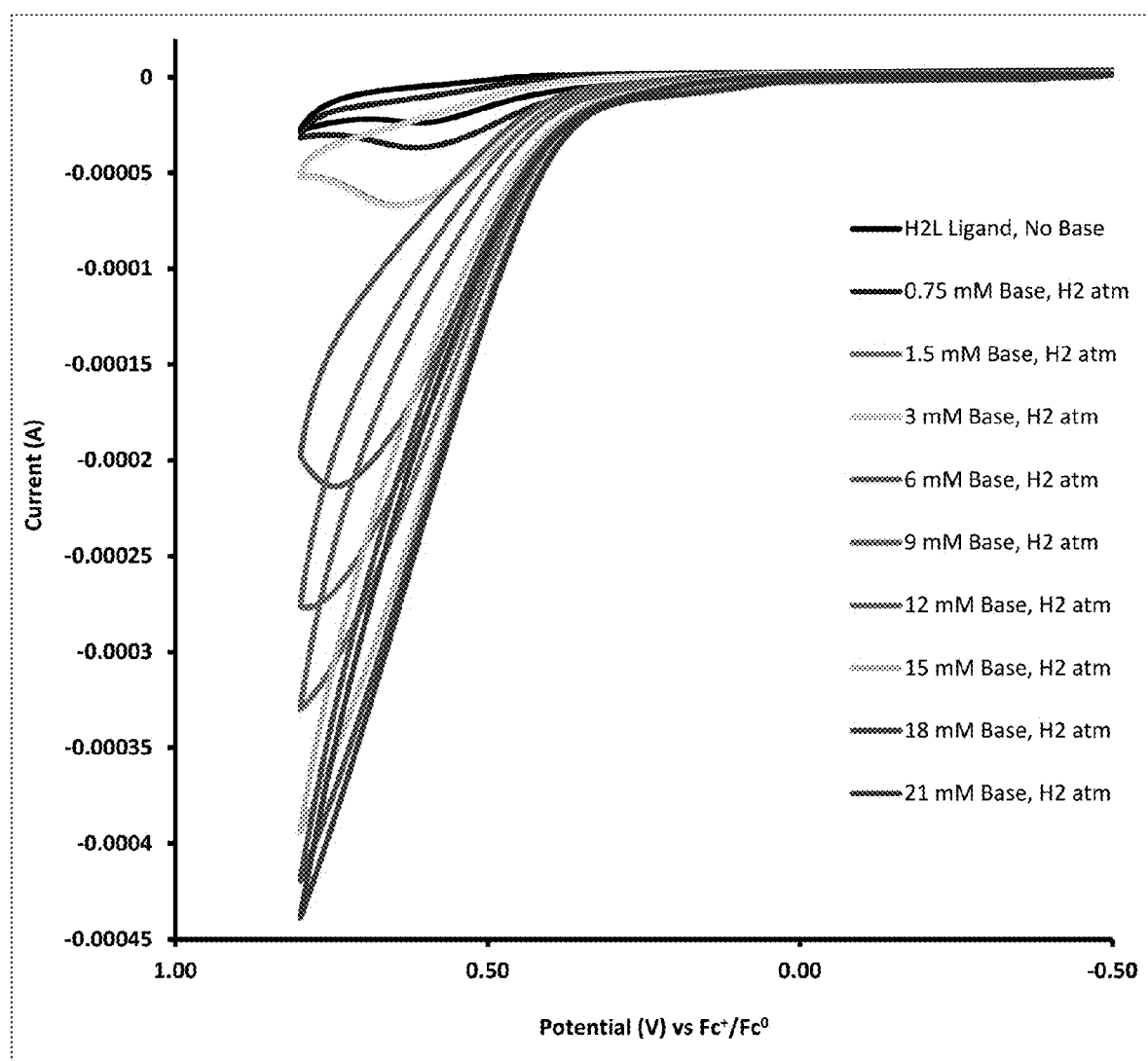
FIG. 7. $H_2L$ HOR base concentration dependent CVs, v=0.5 V/s—$H_2L$ HOR, $H_2$ atmosphere with increasing $[Et_3N]$, vs $Fc^+/Fc^0$ (highest concentration of base at bottom).

As well as electrocatalytic HER, ZnL and $H_2L$ also catalyze HOR. Introduction of triethylamine to methanol solutions of ZnL or $H_2L$ under one atmosphere of $H_2$ results in an increase in anodic current near the irreversible oxidation wave of ZnL or $H_2L$, respectively (FIG. 1C and FIG. 7). For ZnL, the catalytic current shows saturation behavior (FIG. 1D) with near saturation at a base concentration of 30 mM yielding a TOF of 72 s$^{-1}$ with an overpotential of 315 mV. The HOR activity of $H_2L$ ligand was similarly assessed reaching saturation at 21 mM base (FIG. 1D) with a TOF of 32 s$^{-1}$ and an overpotential of 328 mV. The HOR TOFs of ZnL and $H_2L$ are among the highest reported of any homogenous electrocatalyst.

Figure 2:
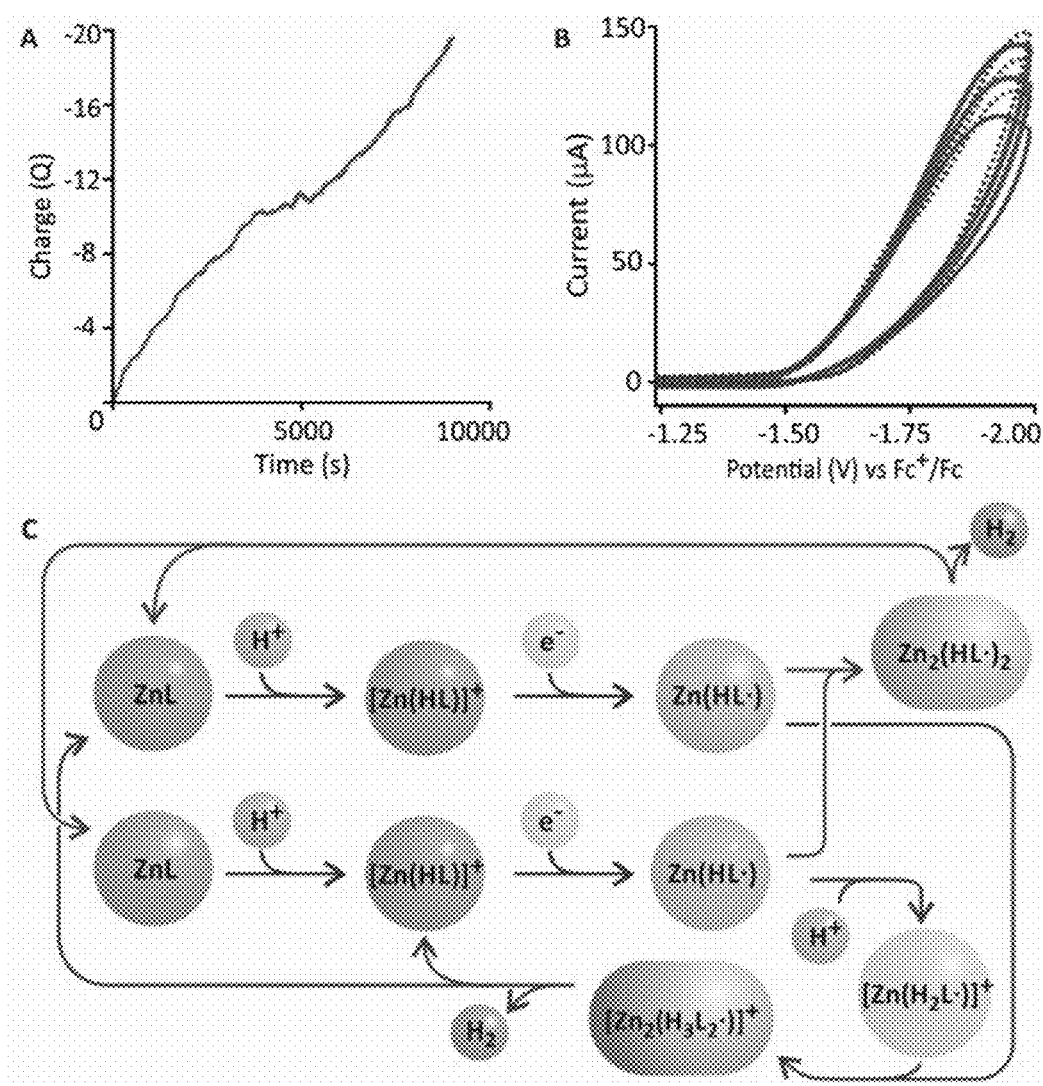
FIG. 2. Mechanistic Studies of $H_2$ evolution. (A) Plot of charge versus time recorded during bulk electrolysis of 0.1 mM ZnL and 12 mM $CH_3COOH$ in methanol with 0.1 M $Bu_4NPF_6$ as supporting electrolyte. (B) Comparisons of experimental (solid) and simulated (dotted) cyclic voltammograms for 3 mM ZnL and 12 mM $CH_3COOH$ in methanol with 0.1 M $Bu_4NPF_6$ as supporting electrolyte at scan rates of (from bottom to top) 0.3, 0.4, and 0.5 V/s. (C) Concurrent catalytic pathways for hydrogen evolution through homo-coupling of neutral Zn(HL.) radicals and hetero-coupling of a neutral Zn(HL.) and cationic $[Zn(H_2L.)]^+$ radicals.
Figure 8:
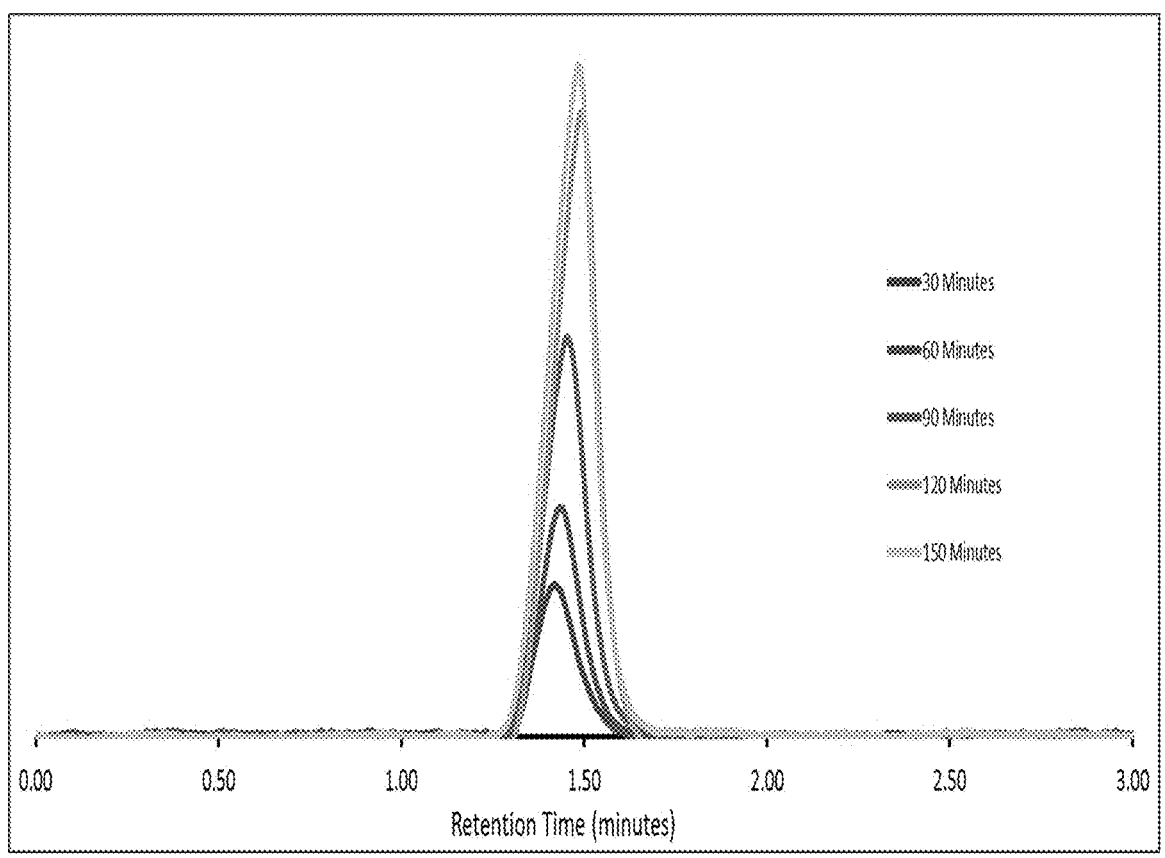
FIG. 8. GC-TCD Readout—GC readouts of gas sampled every 30 minutes during 2.5 hour electrolysis of ZnL.
Figure 21:
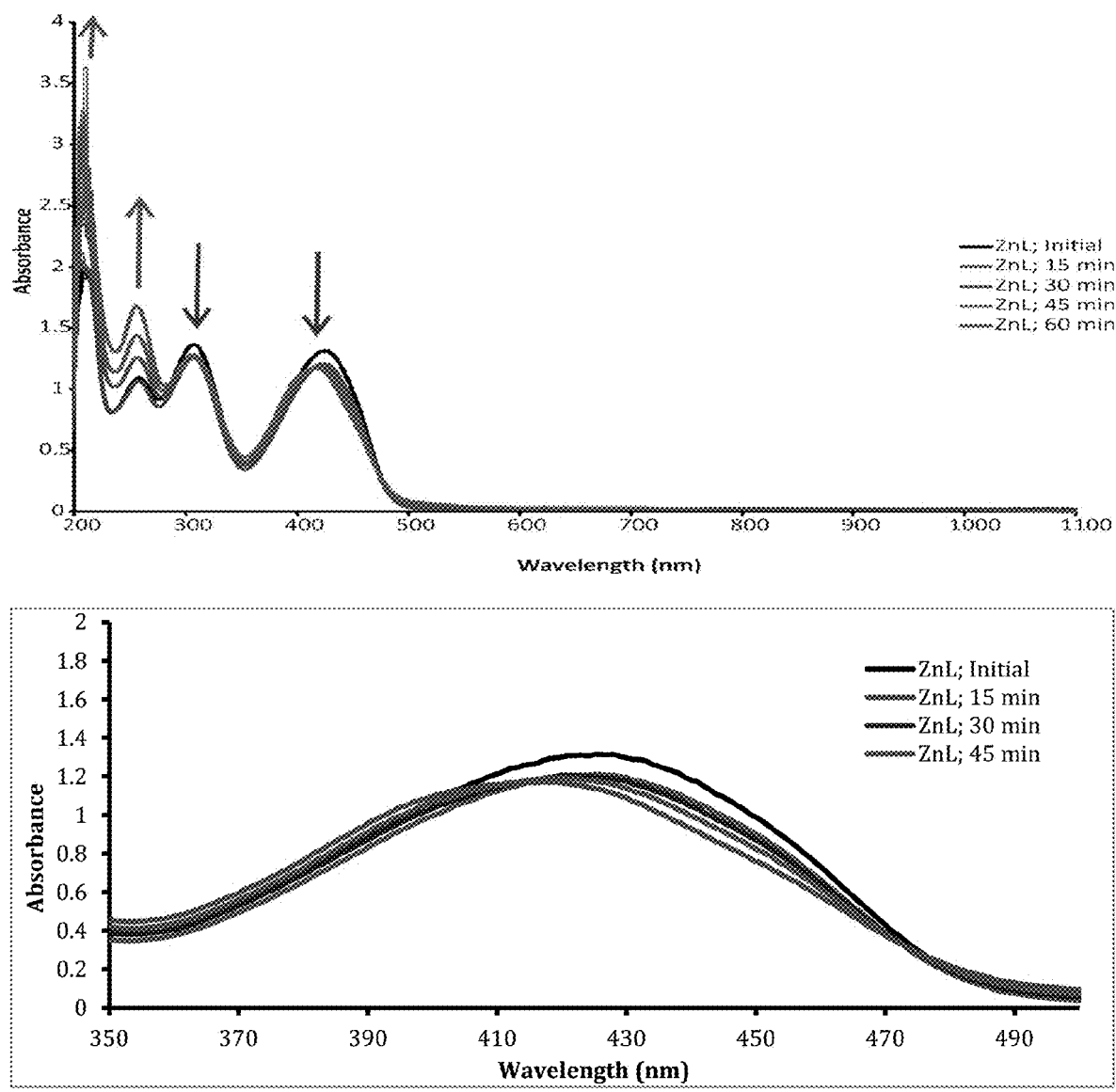
FIG. 21. UV-Vis spectra from Spectroelectrochemical Electrolysis—(Upper) UV spectra recorded every 15 minutes during the electrolysis of 1 mM ZnL under applied potential of −1.7 V in 0.1 M $Bu_4NPF_6$ methanol solution. (Lower) Blow up of 350-500 nm region showing isosbestic point at 400 nm.
Figure 22:
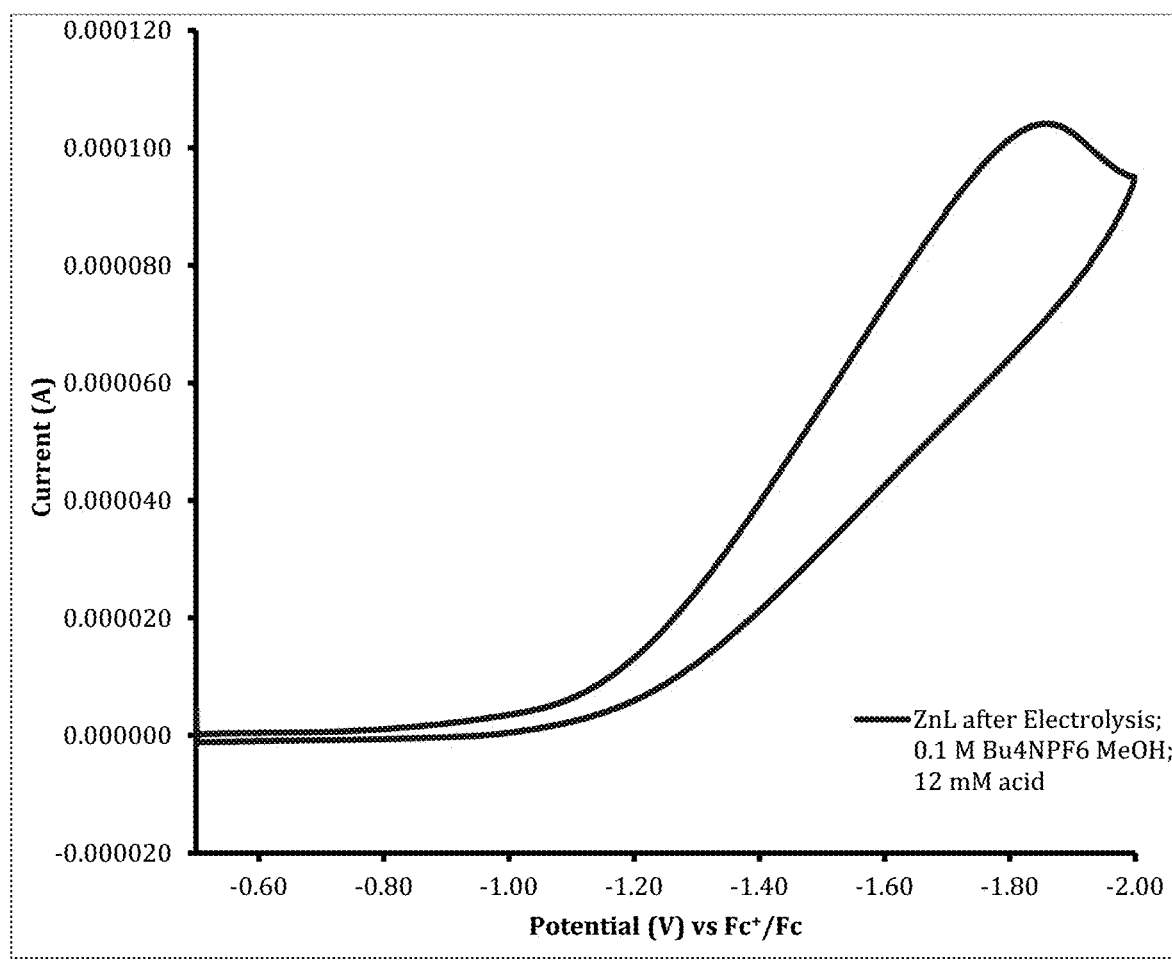
FIG. 22. CV after ZnL electrolysis—CV of ZnL after electrolysis in 0.1 M $Bu_4NPF_6$ methanol solution with 12 mM acetic acid added. v=0.2 V/s vs $Fc^+/Fc^0$.
Figure 23:
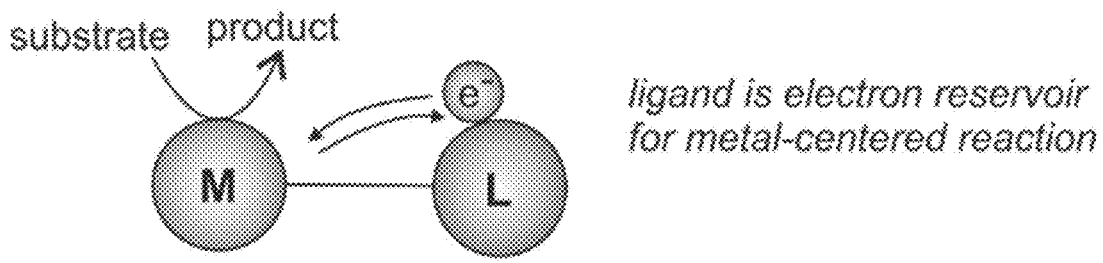
FIG. 23. Overview of reactivity using non-innocent ligands.
Figure 23:
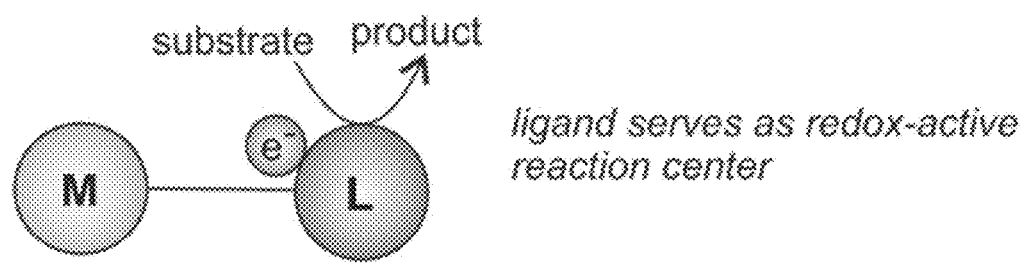
Figure 23:
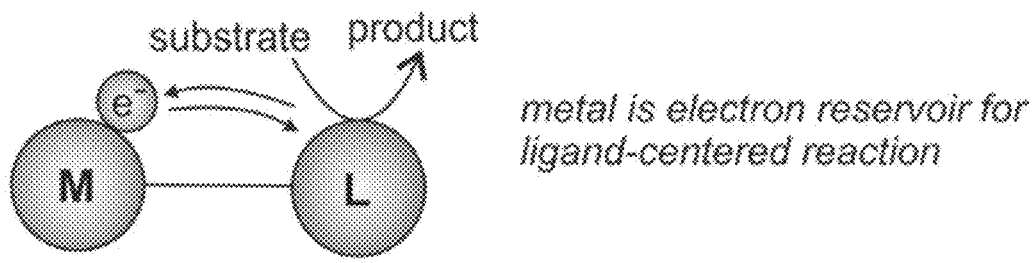

The stability of ZnL as a HER electrocatalyst was further examined by controlled potential coulometry. At an applied potential of −1.7 V versus Fc$^+$/Fc, ZnL evolves $H_2$ from 12 mM acetic acid solutions in methanol with a turnover number (TON) of 37 after 2.5 hours (FIG. 2A) based on a total charge of 19.8 C. The identity of the gaseous product was confirmed as $H_2$ by gas chromatography thermal conductivity (GC-TCD). The integrated peak areas of headspace samples collected during electrolysis (FIG. 8) indicate a minimum faradaic efficiency of 85%. Throughout the electrolysis, the TOF remained consistent at 15 h$^{-1}$ with no signs of decreasing activity. Spectroelectrochemical experiments were performed on 0.1 M $Bu_4NPF_6$ methanol solutions of ZnL with an applied potential of −1.7 V in order to identify the absorption characteristics of the one-electron reduced electrocatalyst, [ZnL]$^-$. UV-Vis spectra were recorded before electrolysis and then measured every 15 minutes during electrolysis showing the growth of the absorption band near 250 nm and a decrease in the absorption band near 430 nm (FIG. 21). A CV was then recorded with addition of 12 mM acetic acid (FIG. 22). An additional control was performed after prolonged reduction in order to rule out ligand decomposition onto electrode surface as possible source of catalysis. After reduction, the working electrode was removed, washed with DI water, and then placed in fresh solution containing no catalyst, upon which no current was observed.

Figure 9:
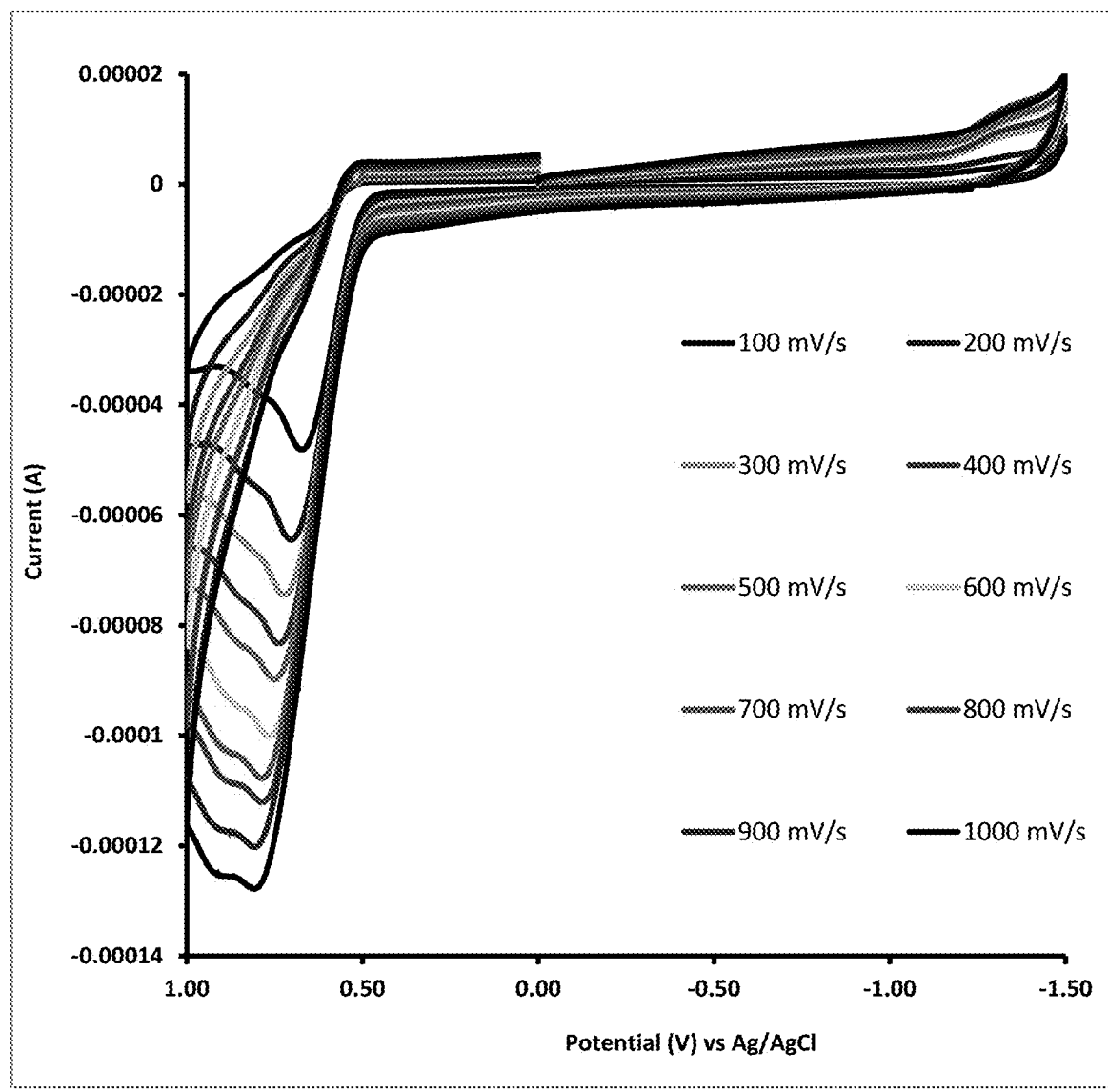
FIG. 9. ZnL Diffusion Limited CV Overlay—0.1 M $Bu_4NPF_6$ methanol solution with 3 mM ZnL run from v=0.1-1.0 V/s vs Ag/AgCl (highest mV/s at bottom).
Figure 10:
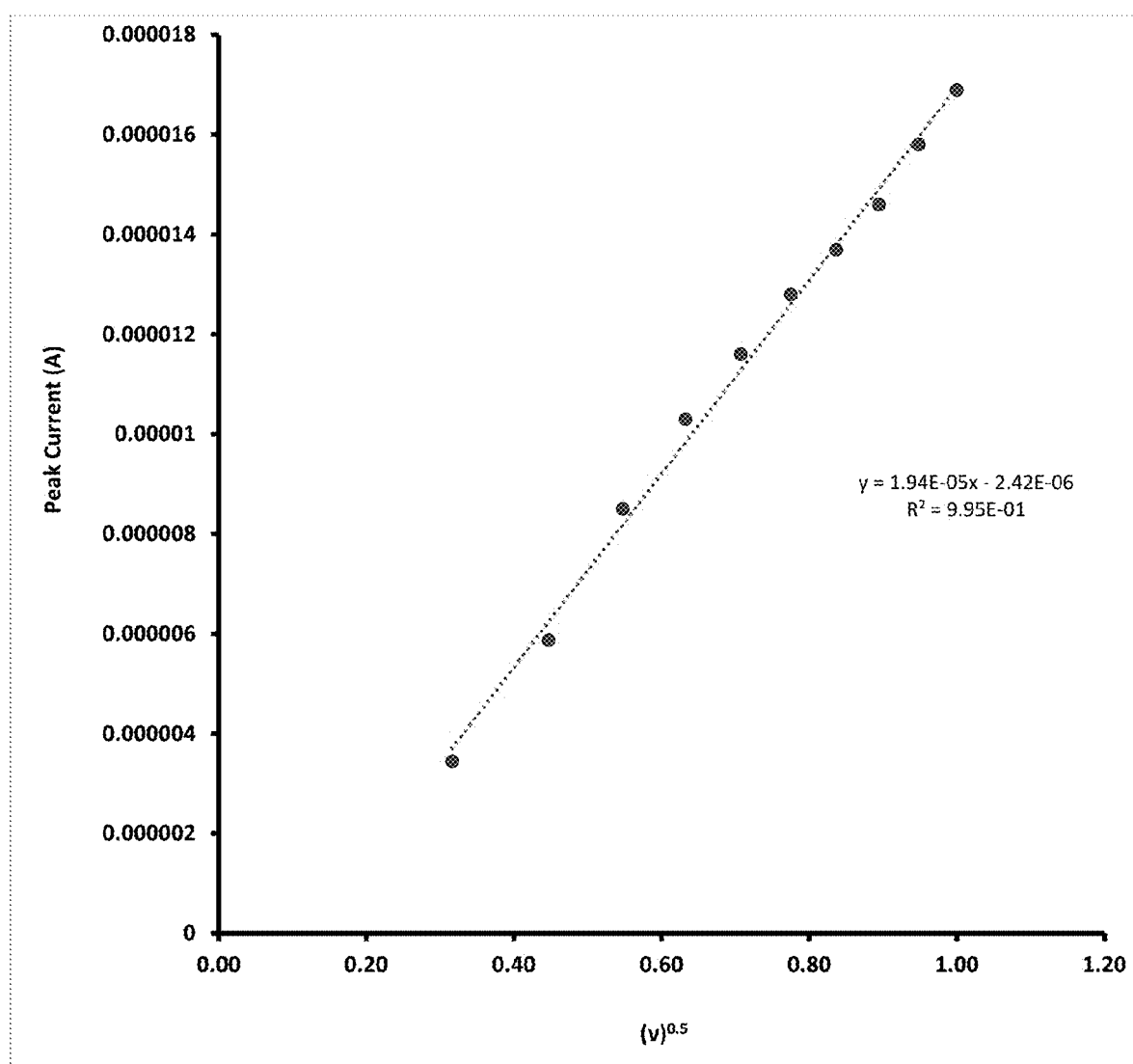
FIG. 10. Peak currents vs square root of scan rate—0.1 M $Bu_4NPF_6$ methanol solutions with 3 mM ZnL, plot showing peak current plotted against the square root of the scan rate from diffusion limited CVs.
Figure 11:
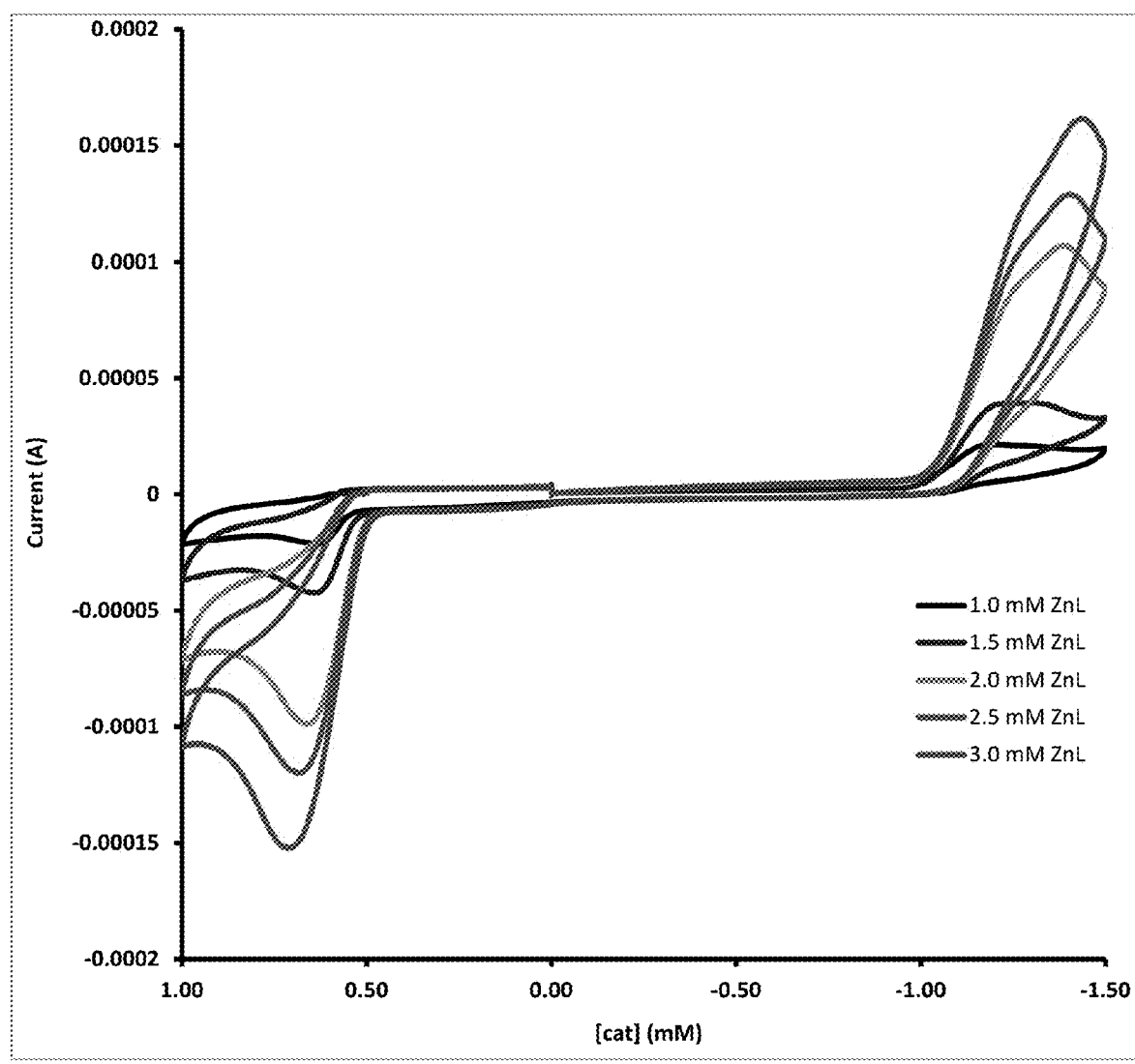
FIG. 11. ZnL concentration dependent CVs, v=0.5 V/s—0.1 M $Bu_4NPF_6$ methanol solution with 12 mM acetic acid added with increasing ZnL concentrations; vs Ag/AgCl (highest ZnL concentration at bottom).
Figure 12:
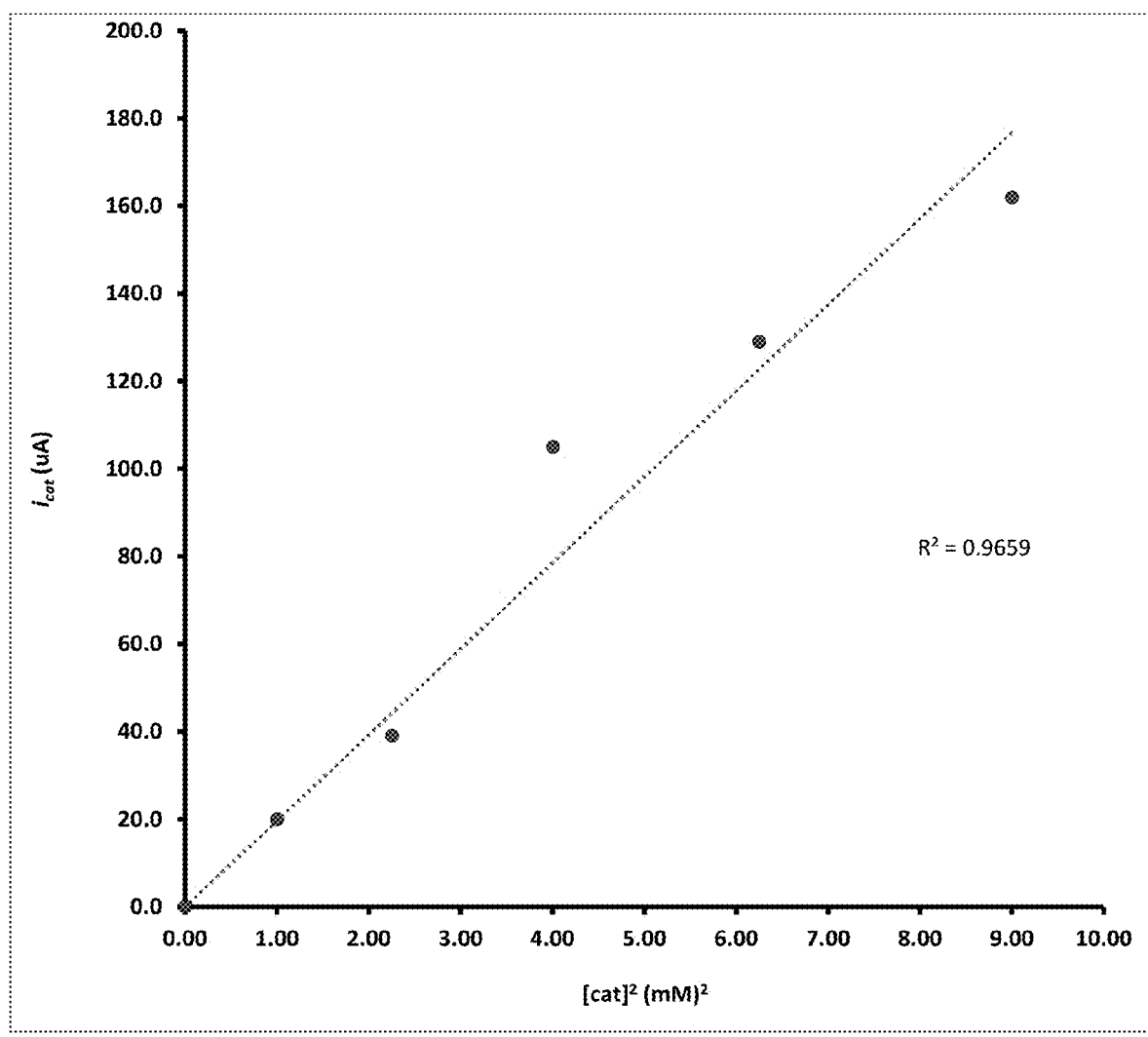
FIG. 12. Plot of $[ZnL]^2$ vs catalytic current, v=0.5 V/s.

To evaluate the HER mechanism of ZnL, we first determined the rate law and measured the H/D kinetic isotope effect. Under acid-dependent conditions, the catalytic current ($i_{cat}$) displays a linear dependence on the square root of the scan rate indicating the current appears limited by acid diffusion to the electrode surface (FIGS. 9-10). Further, under non-saturating acid conditions cat appears directly proportional to [H$^+$] (FIG. 1B) indicating a first-order dependence on acid concentration. Varying the [ZnL] at fixed acid concentrations confirms first-order dependence at catalyst concentrations above 2 mM (FIGS. 11-12). Using the deuterated acid $CD_3CO_2D$, the ZnL catalyst displays a small kinetic isotope effect (KIE) of 1.2.

Several example simulations and calculations were performed, as described herein. However, the scope of the invention is not limited by the results, pathways, or mechanisms exemplified in the simulations.

Figure 13:
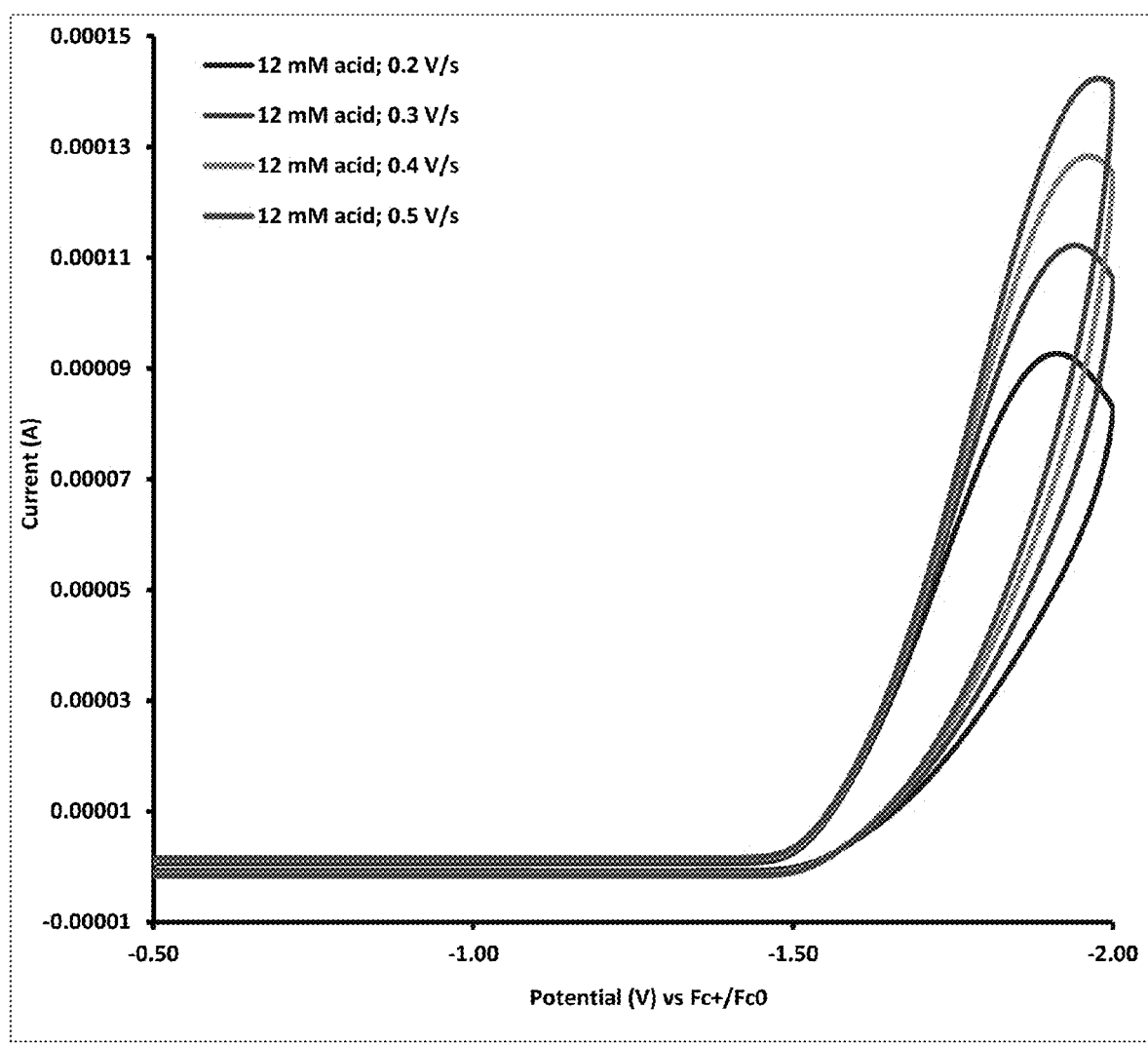
FIG. 13. Simulation of experimental data using DigiElch—ZnL HER CV Simulations of experimental data; 12 mM [acid]; v=0.2-0.5 V/s vs $Fc^+/Fc^0$ (lowest V/s at bottom).
Figure 14:
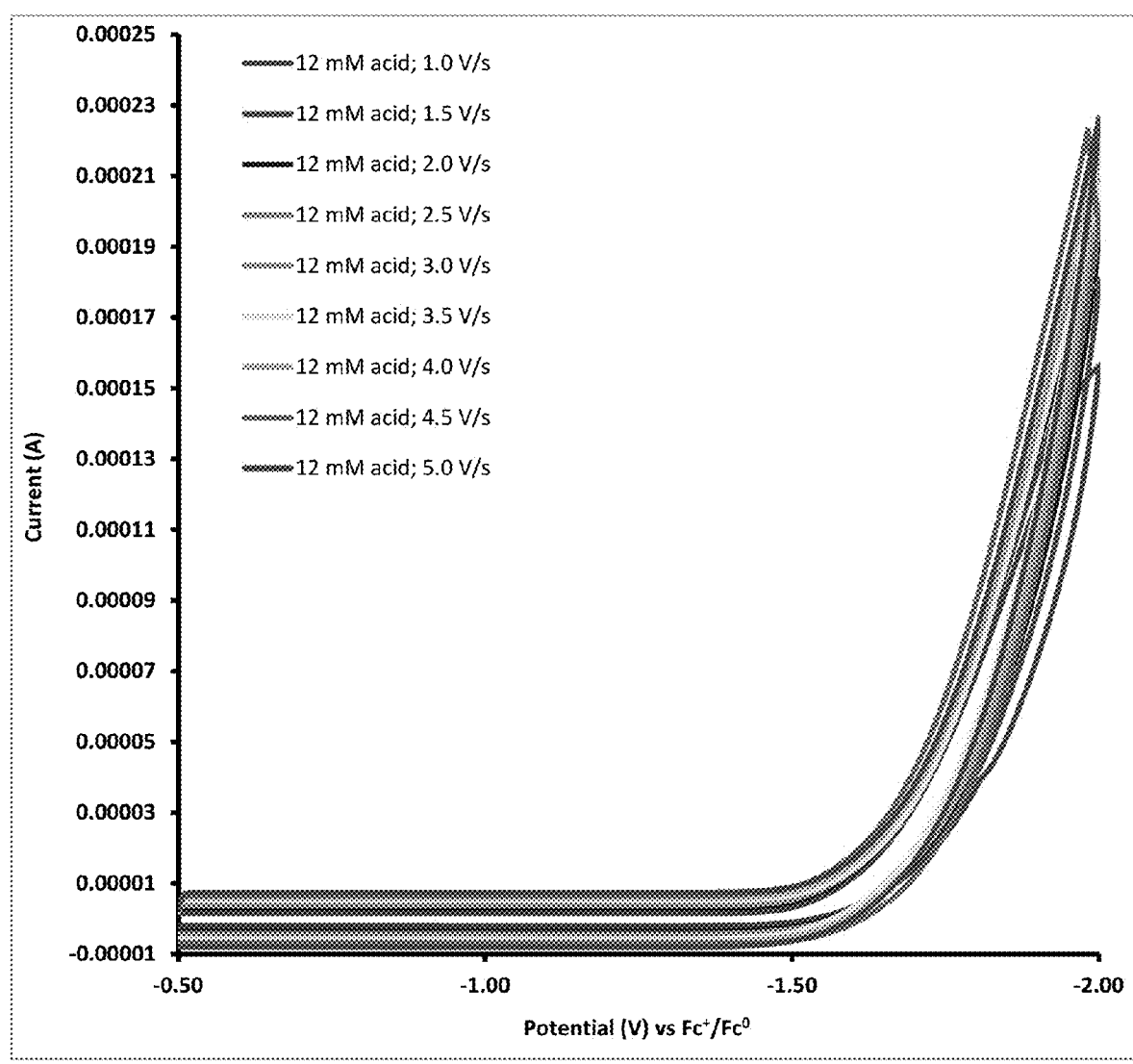
FIG. 14. Simulation of experimental data using DigiElch—ZnL HER CV Simulations of experimental data; 12 mM [acid]; v=0.6-5.0 V/s vs $Fc^+/Fc^0$ (lowest V/s at bottom).
Figure 15:
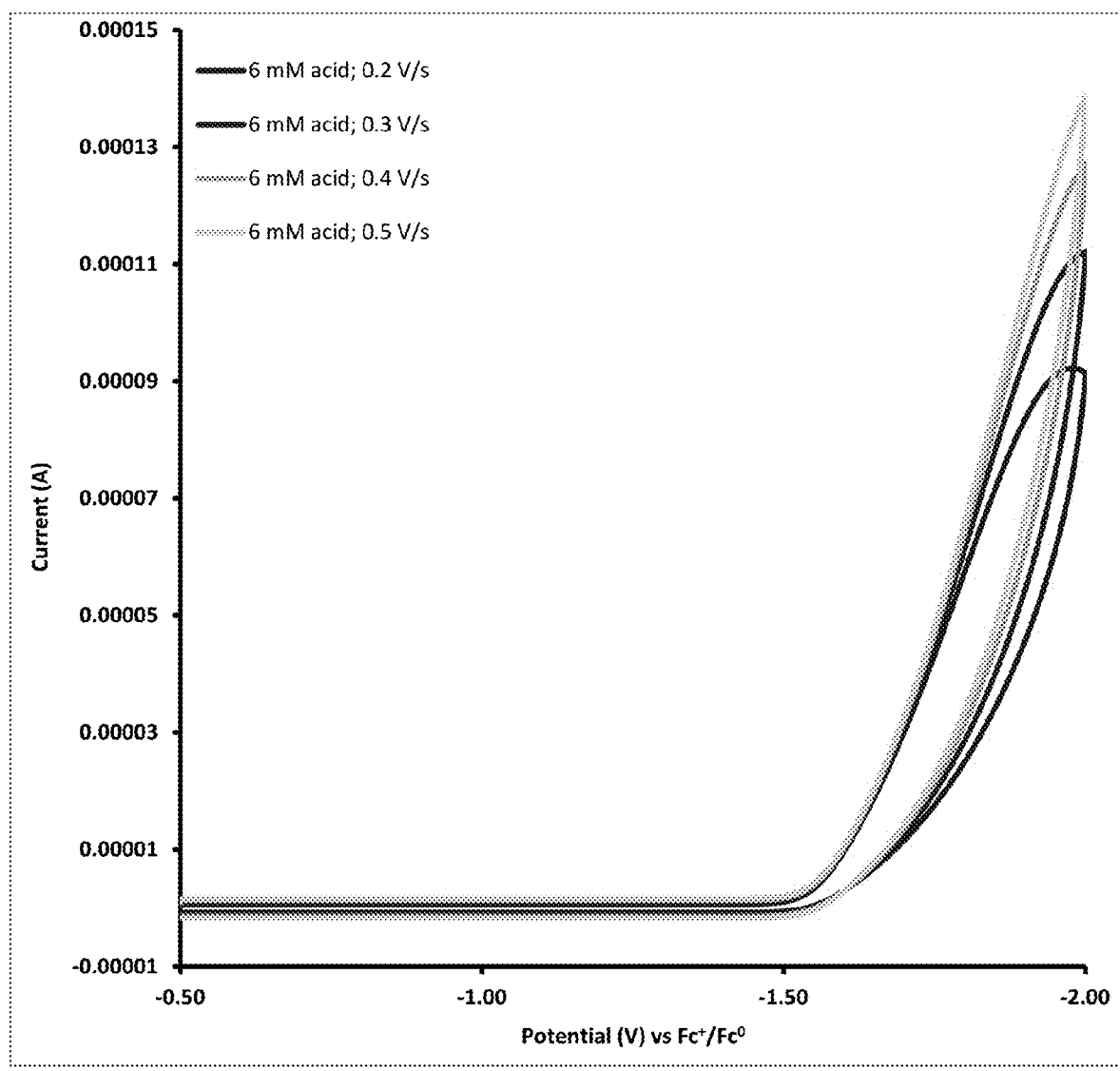
FIG. 15. Simulation of experimental data using DigiElch—ZnL HER CV Simulations of experimental data; 6 mM [acid]; v=0.2-0.5 V/s vs $Fc^+/Fc^0$ (lowest V/s at bottom).

Digital simulations of the cyclic voltammograms (FIG. 2B and Table A1) reveal parallel routes to proton reduction involving homo-coupling of two, neutral Zn(HL·) radicals and hetero-coupling of a neutral Zn(HL·) radical with the cationic radical [Zn(H$_2$L·)]$^+$. The proposed mechanism (FIG. 2C) begins with protonation of ZnL, K=2.4×10$^5$, followed by reduction to Zn(HL·), E°=−1.81 V vs. Fc$^+$/Fc. In the homo-coupling pathway, two Zn(HL·) rapidly combine, $k_f$=3×10$^9$M$^{-1}$ s$^{-1}$, to evolve H$_2$ and regenerate two equivalents of ZnL. In the alternate pathway, one equivalent of Zn(HL·) is further protonated, K=8.8, prior to hetero-coupling. Combination of [Zn(H$_2$L·)]$^+$ with the second equivalent of Zn(HL·), $k_f$=2×10$^{10}$ M$^{-1}$ s$^{-1}$, yields H$_2$ completing the catalytic cycle. The simulated kinetic and thermodynamic parameters reveal that both routes to H$_2$ evolution are operational across a range of experimental conditions (FIGS. 13-15 and Table A2-A3).

Figure 16:
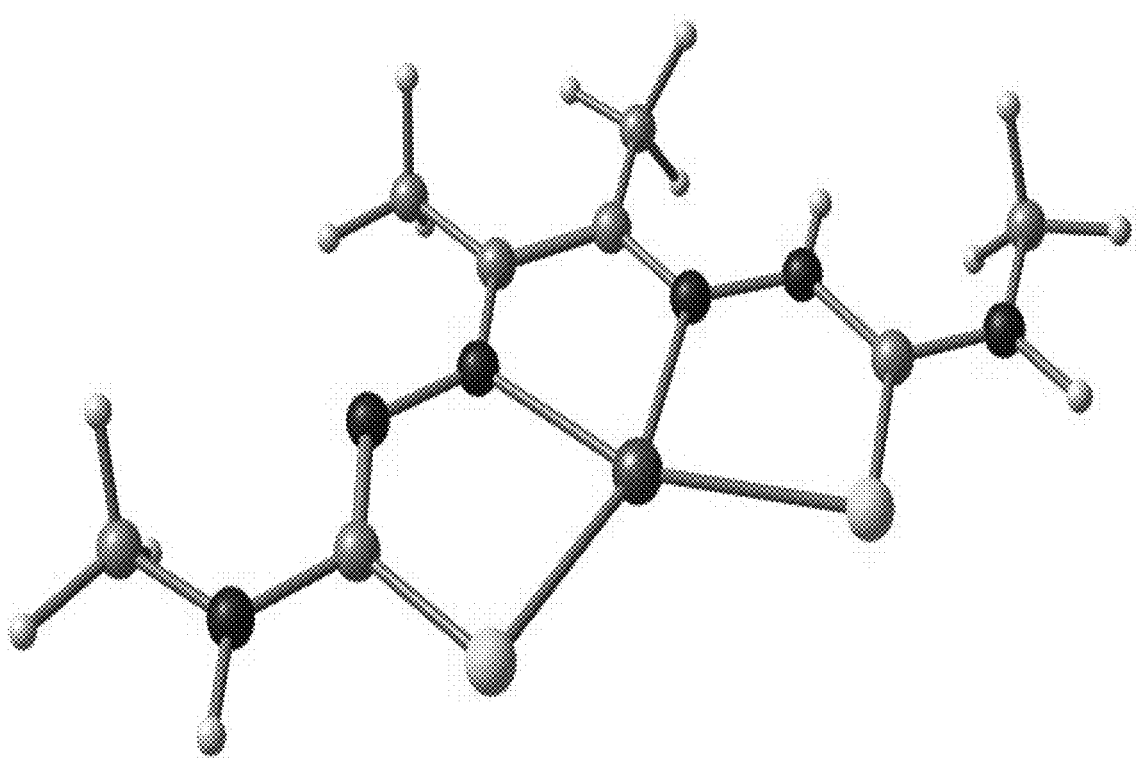
FIG. 16. Optimized structure of $[ZnHL]^+$ with protonation on hydrazino nitrogen.
Figure 17:
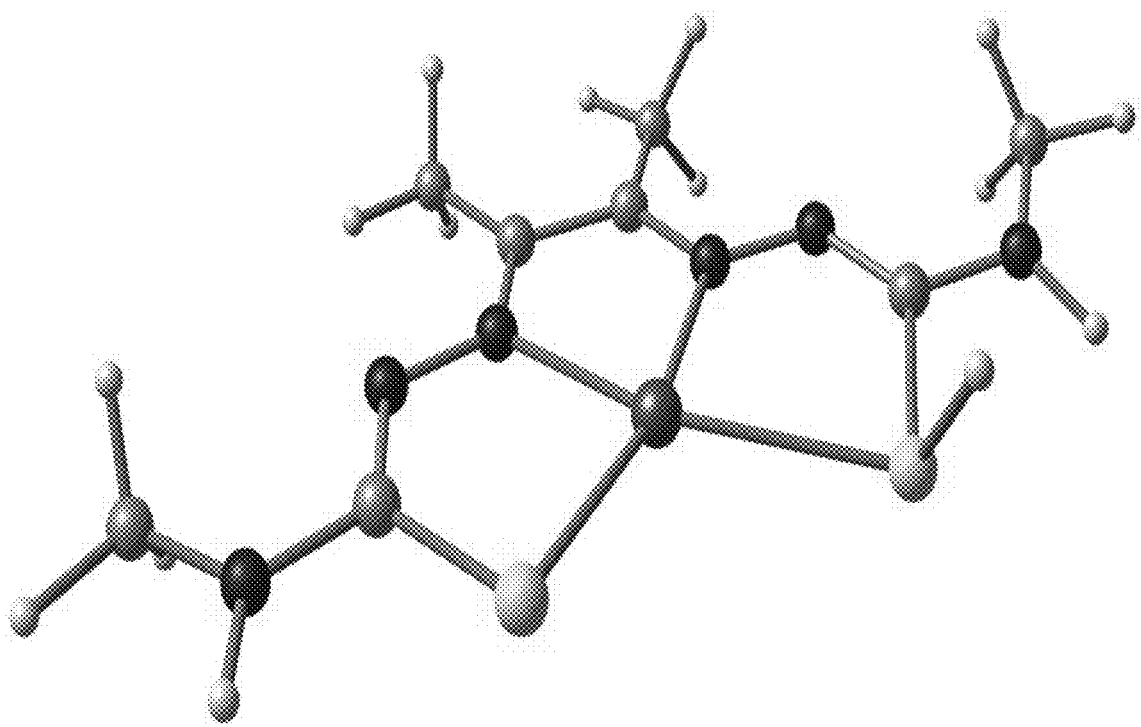
FIG. 17. Optimized structure of $[ZnHL]^+$ with protonation on sulfur.
Figure 18:
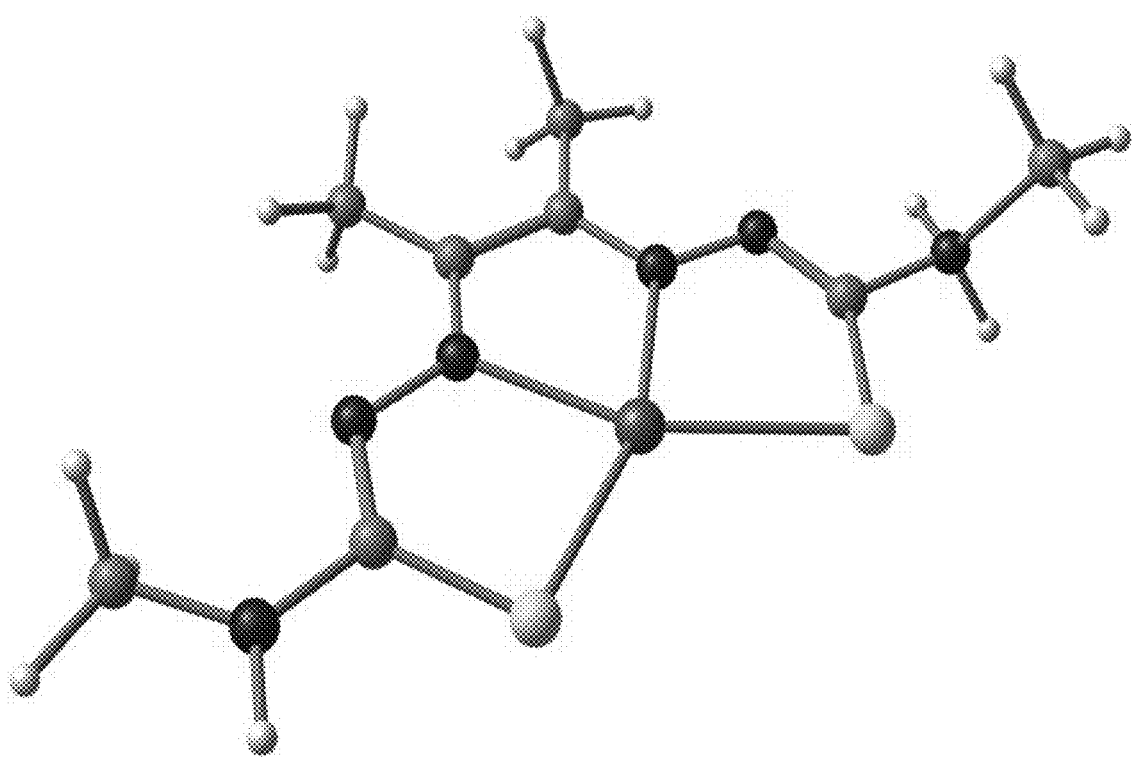
FIG. 18. Optimized structure of $[ZnHL]^+$ with protonation on amine nitrogen.
Figure 19:
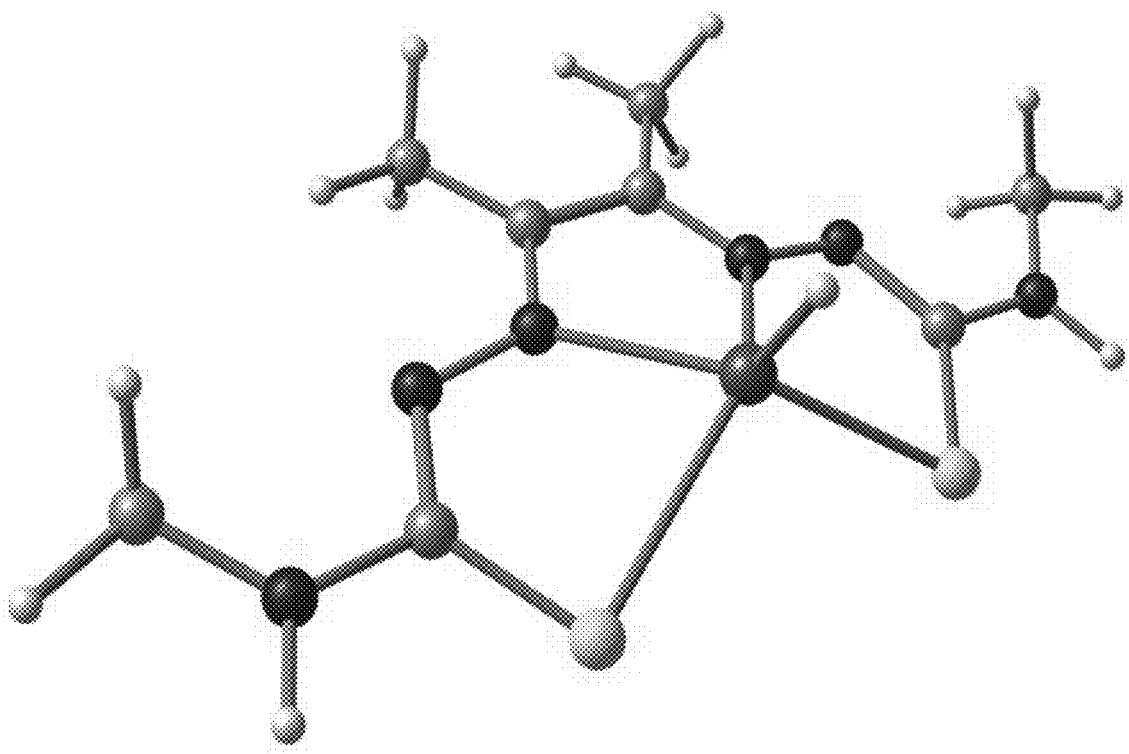
FIG. 19. Optimized structure of $[ZnHL]^+$ with protonation on zinc.

Density functional theory (DFT) calculations using the B97-D functional and the 6-311G(d) basis set, support the proposed catalytic cycle and elucidate the hydrazino nitrogen as the site of protonation. Each of the metal complexes in FIG. 2C was successfully optimized (Table A4-A6). Energies (Table A7) reveal that protonation at the hydrazino nitrogen (FIG. 16) is favored by at least 13.0 kcal/mol relative to other potential basic sites within ZnL (FIGS. 17-19). Evolution of H$_2$ through homo-coupling of two Zn(HL·) radicals is exergonic by 42.6 kcal/mol, while the parallel pathway involving hetero-coupling of Zn(HL·) and [Zn(H$_2$L·)]$^+$ releases 28.8 kcal/mol.

Figure 3:
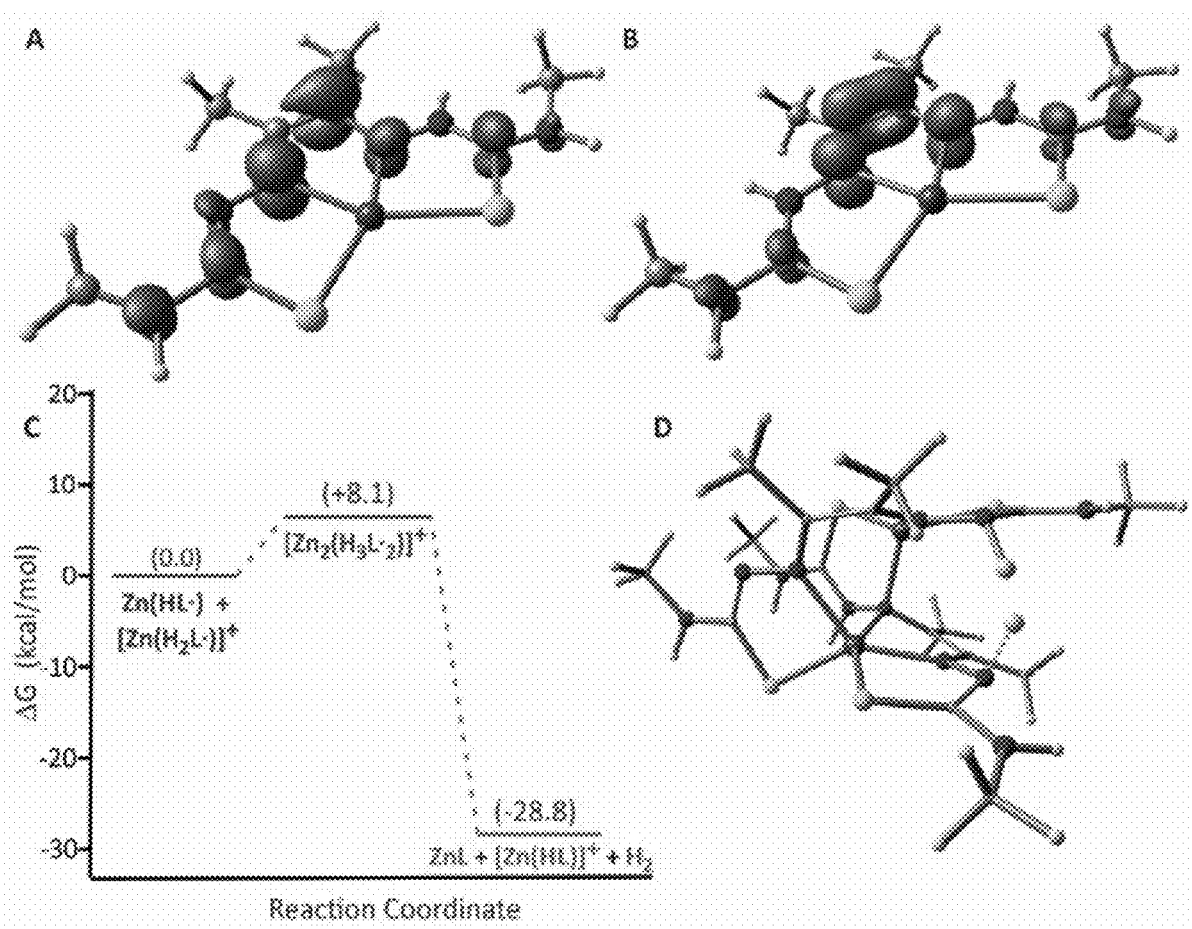
FIG. 3. Energy profile along with spin densities of species involved in catalyzed $H_2$ evolution. Spin-density profiles for Zn(HL.) (A), and $[Zn(H_2L.)]^+$ (B). (C) Relative energies (ZPE corrected) for $H_2$ evolution through the hetero-coupling of Zn(HL.) and $[Zn(H_2L.)]^+$ using the B97-D/6-311G (d) level of theory. (D) Structure of the singlet $[Zn_2(H_3L._2)]^+$ transition state through the hetero-coupling pathway. See FIG. 20 for further information regarding the HER mechanism, analysis of the eigenvector associated with the imaginary frequency i1572 $cm^{-1}$, and the charge densities of atoms for $H_2$ evolution with respect to intrinsic reaction coordinate (IRC).
Figure 20:
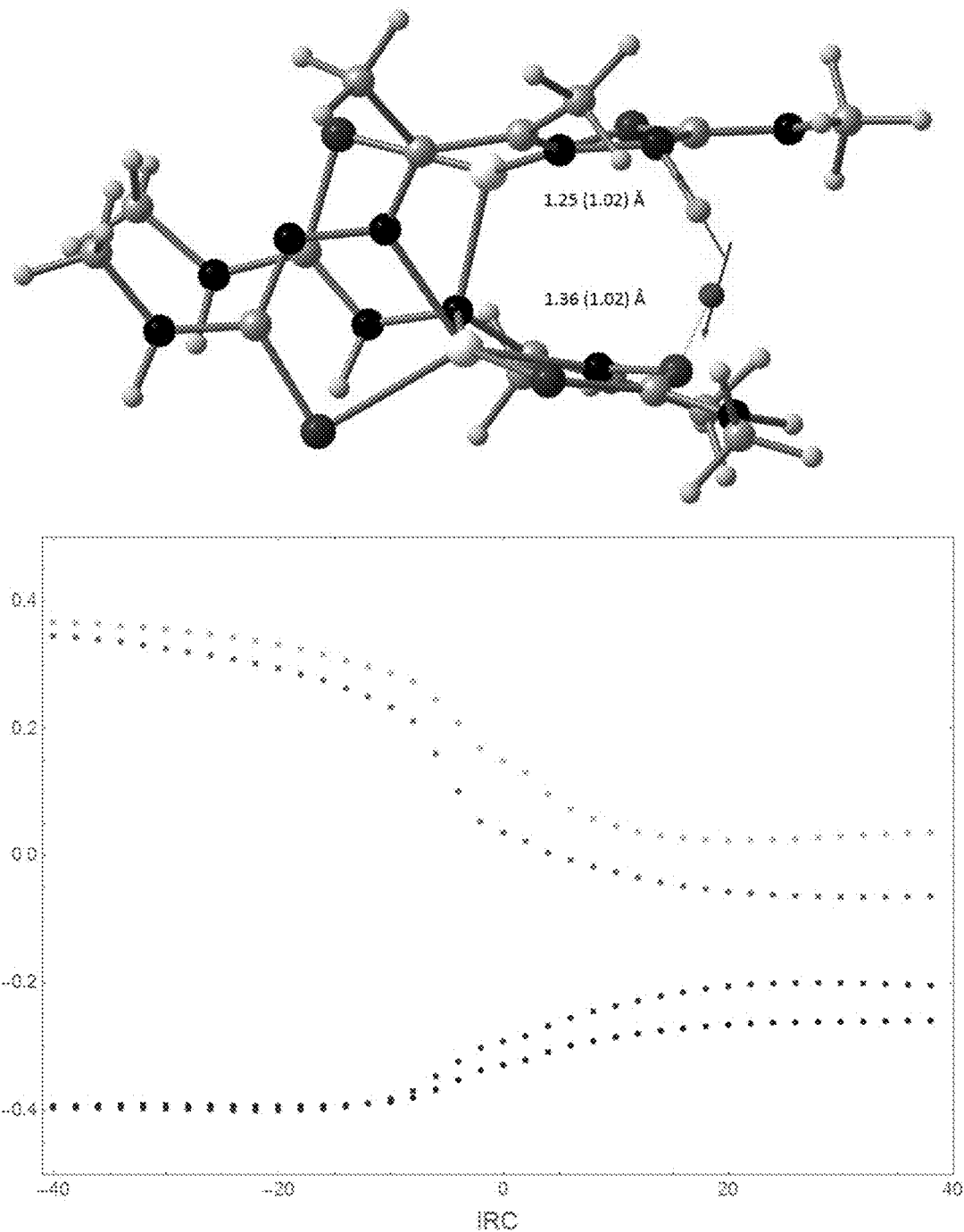
FIG. 20. Transition state analysis of $[Zn_2H_3L._2]^+$—(Upper) Transition state geometry of $[Zn_2H_3L._2]^+$ along the HER pathway, shown with active N—H bond lengths associated with the imaginary frequency i1572 $cm^{-1}$, and equilibrium bond lengths in parentheses. (Lower) Charge densities of atoms near $H_2$ evolution with respect to IRC; N—H of $[Zn(HL.)]^+$ (bottom and top curves), and N—H of $Zn(H_2L.)$ (curves $2^{nd}$ from top and $2^{nd}$ from bottom).

Analyses of the Zn(HL·) and [Zn(H$_2$L·)]$^+$ spin density profiles (FIGS. 3A and 3B) show radical character delocalized on both protonated ligand frameworks. H$_2$ is evolved by radical hetero-coupling, overcoming an 8.1 kcal/mol barrier (FIGS. 3C and 3D). The absence of spin density on Zn for all species involved in the HER, is support for ligand based reduction (Table A8). The transition state (TS) can be described as a dimer with H dissociations from each monomer fragment, along their respective N—H coordinates to form H$_2$ (FIG. 20). This is consistent with N—H bond lengths in the TS of 1.25 Å for Zn(HL·), and 1.36 Å for [Zn(H$_2$L·)]$^+$ compared to respective equilibrium N—H distances, both of 1.02 Å. The longer N—H bond in the TS associated with [Zn(H$_2$L·)]$^+$ may also be attributed to an increased charge density along the forward IRC for both N and H, compared to Zn(HL·) (FIG. 20). The HER from [Zn$_2$H$_3$L·$_2$]$^+$ is thus interpreted as dimeric, where the now charge-reorganized Zn(H$_2$L·) fragment promotes early electron transfer, and is coupled to proton transfer from [Zn(HL·)]$^+$ to form H$_2$.

In summary, some of the non-transition metal complex ZnL and the metal-free ligand H$_2$L disclosed herein appear to represent a fundamentally new class of homogeneous HER and HOR electrocatalysts. Unlike traditional catalysts that employ a metal-hydride as the key intermediate, this new approach facilitates H$_2$ evolution through ligand-centered radical coupling. The combination of the redox active ligand H$_2$L with the non-transition metal Zn constrains redox activity to the ligand, in contrast to transition metal complexes where spin-coupling between the ligand radical and unpaired electrons on the metal may reduce reactivity. The confinement of radical character to the ligand is further evidenced by the catalytic activity of H$_2$L; albeit with higher overpotential than ZnL. The enhanced activity with Zn, in some instances, is understood to be attributed in part to the Lewis acidity of Zn(II), which balances the charge of the anionic ligand, promotes protonation, and lowers the reduction potential. Further, Zn(II) can provide a structural framework for the N$_2$S$_2$ chelate that pre-organizes the radical complexes for H$_2$ evolution.

TABLE A1

Optimized parameters of data fitting, 12 mM [acid]; v = 0.2-0.5 V/s vs Fc$^+$/Fc$^0$

| Charge-transfer Steps | 99% Confidence | E° | α | $k_s$ |
|---|---|---|---|---|
| [ZnHL]$^+$ + e$^-$ = Zn(HL·) | Optimized | −1.8110 | 0.3166 | 0.0070 |
| | Upper Limit | −1.8113 | 0.3166 | 0.0070 |
| | Lower Limit | −1.8107 | 0.3166 | 0.0070 |
| [ZnH$_2$L]$^{2+}$ + e$^-$ = [Zn(H$_2$L·)]$^+$ | Optimized | −1.5872 | 0.3166 | 0.0070 |
| | Upper Limit | −1.5874 | 0.3166 | 0.0070 |
| | Lower Limit | −1.5870 | 0.3166 | 0.0070 |

| Chemical Steps | 99% Confidence | $K_{eq}$ | $k_f$ |
|---|---|---|---|
| ZnL + H$^+$ = [ZnHL]$^+$ | Optimized | 2.42E+05 | 1.28E+13 |
| | Upper Limit | 3.42E+06 | 6.40E+13 |
| | Lower Limit | 1.91E+05 | 1.94E+12 |
| [ZnHL]$^+$ + H$^+$ = [ZnH$_2$L]$^{2+}$ | Optimized | 8.80E+00 | 4.06E+06 |
| | Upper Limit | 8.93E+00 | 6.92E+06 |
| | Lower Limit | 8.68E+00 | 1.20E+06 |
| Zn(HL·) + Zn(HL·) = H$_2$ | Optimized | 4.89E+10 | 3.09E+09 |
| | Upper Limit | 4.96E+10 | 6.51E+09 |
| | Lower Limit | 4.80E+10 | 6.45E+08 |
| Zn(HL·) + [Zn(H$_2$L·)]$^+$ = H$_2$ | Optimized | 9.07E+07 | 2.47E+10 |
| | Upper Limit | 9.19E+07 | 3.95E+10 |
| | Lower Limit | 8.90E+07 | 9.94E+09 |
| [Zn(H$_2$L·)]$^+$ = Zn(HL·) + H$^+$ | Calculated | 1.87E−05 | 8.14E+04 |
| | Upper Limit | 1.87E−05 | 1.07E+05 |
| | Lower Limit | 1.87E−05 | 2.82E+04 |

TABLE A2

Optimized parameters of data fitting, 12 mM [acid]; v = 0.6-5.0 V/s vs Fc$^+$/Fc$^0$

| Charge-transfer Steps | 99% Confidence | E° | α | $k_s$ |
|---|---|---|---|---|

TABLE A2-continued

Optimized parameters of data fitting, 12 mM [acid]; $\nu = 0.6\text{-}5.0$ V/s vs $Fc^+/Fc^o$

| | | | | |
|---|---|---|---|---|
| $[ZnHL]^+ + e^- = Zn(HL\bullet)$ | Optimized | −1.8004 | 0.3166 | 0.007 |
| | Upper Limit | −1.8010 | 0.3166 | 0.007 |
| | Lower Limit | −1.8000 | 0.3166 | 0.007 |
| $[ZnH_2L]^{2+} + e^- = [Zn(H_2L\bullet)]^+$ | Optimized | −1.5264 | 0.3166 | 0.007 |
| | Upper Limit | −1.5274 | 0.3166 | 0.007 |
| | Lower Limit | −1.5254 | 0.3166 | 0.007 |

| Chemical Steps | 99% Confidence | $K_{eq}$ | $k_f$ |
|---|---|---|---|
| $ZnL + H^+ = [ZnHL]^+$ | Optimized | 1364 | 3.20E+13 |
| | Upper Limit | 1442.8 | 8.72E+15 |
| | Lower Limit | 1285.2 | 8.65E+12 |
| $[ZnHL]^+ + H^+ = [ZnH_2L]^{2+}$ | Optimized | 13.438 | 3.06E+09 |
| | Upper Limit | 13.6 | 9.83E+10 |
| | Lower Limit | 13.276 | 9.22E+08 |
| $Zn(HL\bullet) + Zn(HL\bullet) = H_2$ | Optimized | 3.69E+11 | 4.57E+08 |
| | Upper Limit | 3.69E+11 | 5.57E+08 |
| | Lower Limit | 3.68E+11 | 3.57E+08 |
| $Zn(HL\bullet) + [Zn(H_2L\bullet)]^+ = H_2$ | Optimized | 4.44E+08 | 2.72E+11 |
| | Upper Limit | 4.46E+08 | 3.84E+11 |
| | Lower Limit | 4.42E+08 | 1.61E+11 |
| $[Zn(H_2L\bullet)]^+ = Zn(HL\bullet) + H^+$ | Calculated | 1.74E−06 | 2414 |
| | Upper Limit | 1.74E−06 | 2414 |
| | Lower Limit | 1.74E−06 | 2414 |

TABLE A3

Optimized parameters of data fitting, 6 mM [acid]; $\nu = 0.2\text{-}0.5$ V/s vs $Fc^+/Fc^o$

| Charge-transfer Steps | 99% Confidence | $E^0$ | $\alpha$ | $k_s$ |
|---|---|---|---|---|
| $[ZnHL]^+ + e^- = Zn(HL\bullet)$ | Optimized | −1.8431 | 0.3166 | 0.007 |
| | Upper Limit | −1.8562 | 0.3166 | 0.007 |
| | Lower Limit | −1.8333 | 0.3166 | 0.007 |
| $[ZnH_2L]^{2+} + e^- = [Zn(H_2L\bullet)]^+$ | Optimized | −1.6958 | 0.3166 | 0.007 |
| | Upper Limit | −1.7939 | 0.3166 | 0.007 |
| | Lower Limit | −1.5977 | 0.3166 | 0.007 |

| Chemical Steps | 99% Confidence | $K_{eq}$ | $k_f$ |
|---|---|---|---|
| $ZnL + H^+ = [ZnHL]^+$ | Optimized | 32000 | 5.00E+11 |
| | Upper Limit | 6.68E+05 | 1.43E+12 |
| | Lower Limit | 6.04E+03 | 1.04E+10 |
| $[ZnHL]^+ + H^+ = [ZnH_2L]^{2+}$ | Optimized | 19.942 | 2.86E+02 |
| | Upper Limit | 95.717 | 2.86E+03 |
| | Lower Limit | 0.55833 | 2.23E+01 |
| $Zn(HL\bullet) + Zn(HL\bullet) = H_2$ | Optimized | 7.28E+09 | 2.00E+08 |
| | Upper Limit | 1.05E+11 | 1.35E+12 |
| | Lower Limit | 9.08E+08 | 1.35E+06 |
| $Zn(HL\bullet) + [Zn(H_2L\bullet)]^+ = H_2$ | Optimized | 8.58E+07 | 2.00E+12 |
| | Upper Limit | 1.28E+09 | 1.49E+13 |
| | Lower Limit | 1.11E+06 | 1.09E+10 |
| $[Zn(H_2L\bullet)]^+ = Zn(HL\bullet) + H^+$ | Calculated | 1.55E−04 | 4000 |
| | Upper Limit | 1.55E−04 | 4754.6 |
| | Lower Limit | 1.55E−04 | 3245.4 |

TABLE A4

Bond length comparison of calculated HER intermediates

| Structures | | ZnL | $[ZnHL]^+$ | $Zn(HL\bullet)$ | $[ZnH_2L\bullet]^+$ |
|---|---|---|---|---|---|
| Bond Lengths (Å) | Zn—S1 | 2.368 | 2.423 | 2.458 | 2.386 |
| | Zn—S2 | 2.368 | 2.318 | 2.341 | 2.386 |
| | Zn—N2 | 2.116 | 2.118 | 2.059 | 2.061 |
| | Zn—N3 | 2.116 | 2.125 | 2.045 | 2.061 |
| | S1—C1 | 1.774 | 1.719 | 1.728 | 1.732 |
| | C1—N5 | 1.356 | 1.343 | 1.373 | 1.349 |
| | N5—C5 | 1.460 | 1.467 | 1.459 | 1.463 |
| | C1—N1 | 1.339 | 1.373 | 1.351 | 1.361 |
| | N1—N2 | 1.344 | 1.357 | 1.368 | 1.362 |
| | N1—H15 | — | 1.015 | 1.016 | 1.015 |
| | N2—C2 | 1.312 | 1.313 | 1.368 | 1.348 |
| | C2—C3 | 1.478 | 1.470 | 1.427 | 1.436 |
| | C3—N3 | 1.312 | 1.322 | 1.345 | 1.348 |
| | N3—N4 | 1.344 | 1.321 | 1.349 | 1.362 |
| | N4—C4 | 1.339 | 1.361 | 1.329 | 1.361 |
| | C4—S2 | 1.774 | 1.767 | 1.792 | 1.732 |
| | C4—N6 | 1.356 | 1.341 | 1.367 | 1.349 |
| | N6—C8 | 1.460 | 1.469 | 1.458 | 1.463 |

TABLE A5

Bond angle comparison of calculated HER intermediates

| Structures | | ZnL | $[ZnHL]^+$ | $Zn(HL\bullet)$ | $[ZnH_2L\bullet]^+$ |
|---|---|---|---|---|---|
| Bond Angles (°) | S1—Zn—S2 | 118.02 | 119.08 | 116.68 | 117.56 |
| | S1—Zn—N2 | 82.78 | 81.57 | 82.39 | 83.80 |
| | N2—Zn—N3 | 76.43 | 74.94 | 77.40 | 73.34 |
| | N3—Zn—S2 | 82.78 | 84.41 | 85.07 | 83.30 |
| | C1—S1—Zn | 93.70 | 96.92 | 95.10 | 95.54 |
| | N1—N2—C2 | 121.88 | 122.99 | 120.43 | 122.41 |
| | N1—N2—Zn | 122.08 | 119.62 | 119.13 | 118.45 |
| | C2—N2—Zn | 116.04 | 117.39 | 115.19 | 118.59 |
| | C3—N3—Zn | 116.04 | 117.76 | 117.15 | 118.59 |
| | C3—N3—N4 | 121.88 | 122.01 | 121.05 | 122.41 |
| | N4—N3—Zn | 122.08 | 120.23 | 121.44 | 118.45 |

TABLE A6

Computational Input Coordinates

ZnL
0 1

| | | | |
|---|---|---|---|
| Zn | 0.00003000 | −0.87035000 | −0.00021000 |
| S | 1.99717800 | −1.98187000 | 0.39859600 |
| C | 3.02385700 | −0.57568000 | 0.06312600 |
| N | 2.64126500 | 0.68182000 | −0.11295000 |
| N | 1.29611500 | 0.83221600 | −0.13343000 |
| C | 0.74221700 | 2.00306700 | −0.01927000 |
| C | −0.74227000 | 2.00309000 | 0.01908300 |
| N | −1.29622000 | 0.83222900 | 0.13305300 |
| N | −2.64133000 | 0.68180300 | 0.11294100 |
| C | −3.02384000 | −0.57582000 | −0.06295000 |
| S | −1.99721000 | −1.98199000 | −0.39809000 |
| N | 4.35570700 | −0.82176000 | 0.01195100 |
| C | 5.36070300 | 0.19708100 | −0.24871000 |
| C | 1.51592800 | 3.28691200 | 0.08674400 |
| C | −1.51582000 | 3.28710900 | −0.08627000 |
| N | −4.35572000 | −0.82183000 | −0.01172000 |
| C | −5.36071000 | 0.19724100 | 0.24805300 |
| H | 4.64910400 | −1.76944000 | 0.19775300 |
| H | −4.64921000 | −1.76953000 | −0.19732000 |
| H | 6.34217200 | −0.28345000 | −0.24323000 |
| H | 5.33720300 | 0.97919000 | 0.51882200 |
| H | 5.19661500 | 0.66931400 | −1.22332000 |
| H | 2.57356100 | 3.10001400 | −0.10327000 |
| H | 1.41553600 | 3.72317600 | 1.09013800 |
| H | 1.14601100 | 4.03184200 | −0.62751000 |
| H | −2.57412000 | 3.09947900 | 0.09927500 |
| H | −1.14881000 | 4.02987600 | 0.63178900 |

TABLE A6-continued

Computational Input Coordinates

| | | | |
|---|---|---|---|
| H | −1.41150000 | 3.72652300 | −1.08785000 |
| H | −6.34227000 | −0.28309000 | 0.24188600 |
| H | −5.19732000 | 0.66960500 | 1.22273300 |
| H | −5.33643000 | 0.97923600 | −0.51956000 |

[ZnHL]⁺
1 1

| | | | |
|---|---|---|---|
| Zn | 0.000030000 | −0.870350000 | −0.000210000 |
| S | 1.997178000 | −1.981870000 | 0.398596000 |
| C | 3.023857000 | −0.575680000 | 0.063126000 |
| N | 2.641265000 | 0.681820000 | −0.112950000 |
| N | 1.296115000 | 0.832216000 | −0.133430000 |
| C | 0.742210000 | 2.003067000 | −0.019270000 |
| C | −0.742270000 | 2.003090000 | 0.019083000 |
| N | −1.296220000 | 0.832229000 | 0.133053000 |
| N | −2.641330000 | 0.681803000 | 0.112941000 |
| C | −3.023840000 | −0.575820000 | −0.062950000 |
| S | −1.997210000 | −1.981990000 | −0.398090000 |
| N | 4.355707000 | −0.821760000 | 0.011951000 |
| C | 5.360703000 | 0.197081000 | −0.248710000 |
| C | 1.515928000 | 3.286912000 | 0.086744000 |
| C | −1.515820000 | 3.287109000 | −0.086270000 |
| N | −4.355720000 | −0.821830000 | −0.011720000 |
| C | −5.360710000 | 0.197241000 | 0.248053000 |
| H | 4.649104000 | −1.769440000 | 0.197753000 |
| H | −4.649210000 | −1.769530000 | −0.197320000 |
| H | 6.342172000 | −0.283450000 | −0.243230000 |
| H | 5.337203000 | 0.979190000 | 0.518822000 |
| H | 5.196615000 | 0.669314000 | −1.223320000 |
| H | 2.573561000 | 3.100014000 | −0.103270000 |
| H | 1.415536000 | 3.723176000 | 1.090138000 |
| H | 1.146011000 | 4.031842000 | −0.627510000 |
| H | −2.574120000 | 3.099479000 | 0.099275000 |
| H | −1.148810000 | 4.029876000 | 0.631789000 |
| H | −1.411500000 | 3.726523000 | −1.087850000 |
| H | −6.342270000 | −0.283090000 | 0.241886000 |
| H | −5.197320000 | 0.669605000 | 1.222733000 |
| H | −5.336430000 | 0.979236000 | −0.519560000 |
| H | 3.281842792 | 1.442241206 | −0.219812917 |

Zn(HL•)
0 2

| | | | |
|---|---|---|---|
| Zn | 0.000030000 | −0.870350000 | −0.000210000 |
| S | 1.997178000 | −1.981870000 | 0.398596000 |
| C | 3.023857000 | −0.575680000 | 0.063126000 |
| N | 2.641265000 | 0.681820000 | −0.112950000 |
| N | 1.296115000 | 0.832216000 | −0.133430000 |
| C | 0.742210000 | 2.003067000 | −0.019270000 |
| C | −0.742270000 | 2.003090000 | 0.019083000 |
| N | −1.296220000 | 0.832229000 | 0.133053000 |
| N | −2.641330000 | 0.681803000 | 0.112941000 |
| C | −3.023840000 | −0.575820000 | −0.062950000 |
| S | −1.997210000 | −1.981990000 | −0.398090000 |
| N | 4.355707000 | −0.821760000 | 0.011951000 |
| C | 5.360703000 | 0.197081000 | −0.248710000 |
| C | 1.515928000 | 3.286912000 | 0.086744000 |
| C | −1.515820000 | 3.287109000 | −0.086270000 |
| N | −4.355720000 | −0.821830000 | −0.011720000 |
| C | −5.360710000 | 0.197241000 | 0.248053000 |
| H | 4.649104000 | −1.769440000 | 0.197753000 |
| H | −4.649210000 | −1.769530000 | −0.197320000 |
| H | 6.342172000 | −0.283450000 | −0.243230000 |
| H | 5.337203000 | 0.979190000 | 0.518822000 |
| H | 5.196615000 | 0.669314000 | −1.223320000 |
| H | 2.573561000 | 3.100014000 | −0.103270000 |
| H | 1.415536000 | 3.723176000 | 1.090138000 |
| H | 1.146011000 | 4.031842000 | −0.627510000 |
| H | −2.574120000 | 3.099479000 | 0.099275000 |
| H | −1.148810000 | 4.029876000 | 0.631789000 |
| H | −1.411500000 | 3.726523000 | −1.087850000 |
| H | −6.342270000 | −0.283090000 | 0.241886000 |
| H | −5.197320000 | 0.669605000 | 1.222733000 |
| H | −5.336430000 | 0.979236000 | −0.519560000 |
| H | 3.281842792 | 1.442241206 | −0.219812917 |

[ZnH₂L•]⁺
1 2

| | | | |
|---|---|---|---|
| Zn | 0.000030000 | −0.870350000 | −0.000210000 |
| S | 1.997178000 | −1.981870000 | 0.398596000 |
| C | 3.023857000 | −0.575680000 | 0.063126000 |
| N | 2.641265000 | 0.681820000 | −0.112950000 |
| N | 1.296115000 | 0.832216000 | −0.133430000 |
| C | 0.742210000 | 2.003067000 | −0.019270000 |
| C | −0.742270000 | 2.003090000 | 0.019083000 |
| N | −1.296220000 | 0.832229000 | 0.133053000 |
| N | −2.641330000 | 0.681803000 | 0.112941000 |
| C | −3.023840000 | −0.575820000 | −0.062950000 |
| S | −1.997210000 | −1.981990000 | −0.398090000 |
| N | 4.355707000 | −0.821760000 | 0.011951000 |
| C | 5.360703000 | 0.197081000 | −0.248710000 |
| C | 1.515928000 | 3.286912000 | 0.086744000 |
| C | −1.515820000 | 3.287109000 | −0.086270000 |
| N | −4.355720000 | −0.821830000 | −0.011720000 |
| C | −5.360710000 | 0.197241000 | 0.248053000 |
| H | 4.649104000 | −1.769440000 | 0.197753000 |
| H | −4.649210000 | −1.769530000 | −0.197320000 |
| H | 6.342172000 | −0.283450000 | −0.243230000 |
| H | 5.337203000 | 0.979190000 | 0.518822000 |
| H | 5.196615000 | 0.669314000 | −1.223320000 |
| H | 2.573561000 | 3.100014000 | −0.103270000 |
| H | 1.415536000 | 3.723176000 | 1.090138000 |
| H | 1.146011000 | 4.031842000 | −0.627510000 |
| H | −2.574120000 | 3.099479000 | 0.099275000 |
| H | −1.148810000 | 4.029876000 | 0.631789000 |
| H | −1.411500000 | 3.726523000 | −1.087850000 |
| H | −6.342270000 | −0.283090000 | 0.241886000 |
| H | −5.197320000 | 0.669605000 | 1.222733000 |
| H | −5.336430000 | 0.979236000 | −0.519560000 |
| H | 3.281842792 | 1.442241206 | −0.219812917 |
| H | −3.281933702 | 1.442187461 | 0.219910007 |

Protonation of ZnL at sulfur
1 1

| | | | |
|---|---|---|---|
| 30 | 0.000030000 | −0.870350000 | −0.000210000 |
| 16 | 1.997178000 | −1.981870000 | 0.398596000 |
| 6 | 3.023857000 | −0.575680000 | 0.063126000 |
| 7 | 2.641265000 | 0.681820000 | −0.112950000 |
| 7 | 1.296115000 | 0.832216000 | −0.133430000 |
| 6 | 0.742210000 | 2.003067000 | −0.019270000 |
| 6 | −0.742270000 | 2.003090000 | 0.019083000 |
| 7 | −1.296220000 | 0.832229000 | 0.133053000 |
| 7 | −2.641330000 | 0.681803000 | 0.112941000 |
| 6 | −3.023840000 | −0.575820000 | −0.062950000 |
| 16 | −1.997210000 | −1.981990000 | −0.398090000 |
| 7 | 4.355707000 | −0.821760000 | 0.011951000 |
| 6 | 5.360703000 | 0.197081000 | −0.248710000 |
| 6 | 1.515928000 | 3.286912000 | 0.086744000 |
| 6 | −1.515820000 | 3.287109000 | −0.086270000 |
| 7 | −4.355720000 | −0.821830000 | −0.011720000 |
| 6 | −5.360710000 | 0.197241000 | 0.248053000 |
| 1 | 4.649104000 | −1.769440000 | 0.197753000 |
| 1 | −4.649210000 | −1.769530000 | −0.197320000 |
| 1 | 6.342172000 | −0.283450000 | −0.243230000 |
| 1 | 5.337203000 | 0.979190000 | 0.518822000 |
| 1 | 5.196615000 | 0.669314000 | −1.223320000 |
| 1 | 2.573561000 | 3.100014000 | −0.103270000 |
| 1 | 1.415536000 | 3.723176000 | 1.090138000 |
| 1 | 1.146011000 | 4.031842000 | −0.627510000 |
| 1 | −2.574120000 | 3.099479000 | 0.099275000 |
| 1 | −1.148810000 | 4.029876000 | 0.631789000 |
| 1 | −1.411500000 | 3.726523000 | −1.087850000 |
| 1 | −6.342270000 | −0.283090000 | 0.241886000 |
| 1 | −5.197320000 | 0.669605000 | 1.222733000 |
| 1 | −5.336430000 | 0.979236000 | −0.519560000 |
| 1 | 2.274340046 | −3.233237278 | 0.753787688 |

TABLE A6-continued

Computational Input Coordinates

Protonation at Amine Nitrogen
1 1

| | | | |
|---|---|---|---|
| Zn | 0.000030000 | −0.870350000 | −0.000210000 |
| S | 1.997178000 | −1.981870000 | 0.398596000 |
| C | 3.023857000 | −0.575680000 | 0.063126000 |
| N | 2.641265000 | 0.681820000 | −0.112950000 |
| N | 1.296115000 | 0.832216000 | −0.133430000 |
| C | 0.742210000 | 2.003067000 | −0.019270000 |
| C | −0.742270000 | 2.003090000 | 0.019083000 |
| N | −1.296220000 | 0.832229000 | 0.133053000 |
| N | −2.641330000 | 0.681803000 | 0.112941000 |
| C | −3.023840000 | −0.575820000 | −0.062950000 |
| S | −1.997210000 | −1.981990000 | −0.398090000 |
| N | 4.355707000 | −0.821760000 | 0.011951000 |
| C | 5.360703000 | 0.197081000 | −0.248710000 |
| C | 1.515928000 | 3.286912000 | 0.086744000 |
| C | −1.515820000 | 3.287109000 | −0.086270000 |
| N | −4.355720000 | −0.821830000 | −0.011720000 |
| C | −5.360710000 | 0.197241000 | 0.248053000 |
| H | 4.649104000 | −1.769440000 | 0.197753000 |
| H | −4.649210000 | −1.769530000 | −0.197320000 |
| H | 6.342172000 | −0.283450000 | −0.243230000 |
| H | 5.337203000 | 0.979190000 | 0.518822000 |
| H | 5.196615000 | 0.669314000 | −1.223320000 |
| H | 2.573561000 | 3.100014000 | −0.103270000 |
| H | 1.415536000 | 3.723176000 | 1.090138000 |
| H | 1.146011000 | 4.031842000 | −0.627510000 |
| H | −2.574120000 | 3.099479000 | 0.099275000 |
| H | −1.148810000 | 4.029876000 | 0.631789000 |
| H | −1.411500000 | 3.726523000 | −1.087850000 |
| H | −6.342270000 | −0.283090000 | 0.241886000 |
| H | −5.197320000 | 0.669605000 | 1.222733000 |
| H | −5.336430000 | 0.979236000 | −0.519560000 |
| H | 4.370833470 | −0.021327902 | −0.587281548 |

Protonation on Zinc
1 1

| | | | |
|---|---|---|---|
| Zn | 0.000030000 | −0.870350000 | −0.000210000 |
| S | 1.997178000 | −1.981870000 | 0.398596000 |
| C | 3.023857000 | −0.575680000 | 0.063126000 |
| N | 2.641265000 | 0.681820000 | −0.112950000 |
| N | 1.296115000 | 0.832216000 | −0.133430000 |
| C | 0.742210000 | 2.003067000 | −0.019270000 |
| C | −0.742270000 | 2.003090000 | 0.019083000 |
| N | −1.296220000 | 0.832229000 | 0.133053000 |
| N | −2.641330000 | 0.681803000 | 0.112941000 |
| C | −3.023840000 | −0.575820000 | −0.062950000 |
| S | −1.997210000 | −1.981990000 | −0.398090000 |
| N | 4.355707000 | −0.821760000 | 0.011951000 |
| C | 5.360703000 | 0.197081000 | −0.248710000 |
| C | 1.515928000 | 3.286912000 | 0.086744000 |
| C | −1.515820000 | 3.287109000 | −0.086270000 |
| N | −4.355720000 | −0.821830000 | −0.011720000 |
| C | −5.360710000 | 0.197241000 | 0.248053000 |
| H | 4.649104000 | −1.769440000 | 0.197753000 |
| H | −4.649210000 | −1.769530000 | −0.197320000 |
| H | 6.342172000 | −0.283450000 | −0.243230000 |
| H | 5.337203000 | 0.979190000 | 0.518822000 |
| H | 5.196615000 | 0.669314000 | −1.223320000 |
| H | 2.573561000 | 3.100014000 | −0.103270000 |
| H | 1.415536000 | 3.723176000 | 1.090138000 |
| H | 1.146011000 | 4.031842000 | −0.627510000 |
| H | −2.574120000 | 3.099479000 | 0.099275000 |
| H | −1.148810000 | 4.029876000 | 0.631789000 |
| H | −1.411500000 | 3.726523000 | −1.087850000 |
| H | −6.342270000 | −0.283090000 | 0.241886000 |
| H | −5.197320000 | 0.669605000 | 1.222733000 |
| H | −5.336430000 | 0.979236000 | −0.519560000 |
| H | 0.000293000 | −2.650349596 | −0.001380325 |

Hydrogen
0 1

| | | | |
|---|---|---|---|
| H | 3.259348439 | 4.169555780 | −0.124845483 |
| H | 3.259348439 | 4.169555780 | −0.864845483 |

TABLE A7

Comparison of calculated energies for various protonation sites on ZnL

| Site of Protonation | Sum of Electronic and Thermal Free Energies (kcal/mole) |
|---|---|
| S-Protonation | +1300 |
| Hydrazino N-Protonation | 0 |
| Amine N-Protonation | +13 |
| Zn-Protonation | +14 |

TABLE A8

α-β spin density comparison for radical species: Zn(HL•) and [ZnH$_2$L•]$^+$

| | Spin-Density (α-β) | |
|---|---|---|
| Atom | Zn(HL•) | [ZnH$_2$L•]$^+$ |
| C1 | 0.096320 | 0.072671 |
| C2 | 0.298443 | 0.211249 |
| C3 | — | 0.211171 |
| C4 | 0.094069 | 0.072688 |
| N2 | 0.125707 | 0.192627 |
| N3 | 0.259371 | 0.192651 |
| N4 | 0.022704 | — |
| N5 | — | 0.033882 |
| N6 | 0.026308 | 0.033891 |
| S1 | 0.014559 | — |
| S2 | 0.008889 | — |

Example Set B: HER of Cu Complexes

The compounds discussed in Example Set B include $H_2L^2$, $ML^1$, and $ML^2$.

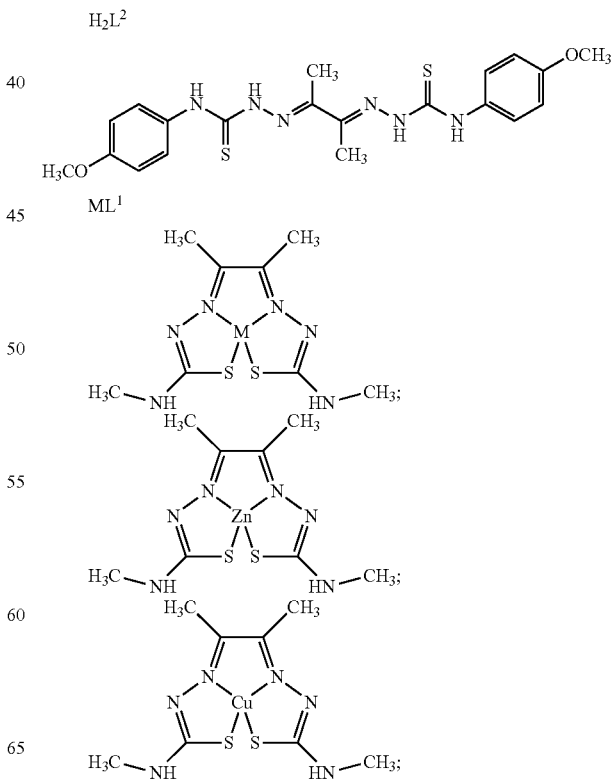

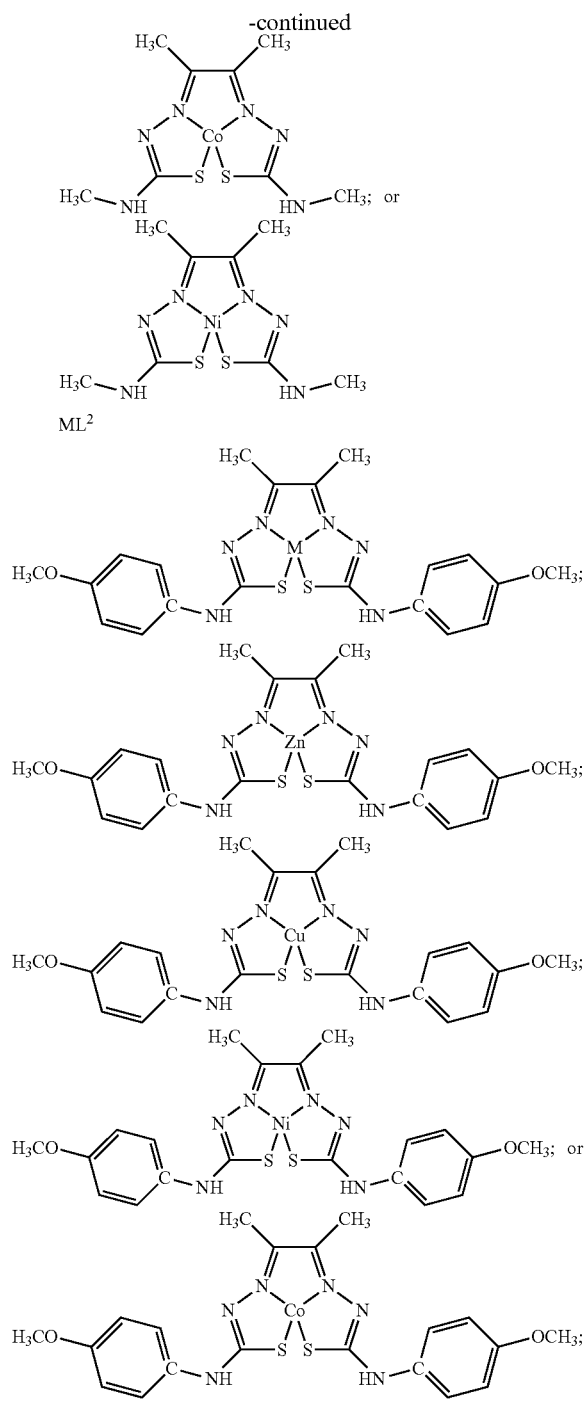

Materials and Methods for Example Set B

Electrochemical Methods

All cyclic voltammetry (CV) and controlled potential coulometry (CPC) measurements were recorded using a Gamry Interface potentiostat/galvanostat, which was connected to a glassy carbon working electrode (6.5 mm diameter, surface =0.07 cm$^2$), a platinum wire counter electrode, and Ag/AgCl reference electrode. Before use, the working electrode was polished using an aqueous alumina slurry. The working and counter electrodes were cleaned before use by washing with water, ethanol, isopropanol, acetone and then sonication for 10 minutes in acetonitrile. CV measurements were conducted using a three-neck electrochemical cell that was washed and dried in an oven overnight before use. All electrochemical experiments were conducted under a $N_2$ atmosphere. All CPC measurements were conducted using a two chambered glass electrolysis cell with working and auxiliary compartments separated by a frit, with a volume of 10 mL in each, washed and dried the night before use. The working compartment was fitted with a glassy carbon working electrode and an Ag/AgCl reference electrode. The auxiliary compartment was fitted with a Pt wire counter electrode. The working compartment contained 0.292 M acetic acid added to a 0.1 M $Bu_4NPF_6$ acetonitrile or DMF solution, while the auxiliary compartment was filled with 0.1 M $Bu_4NPF_6$ acetonitrile or DMF solution. Both compartments were purged for 15 min with $N_2$ prior to electrolysis. A control (blank) CPC study was conducted and subtracted from experimental results (supporting information). Electrolysis measurements were performed after addition of 0.6 mM $CuL^1$ to the working compartment for several time durations. The evolved gas was subjected to GC-TCD analysis at the end of the electrolysis using a Gow-Mac series 400 GC-TCD equipped with a molecular sieve column for product detection. The column was heated to 130° C. under $N_2$ gas flow with 250 μL injection samples injected onto the column to confirm $H_2$ as the gaseous product.

Overpotential Determination

Overpotential can be defined as the difference between the thermodynamic and equilibrium potentials for a given reaction and the potential at which the reaction occurs under a set of specific conditions. In the case of $H_2$ evolution or oxidation, when either the equilibrium potential for the standard state $H^+/H_2$ couple ($E°_{H+}$) is not known for some particular solvent, or a reliable pKa scale is unavailable, the direct measurement of the equilibrium potential for the reduction of protons ($E_{H+}$) can be accomplished through an open circuit potential (OCP) measurements, as described by Appel and Helm (ACS Catal., 2014, Vol. 4, pp. 630-633; DOI: 10.1021/cs401013v). Using this method provides an accurate determination of the equilibrium potential for the $H^+/H_2$ couple under a wide range of acids and bases, as well as solvents or mixtures of solvents. This method has proven valuable for the determination of $E_{H+}$ of protic ionic liquids and various acid base pairs in acetonitrile DMF and/or water. The accurate determination of overpotential can sometimes require an estimation of $E_{cat/2}$ and $E_{H+}$, each of which can change, depending on the reaction conditions. The value for the potential for catalysis should be related to the catalytic current, and therefore, we use $E_{cat/2}$. This combined with a value for $E_{H+}$, obtained through OCP measurements allows for calculation of the overpotential (η) for proton reduction by $CuL^1$ under some specific experimental conditions. The overpotential can then be estimated as, η=|($E_{OCP}-E_{cat/2}$)|, where $E_{OCP}$ is the measured open circuit potential measured under catalytic conditions specific for each reaction, and $E_{cat/2}$ is the potential at one-half the maximum of the catalytic current measured for the catalyzed reduction of protons (see sample calculations).

Faradaic Efficiency Determination

Evolved gas from the cathode compartment displaced water in a cylinder with radius 1.12 cm by a height of 2.16 cm. Using the equation for the volume of a cylinder, V=π(r)$^2$h, we can calculate the volume displaced. This is calculated to be 8.51 mL. Using the conversion factor of 22.4 L of any ideal gas per one mole of gas allows us to quantify the number of moles of $H_2$ evolved as 3.80+10$^4$ moles. This value can then be compared to the theoretical number of moles of $H_2$ evolved based on charge determined earlier, 4.40×10$^4$. Faradaic efficiency is defined as moles of $H_2$ quantified/moles of $H_2$ theoretical based on charge ×100%. This corresponds with a minimum Faradic efficiency of 86.0%.

Turnover Frequency Determination $$i_{cat}=nFA[cat]\sqrt{Dk[H^+]^2} \quad (B1)$$

Equation B1 details the relationship between the catalytic current $i_{cat}$, the catalyst concentration [cat], and the acid concentration [$H^+$] for a catalytic reaction that is second-order in acid and first-order in catalyst. The terms n, F, A, and D are the normal electrochemical terms related to the number of electrons transferred, Faraday's constant, area of the electrode (0.07 cm$^2$), and diffusion constant, respectively.

Equation B2 (Randle-Sevcik equation) provides the relationship between the peak current ($i_p$), catalyst concentration, and scan rate (v) in the absence of acid. The factor of 0.4463 is related to the diffusion equations, R is the gas constant, and T is temperature in K. The other terms are the same as in equation B 1.

$$i_p = 0.4463FA[cat]\sqrt{\frac{FvD}{RT}} \quad (B2)$$

Thus, the ratio of $i_{cat}/i_p$ (equation B3) is obtained from the quotient equations B1 and B2.

$$\frac{i_{cat}}{i_p} = \frac{n}{0.4463}\sqrt{\frac{RTk[H^+]^2}{Fv}} \quad (B3)$$

Under pseudo first-order conditions where $k_{obs}=k[H^+]^2$, equation B3 simplifies to B4.

$$\frac{i_{cat}}{i_p} = \frac{n}{0.4463}\sqrt{\frac{RTk_{obs}}{Fv}} \quad (B4)$$

Equation B4 can be simplified further to equation B5, when n=2, and when at scan rate independent conditions can be used to estimate the observed rate constant or turnover frequency (TOF) (see sample calculations).

$$k_{obs}=1.94 \times v[i_{cat}/i_p]^2 \quad (B5)$$

X-ray Photoelectron Spectroscopy of Electrode Adsorbed Films

CPEs of 0.6 mM CuL$^1$ with 0.292 M acetic acid added in 0.1 M Bu$_4$NPF$_6$ DMF and ACN solutions were run for 23.5 and 4.2 hours, respectively. After completion of electrolysis, the working electrode was removed and washed with DI water. A visible red-brown film persisted on the electrode surface. The films were scraped off using a spatula, collected onto wax paper, and transferred to a glass vial, which was sealed and wrapped with parafilm. XPS analysis was conducted by the Nanoscale Characterization Facility at the University of Indiana (Bloomington, Ind.) using a PHI VersaProbe II Scanning X-ray Microprobe system.

Computational Methods

Initial calculations were performed using M06, B3LYP and B97-D. Based on energetic minima results, B3LYP was chosen for use as the functional for subsequent calculations. Optimizations were performed in the gas phase using density functional theory (DFT) employing the B3LYP exchange correlation functional, and the 6-311G(d,p) basis set for all atoms as implemented in the Gaussian09 suite of programs for electronic structure and ChemCraft was used for graphics visualization. All optimizations were performed under tight constraints, with no symmetry imposed. All input coordinates are available below.

Sample Calculations

Overpotential calculation at the potential of half catalytic current ($E_{cat/2}$); CuL$^1$ HER:

$$\eta = \text{Overpotential} = |(E_{BH+(OCP)})-(E_{cat/2})|$$

$$\eta = |[-0.50-(-2.20\ V)]|$$

$$\eta = 1.7\ V\ \text{vs}\ Fc^+/Fc^0$$

Determination of CuL$^1$ Diffusion Coefficient ($D_0$) (Acetonitrile):

$$\text{Slope}=3.22E-5=0.4463FA[cat][(FD_0/RT)]^{0.5}$$

A=0.071 cm$^2$
[cat]=6E−7 moles/cm$^3$
F=96485 C/mole e$^-$
R=ideal gas constant
T=298 K
$D_0$=7.9E−6 cm$^2$/s in acetonitrile Determination of CuL$^1$ Diffusion Coefficient ($D_0$) (DMF):

$$\text{Slope}=3E-5=0.4463FA[cat][(FD_0/RT)]^{0.5}$$

A=0.071 cm$^2$
[cat]=6E−7 moles/cm$^3$
F=96485 C/mole e$^-$
R=ideal gas constant
T=298 K
$D_0$=9.35E−6 cm$^2$/s in DMF TOF$_{max}$ Sample Calculation for CuL$^1$ in acetonitrile:

Using equation B5, at scan-rate independent conditions, when v=0.2 v/s and when $i_{cat}$=2250 μA and $i_p$=14 μA $$\frac{i_{cat}}{i_p} = 160.71$$

$$TOF_{max}/k_{obs} = 10000\ s^{-1}$$

TOF$_{max}$ Sample Calculation for CuL$^1$ in Dimethylformamide:

Using equation B5, at scan rate independent conditions, when v=1.0 v/s, and when $i_{cat}$=1490 μA and $i_p$=29 μA $$\frac{i_{cat}}{i_p} = 51.44$$

$$TOF_{max}/k_{obs} = 5410\ s^{-1}$$

Sample Calculations CuL$^1$ Electrolysis in Acetonitrile:
Trial 1: Total charge=$Q_{with\ cat}-Q_{blank}=Q_{net}$ 60.49 C−0.0576 C=60.43

Theoretical Moles of Hydrogen Made via Total Charge:

60.43 C×(1 mol $e^-$/96485 C)×(1 mol $H_2$/2 mol $e^-$)=moles $H_2$ theoretical

Moles $H_2$ theoretical=0.00031 moles $H_2$ based on charge from electrolysis

Trial 1: $CuL^1$ TON Calculation:

TON=Moles of $H_2$ Produced/Moles of $CuL^1$ Used

TON=(0.00031 moles $H_2$ produced)/(0.000006 moles $CuL^1$ used)

TON=51.7

Trial 2: Total Charge=$Q_{with\ cat}$-$Q_{blank}$=$Q_{net}$ 84.74 C-0.0576 C=84.68

Theoretical moles of Hydrogen made via Total Charge 84.68 C×(1 mol $e^-$/96485 C)×(1 mol $H_2$/2 mol $e^-$)=moles $H_2$ theoretical Moles $H_2$ Theoretical=0.00044 moles $H_2$ based on charge from electrolysis Trial 2: $CuL^1$ TON Calculation:

TON=Moles of $H_2$ Produced/Moles of $CuL^1$ Used

TON=(0.00044 moles of $H_2$ produced)/(0.000006 moles $CuL^1$ used)

TON=73.3

Sample Calculations $CuL^1$ Electrolysis in DMF

Trial 1: Total charge=$Q_{with\ cat}$-$Q_{blank}$=$Q_{net}$ 67.03 C-0.0682 C=66.96 C Theoretical Moles of Hydrogen made via total Charge:

66.96×(1 mol $e^-$/96485 C)×(1 mol $H_2$/2 mol $e^-$)=moles of $H_2$ theoretical Moles $H_2$ Theoretical=0.00035 moles $H_2$ based on charge from electrolysis Trial 1: $CuL^1$ TON Calculation:

TON=Moles of $H_2$ Produced/Moles of $CuL^1$ Used

TON=(0.00035 moles of $H_2$ produced)/(0.000006 moles $CuL^1$ used)

TON=58.3

Trial 2: Total Charge=$Q_{with\ cat}$-$Q_{blank}$=$Q_{net}$ 85.06 C-0.682 C=85 C Theoretical Moles of Hydrogen made via total Charge:

85×(1 mol $e^-$/96485 C)×(1 mol $H_2$/2 mol $e^-$)=moles of $H_2$ theoretical

Moles $H_2$ Theoretical=0.00044 moles $H_2$ based on charge from electrolysis

Trial 2: $CuL^1$ TON Calculation:

TON=Moles of $H_2$ Produced/Moles of $CuL^1$ Used

TON=(0.00044 moles of $H_2$ produced)/(0.000006 moles $CuL^1$ used)

TON=73.3

Trial 2: $CuL^1$ Faradaic Efficiency Calculation:

Faradaic efficiency =

(moles of $H_2$ quantified)/(moles of $H_2$ theoretical based on charge)×

100% = (0.000356 moles)/(0.00044 Moles)×100% =

81% Faradaic Efficiency

Crystallographic Details

A light-purple plate 0.26×0.10×0.01 mm³ crystal of $[CuL^1H_2]^{2+}$, grown through liquid-liquid diffusion of pentane into methanol/acetonitrile solution of 1 mM $CuL^1$ with four drops of perchloric acid added, was mounted on a CryoLoop for collection of x-ray data on an Agilent Technologies/Oxford Diffraction Gemini CCD diffractometer. The CrysAlisPro[1] CCD software package (v 1.171.36.32) was used to acquire a total of 772 forty-five second frame ω-scan exposures of data at 100K to a 2θ max=57.42° using monochromated MoKα radiation (0.71073 Å) from a sealed tube. Frame data were processed using CrysAlisPro[1] RED to determine final unit cell parameters: a=8.7724(3) Å, b=9.3218(3) Å, c=12.1476(5) Å, α=100.149(3), β=107.682(3)°, γ=97.493(3)°, V=913.55(6) Å³, $D_{calc}$=1.901 Mg/m³, Z=2 to produce raw hkl data that were then corrected for absorption (transmission min./max.=0.848/1.000; μ=1.769 mm$^{-1}$) using SCALE3 ABSPACK. The structure was solved by Direct methods in the space group P-1 using SHELXS and refined by least squares methods on $F^2$ using SHELXL. Non-hydrogen atoms were refined with anisotropic atomic displacement parameters. Imine H's were located by difference maps and refined isotropically. Methyl hydrogen atoms were placed in their geometrically generated positions and refined as a riding model and these atoms were assigned U(H)=1.5×Ueq. For all 4720 unique reflections (R(int) 0.040) the final anisotropic full matrix least-squares refinement on $F^2$ for 264 variables converged at R1=0.044 and wR2=0.075 with a GOF of 1.06.

TABLE B1

Bond lengths (Å) for $[Cu(L^1H_2)(ClO_4)]ClO_4$.

| | | | |
|---|---|---|---|
| Cu(1)—N(1) | 1.9579(18) | C(2)—C(4) | 1.483(3) |
| Cu(1)—N(4) | 1.9557(18) | C(3)—H(3A) | 0.9600 |
| Cu(1)—S(1) | 2.2462(6) | C(3)—H(3B) | 0.9600 |
| Cu(1)—S(2) | 2.2593(6) | C(3)—H(3C) | 0.9600 |
| S(1)—C(5) | 1.714(2) | C(4)—H(4A) | 0.9600 |
| S(2)—C(6) | 1.711(2) | C(4)—H(4B) | 0.9600 |
| N(1)—C(1) | 1.282(3) | C(4)—H(4C) | 0.9600 |
| N(1)—N(2) | 1.355(3) | C(7)—H(7A) | 0.9600 |
| N(2)—C(5) | 1.360(3) | C(7)—H(7B) | 0.9600 |
| N(2)—H(2N) | 0.78(3) | C(7)—H(7C) | 0.9600 |
| N(3)—C(5) | 1.311(3) | C(8)—H(8A) | 0.9600 |
| N(3)—C(7) | 1.448(3) | C(8)—H(8B) | 0.9600 |
| N(3)—H(3N) | 0.76(3) | C(8)—H(8C) | 0.9600 |
| N(4)—C(2) | 1.287(3) | Cl(1)—O(2) | 1.4223(17) |
| N(4)—N(5) | 1.364(2) | Cl(1)—O(4) | 1.4274(18) |
| N(5)—C(6) | 1.356(3) | Cl(1)—O(3) | 1.4503(17) |
| N(5)—H(5N) | 0.78(2) | Cl(1)—O(1) | 1.4541(17) |
| N(6)—C(6) | 1.319(3) | Cl(2)—O(8) | 1.4231(19) |
| N(6)—C(8) | 1.465(3) | Cl(2)—O(7) | 1.4307(19) |
| N(6)—H(6N) | 0.78(3) | Cl(2)—O(6) | 1.430(2) |
| C(1)—C(3) | 1.484(3) | Cl(2)—O(5) | 1.4506(18) |
| C(1)—C(2) | 1.501(3) | | |

TABLE B2

Bond angles (°) for $[Cu(L^1H_2)(ClO_4)]ClO_4$.

| | | | |
|---|---|---|---|
| N(1)—Cu(1)—N(4) | 78.80(7) | C(2)—C(4)—H(4A) | 109.5 |
| N(1)—Cu(1)—S(1) | 86.88(6) | C(2)—C(4)—H(4B) | 109.5 |
| N(4)—Cu(1)—S(1) | 165.50(5) | H(4A)—C(4)—H(4B) | 109.5 |
| N(1)—Cu(1)—S(2) | 164.38(6) | C(2)—C(4)—H(4C) | 109.5 |
| N(4)—Cu(1)—S(2) | 86.08(5) | H(4A)—C(4)—H(4C) | 109.5 |
| S(1)—Cu(1)—S(2) | 108.02(2) | H(4B)—C(4)—H(4C) | 109.5 |
| C(5)—S(1)—Cu(1) | 95.64(8) | N(3)—C(5)—N(2) | 116.5(2) |
| C(6)—S(2)—Cu(1) | 95.99(7) | N(3)—C(5)—S(1) | 121.83(19) |
| C(1)—N(1)—N(2) | 123.56(18) | N(2)—C(5)—S(1) | 121.63(17) |
| C(1)—N(1)—Cu(1) | 118.13(15) | N(6)—C(6)—N(5) | 117.3(2) |
| N(2)—N(1)—Cu(1) | 118.19(14) | N(6)—C(6)—S(2) | 120.89(17) |

TABLE B2-continued

Bond angles (°) for [Cu(L¹H₂)(ClO₄)]ClO₄.

| | | | |
|---|---|---|---|
| N(1)—N(2)—C(5) | 117.61(19) | N(5)—C(6)—S(2) | 121.84(16) |
| N(1)—N(2)—H(2N) | 121(2) | N(3)—C(7)—H(7A) | 109.5 |
| C(5)—N(2)—H(2N) | 121(2) | N(3)—C(7)—H(7B) | 109.5 |
| C(5)—N(3)—C(7) | 124.8(2) | H(7A)—C(7)—H(7B) | 109.5 |
| C(5)—N(3)—H(3N) | 119(2) | N(3)—C(7)—H(7C) | 109.5 |
| C(7)—N(3)—H(3N) | 116(2) | H(7A)—C(7)—H(7C) | 109.5 |
| C(2)—N(4)—N(5) | 122.83(19) | H(7B)—C(7)—H(7C) | 109.5 |
| C(2)—N(4)—Cu(1) | 118.03(15) | N(6)—C(8)—H(8A) | 109.5 |
| N(5)—N(4)—Cu(1) | 119.13(14) | N(6)—C(8)—H(8B) | 109.5 |
| C(6)—N(5)—N(4) | 116.86(18) | H(8A)—C(8)—H(8B) | 109.5 |
| C(6)—N(5)—H(5N) | 120.5(19) | N(6)—C(8)—H(8C) | 109.5 |
| N(4)—N(5)—H(5N) | 119.9(19) | H(8A)—C(8)—H(8C) | 109.5 |
| C(6)—N(6)—C(8) | 123.5(2) | H(8B)—C(8)—H(8C) | 109.5 |
| C(6)—N(6)—H(6N) | 117(2) | O(2)—Cl(1)—O(4) | 110.85(12) |
| C(8)—N(6)—H(6N) | 119(2) | O(2)—Cl(1)—O(3) | 109.38(11) |
| N(1)—C(1)—C(3) | 125.2(2) | O(4)—Cl(1)—O(3) | 110.25(11) |
| N(1)—C(1)—C(2) | 112.56(18) | O(2)—Cl(1)—O(1) | 110.29(11) |
| C(3)—C(1)—C(2) | 122.2(2) | O(4)—Cl(1)—O(1) | 109.21(10) |
| N(4)—C(2)—C(4) | 124.6(2) | O(3)—Cl(1)—O(1) | 106.78(12) |
| N(4)—C(2)—C(1) | 112.47(19) | O(8)—Cl(2)—O(7) | 109.28(13) |
| C(4)—C(2)—C(1) | 122.83(19) | O(8)—Cl(2)—O(6) | 110.09(14) |
| C(1)—C(3)—H(3A) | 109.5 | O(7)—Cl(2)—O(6) | 109.35(12) |
| C(1)—C(3)—H(3B) | 109.5 | O(8)—Cl(2)—O(5) | 109.98(11) |
| H(3A)—C(3)—H(3B) | 109.5 | O(7)—Cl(2)—O(5) | 109.47(12) |
| C(1)—C(3)—H(3C) | 109.5 | O(6)—Cl(2)—O(5) | 108.65(11) |
| H(3A)—C(3)—H(3C) | 109.5 | | |
| H(3B)—C(3)—H(3C) | 109.5 | | |

TABLE B3

Kinetic Isotope Effect: CH₃COOH vs CD₃COOD

| % D-Acid | $i_{cat}$ (uA) | TOF (s⁻¹) | KIE |
|---|---|---|---|
| 0.00 | 2250 | 10021.68 | 1 |
| 20.00 | 1837 | 6680.269 | 1.500192 |
| 40.00 | 1257 | 3127.852 | 3.204015 |
| 60.00 | 1045 | 2161.764 | 4.635883 |
| 80.00 | 910 | 1639.3 | 6.113392 |
| 100.00 | 819 | 1327.833 | 7.547398 |

TABLE B4

Computational Input Coordinates

CuL¹
0 2

| | | | |
|---|---|---|---|
| Cu | 1.431847450 | −0.488032580 | 0.446112510 |
| S | 2.332615610 | −0.119942340 | 2.552696700 |
| S | 2.858402730 | −1.722415690 | −0.909505780 |
| N | −0.257435500 | 0.971116720 | 2.468152050 |
| N | −0.172027540 | 0.534274340 | 1.177021620 |
| N | 0.574079220 | −1.034389140 | −2.391256330 |
| N | 0.223704470 | −0.461096440 | −1.204115870 |
| C | 0.866804360 | 0.696900310 | 3.160702940 |
| C | −1.156654600 | 0.726779040 | 0.313291070 |
| C | 1.780157800 | −1.630949380 | −2.329823970 |
| C | −0.928456430 | 0.172470660 | −1.041194200 |
| C | −2.430852170 | 1.445672040 | 0.707410510 |
| C | −1.949721220 | 0.325466600 | −2.151313540 |
| N | 0.905903760 | 1.099112750 | 4.470338340 |
| N | 2.249331710 | −2.229486700 | −3.469048500 |
| C | 1.542073250 | −2.300940750 | −4.757663730 |
| C | −0.256906930 | 1.621968390 | 5.210058210 |
| H | −0.736089590 | 2.427871470 | 4.633939270 |
| H | 0.095862870 | 2.020878310 | 6.174487110 |
| H | −1.009760380 | 0.833110030 | 5.396764760 |
| H | −3.052880760 | 1.693994160 | −0.164430810 |
| H | −2.187359810 | 2.369822740 | 1.257044200 |
| H | −3.027972700 | 0.817502200 | 1.394048690 |
| H | 2.232241150 | −2.034661770 | −5.577035900 |
| H | 0.709065320 | −1.588742850 | −4.742827890 |

TABLE B4-continued

Computational Input Coordinates

| | | | |
|---|---|---|---|
| H | 1.143750430 | −3.316026930 | −4.940576080 |
| H | −1.595749020 | −0.186808630 | −3.055724620 |
| H | −2.117801900 | 1.390722990 | −2.392856600 |
| H | −2.924379830 | −0.103170090 | −1.856998090 |
| H | 1.714229460 | 0.779113230 | 5.003296850 |
| H | 3.143979070 | −2.710111620 | −3.380991940 |

[CuL¹H]⁺
1 2

| | | | |
|---|---|---|---|
| Cu | 1.431847450 | −0.488032580 | 0.446112510 |
| S | 2.332615610 | −0.119942340 | 2.552696700 |
| S | 2.858402730 | −1.722415690 | −0.909505780 |
| N | −0.257435500 | 0.971116720 | 2.468152050 |
| N | −0.172027540 | 0.534274340 | 1.177021620 |
| N | 0.574079220 | −1.034389140 | −2.391256330 |
| N | 0.223704470 | −0.461096440 | −1.204115870 |
| C | 0.866804360 | 0.696900310 | 3.160702940 |
| C | −1.156654600 | 0.726779040 | 0.313291070 |
| C | 1.780157800 | −1.630949380 | −2.329823970 |
| C | −0.928456430 | 0.172470660 | −1.041194200 |
| C | −2.430852170 | 1.445672040 | 0.707410510 |
| C | −1.949721220 | 0.325466600 | −2.151313540 |
| N | 0.905903760 | 1.099112750 | 4.470338340 |
| N | 2.249331710 | −2.229486700 | −3.469048500 |
| C | 1.542073250 | −2.300940750 | −4.757663730 |
| C | −0.256906930 | 1.621968390 | 5.210058210 |
| H | −0.736089590 | 2.427871470 | 4.633939270 |
| H | 0.095862870 | 2.020878310 | 6.174487110 |
| H | −1.009760380 | 0.833110030 | 5.396764760 |
| H | −3.052880760 | 1.693994160 | −0.164430810 |
| H | −2.187359810 | 2.369822740 | 1.257044200 |
| H | −3.027972700 | 0.817502200 | 1.394048690 |
| H | 2.232241150 | −2.034661770 | −5.577035900 |
| H | 0.709065320 | −1.588742850 | −4.742827890 |
| H | 1.143750430 | −3.316026930 | −4.940576080 |
| H | −1.595749020 | −0.186808630 | −3.055724620 |
| H | −2.117801900 | 1.390722990 | −2.392856600 |
| H | −2.924379830 | −0.103170090 | −1.856998090 |
| H | 1.714229460 | 0.779113230 | 5.003296850 |
| H | 3.143979070 | −2.710111620 | −3.380991940 |
| H | 0.002279216 | −1.014134076 | −3.211399298 |

CuL¹H
0 1

| | | | |
|---|---|---|---|
| Cu | 1.431847450 | −0.488032580 | 0.446112510 |
| S | 2.332615610 | −0.119942340 | 2.552696700 |
| S | 2.858402730 | −1.722415690 | −0.909505780 |
| N | −0.257435500 | 0.971116720 | 2.468152050 |
| N | −0.172027540 | 0.534274340 | 1.177021620 |
| N | 0.574079220 | −1.034389140 | −2.391256330 |
| N | 0.223704470 | −0.461096440 | −1.204115870 |
| C | 0.866804360 | 0.696900310 | 3.160702940 |
| C | −1.156654600 | 0.726779040 | 0.313291070 |
| C | 1.780157800 | −1.630949380 | −2.329823970 |
| C | −0.928456430 | 0.172470660 | −1.041194200 |
| C | −2.430852170 | 1.445672040 | 0.707410510 |
| C | −1.949721220 | 0.325466600 | −2.151313540 |
| N | 0.905903760 | 1.099112750 | 4.470338340 |
| N | 2.249331710 | −2.229486700 | −3.469048500 |
| C | 1.542073250 | −2.300940750 | −4.757663730 |
| C | −0.256906930 | 1.621968390 | 5.210058210 |
| H | −0.736089590 | 2.427871470 | 4.633939270 |
| H | 0.095862870 | 2.020878310 | 6.174487110 |
| H | −1.009760380 | 0.833110030 | 5.396764760 |
| H | −3.052880760 | 1.693994160 | −0.164430810 |
| H | −2.187359810 | 2.369822740 | 1.257044200 |
| H | −3.027972700 | 0.817502200 | 1.394048690 |
| H | 2.232241150 | −2.034661770 | −5.577035900 |
| H | 0.709065320 | −1.588742850 | −4.742827890 |
| H | 1.143750430 | −3.316026930 | −4.940576080 |
| H | −1.595749020 | −0.186808630 | −3.055724620 |
| H | −2.117801900 | 1.390722990 | −2.392856600 |
| H | −2.924379830 | −0.103170090 | −1.856998090 |

TABLE B4-continued

Computational Input Coordinates

| | | | |
|---|---|---|---|
| H | 1.714229460 | 0.779113230 | 5.003296850 |
| H | 3.143979070 | −2.710111620 | −3.380991940 |
| H | 0.002279216 | −1.014134076 | −3.211399298 |

CuL$^1$H (Triplet)
0 3

| | | | |
|---|---|---|---|
| Cu | 1.431847450 | −0.488032580 | 0.446112510 |
| S | 2.332615610 | −0.119942340 | 2.552696700 |
| S | 2.858402730 | −1.722415690 | −0.909505780 |
| N | −0.257435500 | 0.971116720 | 2.468152050 |
| N | −0.172027540 | 0.534274340 | 1.177021620 |
| N | 0.574079220 | −1.034389140 | −2.391256330 |
| N | 0.223704470 | −0.461096440 | −1.204115870 |
| C | 0.866804360 | 0.696900310 | 3.160702940 |
| C | −1.156654600 | 0.726779040 | 0.313291070 |
| C | 1.780157800 | −1.630949380 | −2.329823970 |
| C | −0.928456430 | 0.172470660 | −1.041194200 |
| C | −2.430852170 | 1.445672040 | 0.707410510 |
| C | −1.949721220 | 0.325466600 | −2.151313540 |
| N | 0.905903760 | 1.099112750 | 4.470338340 |
| N | 2.249331710 | −2.229486700 | −3.469048500 |
| C | 1.542073250 | −2.300940750 | −4.757663730 |
| C | −0.256906930 | 1.621968390 | 5.210058210 |
| H | −0.736089590 | 2.427871470 | 4.633939270 |
| H | 0.095862870 | 2.020878310 | 6.174487110 |
| H | −1.009760380 | 0.833110030 | 5.396764760 |
| H | −3.052880760 | 1.693994160 | −0.164430810 |
| H | −2.187359810 | 2.369822740 | 1.257044200 |
| H | −3.027972700 | 0.817502200 | 1.394048690 |
| H | 2.232241150 | −2.034661770 | −5.577035900 |
| H | 0.709065320 | −1.588742850 | −4.742827890 |
| H | 1.143750430 | −3.316026930 | −4.940576080 |
| H | −1.595749020 | −0.186808630 | −3.055724620 |
| H | −2.117801900 | 1.390722990 | −2.392856600 |
| H | −2.924379830 | −0.103170090 | −1.856998090 |
| H | 1.714229460 | 0.779113230 | 5.003296850 |
| H | 3.143979070 | −2.710111620 | −3.380991940 |
| H | 0.002279216 | −1.014134076 | −3.211399298 |

[CuL$^1$H$_2$]$^+$
1 1

| | | | |
|---|---|---|---|
| Cu | 1.201842280 | −0.715405322 | 0.506889342 |
| S | 2.102610440 | −0.347315082 | 2.613473532 |
| S | 2.628397560 | −1.949788432 | −0.848728948 |
| N | −0.487440670 | 0.743743978 | 2.528928882 |
| N | −0.402032710 | 0.306901598 | 1.237798452 |
| N | 0.344074050 | −1.261761882 | −2.330479498 |
| N | −0.006300700 | −0.688469182 | −1.143339038 |
| C | 0.636799190 | 0.469527568 | 3.221479772 |
| C | −1.386659770 | 0.499406298 | 0.374067902 |
| C | 1.550152630 | −1.858322122 | −2.269047138 |
| C | −1.158461600 | −0.054902082 | −0.980417368 |
| C | −2.660857340 | 1.218299298 | 0.768187342 |
| C | −2.179726390 | 0.098093858 | −2.090536708 |
| N | 0.675898590 | 0.871740008 | 4.531115172 |
| N | 2.019326540 | −2.456859442 | −3.408271668 |
| C | 1.312068080 | −2.528313492 | −4.696886898 |
| C | −0.486912100 | 1.394595648 | 5.270835042 |
| H | −0.966094760 | 2.200498728 | 4.694716102 |
| H | −0.134142300 | 1.793505568 | 6.235263942 |
| H | −1.239765550 | 0.605737288 | 5.457541592 |
| H | −3.282885930 | 1.466621418 | −0.103653978 |
| H | −2.417364980 | 2.142449998 | 1.317821032 |
| H | −3.257977870 | 0.590129458 | 1.454825522 |
| H | 2.002235980 | −2.262034512 | −5.516259068 |
| H | 0.479060150 | −1.816115592 | −4.682051058 |
| H | 0.913745260 | −3.543399672 | −4.879799248 |
| H | −1.825754190 | −0.414181372 | −2.994947788 |
| H | −2.347807070 | 1.163350248 | −2.332079768 |
| H | −3.154385000 | −0.330542832 | −1.796221258 |
| H | 1.484224290 | 0.551740488 | 5.064073682 |
| H | 2.913973900 | −2.937484362 | −3.320215108 |
| H | −0.227725954 | −1.241506818 | −3.150622466 |
| H | −1.284747732 | 1.209226221 | 2.913152425 |

CuL·$^1$H$_2$—N1H
0 2

| | | | |
|---|---|---|---|
| Cu | 1.201842280 | −0.715405322 | 0.506889342 |
| S | 2.102610440 | −0.347315082 | 2.613473532 |
| S | 2.628397560 | −1.949788432 | −0.848728948 |
| N | −0.487440670 | 0.743743978 | 2.528928882 |
| N | −0.402032710 | 0.306901598 | 1.237798452 |
| N | 0.344074050 | −1.261761882 | −2.330479498 |
| N | −0.006300700 | −0.688469182 | −1.143339038 |
| C | 0.636799190 | 0.469527568 | 3.221479772 |
| C | −1.386659770 | 0.499406298 | 0.374067902 |
| C | 1.550152630 | −1.858322122 | −2.269047138 |
| C | −1.158461600 | −0.054902082 | −0.980417368 |
| C | −2.660857340 | 1.218299298 | 0.768187342 |
| C | −2.179726390 | 0.098093858 | −2.090536708 |
| N | 0.675898590 | 0.871740008 | 4.531115172 |
| N | 2.019326540 | −2.456859442 | −3.408271668 |
| C | 1.312068080 | −2.528313492 | −4.696886898 |
| C | −0.486912100 | 1.394595648 | 5.270835042 |
| H | −0.966094760 | 2.200498728 | 4.694716102 |
| H | −0.134142300 | 1.793505568 | 6.235263942 |
| H | −1.239765550 | 0.605737288 | 5.457541592 |
| H | −3.282885930 | 1.466621418 | −0.103653978 |
| H | −2.417364980 | 2.142449998 | 1.317821032 |
| H | −3.257977870 | 0.590129458 | 1.454825522 |
| H | 2.002235980 | −2.262034512 | −5.516259068 |
| H | 0.479060150 | −1.816115592 | −4.682051058 |
| H | 0.913745260 | −3.543399672 | −4.879799248 |
| H | −1.825754190 | −0.414181372 | −2.994947788 |
| H | −2.347807070 | 1.163350248 | −2.332079768 |
| H | −3.154385000 | −0.330542832 | −1.796221258 |
| H | 1.484224290 | 0.551740488 | 5.064073682 |
| H | 2.913973900 | −2.937484362 | −3.320215108 |
| H | −0.227725954 | −1.241506818 | −3.150622466 |
| H | −1.284747732 | 1.209226221 | 2.913152425 |

CuL·$^1$H$_2$—N4H
0 2

| | | | |
|---|---|---|---|
| Cu | 1.431847450 | −0.488032580 | 0.446112510 |
| S | 2.332615610 | −0.119942340 | 2.552696700 |
| S | 2.858402730 | −1.722415690 | −0.909505780 |
| N | −0.257435500 | 0.971116720 | 2.468152050 |
| N | −0.172027540 | 0.534274340 | 1.177021620 |
| N | 0.574079220 | −1.034389140 | −2.391256330 |
| N | 0.223704470 | −0.461096440 | −1.204115870 |
| C | 0.866804360 | 0.696900310 | 3.160702940 |
| C | −1.156654600 | 0.726779040 | 0.313291070 |
| C | 1.780157800 | −1.630949380 | −2.329823970 |
| C | −0.928456430 | 0.172470660 | −1.041194200 |
| C | −2.430852170 | 1.445672040 | 0.707410510 |
| C | −1.949721220 | 0.325466600 | −2.151313540 |
| N | 0.905903760 | 1.099112750 | 4.470338340 |
| N | 2.249331710 | −2.229486700 | −3.469048500 |
| C | 1.542073250 | −2.300940750 | −4.757663730 |
| C | −0.256906930 | 1.621968390 | 5.210058210 |
| H | −0.736089590 | 2.427871470 | 4.633939270 |
| H | 0.095862870 | 2.020878310 | 6.174487110 |
| H | −1.009760380 | 0.833110030 | 5.396764760 |
| H | −3.052880760 | 1.693994160 | −0.164430810 |
| H | −2.187359810 | 2.369822740 | 1.257044200 |
| H | −3.027972700 | 0.817502200 | 1.394048690 |
| H | 2.232241150 | −2.034661770 | −5.577035900 |
| H | 0.709065320 | −1.588742850 | −4.742827890 |
| H | 1.143750430 | −3.316026930 | −4.940576080 |
| H | −1.595749020 | −0.186808630 | −3.055724620 |
| H | −2.117801900 | 1.390722990 | −2.392856600 |
| H | −2.924379830 | −0.103170090 | −1.856998090 |
| H | 1.714229460 | 0.779113230 | 5.003296850 |
| H | 3.143979070 | −2.710111620 | −3.380991940 |
| H | 0.002279216 | −1.014134076 | −3.211399298 |
| H | −0.537578235 | −0.345922291 | −1.882139314 |

Results and Discussion for Example B

Synthesis and Electrochemical Characterization

Figure 24:
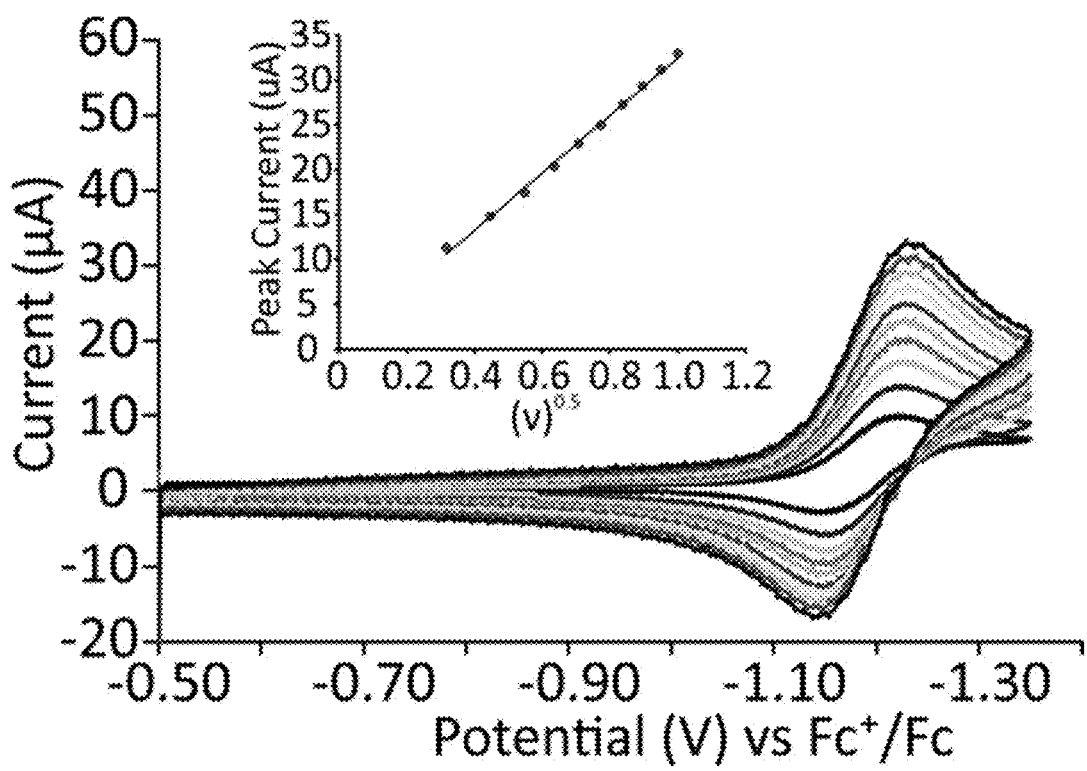
FIG. 24. Electrochemical Characterization—CVs of $CuL^1$ in 0.1 M $Bu_4NPF_6$ ACN solution at scan rates of (from inside to outside, at peak) 0.1, 0.2, 0.3, 0.4, 0.5, 0.6, 0.7, 0.8, 0.9, and 1.0 V/s.CuL$^1$. (Inset: Cottrell plot of peak current vs square root of scan rate.)

The CuL$^1$ compound was isolated as an air-stable burgundy solid from H$_2$L$^1$ and copper(II) acetate as previously reported previously (Betts et al., Angew. Chem. Int. Ed. 2008, Vol. 44, pp. 8416-8419—DOI: 10.1002/anie.200801936; Christlieb et al., Dalton Trans. 2007, pp. 5043-5054—DOI: 10.1039/B705087A). The cyclic voltammogram (CV) of CuL$^1$ in acetonitrile (ACN) or dimethylformamide (DMF) containing 0.1 M Bu$_4$NPF$_6$ as supporting electrolyte displays a reversible Cu$^{II/I}$ event at −1.20 V vs. ferrocenium/ferrocene (Fc$^+$/Fc) consistent with prior reports. Additional CV data collected at multiple scan rates from 0.1 to 1.0 V/s in ACN (FIG. 24) and DMF (data not shown) were used to construct Cottrell plots (FIG. 24 inset) establishing that the Cu$^{II/I}$ reduction is diffusion limited and demonstrating the potential of CuL$^1$ as a homogeneous electrocatalyst. The slope of the plot yields a diffusion coefficient of 7.9×10$^{-6}$ cm$^2$/s in ACN and 9.35×10$^{-6}$ cm$^2$/s in DMF. The formal Cu$^{III/II}$ couple was observed at 0.24 V vs Fc$^+$/Fc in DMF and ACN in line with prior reports, but this event was not further evaluated in the current study.

Homogeneous Catalytic Hydrogen Evolution: Cyclic Voltammetry and KIE

Figure 25:
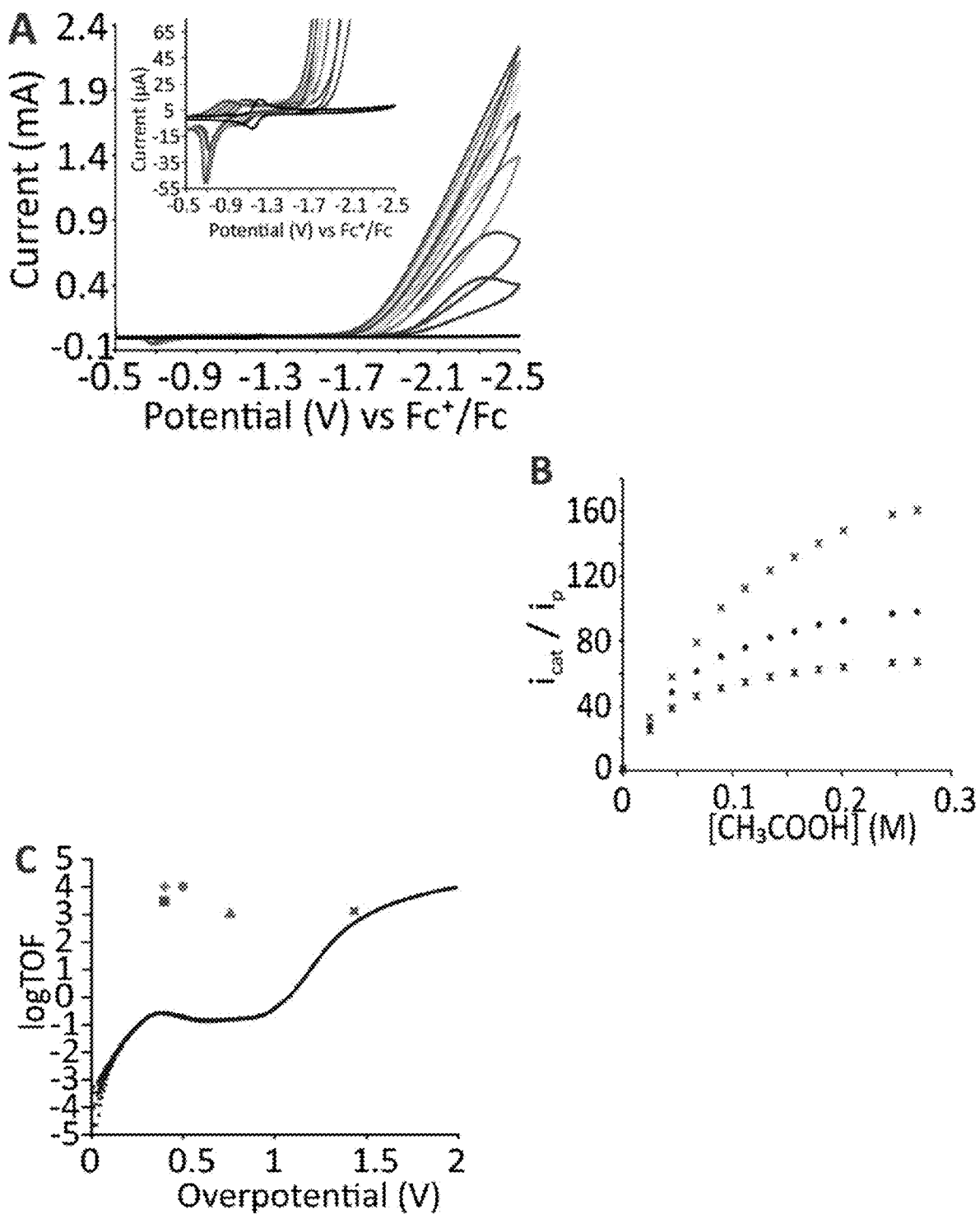
FIG. 25. Homogeneous Catalytic Hydrogen Evolution: Cyclic Voltammetry (A) CVs (from bottom to top) of 0.6 mM CuL$^1$ in 0.1M Bu$_4$NPF$_6$ ACN with 0.0244 M CH$_3$COOH, 0.0448 M CH$_3$COOH, 0.0896 M CH$_3$COOH, 0.134 M CH$_3$COOH, 0.179 M CH$_3$COOH, 0.244 M CH$_3$COOH, and 0.269 M CH$_3$COOH, (Inset: Blow up of CV showing shift of Cu$^{II/I}$ reduction event.); (B) Plot of $i_{cat}/i_p$ vs [CH$_3$COOH] for 0.60 mM CuL$^1$ at scan rates of 0.20 (×), 0.50 (●) and 1.00 (*) V/s; (C) Catalytic Tafel Plot of CuL$^1$ with comparison of performance for hydrogen evolution with those of others reported in literature. ◆: Co$^{II}$(dmgH)$_2$py; ●: [Ni(P$_2^{Ph}$N$^{Ph}$)$_2$]$^{2+}$; ■: NiL$^2$; ▲:ZnL$^1$; ×:H$_2$L$^1$.

Addition of acetic acid exceeding 24 mM to 0.6 mM ACN solutions of CuL$^1$ shifts the Cu$^{II/I}$ reduction potential from −1.20 V to −0.95 V and introduces a catalytic cathodic current at −1.70 V vs Fc$^+$/Fc (FIG. 25A). The +0.25 V shift is consistent with a single protonation event prior to the initial electrochemical reduction. The ratio of the catalytic current to the peak current displays linear dependence on the acid concentration up to 0.157 M, indicating a second-order dependence of the catalytic rate on the acid concentration. At concentrations greater than 0.157 M the current response begins to plateau, reaching an acid independent region at concentrations of 0.269 M, (FIG. 25B). This transition from second-order to zero-order dependence requires a pre-equilibrium step(s) involving two protons that precedes the rate determining step for H$_2$ elimination. The current becomes scan rate independent at 0.2 V/s. Under these conditions the i$_p$ of the Cu$^{II/I}$ reduction event, 14.0 µA, and the i$_{cat}$ max from the acid-independent region, 2.25 mA, correspond with a maximum i$_{cat}$/i$_p$ value of 161, affording a TOF of 10,000 s$^{-1}$.

Figure 26:
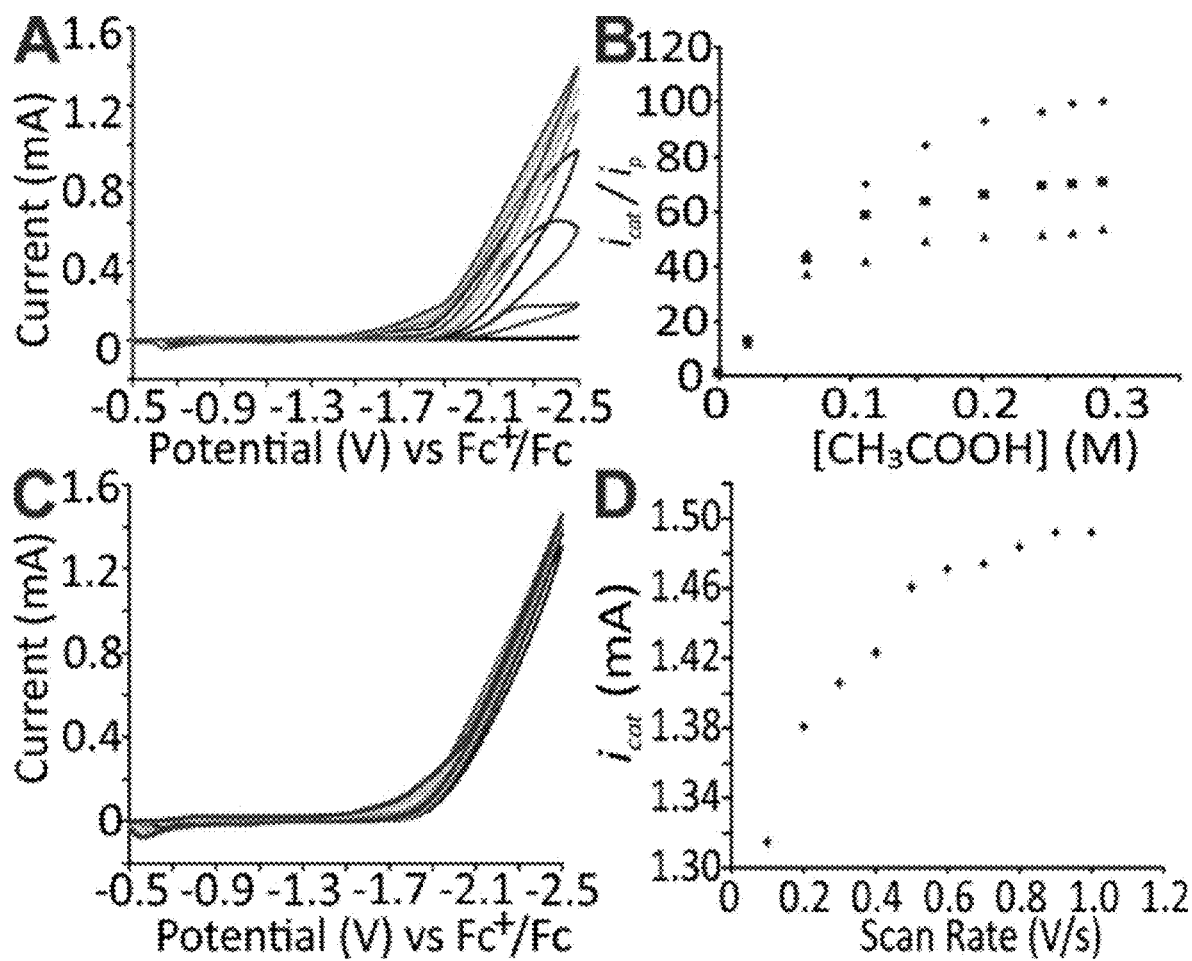
FIG. 26. Cyclic Voltammetry—(A) CVs (from bottom to top) of 0.6 mM CuL$^1$ in 0.1M Bu$_4$NPF$_6$ DMF with 0.0244 M CH$_3$COOH, 0.0672 M CH$_3$COOH, 0.112 M CH$_3$COOH, 0.157 M CH$_3$COOH, 0.202 M CH$_3$COOH, 0.246 M CH$_3$COOH, 0.269 M CH$_3$COOH, and 0.292 M CH$_3$COOH. (B) Plot of $i_{cat}/i_p$ vs [CH$_3$COOH] for 0.6 mM CuL$^1$ at scan rates of 0.20 (◆), 0.50 (■) and 1.00 (▲) V/s. (C) CVs of 0.6 mM CuL$^1$ in 0.1M Bu$_4$NPF$_6$ DMF with 0.292 M CH$_3$COOH at scan rates from 0.1 to 1.0 V/s. (D) Plot of cat vs scan rate for 0.6 mM CuL$^1$ in 0.1M Bu$_4$NPF$_6$ DMF with 0.292 M CH$_3$COOH.

The electrocatalytic activity of 0.6 mM CuL$^1$ with acetic acid was also assessed in DMF. An increase in current at −1.9 V vs Fc$^+$/Fc is observed upon increasing additions of acetic acid (FIG. 26A). At concentrations of acid greater than 0.292 M, the current saturates reaching a maximum cat of 1.49 mA (FIG. 26B). Acid addition results in a shift of the Cu$^{II/I}$ potential from −1.20 V to −0.95 V, as observed in ACN, attributed to a single protonation event prior to reduction. Catalytic current becomes independent of scan rate above 1.0 V/s (FIG. 26C and 26D). Under these conditions i$_{cat}$ is 1490 µA and i$_p$ is 29 µA giving a TOF of 5140 s$^{-1}$, which is significantly lower than the TOF in ACN.

The Tafel plot of the log TOF versus overpotential for CuL$^1$ (FIG. 25C) displays the TOF as a function of the applied overpotential. CuL$^1$ displays the highest maximum logTOF values reported to date of any homogeneous ligand-centered electrocatalyst, reaching a maximum of 3.99. The CuL$^1$ electrocatalyst maintains a logTOF value greater than one, with applied overpotentials greater than 1.2 V. Overpotentials less than 1.2 V result in significantly decreased TOF values, correlating with negative or near zero logTOF values. The local maxima observed near 0.4 V is indicative of the pre-catalytic Cu$^{II/I}$ reduction, which has anodic shift of 0.25 V during catalysis. The maximum logTOF for CuL$^1$ of 3.99 requires a large overpotential of 2.0 V.

Analysis of the CVs of CuL$^1$ under catalytic HER conditions appear to reveal a new oxidation event at a potential of −0.65 V Fc$^+$/Fc during the return anodic scan (FIG. 25A inset), which is assigned to the Cu(II/I) couple of the diprotonated copper(I) intermediate, [CuL$^1$H$_2$]$^+$. This event is 300 mV more positive than the Cu(II/I) couple of the monoprotonated [CuL$^1$H]$^+$, which in turn is 250 mV more positive than the CuL$^1$. The intensity of the peak current at −0.65 V demonstrates scan rate dependence typical of diffusion controlled behavior (FIG. 26C) confirming it is not due to an adsorbed species.

As noted above, the catalysis is second-order in acid in the acid dependent regime. To determine the order with respect to the catalyst, the concentration of CuL$^1$ was varied from 0.1 to 1.0 mM in solution containing 0.15 M acetic acid. A plot of catalyst concentration versus peak current reveals a linear relationship, confirming a first-order dependence on the concentration of the catalyst and an overall third-order process.

Figure 27:
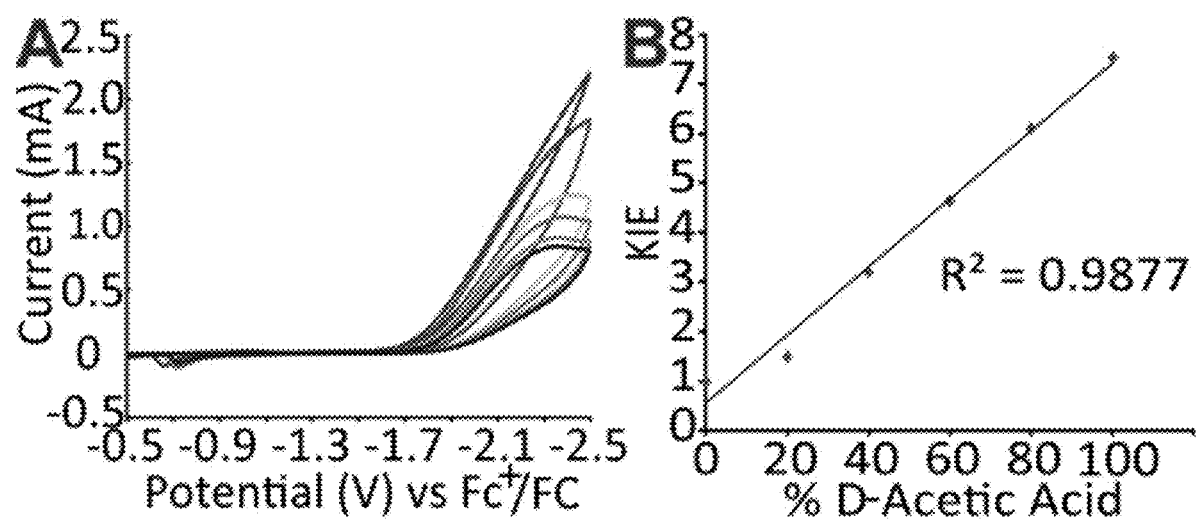
FIG. 27. Kenetic Isotope Effects (KIE)—(A) CVs of 0.6 mM CuL$^1$ in 0.1 M Bu$_4$NPF$_6$ ACN solution with 0.269 M acetic acid at (from top to bottom) 0 mole % of CD$_3$COOD, 20 mole % of CD$_3$COOD, 40 mole % of CD$_3$COOD, 60 mole % of CD$_3$COOD, 80 mole % of CD$_3$COOD, and 100 mole % of CD$_3$COOD mole % of CD$_3$COOD. (B) Plot of KIE vs % CD$_3$COOD.

To further evaluate the HER mechanism of CuL$^1$, the H/D kinetic isotope effect (KIE) was measured. CuL$^1$ displays a large KIE of 7.54 using 100% CD$_3$CO$_2$D. The high KIE value observed when using 100% CD$_3$CO$_2$D is distinct from the inverse KIEs reported for some HER catalysts proceeding through metal-hydrides, but similar to that observed for a ligand-centered Re-thiolate HER catalyst. Since CuL$^1$ HER catalysis is second-order in [H$^+$], a proton inventory study was conducted to determine the number of protons involved in the rate determining step. Cyclic voltammograms collected with variable quantities of CH$_3$CO$_2$H and CD$_3$CO$_2$D were used to generate plots of KIE versus the percent fraction of CD$_3$CO$_2$D (FIGS. 27A & 27B). The plot yields a linear fit consistent with the involvement of a single proton in the rate determining step.

Controlled Potential Electrolysis

Figure 28:
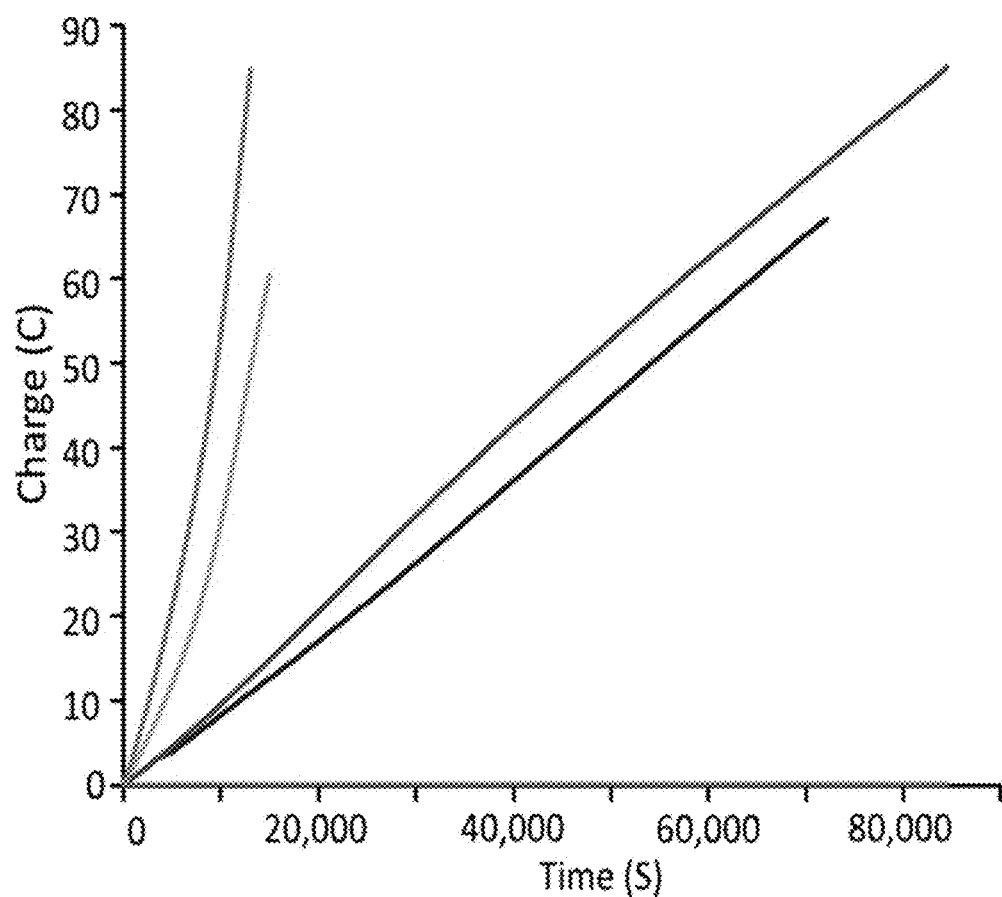
FIG. 28. Controlled Potential Electrolysis (CPE)—CPE of 0.6 mM CuL$^1$ in 0.1 M Bu$_4$NPF$_6$ ACN (left-most and second from left) or 0.1 M Bu$_4$NPF$_6$ DMF (second from right and right-most) solutions with 0.292 M CH$_3$COOH added; 0.1 M Bu$_4$NPF$_6$ DMF with 0.292 M CH$_3$COOH, no CuL$^1$ (overlaps with x-axis, zero apparent charge)).
Figure 41:
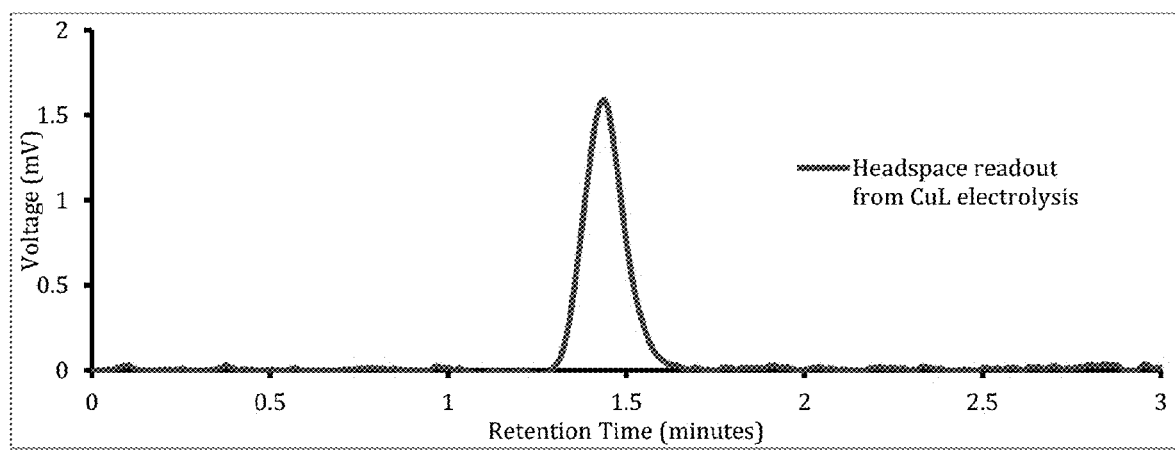
FIG. 41. GC-TCD readout for gaseous product identification from electrolysis
Figure 42:
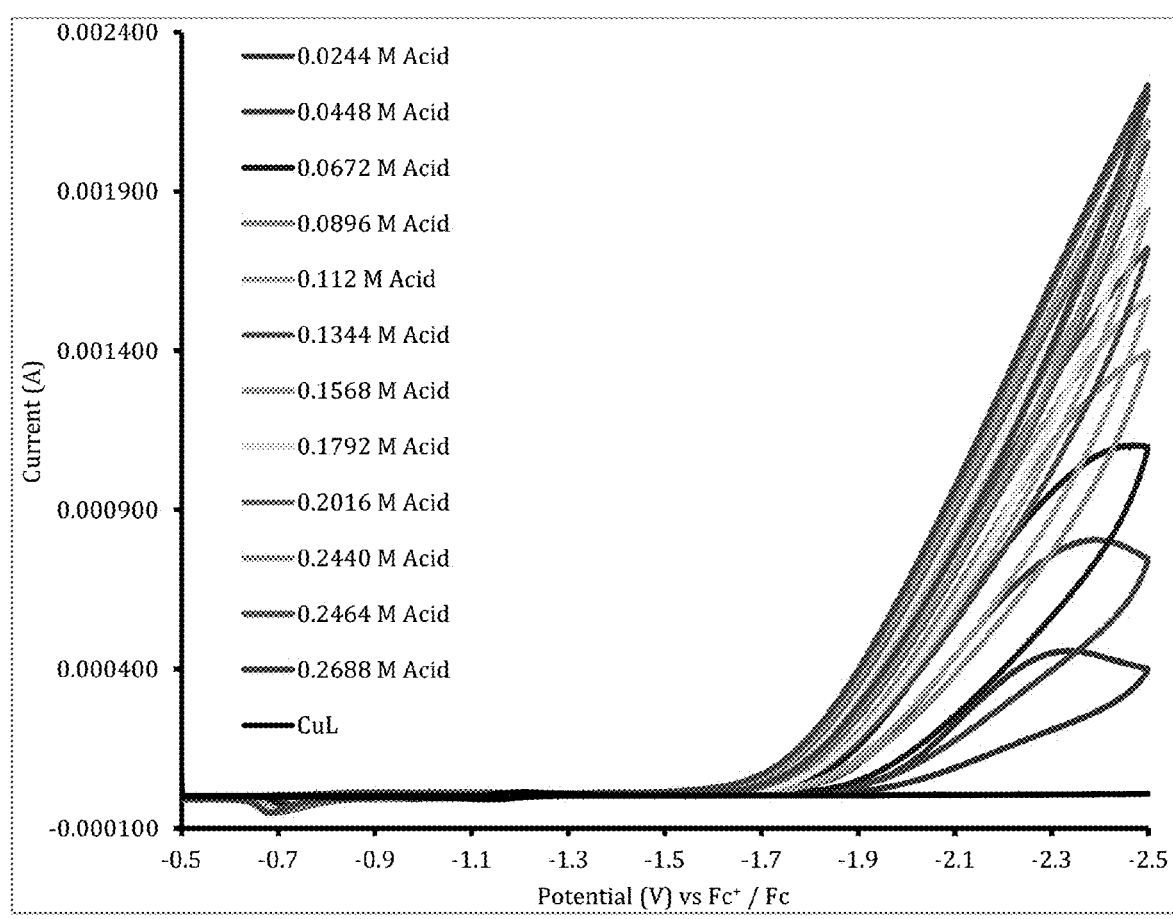
FIG. 42. 0.6 mM CuL$^1$ in 0.1 M Bu$_4$NPF$_6$ acetonitrile HER CVs scanned at 0.2 V/s.
Figure 43:
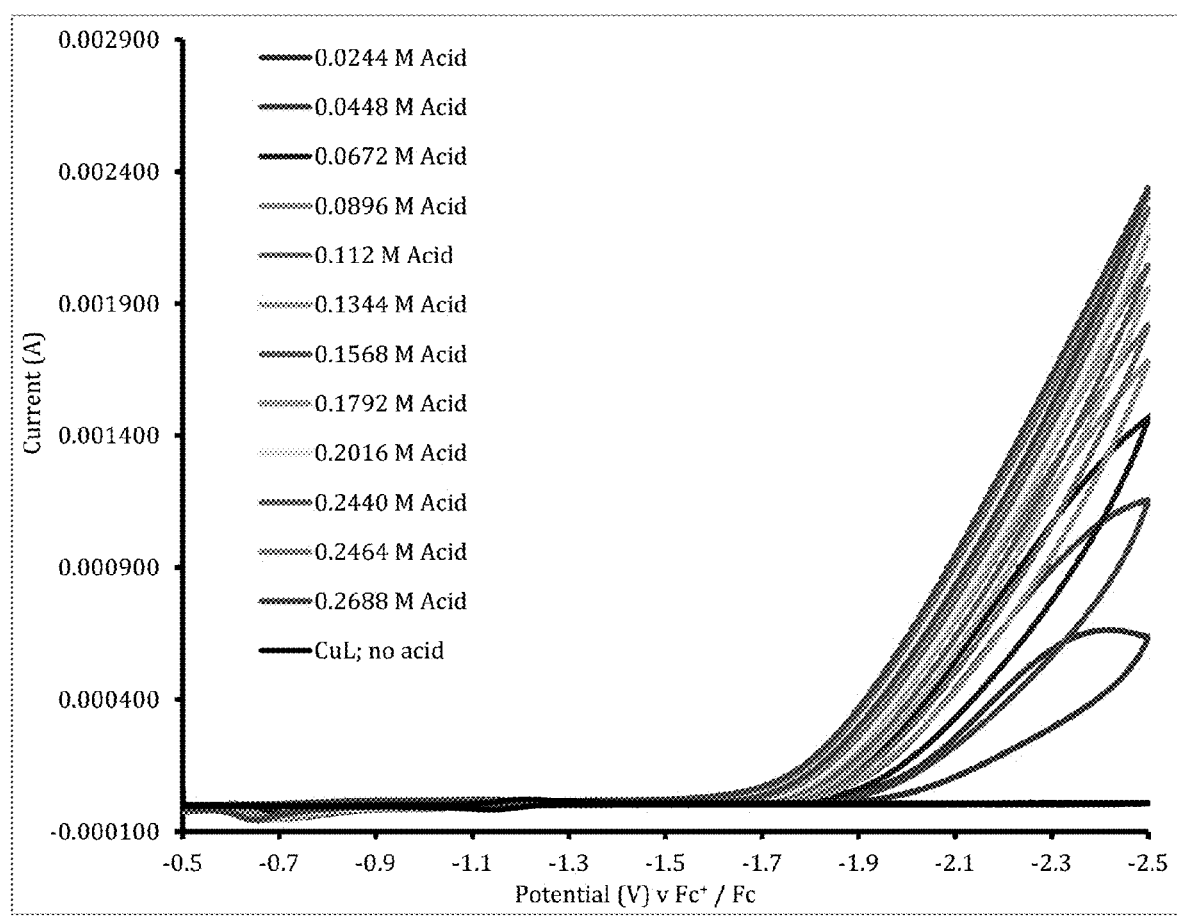
FIG. 43. 0.6 mM CuL$^1$ in 0.1 M Bu$_4$NPF$_6$acetonitrile HER CVs scanned at 0.5 V/s.
Figure 44:
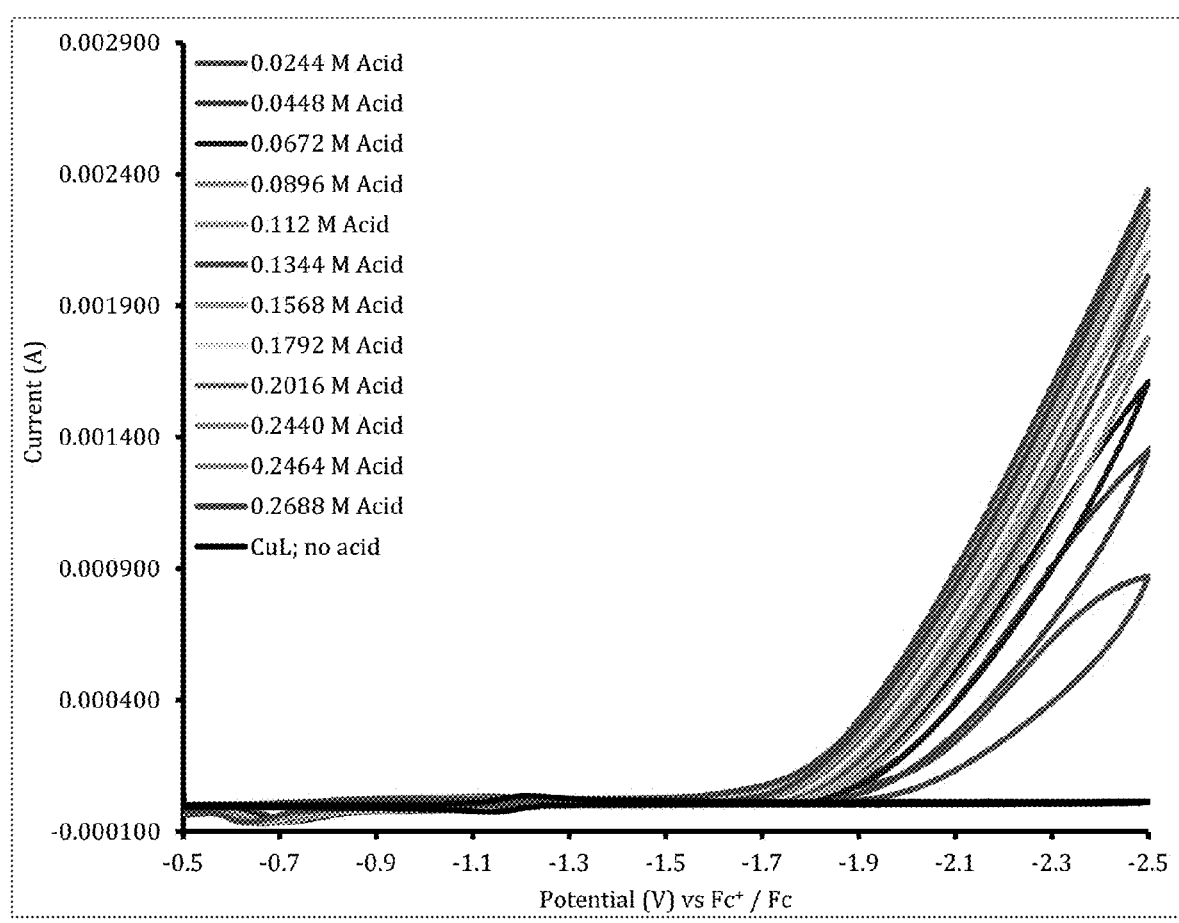
FIG. 44. 0.6 mM CuL$^1$ in 0.1 M Bu$_4$NPF$_6$ acetonitrile HER CVs scanned at 1.0 V/s.
Figure 45:
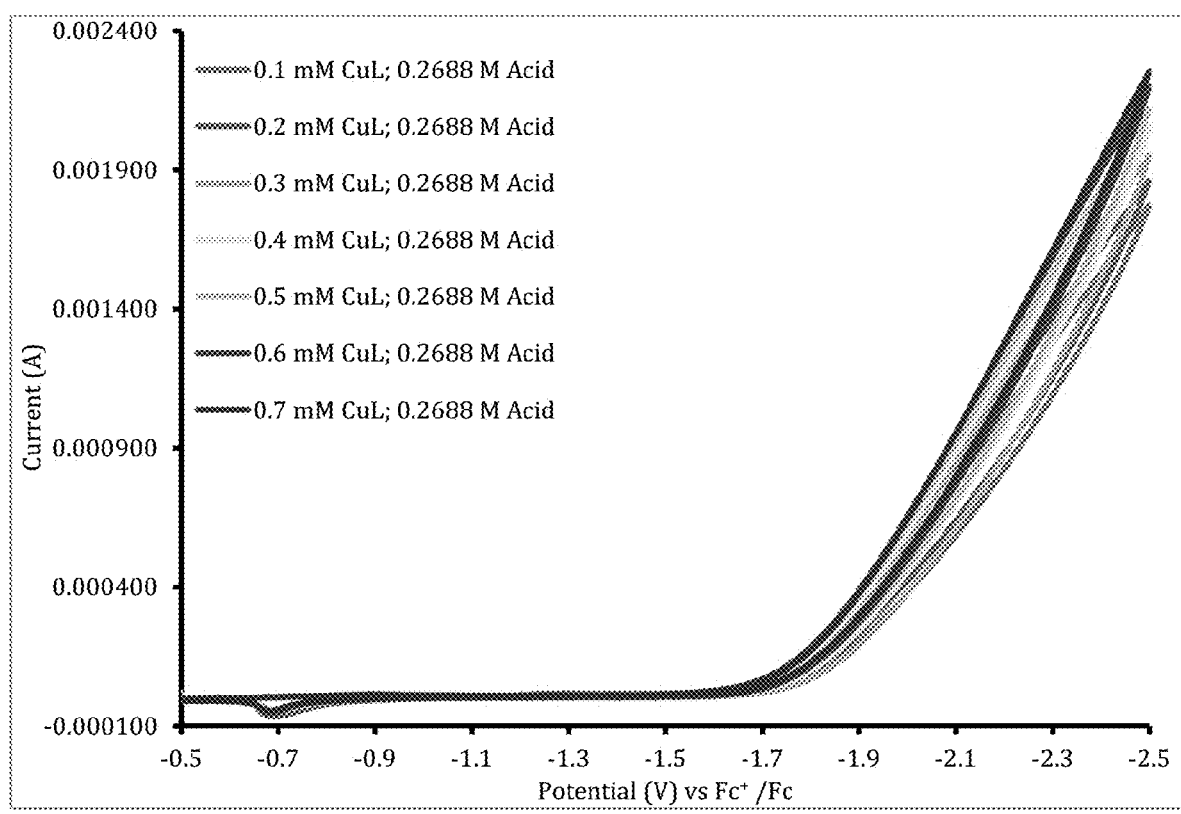
FIG. 45. [CuL$^1$] dependence in 0.1 M Bu$_4$NPF$_6$ acetonitrile with 0.269 M CH$_3$COOH HER CVs.
Figure 46:
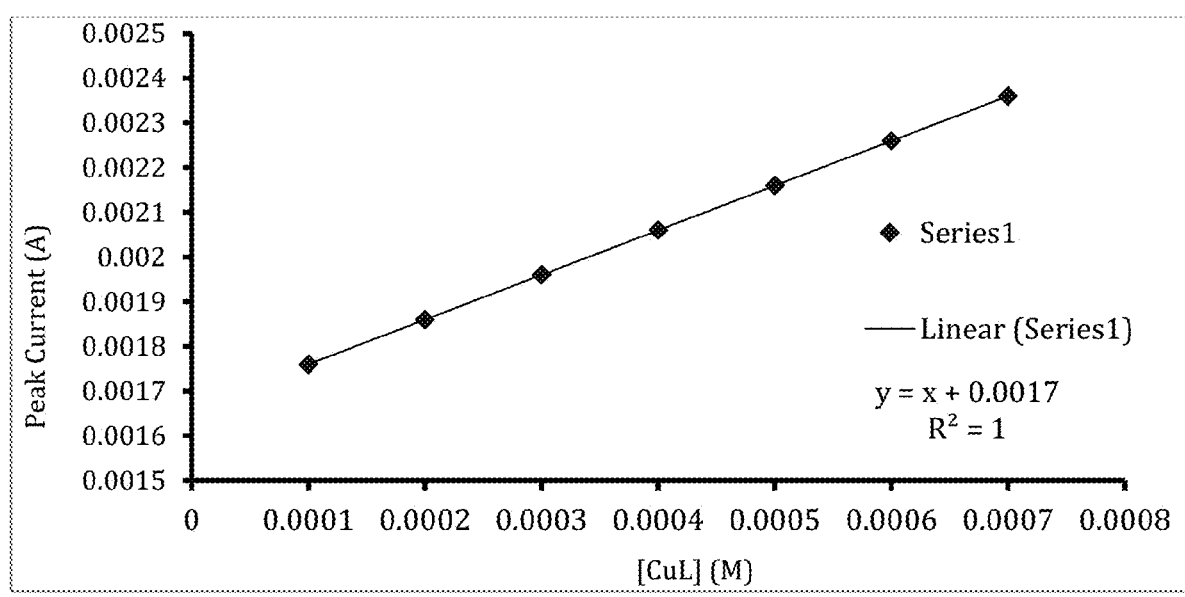
FIG. 46. Plot of $i_p$ vs [CuL$^1$] in 0.1 M Bu$_4$NPF$_6$ acetonitrile with 0.269 M CH$_3$COOH.
Figure 47:
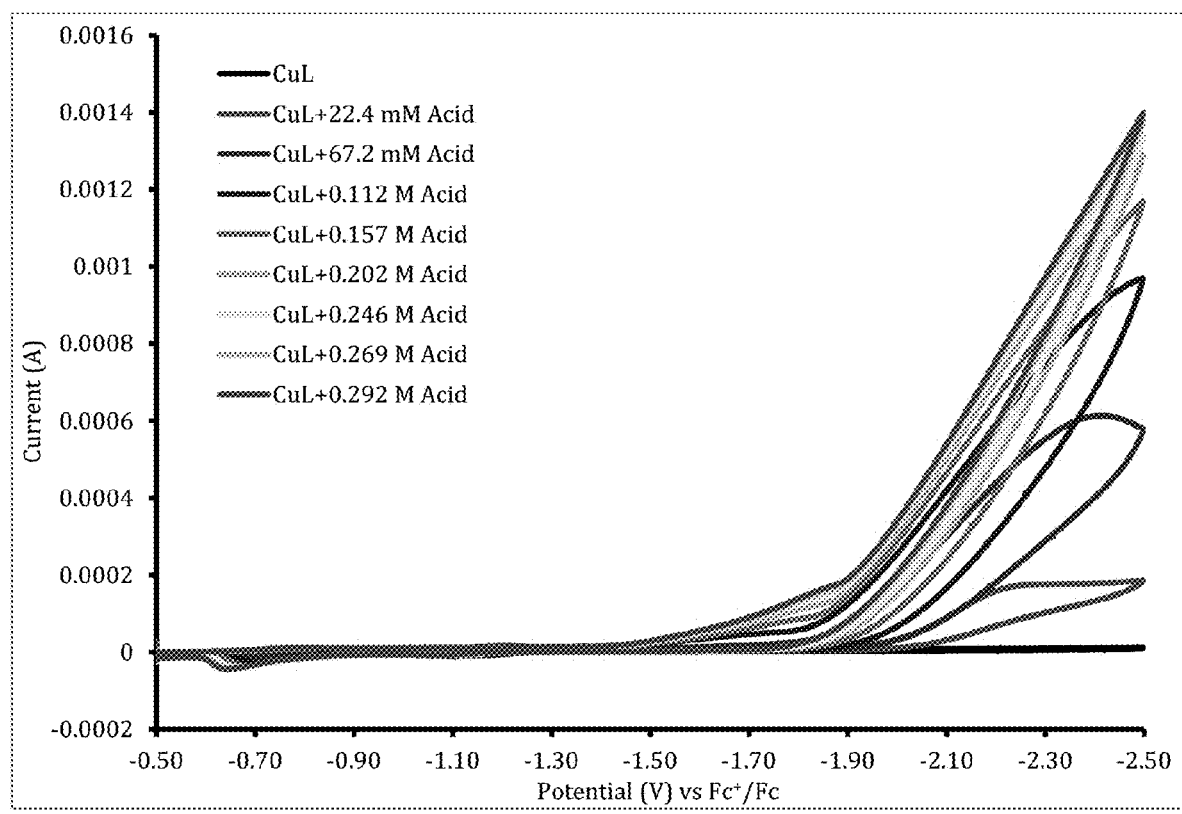
FIG. 47. 0.6 mM CuL$^1$ in 0.1 M Bu$_4$NPF$_6$ DMF; HER CVs scanned at 0.2 V/s.
Figure 48:
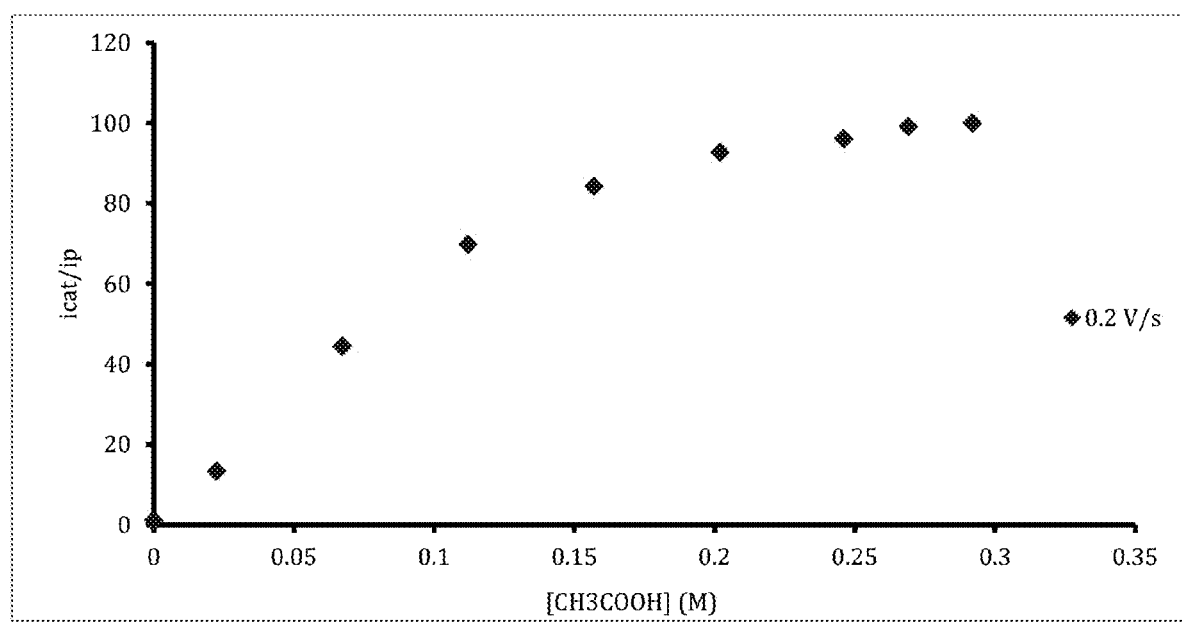
FIG. 48. Plot of $i_{cat}/i_p$ vs [CH$_3$COOH]; v=0.2 V/s.
Figure 49:
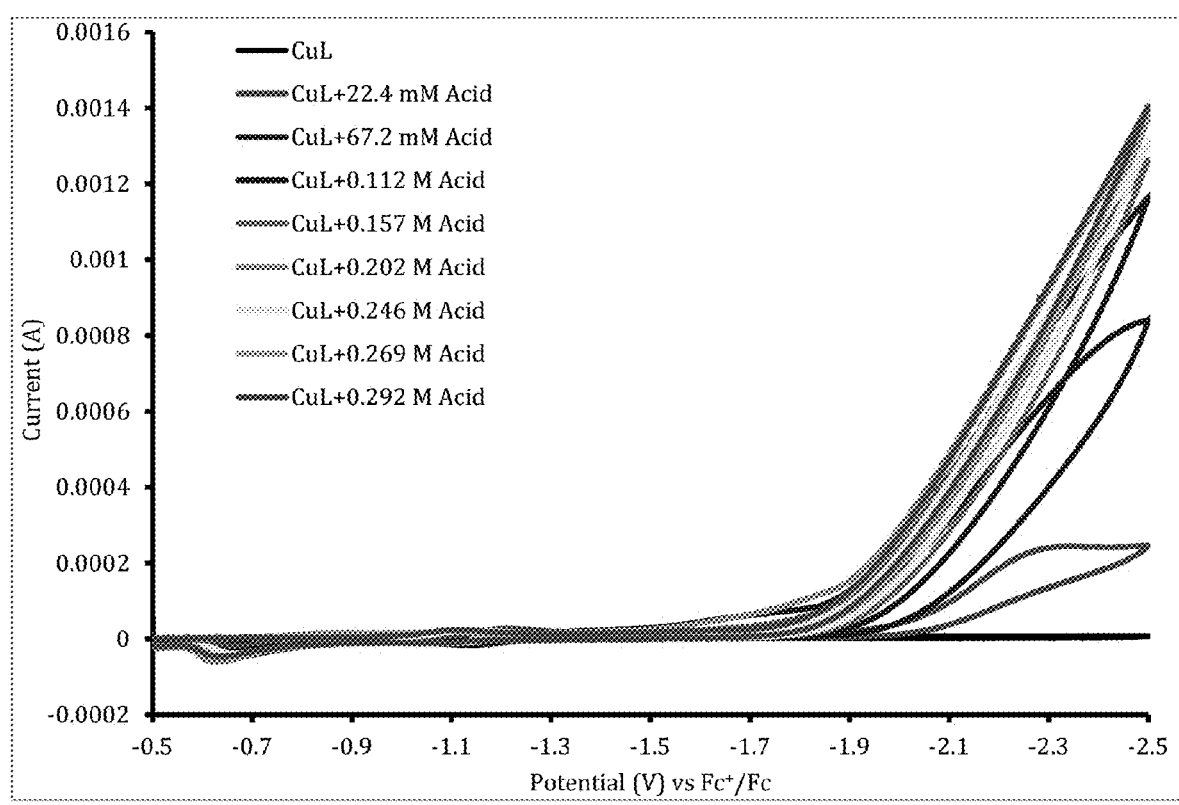
FIG. 49. 0.6 mM CuL$^1$ in 0.1 M Bu$_4$NPF$_6$ DMF; HER CVs scanned at 0.5 V/s.
Figure 50:
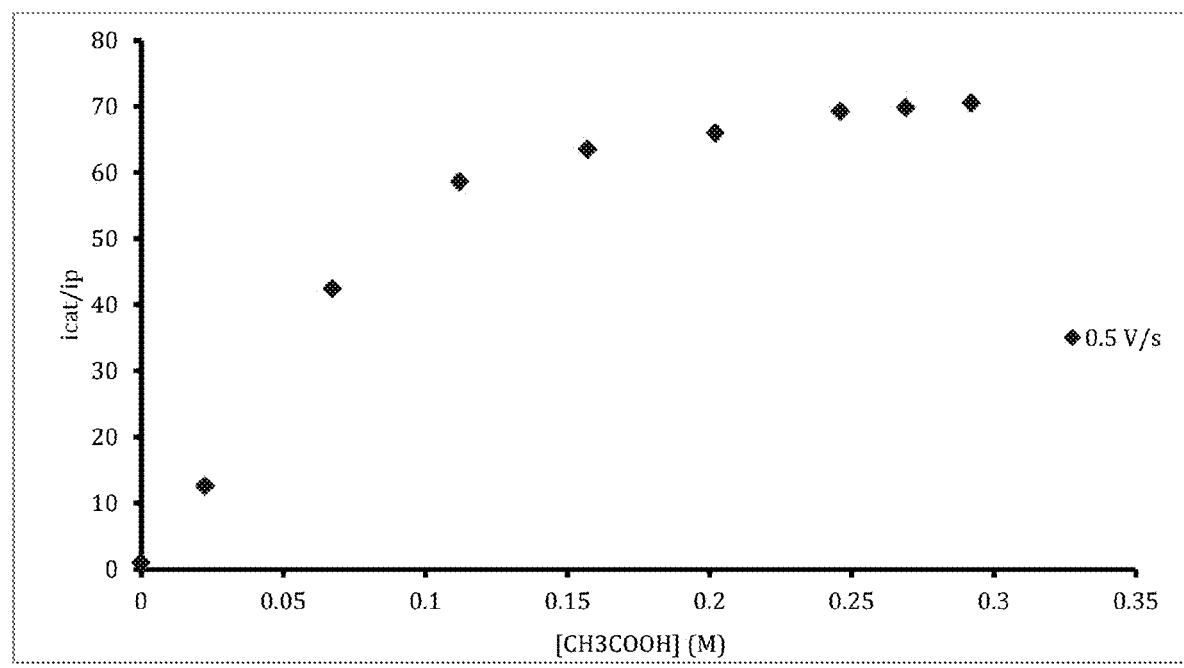
FIG. 50. Plot of $i_{cat}/i_p$ vs [CH$_3$COOH]; v=0.5 V/s.
Figure 51:
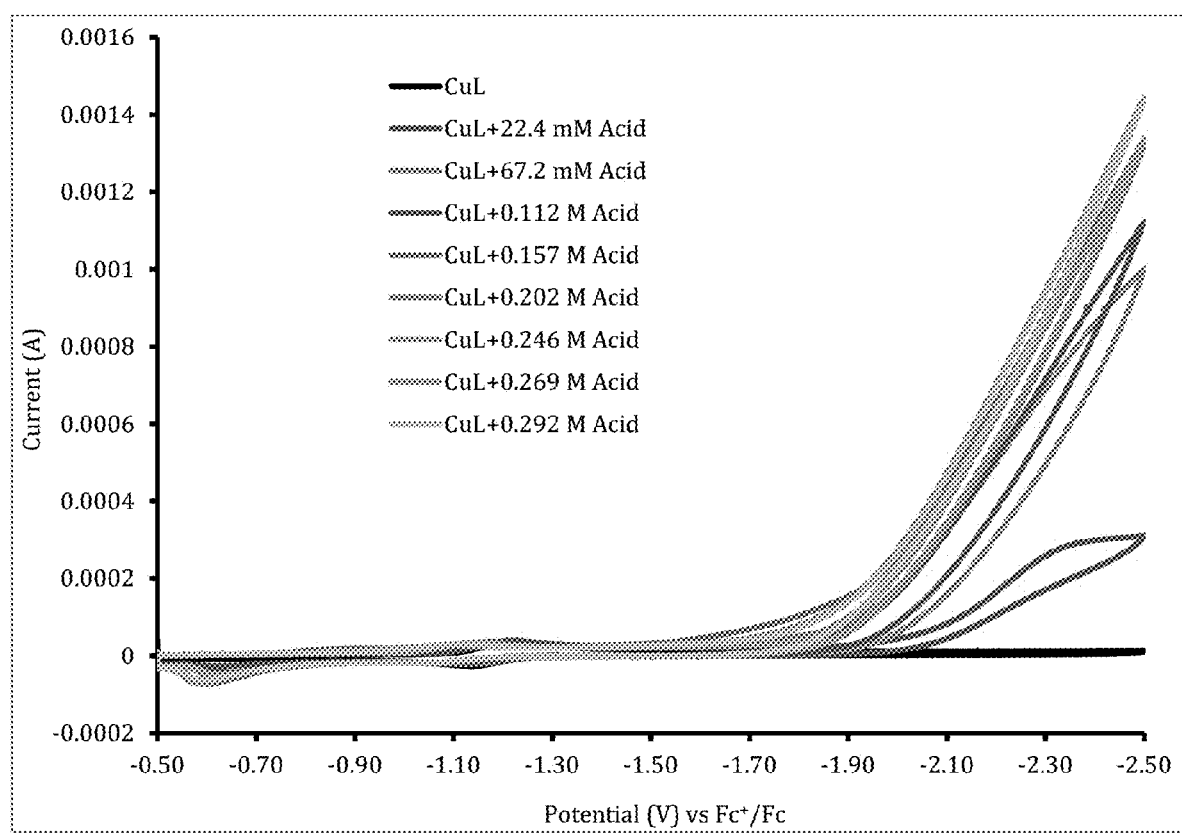
FIG. 51. 0.6 mM CuL$^1$ in 0.1 M Bu$_4$NPF$_6$ DMF; HER CVs scanned at 1.0 V/s.
Figure 52:
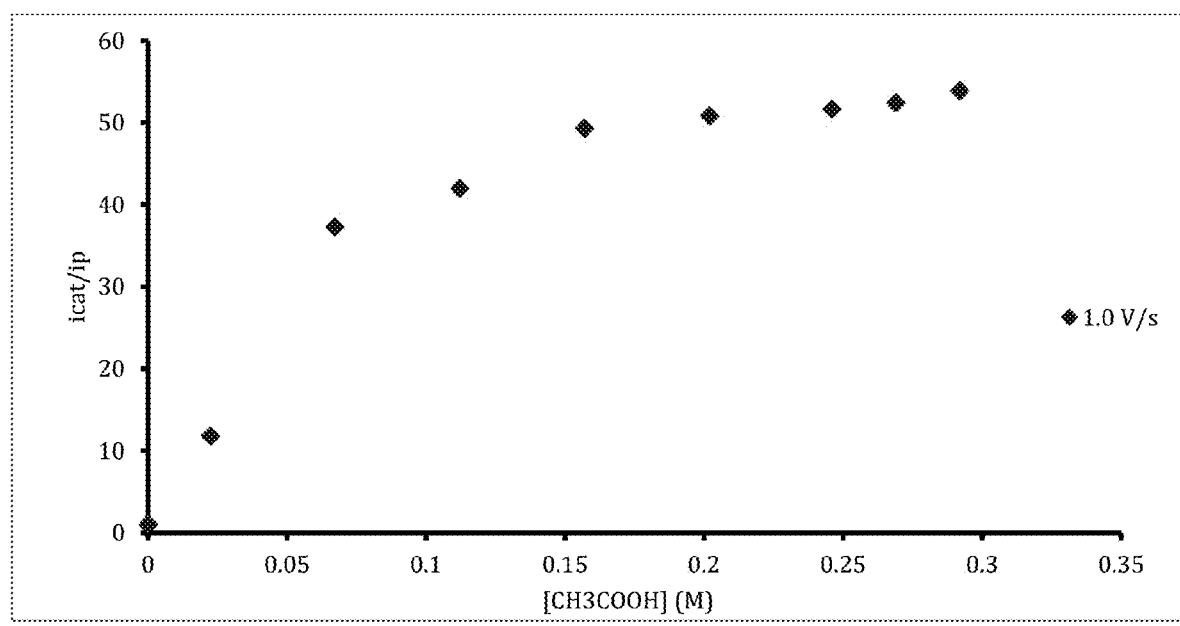
FIG. 52. Plot of $i_{cat}/i_p$ vs [CH$_3$COOH]; v=1.0 V/s.
Figure 53:
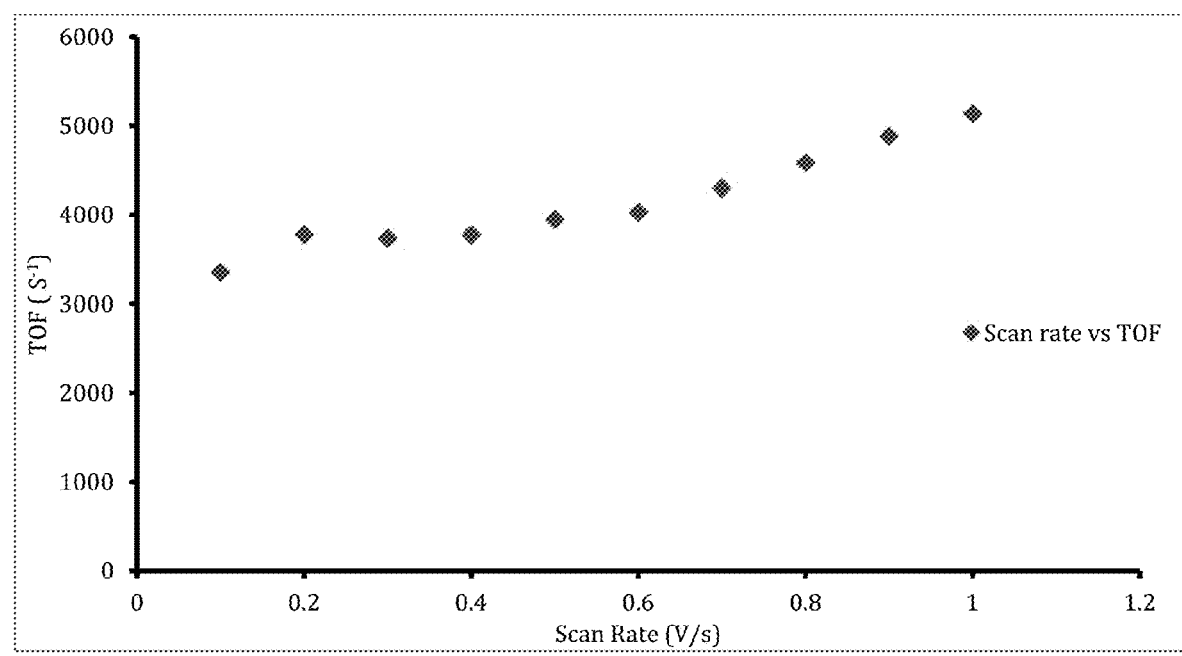
FIG. 53. Plot of scan rate vs TOF for CuL$^1$ in DMF.
Figure 54:
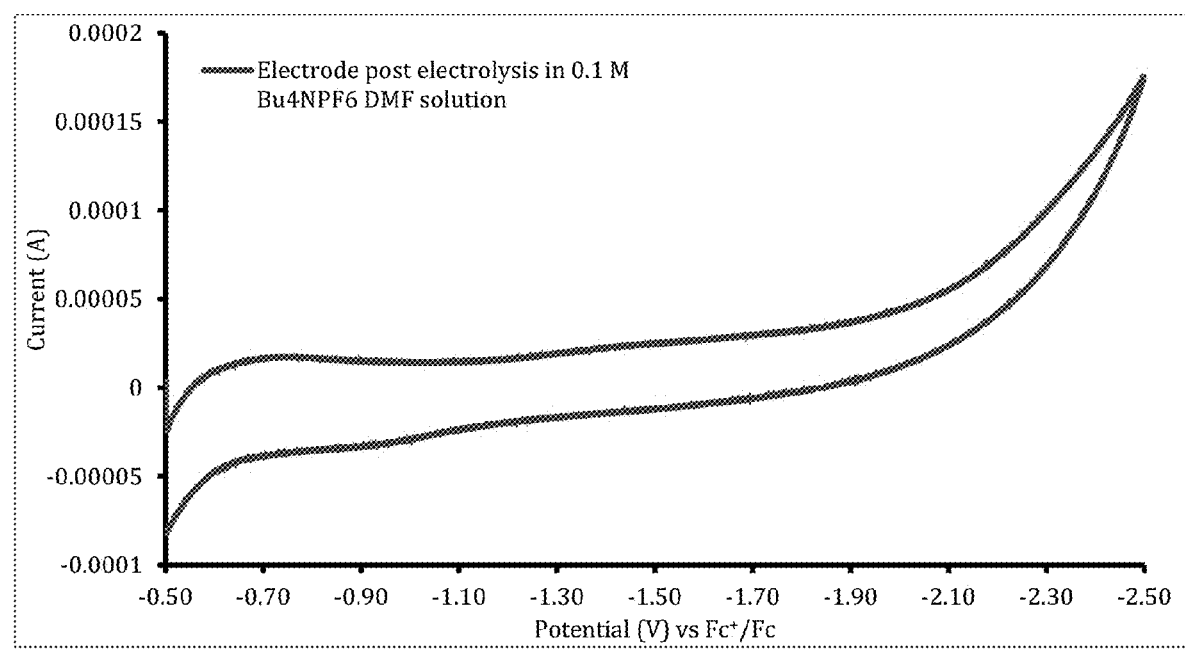
FIG. 54. Dip test post electrolysis in DMF.

A series of controlled potential electrolysis (CPE) experiments were performed using 0.6 mM CuL$^1$ and 0.292 M acetic acid, with potential held at −1.65 V vs Fc$^+$/Fc, in both DMF and ACN (Table B5). Electrolysis in 0.1 M Bu$_4$NPF$_6$ DMF solutions was allowed to run for 84,400 seconds (23.4 hours) resulting in a total charge passed of 85.0 C, corresponding to 4.4×10$^{-4}$ moles of H$_2$ produced with a turnover number (TON) of 73.3. Gas analysis of the headspace using gas chromatography thermal conductivity (GC-TCD) confirms H$_2$ as the gaseous product (FIG. 41). The charge increases linearly over time with no signs of degradation or decrease in activity over 23 hours (FIG. 28). A second CPE in DMF over 72,120 seconds (20 hours) yielded comparable results giving a slightly lower charge of 67.0 C, producing 3.5×10$^{-4}$ moles of H$_2$ corresponding with a TON of 58.3.

TABLE B5

Summary of CPE Results

| Entry | Solvent | Duration (S$^{-1}$) | Charge (C) | Moles of H$_2$ Produced (×10$^{-4}$) | TON |
|---|---|---|---|---|---|
| 1 | ACN | 15,000 | 60.4 | 3.1 | 52 |
| 2 | ACN | 13,000 | 84.7 | 4.4 | 73 |
| 3 | DMF | 84,400 | 67.0 | 3.5 | 58 |
| 4 | DMF | 72,120 | 85.0 | 4.4 | 73 |

The CPEs performed in 0.1 M Bu$_4$NPF$_6$ ACN passed similar charge, giving values of 60.4 and 84.7 C corresponding to TON values of 51.7 and 73.3, over shorter electrolysis times of 15,000 and 13,000 seconds, respectively (FIG. 28). The current in ACN is higher than in DMF, resulting in a steeper slope in the charge-time plots, consistent with relative TOFs from CV studies. Electrolysis beyond 15,000 seconds in ACN is complicated by diffusion across the frit from the working to auxiliary compartment. This results in the appearance of a brown, cloudy mixture in the auxiliary compartment concurrent with the plateauing of charge. This phenomenon was consistently observed in ACN, but was absent in DMF.

Control Experiments

Figure 29:
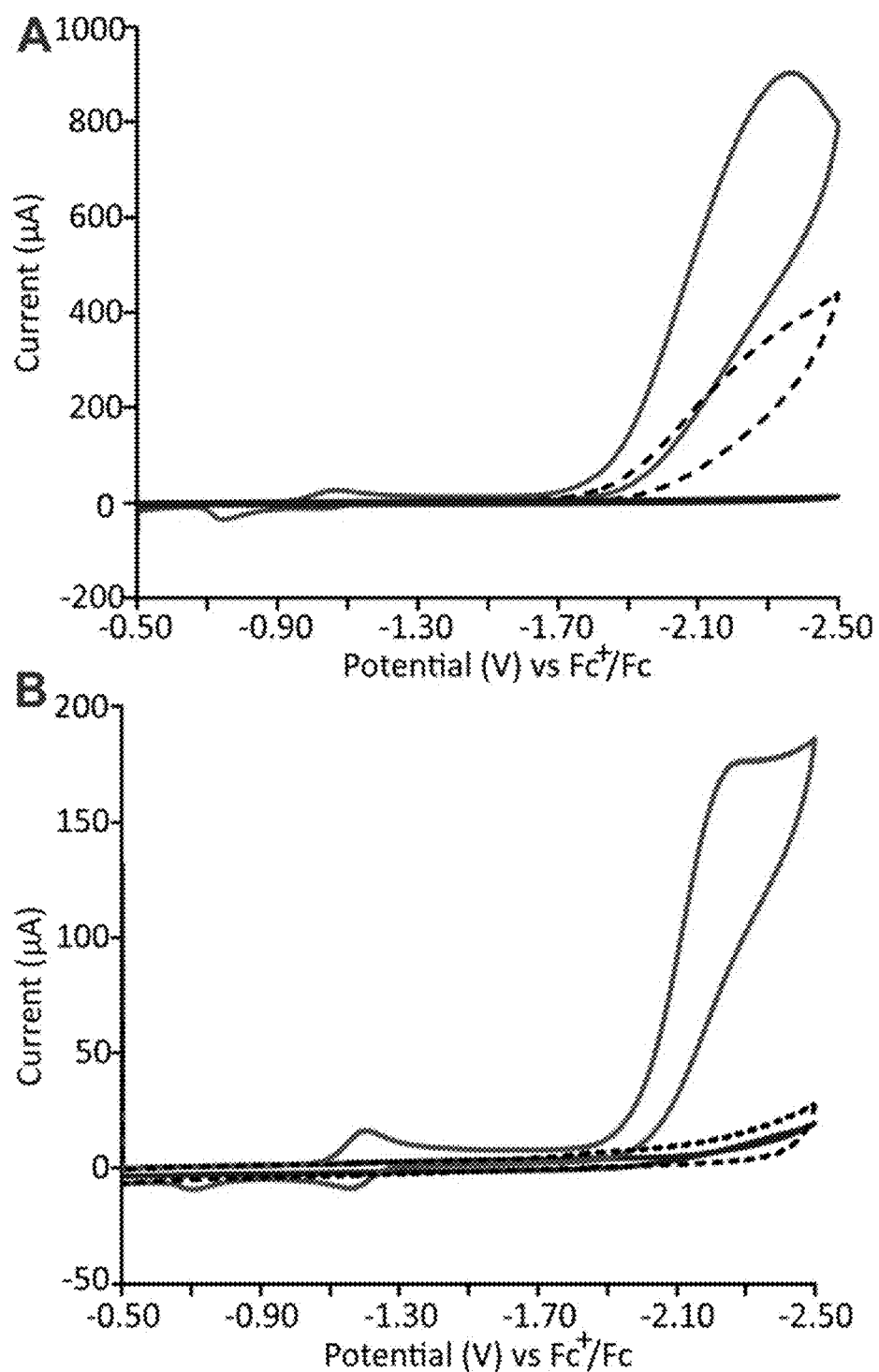
FIG. 29. Control Experiments—(A) CVs run in 0.1 M Bu$_4$NPF$_6$ ACN solutions, showing blank ACN (bottom), with 0.0672 M acetic acid added (dashed—middle), and with 0.0672 M acetic acid and 0.6 mM CuL$^1$ (top). (B) CVs run in 0.1 M Bu$_4$NPF$_6$ DMF solutions, showing blank DMF (solid), with 0.0224 M acetic acid added (dashed), and with 0.0224 M acetic acid and 0.6 mM CuL$^1$ (top).

A series of control experiments were performed to confirm $CuL^1$ as the electrocatalyst. First, CVs were recorded on ACN and DMF solutions containing only acetic acid. Addition of 67.2 mM acetic acid to 0.1 M $Bu_4NPF_6$ ACN solutions resulted in an observable current of 300 µA (FIG. 29A). However, after 2 CV cycles the current drops to a stable value near 100 µA. Upon addition of 0.6 mM $CuL^1$, the current increases to 900 µA (FIG. 29A). In DMF addition of 22.4 mM acetic acid results in a modest current increase of ~5 µA (FIG. 29B). Addition of 0.6 mM $CuL^1$ to this solution resulted in an increase in current, giving a value of 200 µA (FIG. 29B). At more cathodic potentials, a substantial change in the CVs of $CuL^1$ with 22.4 mM acetic acid added is observed with current increase onset potentials near −1.7 V vs $Fc^+/Fc$ (FIG. 29B). These control experiments identify $CuL^1$ as the source of the catalytic activity, but do not exclude the possibility that it may be the precursor to an adsorbed catalyst.

To probe for adsorption of the $CuL^1$ on the electrode surface prior to catalysis, a "soak test" was performed using the methods of Dempsey and co-workers (Lee at al., *Inorg. Chem.* 2017, Vol. 56, pp. 1988-1998—DOI: 10.1021/acs.inorgchem.6b02586). The working electrode was immersed overnight in a 0.1 M $Bu_4NPF_6$ ACN solution containing 0.6 mM $CuL^1$ and 0.292 M acetic acid. It was then removed, washed with DI water, and placed into a fresh solution of 0.1 M $Bu_4NPF_6$ ACN, with no added acid or catalyst. The resulting CV displayed no redox events indicating no detectable adsorption of $CuL^1$ derived species under these conditions.

Figure 62:
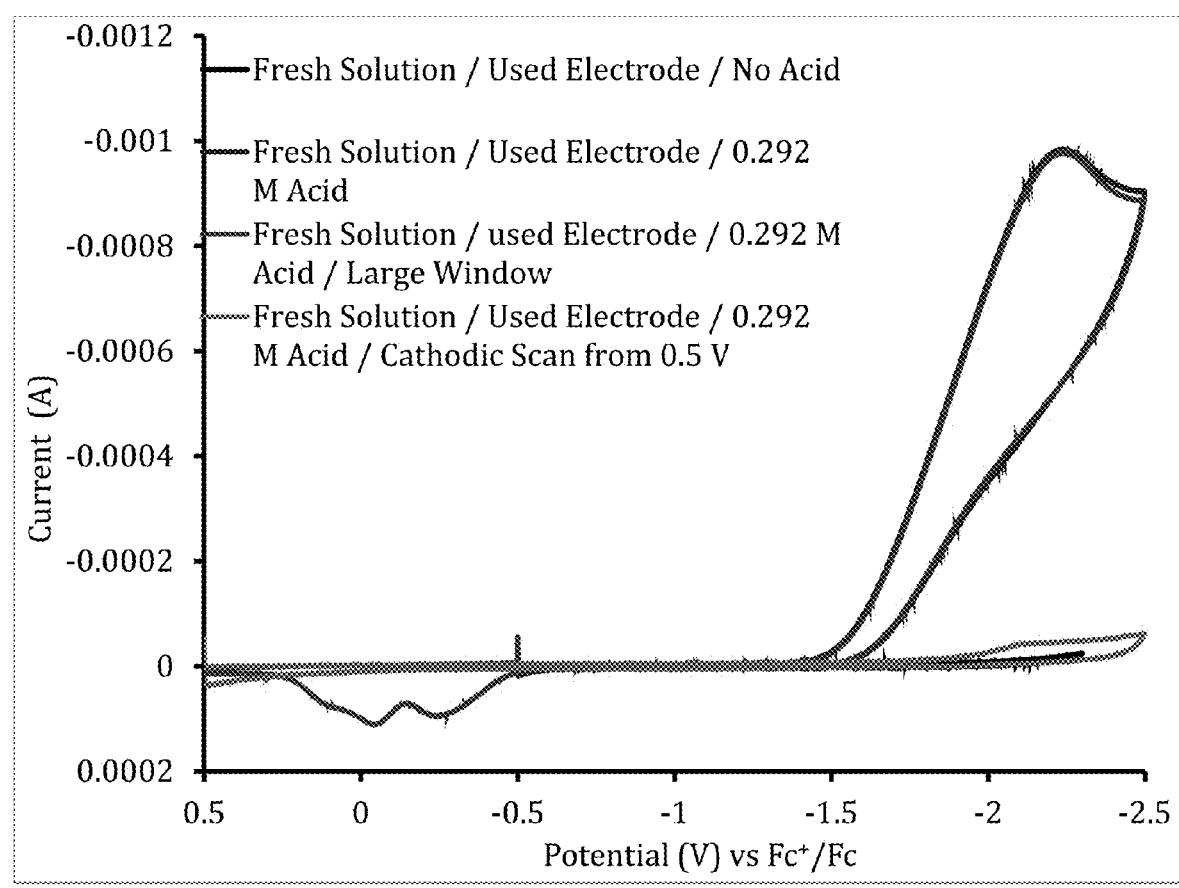
FIG. 62. Post CV dip-test after 50 CV Cycles.
Figure 63:
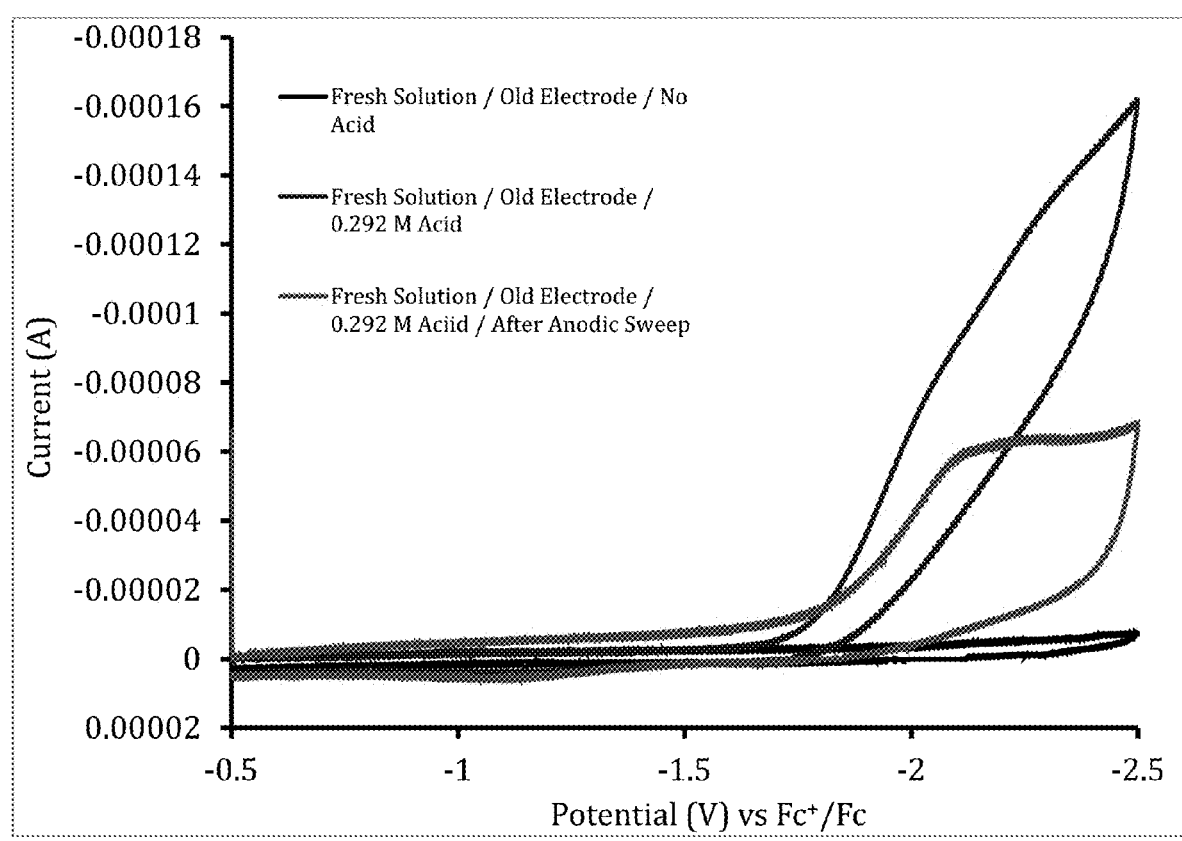
FIG. 63. Post CV dip-test after 50 CV Cycles.

A second series of controls were performed to evaluate if a catalytically active adsorbed species forms during CV catalysis. These post-CV "dip-tests" were conducted after 10 cycles and 50 cycles (See FIGS. 62 and 63). During the 50 cycles from −0.5 to −2.3 V vs. $Fc^+/Fc$ on 0.6 mM $CuL^1$ solutions under acid saturated conditions the current reaches a maximum value of ~1.5 mA. The working electrode was removed, washed with DI water, and immersed into a fresh solution of 0.1 M $Bu_4NPF_6$ ACN or DMF. The resulting CVs showed no significant Faradaic current in the window from −0.5 to −2.3 V. Upon addition of 0.292 M acetic acid, a catalytic current of 1 mA was observed at −1.7 V. After we extended the scan window to include 0.4 V, the catalytic current at −1.7 V is absent. This confirms that at least some of the HER catalysis results from adsorbed $CuL^1$ species.

To probe if all of the catalytic activity results from adsorbed catalysts, we repeated the post-CV "dip-test" after 10 cycles from −0.5 to −2.5 V vs. $Fc^+/Fc$ on 0.6 mM $CuL^1$ solutions under acid saturated conditions, again reaching maximum current values of ~1.5 mA. The working electrode was removed, washed with DI water, and immersed into a fresh solution of 0.1 M $Bu_4NPF_6$ DMF. As before, the resulting CVs showed no observable Faradaic current in the window from −0.5 to −2.5 V. CVs following addition of 0.292 M acetic acid that also showed only 400 µA of current −1.7 V. While these results indicate that surface adsorbed $CuL^1$ is responsible for some of the catalytic current after as few as 10 cycles, they show that the majority of HER activity under homogeneous conditions is due to dissolved $CuL^1$ complex.

Figure 30:
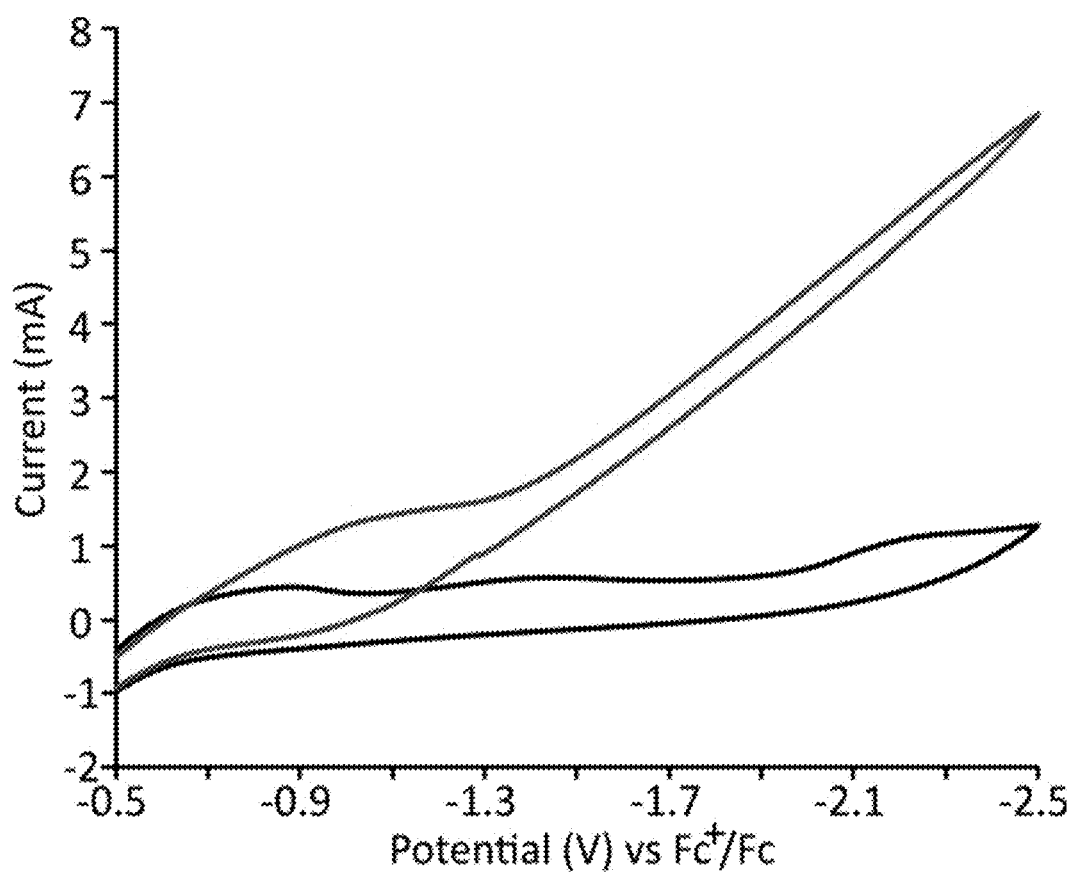
FIG. 30. Post-electrolysis "dip-test" of film—Performed on working electrode post CPE. Electrode washed with D.I water and immersed into a fresh solution of 0.1 M Bu$_4$NPF$_6$ ACN (bottom), and upon addition of 0.292 M CH$_3$COOH (top).

In addition, a post-electrolysis "dip-test" was performed following CPE studies of $CuL^1$ catalyzed HER. Under these conditions, a substantial amount of surface adsorbed $CuL^1$ derived complex is expected. After both CPEs in DMF and ACN, the working electrode was removed, washed with DI water, and immersed into a fresh 0.1 M $Bu_4NPF_6$ DMF/ACN solution. The CV was collected. In contrast to the post-CV "dip-tests", the electrode displays three reduction events at −0.9 V, −1.4 V and −2.1 V vs $Fc^+/Fc$. The first two events are near the observed Cu(II/I) reductions potentials of $[CuL^1H]^+$ and $CuL^1$, respectively. The most cathodic event is near the reduction potential of $H_2L^1$. Upon addition of 0.292 M acetic acid to the solution, current increases and catalysis is observed (FIG. 30).

Figure 31:
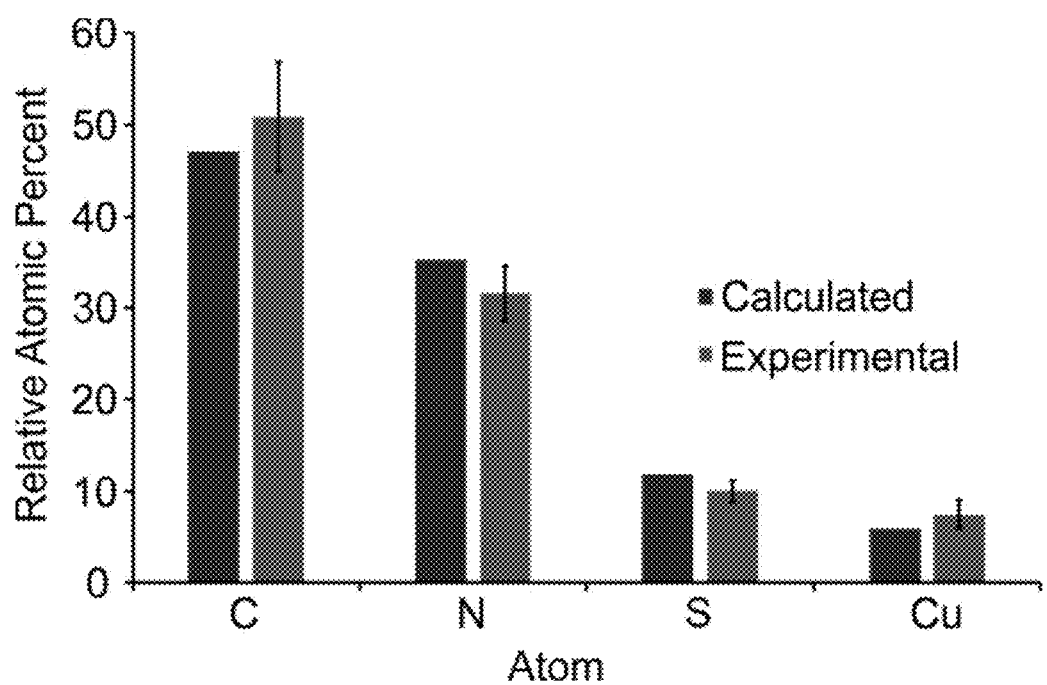
FIG. 31. Film analysis—Calculated (left bar) and XPS experimental (right bar) relative atomic mass percent for post-electrolysis CuL$^1$ derived films. Error bars show ±3σ for 4 experimental measurements.
Figure 61:
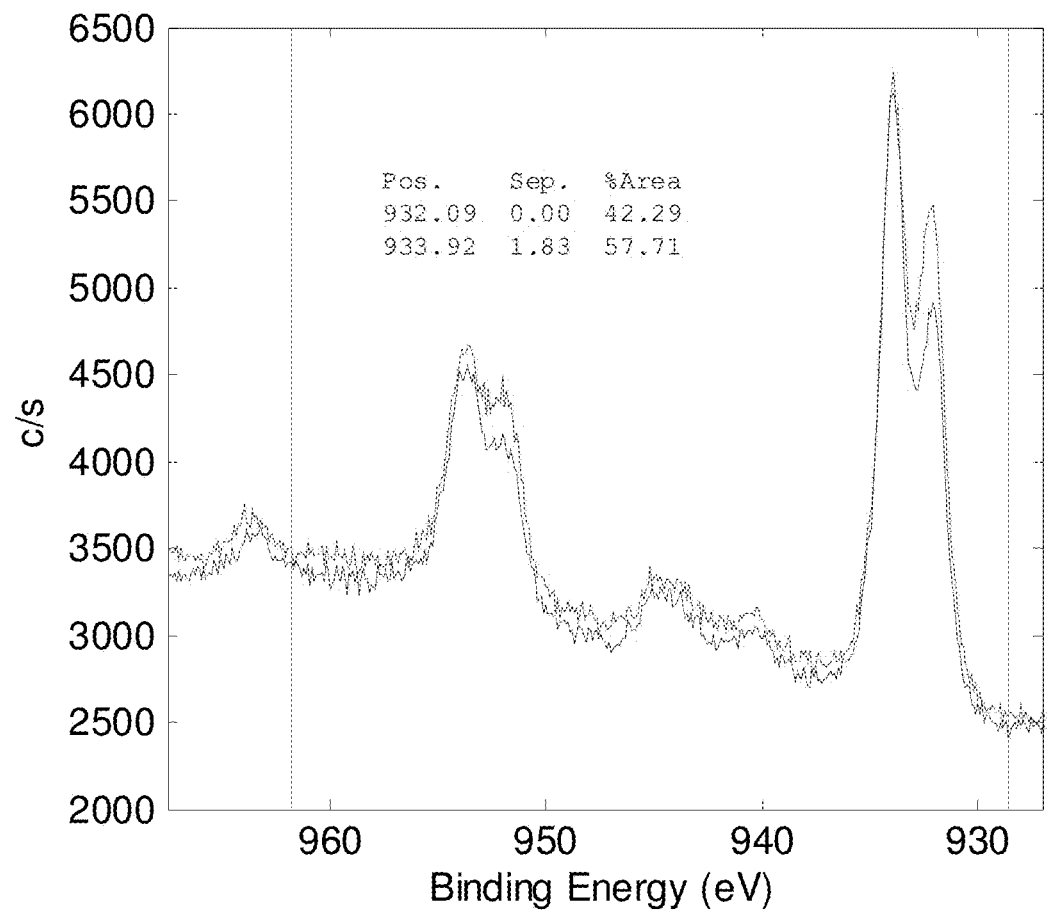
FIG. 61. High resolution (top) XPS of copper atoms and low resolution of entire adsorbed film (bottom).
Figure 61:
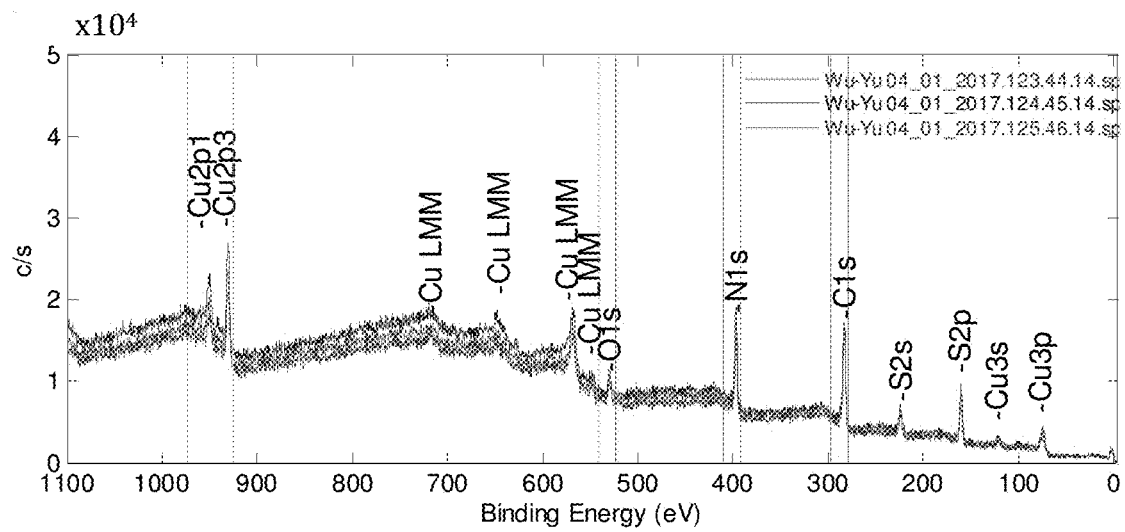

Analysis of the films following electrolysis in DMF and ACN by x-ray photoelectron spectroscopy revealed atomic percentages consistent with $CuL^1$, FIG. 31. The results are inconsistent with the formation of nanoparticles consisting of metallic Cu, copper oxides, or copper sulfides. The data from the two solvents are indistinguishable. High resolution XPS (see above and FIG. 61) confirms the presence of Cu ions and is inconsistent with metallic Cu.

Protonated Derivatives of $CuL^1$

A series of protonated derivatives of $CuL^1$ were evaluated as potential catalytically relevant intermediates. These include the mono- and di-protonated Cu(II) complexes [CuLH] and $[CuLH_2]^{2+}$ and the Cu(I) analogue CuLH.

Figure 32:
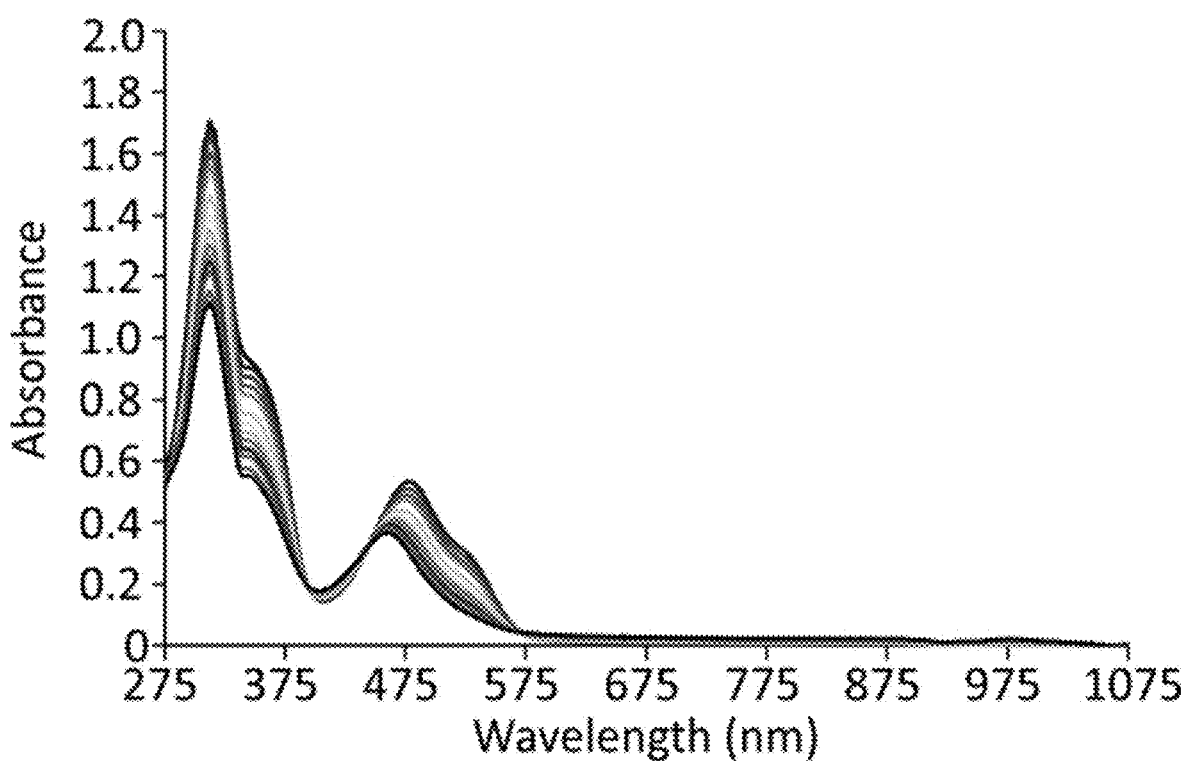
FIG. 32. UV-Visible spectrum of CuL$^1$—titrated with CH$_3$COOH (from top to bottom); 0.022 M, 0.044 M, 0.056 M, 0.067 M, 0.089 M, 0.112 M, 0.134 M, 0.157 M, 0.202 M, 0.244 M, 0.269 M, 0.292 M, 0.337 M, and 0.382 M.

To confirm that $[CuUH]^+$ is present in solution under catalytic conditions, acid titrations were monitored by UV-visible spectroscopy. The spectrum of 0.6 mM $CuL^1$ in deoxygenated DMF shows absorbance bands at 310, 375, 475 and 520 nm. The solution was titrated with acetic acid, increasing in concentration from 0.022 M to 0.382 M (FIG. 32). The absorbance bands of $CuL^1$ decrease in intensity, concurrent with increases at 405 and 460 nm consistent with the formation of $[CuL^1H]^+$. The proposed protonation site is the hydrizino N, in line with previous reports and density functional theory computations (vide infra).

Figure 55:
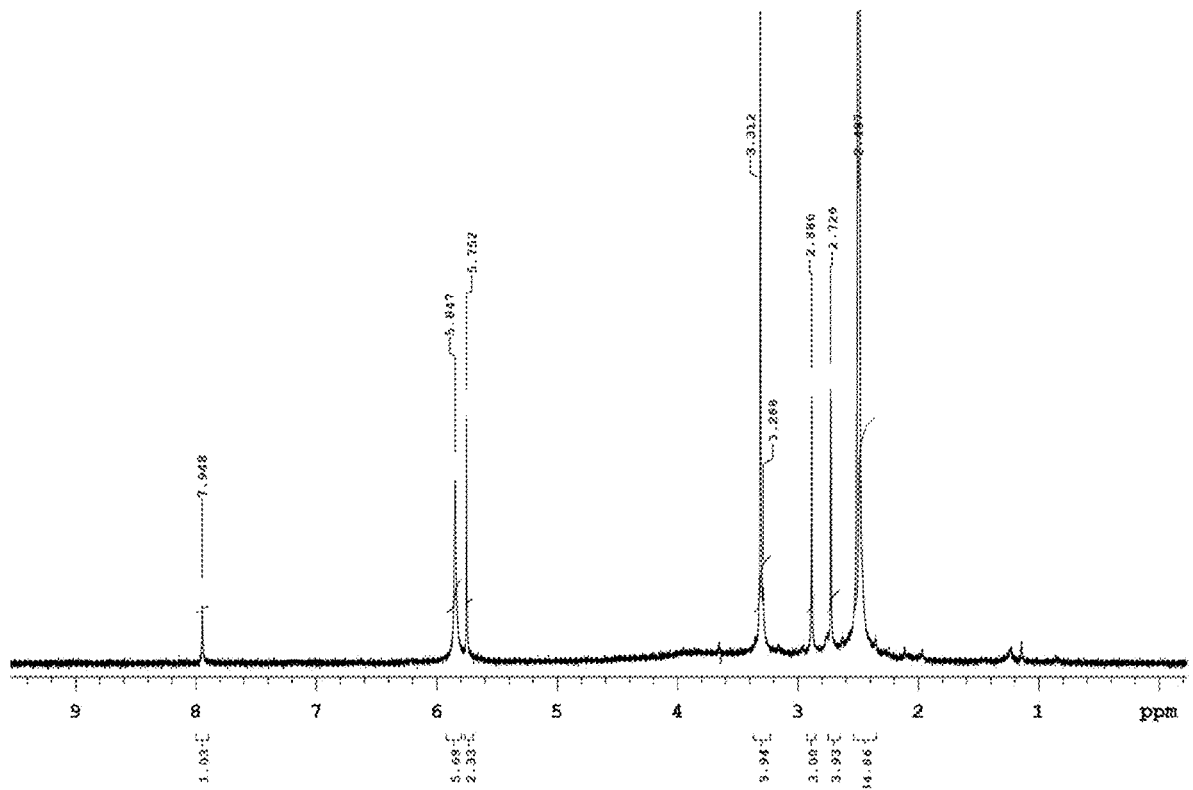
FIG. 55. $^1$H NMR spectrum of [CuL$^1$]$^-$.
Figure 56:
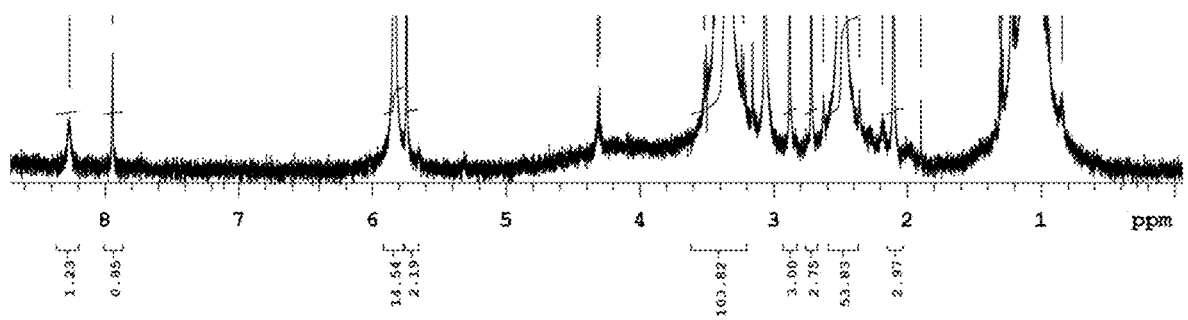
FIG. 56. $^1$H NMR spectrum of [CuL$^1$H]$^+$.
Figure 57:
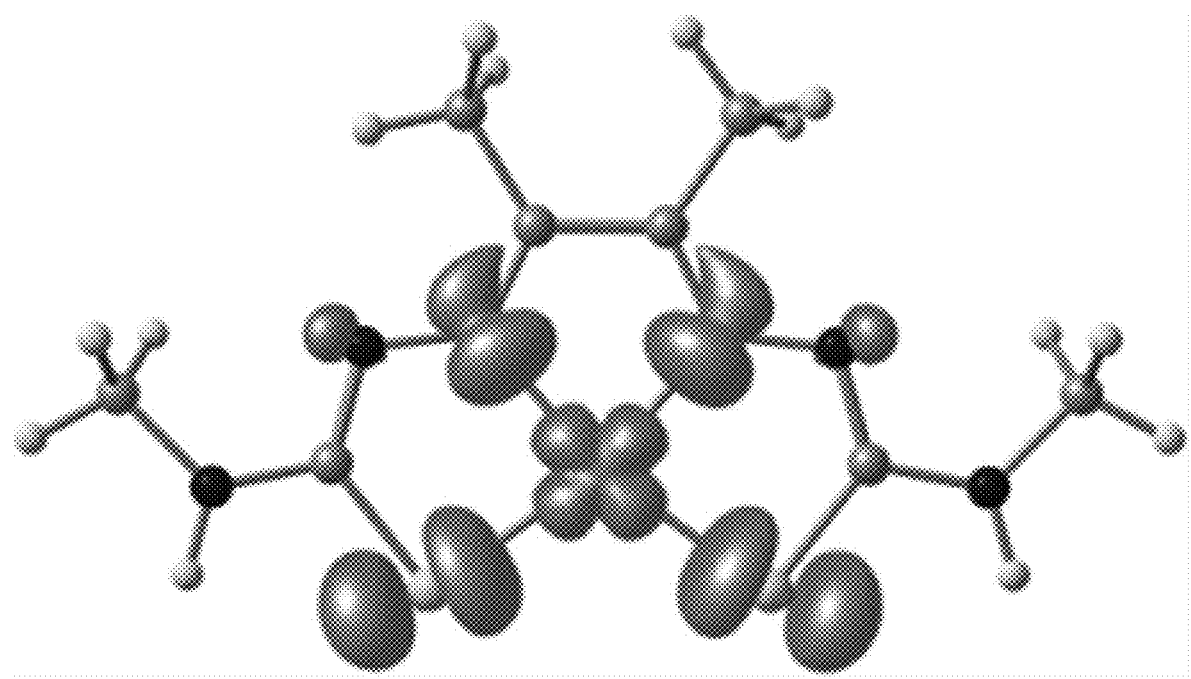
FIG. 57. Spin-density map of CuL$^1$ (S=1/2).
Figure 58:
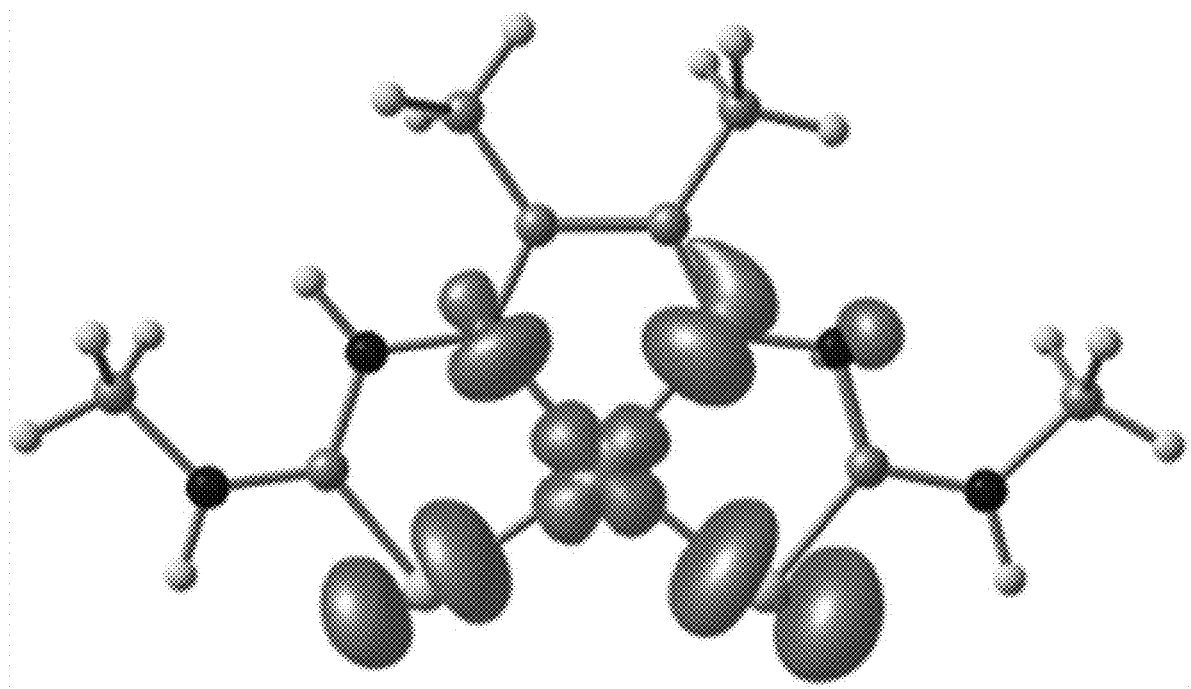
FIG. 58. Spin-density map of [CuL$^1$H]$^+$.

To characterize the monoprotonated Cu(I) species, $CuL^1H$, $CuL^1$ was first reduced and then protonated. In an Ar filled glove box, $CuL^1$ was dissolved in DMSO-$d_6$. Upon addition of one equivalent of cobaltocence, the solution changed color from red to light purple. The solution was stirred for 15 minutes to obtain the reduced anionic copper complex, $[CuL^1]^-$. An aliquot was added to an NMR tube for analysis. The $^1H$ NMR spectrum of $[CuL^1]^-$ displays the expected peaks. Chemical shifts at 2.73, 2.89, and 7.95 ppm are assigned to the methyl backbone $CH_3$, $NH(CH_3)$, and $NH(CH_3)$, respectively, and integrate with a ratio of 3:3:1 (FIG. 55). Addition of one equivalent of $HBF_4$ to the $[CuL^1]^-$ solution results in a color change from light purple to orange. An aliquot was taken and analyzed by $^1H$ NMR. Each of the peaks observed in $[CuL^1]^-$ are still present, along with a new peak at 8.27 ppm, which integrates to 1 (FIG. 56). The new peak is assigned to the protonation of the hydrazino nitrogen. The chemical shift is inconsistent with metal-centered protonation, which would result in a copper hydride with a negative chemical shift.

Our $CH_3COOH$ titration studies of diprotonated Cu(II) complex $[CuL^1H_2]^{2+}$ show no evidence of a second protonation event under catalytic conditions. Although $[CuL^1H_2]^{2+}$ is not catalytically relevant, x-ray quality crystals of $[CuL^1H_2]^{2+}$ were obtained from perchloric acid solution.

Figure 33:
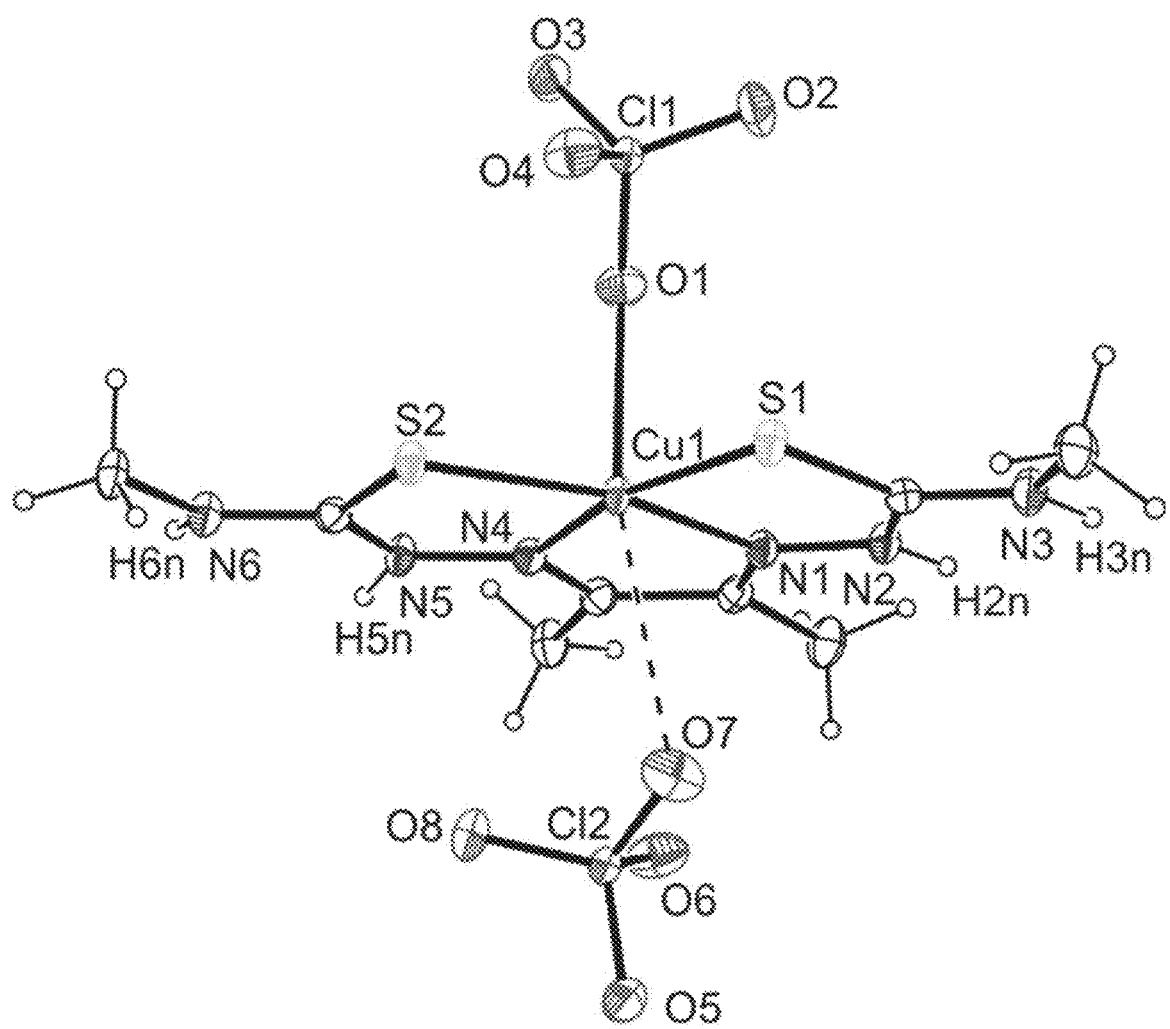
FIG. 33. ORTEP representation of [Cu(L$^1$H$_2$)(ClO$_4$)]ClO$_4$—Selected distances (Å): Cu—N1 1.9579(18), Cu—N4 1.9557(18), Cu—S1 2.2462(6), Cu—S2 2.2593(6), Cu—O1 2.5166(16), Cu . . . O7 2.9233(19), N2-H2n 0.78(3), N3-H3n 0.76(3), N4-N5 1.364(2), N5-H5n 0.78(2), N6-H6n 0.78(3). Selected angles (°): N1-Cu—N4 78.80(7), N1-Cu—S1 86.88(6), N4-Cu—S(2) 86.08(5), S1-Cu—S2 108.02(2), N2-N1-Cu 118.19(14), N1-N2-H2n 121(2), N5-N4-Cu 119.13(14), N4-N5-H5n 119.9(19).

The ORTEP representation shows protonation of both hydrizino nitrogens, axial coordination of one perchlorate, and axial association of the second perchlorate, FIG. 33. A complete description of the crystallographic details is provided above.

Proposed Homogeneous HER Mechanism

Figure 34:
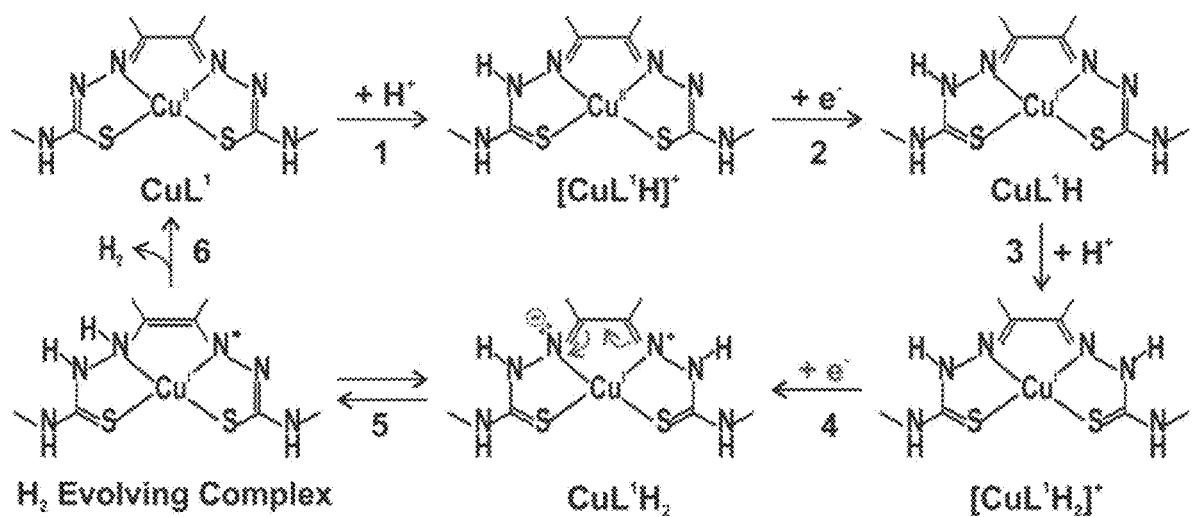
FIG. 34. Proposed mechanism of hydrogen evolution by CuL$^1$.

A proposed CECE mechanism for homogenous HER catalyzed by $CuL^1$ is shown in FIG. 34. Step 1 is an initial chemical (C) event involving protonation of the hydrazino nitrogen on $CuL^1$ to yield $[CuL^1H]^+$. This is followed by an electrochemical step (E) assigned as a metal-centered reduction giving the neutral Cu(I) species, $CuL^1H$. Step 3 is a chemical step involving protonation on the other hydrazino nitrogen, affording the Cu(I) cation, $[CuL^1H_2]^+$. Step 4 is the final electrochemical step, a proposed ligand-centered reduction to give the neutral species, $CuL^1H_2$. The $CuL^1H_2$ complex can be regarded as Cu(I) coordinated by a nitrogen-centered radical. Step 5 shows double bond rearrangement, resulting in an anionic coordinated nitrogen. This anionic nitrogen induces an internal proton transfer, a tautomerism that has been observed in many thiosemicarbazone complexes, leading to formation of the $H_2$ evolving complex. Finally, in step 6, hydrogen is evolved through hydrogen atom or proton/hydride coupling at the adjacent N—H bonds.

The proposed mechanism is consistent with the experimentally determined rate law and the KIE study. Both protons are added to a single $CuL^1$ complex prior to the rate determining step (r.d.s.) consistent with the first-order catalyst and second-order proton dependence on current. The proton inventory study suggests that a single proton is involved in the r.d.s. This favors tautomerization, step 5, over hydrogen evolution, step 6, as the rate limiting event. The solvent dependency of the TOF further supports this interpretation. The TOF in DMF is approximately one-half that in ACN. This is attributed to H-bonding interactions between DMF and ligand N—H groups. These stabilizing interactions retard the rate limiting tautomerization step in DMF relative to ACN. To assess the viability of this mechanism, density functional theory computations on all proposed species were performed.

Density Functional Theory Investigations

Figure 35:
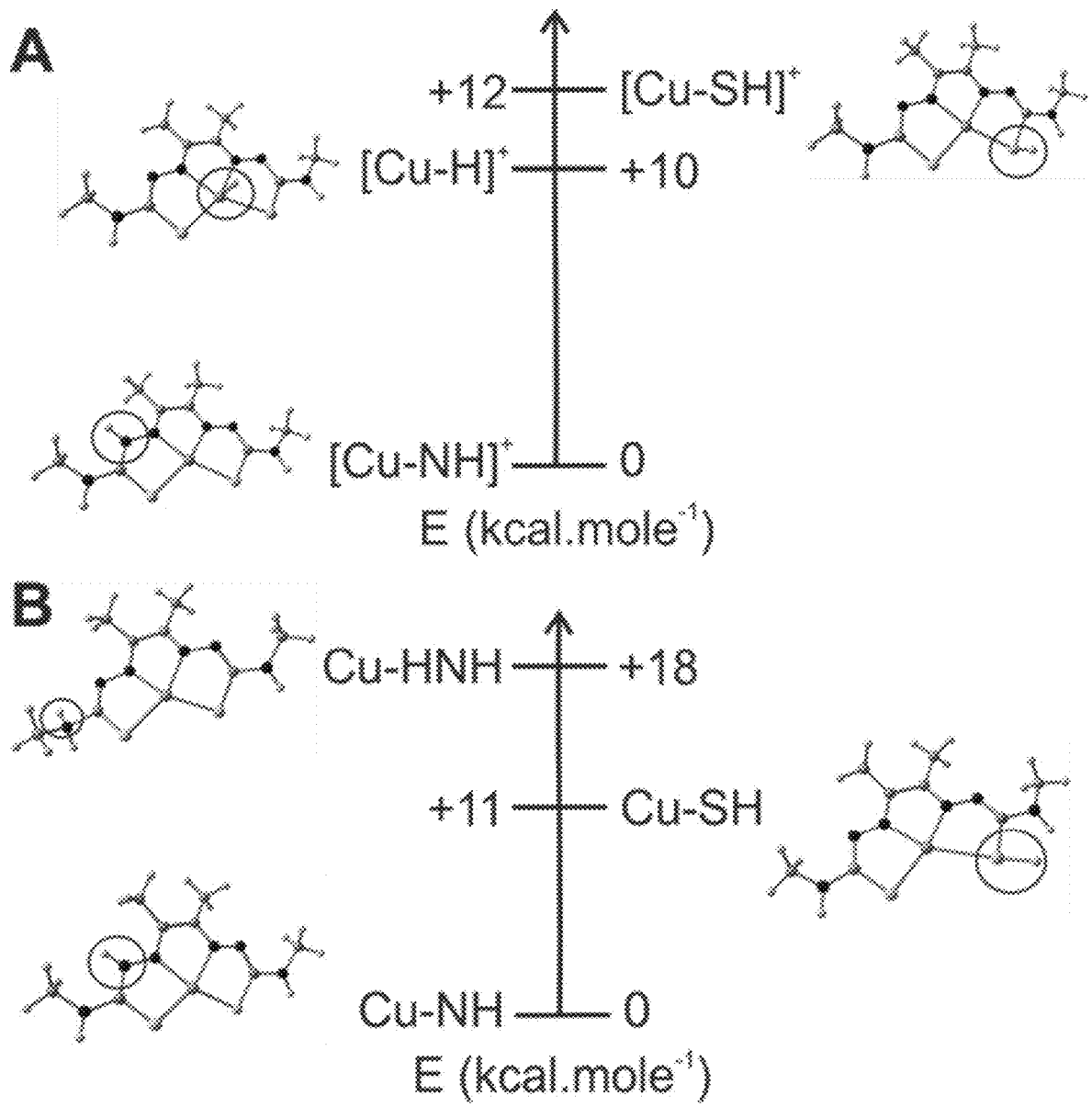
FIG. 35. Energetic Stability from DFT—(A) Energetic stability of protonated species, [CuL$^1$H]$^+$ (S=½). (B) Energetic Stability of protonated/reduced species, CuL$^1$H (S=0), B3LYP/6-311g(d,p).

All proposed complexes in FIG. 34 were assessed using density functional theory (DFT) using the B3LYP hybrid functional and the 6-311g(d,p) basis set. First, we evaluated the protonation event associated with step 1. Calculations on the singly protonated intermediate, $[CuL^1H]^+$, support our assignment of the hydrazino nitrogen as the site of protonation. For $[CuL^1H]^+$ (S=1/2), the Cu, S, N3 (hydrazino), N4 (coordinated), and N6 (pendant amine) were evaluated as possible protonation sites. In each structure, the geometry and frequencies were optimized and the energies minimized. The hydrizino protonated geometry is energetically preferred, lying 10 kcal/mole lower than the metal-hydride (FIG. 35A). Protonation at S is less favored by 12 kcal/mole and attempts to optimize structures with protonation on N4 and N6 resulted in migration of the hydrogen onto the hydrazino nitrogen.

Figure 59:
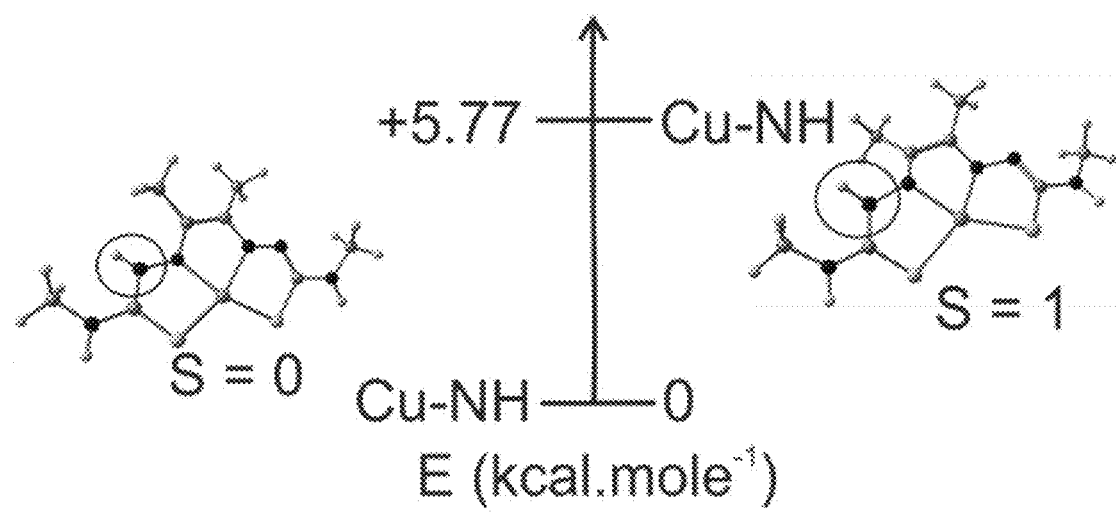
FIG. 59. Energetic stability of the protonated/reduced species, CuL$^1$H, in the singlet (S=0) and triplet (S=1) electronic states.
Figure 60:
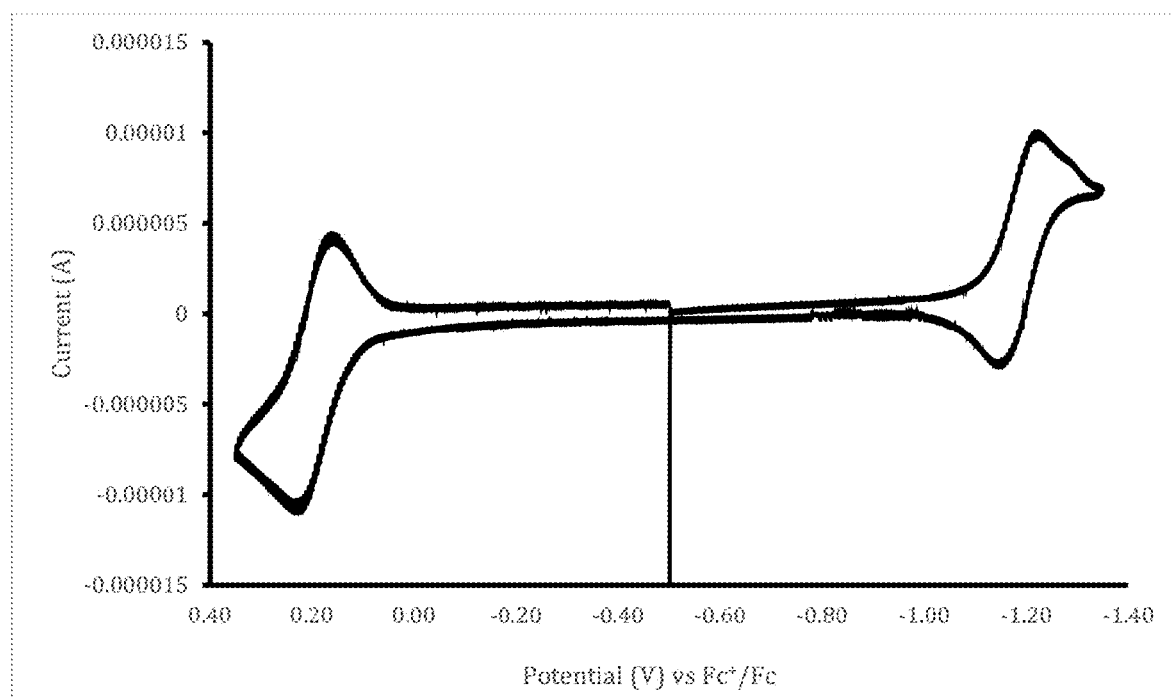
FIG. 60. Full CV of CuL$^1$.

Next, the one-electron reduced protonated species, $CuL^1H$ (S=0) (FIG. 35B), was examined to determine if reduction, step 2, impacts the location of the proton. Computed free energies for structures with protonation at Cu, S, and each N, clearly indicate that protonation on the hydrazino N is still favored. Protonation at S is disfavored by 11 kcal/mole, while protonation at the pendant amine is less favored by 18 kcal/mole. Attempts to optimize $CuL^1H$ with protonation at the coordinated nitrogen again resulted in migration of hydrogen onto the hydrazino nitrogen. We also considered $CuL^1H$ with protonation on the hydrazino nitrogen in its triplet electronic configuration (S=1). However, it is 5.77 kcal/mole higher in energy (see FIG. 59), confirming the nature of the first reduction as metal based.

Figure 36:
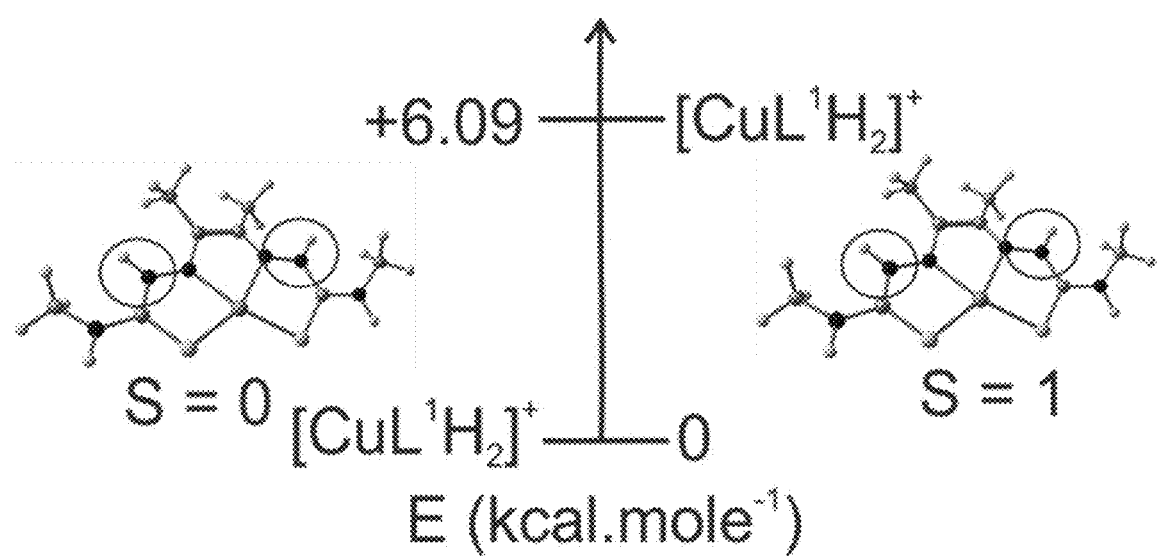
FIG. 36. Energetic Stability from DFT—Energetic stability of the protonated/reduced/protonated species, [CuL$^1$H$_2$]$^+$, in the singlet (S=0) and triplet (S=1) electronic states, B3LYP/6-311g(d,p).

Step 3 of the proposed mechanism involves addition of a second proton to $CuL^1H$. Energy minimizations of the doubly protonated, singly reduced intermediate, $[CuL^1H_2]^+$ in both the singlet (S=0) and triplet (S=1) electronic states were performed. For each spin state, the copper, the opposing hydrazino nitrogen (N1), sulfur (S2), the pendant amine (N6) and the coordinated nitrogen (N4) were all considered as the second protonation site. In both electronic states, protonation on the opposing hydrazino nitrogen (N1) is favored over all other protonation sites by at least 8 kcal/mole. Comparison of the singlet and triplet state the energies for protonation on N4 indicate the singlet is more stable by 6.09 kcal/mole (FIG. 36).

Figure 37:
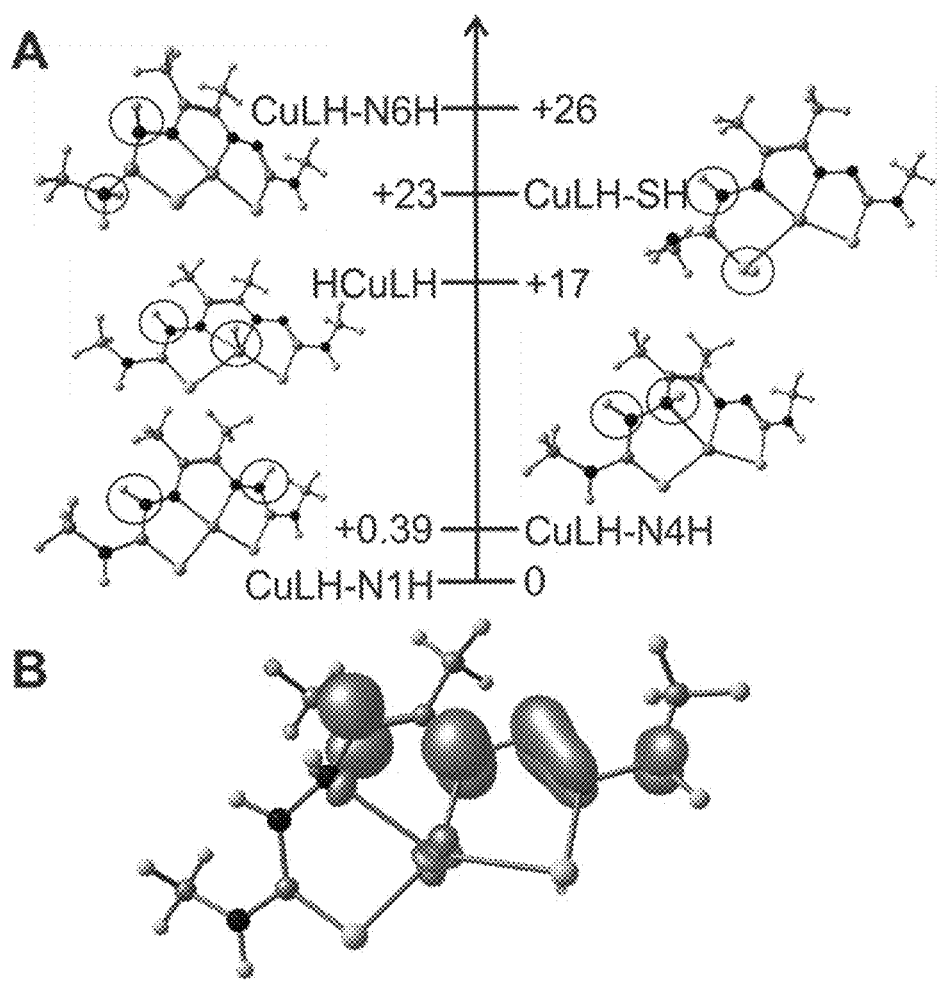
FIG. 37. Energetic Stability from DFT—(A) Energetic stability of CuL$^1$H$_2$ (S=½). (B) Spin-density map of CuL.$^1$H$_2$ with second protonation on N4, B3LYP/6-311g(d, p).

The addition of the second electron, step 4, leads to formation of the hydrogen evolving complex $CuL^1H_2$ through proposed rearrangement, step 5. The geometry and frequencies of $CuL^1H_2$ were optimized with one proton located on N3 while considering multiple sites for the second proton including the copper, the opposing hydrazino nitrogen (N1), sulfur (S2) the pendant amine (N6) and the coordinated nitrogen (N4). Energy minimizations indicate that placement of the second proton on N1 or N4 nitrogen are most favored, by at least 17 kcal/mole, compared to all other sites (FIG. 37A). Notably, energies for protonation at N1 and N4 differ by only 0.39 kcal/mole, indicating that the tautomerization associated with step 5 in the proposed mechanism is viable. Further, examination of the spin-density (SD) shows that the second reduction is primarily ligand based, with 34% on N2, 38% on C4, 14% on N1, 8% on N5, and only 3% on Cu (FIG. 37B).

Discussion

The complexes cited herein present intriguing reactivity as the ligand can participate in electron transfer events, either with or without a transition metal—rendering it "non-innocent" in some instances. Additionally, the ligands can be protonated generating various tautomeric forms—rendering it not only non-innocent, but also "promiscuous" in some instances. The combination of these two factors can be dependent on the identity of the metal ion, and, in some instances, can result in three types of HER reactivity: a) ligand-assisted metal reactivity with Ni, b) ligand-centered reactivity with Zn, and c) metal-assisted ligand reactivity with Cu.

Figure 38:
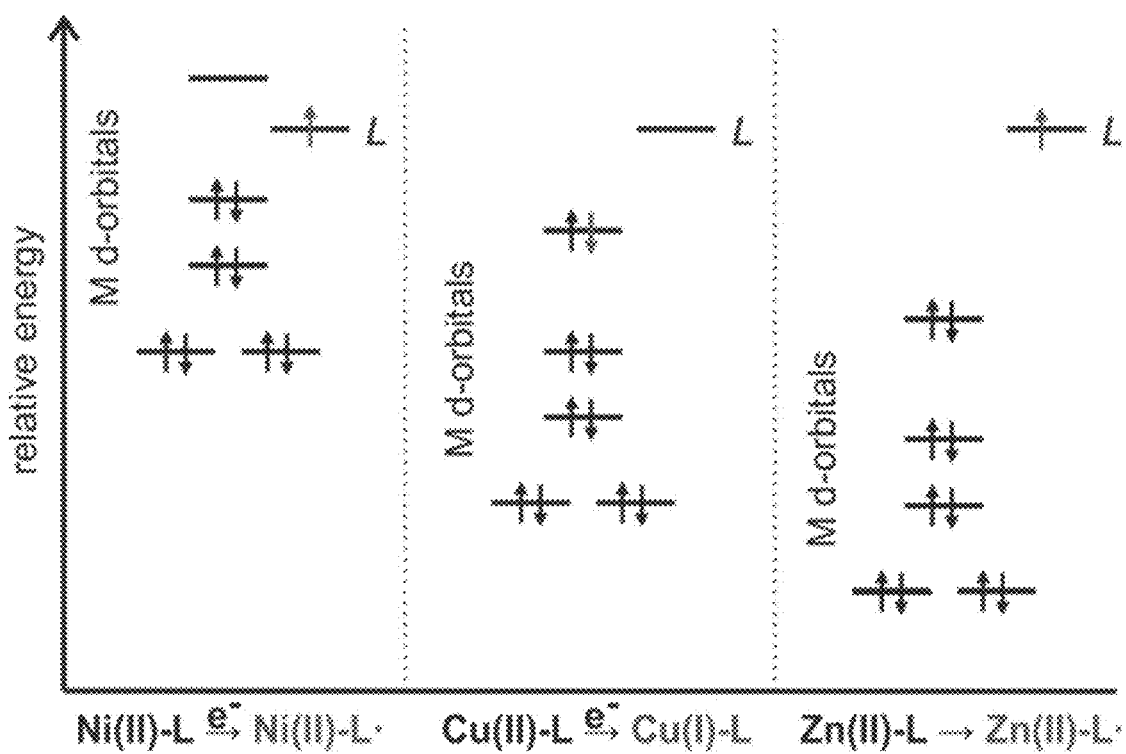
FIG. 38. Qualitative frontier molecular orbital diagram highlighting site of reduction.
Figure 39:
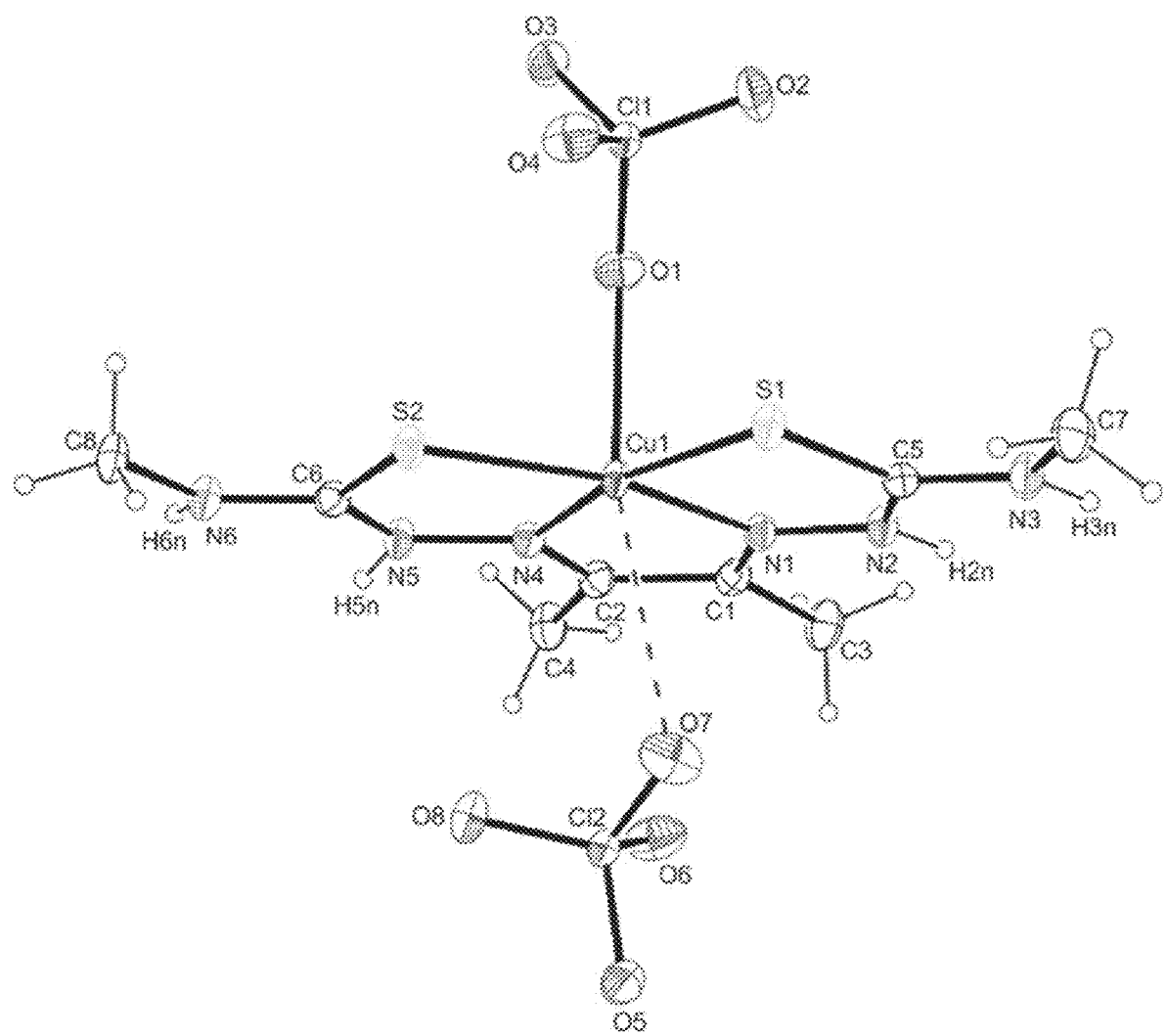
FIG. 39. Full ORTEP view of [Cu(L$^1$H$_2$)(ClO$_4$)]ClO$_4$.
Figure 40:
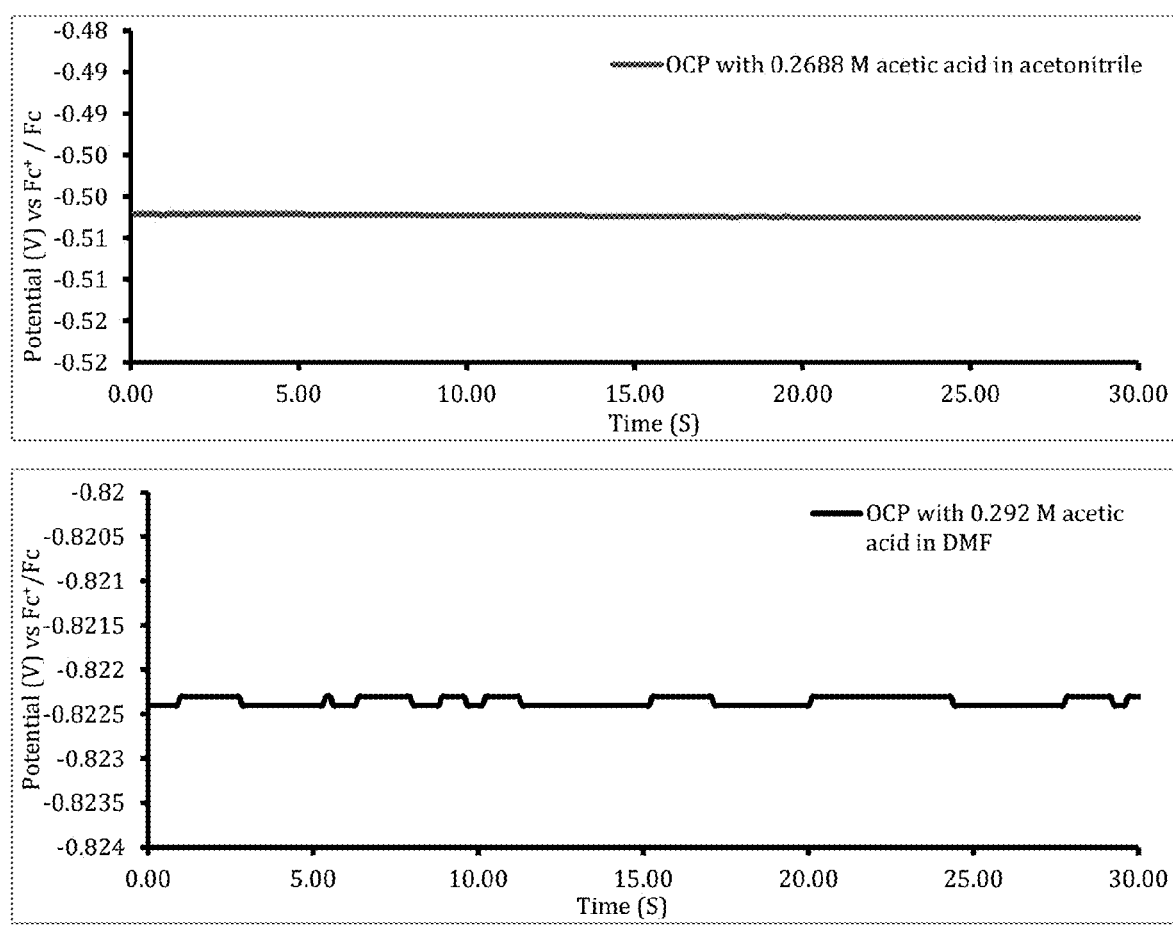
FIG. 40. Open circuit potential measurement in 0.1 M Bu$_4$NPF$_6$ acetonitrile solution (top) and in 0.1 M Bu$_4$NPF$_6$ DMF solution (bottom) with 0.269 M acetic acid added.

In some examples, the impact of the metal is manifested in the initial protonation and initial reduction sites. For both $CuL^1$ and $ZnL^1$, a hydrazino N is protonated prior to the initial reduction. The initial site of reduction can be rationalized based on the relative energies of the metal d-orbitals and an unoccupied ligand centered orbital, FIG. 38. The metal d-orbital energies decrease from $Ni^{2+}$ to $Cu^{2+}$ to $Zn^{2+}$ with increasing effective nuclear charge. For $Ni^{2+}$, a vacant ligand centered orbital lies below the vacant metal $d_{z^2}$ orbital yielding a ligand-centered radical upon reduction. For $Cu^{2+}$, the stabilized d-orbital manifold falls below the ligand-centered orbital resulting in metal-centered reduction. For $Zn^{2+}$, the d-orbitals are filled required ligand-centered reduction. Additionally, the site of reduction and the localization of spin-density can impact the site of protonation. For Cu, the proton remains on the hydrizino nitrogen after metal-centered reduction. In contrast, for Ni the ligand-centered reduction favors double bond rearrangement similar to step 5 in FIG. 34. As a result, the tautomers with protonation of the hydrizino N and anionic coordinated N have similar energies. For Zn, the tautomer with the proton remaining on the hydrizino N remains favored after ligand-centered reduction.

In some embodiments, the mechanism for $H_2$ evolution is a consequence of the initial protonation and reduction sites. For Ni, some has posited that the second reduction is metal-based, generating a nucleophilic $d^9$ Ni(I) center. Further protonation is proposed to occur at the metal generating a $Ni^{III}$-hydride as the catalytically active species for $H_2$ evolution. In this context, $NiL^2$ can demonstrate ligand-assisted metal reactivity, in which the ligand serves as an auxiliary redox site to facilitate two-electron chemistry at the metal. This can be a common role for redox active ligands in transition metal catalysis. In contrast, the HER chemistry of $ZnL^1$ can be ligand-centered. Its HER mechanism can localize all chemical and electrochemical steps on the ligand, with the metal providing structural support. As in the case of $NiL^2$, initial protonation and reduction is ligand-centered, however, the $d^{10}$ Zn(II), in some instances, is incapable of undergoing a second reduction and HER proceeds via a bimolecular process.

The HER chemistry of $CuL^1$ displays a less common type of mechanism with redox non-innocent ligands, which we defined as metal-assisted ligand-centered reactivity. The initial metal-centered reduction leads to a $d^{10}$ Cu(I), which is isoelectronic with $ZnL^1$. As such, it can accommodate subsequent ligand-based protonation and reduction events with evolution of $H_2$ from the ligand-center. In this context, the metal serves as the auxiliary redox site, which can facilitate two-electron chemistry at the ligand.

$CuL^1$ demonstrates a metal-assisted ligand-centered mechanism, in some instances. The redox non-innocence and protonation promiscuity of the ligand provides for a variety of HER mechanisms, some of which can be dependent on the metal ion. The $CuL^1$ system exhibits the highest reported TOF of any ligand-centered homogeneous HER catalysts to date. However, its high activity can sometimes require large overpotential. Nonetheless, the metal-assisted ligand reactivity of $CuL^1$ provides a new template for future HER electrocatalysts that, in some instances, function without the participation of a metal-hydride. The current study demonstrates that non-innocent ligands can work in conjunction with a redox-active metal to promote ligand-centered reactivity. This represents a new approach to the development of electrocatalysts for HER and, possibly, the activation of other small molecules.

Example Set C: Example Syntheses and Electrochemical Investigations of Alkoxy Derivatives Alkoxy derivatives were prepared as shown in the scheme below.

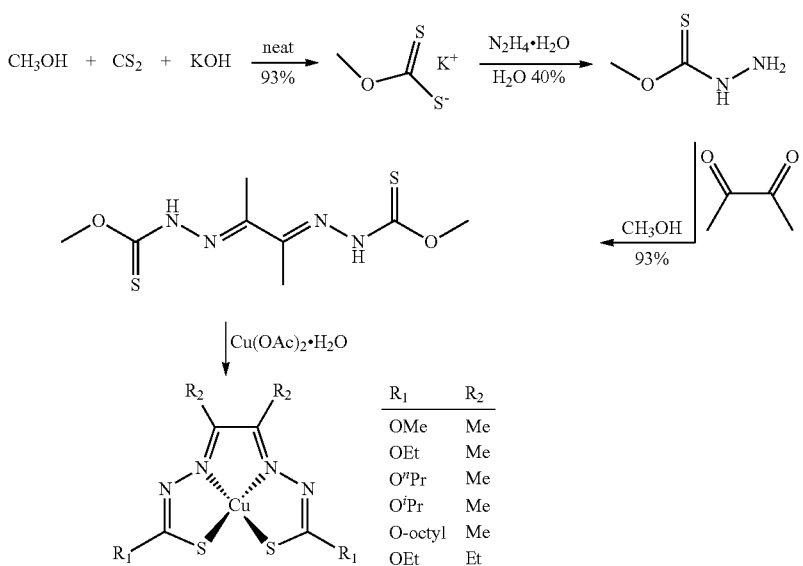

The hydrazinecarbothioc acid O-alkyl esters were prepared and condensed with diones. This was followed by metalation (shown here as Cu acetate). Characterization of their Cu(II) complexes reveals only small structural and spectroscopic changes relative to their bis-thiosemicarbazone counterparts. However, electro-chemical investigations reveal anodic shifts of ~340 mV in the $Cu^{II/I}$ reduction. The results demonstrate the ability to modulate the potential by variation of the thiosemicarbazone N-termini without imparting large structural changes. The synthetic strategies highlighted in the scheme provide examples of the design of new molecular catalysts, the synthesis of catalysts with extended structures, and the covalent attachment of catalysts to electrode surfaces.

Example Set D: Example Syntheses

A series of compounds can be synthesized containing transition metal-(Cu), non-transition metal-(Zn), and metal-free derivatives of symmetric ($R_1=R_2$) derivatives ($H_2L^{1-4}$) and the corresponding asymmetric derivatives ($H_2L^{5-8}$) in which $R_2$ is an ethoxy group, as in the scheme below.

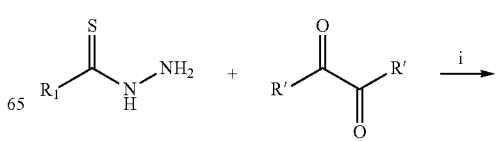

-continued

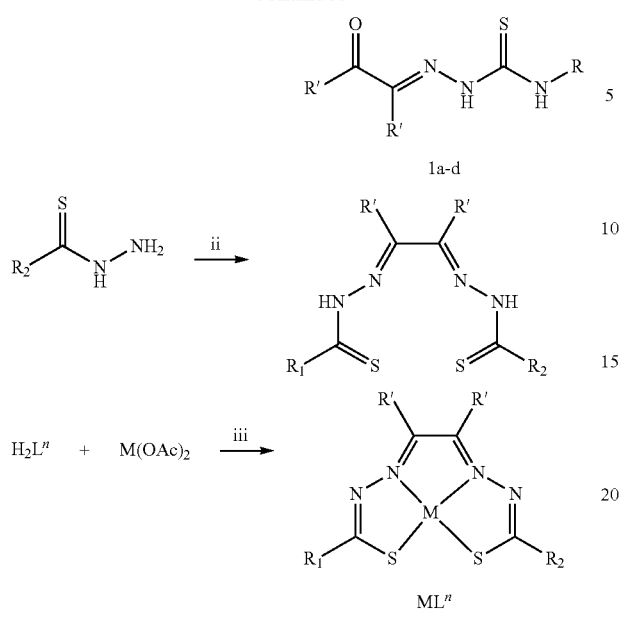

ML[n]

| n | R₁ | R₂ |
|---|---|---|
| 1 | NHCH₃ | NHCH₃ |
| 2 | NHPh | NHPh |
| 3 | NHCH₂CF₃ | NHCH₂CF₃ |
| 4 | N(C₃H₇)₂ | N(C₃H₇)₂ |
| 5 | NHCH₃ | OCH₂CH₃ |
| 6 | NHPh | OCH₂CH₃ |
| 7 | NHCH₂CF₃ | OCH₂CH₃ |
| 8 | N(C₃H₇)₂ | OCH₂CH₃ | i) H₂O, cat. HCl, 0°-5 C., 2 h; ii) 1a-d, EtOH, cat. HCl, 12 h;
iii) MeOH, reflux, 4 h The bis-thiosemicarbazone ligands $H_2L^{1-4}$ and their Cu and Zn complexes have been prepared. The asymmetric ligand $H_2L^5$, was prepared by condensation of 1a with the N-amino-O-ethylthiocarbamate (prepared from ethanol, CS₂, and NH₂NH₂.H₂O) in 50-70% yield (see above). Addition of Cu(OAc)₂ in methanol yields $CuL^5$ as a dark brown precipitates upon reflux. Spectroscopic characterization reveals a similar ligand environment as $CuL^1$ and related derivatives. The x-ray structure of $CuL^5$, confirms the asymmetric N₂S₂ environment.

Example Set E: Examples of Asymmetric Formulas

A series of asymmetric ligands has been synthesized, according to the scheme below.

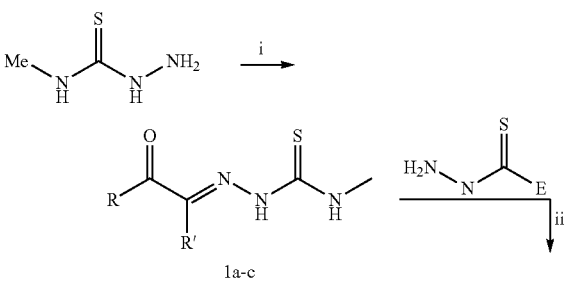

-continued

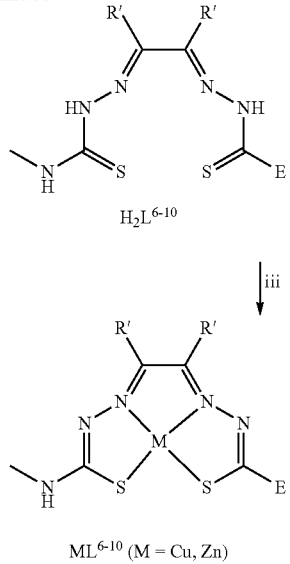

$H_2L^{6-10}$

ML[6-10] (M = Cu, Zn)

$i = $ R'C(O)C(O)R, H₂O, cat. HCl, 0-5° C., 2 h.

ii = EtOH, cat. HCl, 12 h.
iii = MeOH, M(OAc)2, relux 4 h.

| L[n] | E |
|---|---|
| 6 | N(iPr)₂ |
| 7 | NHPh |
| 8 | NHCH₂CF₃ |
| 9 | OCH₃ |
| 10 | OCH₂CH₃ | a R = R' = CH₃
b R = R' = CH₂CH₃
c R = CH₃, R' = Ph

Ligands $H_2L^{10a-c}$ have been prepared by condensation of 1a-c with the N-amino-O-ethylthiocarbamate (prepared from ethanol, CS₂, and NH₂NH₂.H₂O) in 50-70% yield. Addition of Cu(OAc)₂ in methanol yields $CuL^{10a-c}$ as a dark brown precipitates upon reflux. Spectroscopic characterization reveals a similar ligand environment as $CuL^1$ and related derivatives. The x-ray structure of $CuL^{10a}$, confirms the asymmetric N₂S₂ environment. $H_2L^{8a}$ and $CuL^{8a}$ were also prepared.

The CVs of $CuL^{10a-c}$ in acetonitrile (0.1 M TBAHFP) show a quasireversible reduction and oxidation. For $CuL^{10a}$, the $Cu^{II/I}$ reduction occurs at −1010 mV with the formal $Cu^{III/II}$ couple observed at +448 mV. These values lie between the respective potentials of the symmetric derivatives $CuL^1$ and $CuL^5$. Substitution of the backbone methyl groups with ethyl results in a small, but measurable cathodic shift to −1030 mV for the $Cu^{II/I}$. Incorporation of phenyl substituent in the backbone, $CuL^{10c}$c, yields a larger shift in the $Cu^{II/I}$ potential to −850 mV. Notably, the $Cu^{II/I}$ reduction of $CuL^{10c}$ is more accessible than in the symmetric $CuL^5$. This confirms modification of backbone R groups as a viable strategy to tune potential. Also, the CH₂CF₃ group of $CuL^{8a}$ shifts the $Cu^{III/II}$ potential to +70 mV with relative to $CuL^1$ in DMF.[40]

Figure 64:
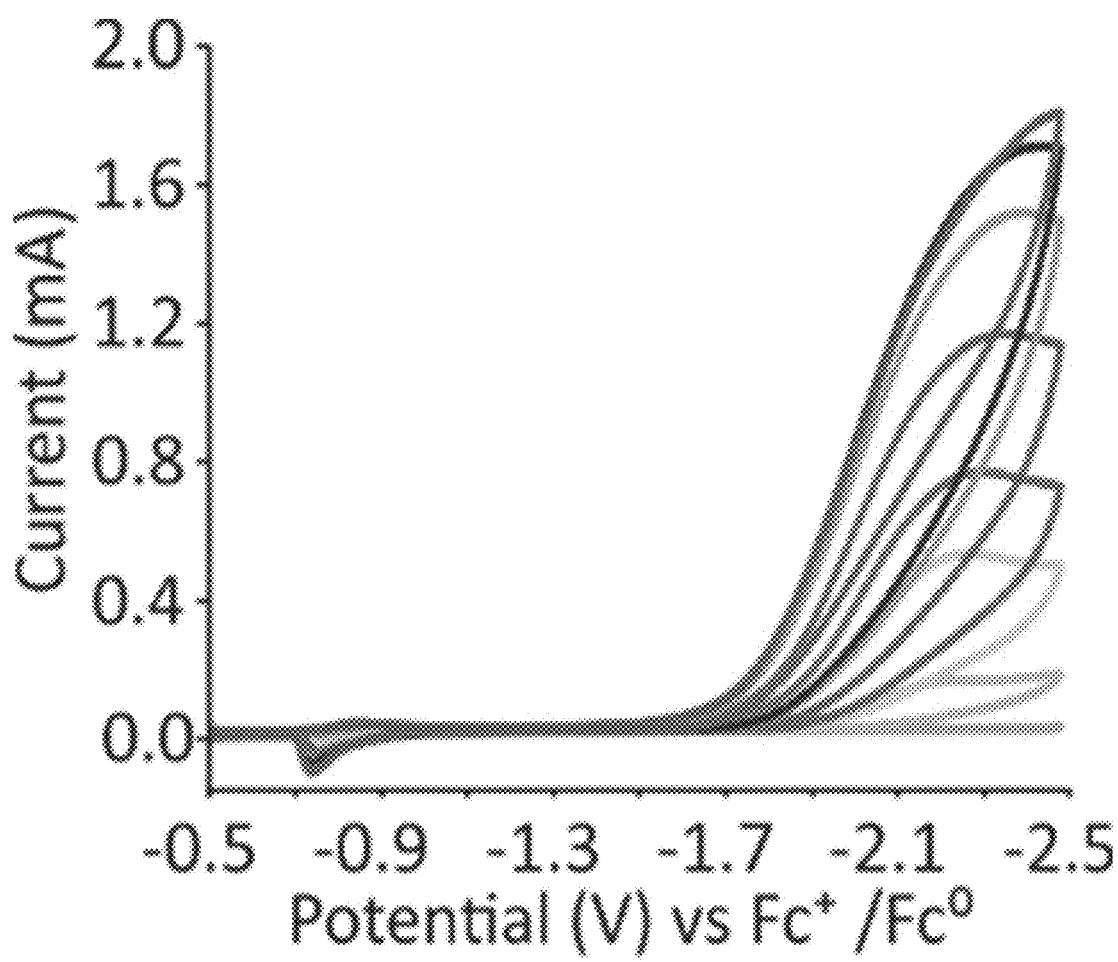
FIG. 64. CV of Asymmetric Cu ligand—CVs of CuL$^{10a}$ in CH$_3$CN with increasing [H$^+$].

Initial CVs confirm the HER activity of $CuL^{10b,c}$ in acetonitrile. Addition of acetic acid to $CuL^{10c}$ increases catalytic current at −1.5 V, FIG. 64. The current is first-order in [acid] until it reaches acid independence at [acid]>0.093

M. The maximum catalytic currents stabilizes at 1.80 mA associated with a maximum $i_{cat}/i_p$ value of 43.8 (v=1.0 V/s), affording a TOF of 15,600 s$^{-1}$ assuming the mechanism is bimolecular, as observed for CuL$^1$. An overpotential of 1.5 V was determined by open circuit potential methods. CuL$^{10b}$ has similar HER electrocatalytic activity.

Example Set F: Glassy Carbon Electrode (GCE) Preparation and Results

Figure 65:
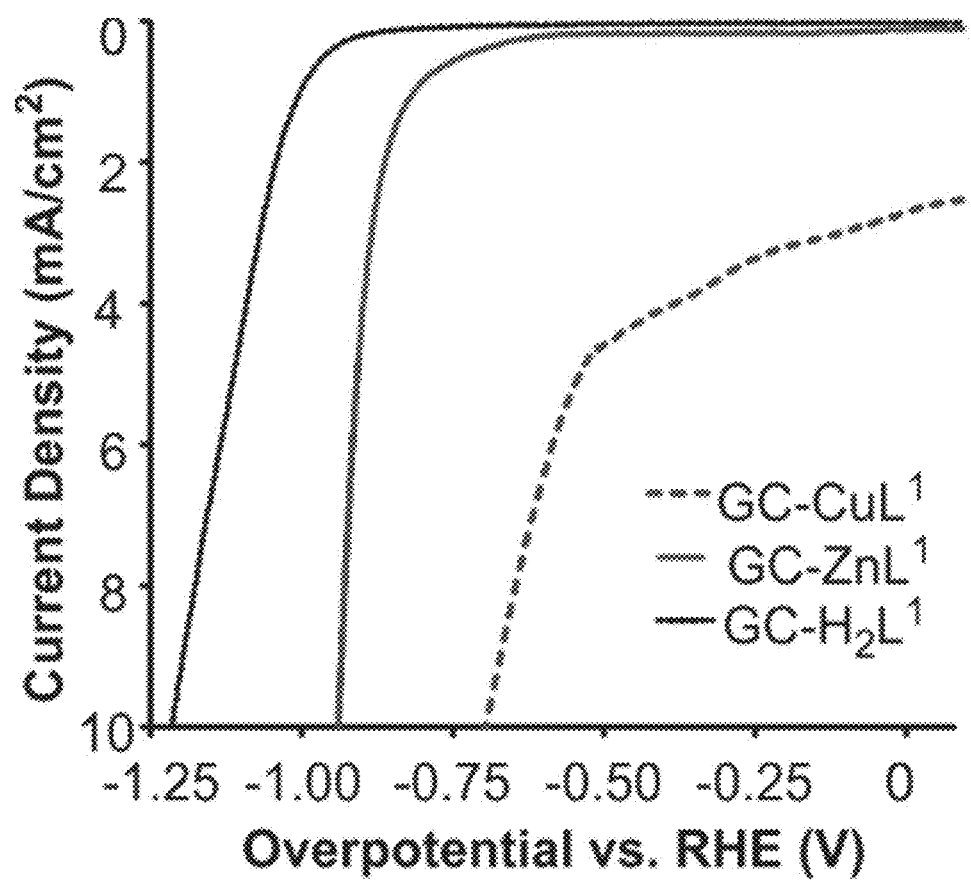
FIG. 65. GCE (Glass Carbon Electrode) polarization curves—Polarization curves in 0.5 H$_2$SO$_{4\ (aq)}$ with modified GCE (working), Pt (counter), and Ag/AgCl (3.5 M KCl) (reference) electrodes.

H$_2$L$^1$ and its Cu and Zn complexes (See Example Set B) are insoluble in water making them ideal candidates for preparing modified GCEs. GC-H$_2$L$^1$, GC-ZnL$^1$, and GC-CuL$^1$ were prepared by dropcast of from 20 nmol to 200 nmol of the appropriate catalyst on 5 mm GCE disks and curing of the resulting films. Electrodes were thoroughly dried and stored in air prior to use. The Electrochemical Impedance Spectroscopic (EIS) data for GC-CuL$^1$ is consistent with a contact resistance of 14Ω. The charge transfer resistance, which has an impact on overpotential, of GC-CuL$^1$ is 1760Ω. This relatively low charge transfer resistance could be attributed to the ease of electron transfer within the planar, conjugated framework of CuL$^1$. Results for ZnL$^1$ are similar. Initial CV studies confirm HER activity of the surface confined catalysts. From the polarization curves, the overpotential required to achieve a current density of 10 mA/cm$^2$ is 699 mV for GC-CuL$^1$, FIG. 65. GC-ZnL$^1$ and GC-H$_2$L$^1$ have higher overpotential of 940 mV and 1200 mV, respectively.

Example Set G: Carbon Paste Electrodes (CPE)—Fabrication and Surface Analysis

CPEs modified with H$_2$L$^1$, CuL$^1$ and ZnL$^1$ (from Example Set B) were prepared by mixing graphite fine powder with and 0.5 wt % of the appropriate catalyst in dichloromethane and sonicating for 15 min. The mixture was dried under an infrared lamp for 30 min. Paraffin oil (20 wt %) was added and the resulting slurry was carefully mixed to form the carbon paste. The paste was pressed into a plastic tube and a Cu wire was inserted to establish electrical contact. The electrode surface was polished with weighing paper and washed with deionized water. Finally, 2 μL of a Nafion (5% in isopropanol) was added to the polished surface and the chemically modified CPE was dried under an infrared heating lamp for 15 min. CPEs were stored in air.

The CPE-CuL$^1$ surface was imaged using SEM and the impedance measured by EIS. The SEM images show clear and homogeneous graphite layers with uniformly distributed pores, FIG. 66a. The surface porosity should allow for sufficient ion diffusion from the bulk to the catalysts embedded in the electrode film. Resistance between the CPE-CuL$^1$ and solution was measured by EIS. Data collected over a frequency range of 10$^{-2}$ to 10$^5$ Hz at an applied overpotential of 1.3 V were used to construct a Nyquist plot, FIG. 66b. Fitting of the data yields a resistance between the electrode surface and electrolyte of 12.3Ω, a charge transfer resistance within the electrode of 508Ω, a capacitive component indicative of space charges or electrical dipoles in the sample. Overall, resistance for the CPEs is significantly smaller than the modified GCEs in Example Set F.

Figure 66:
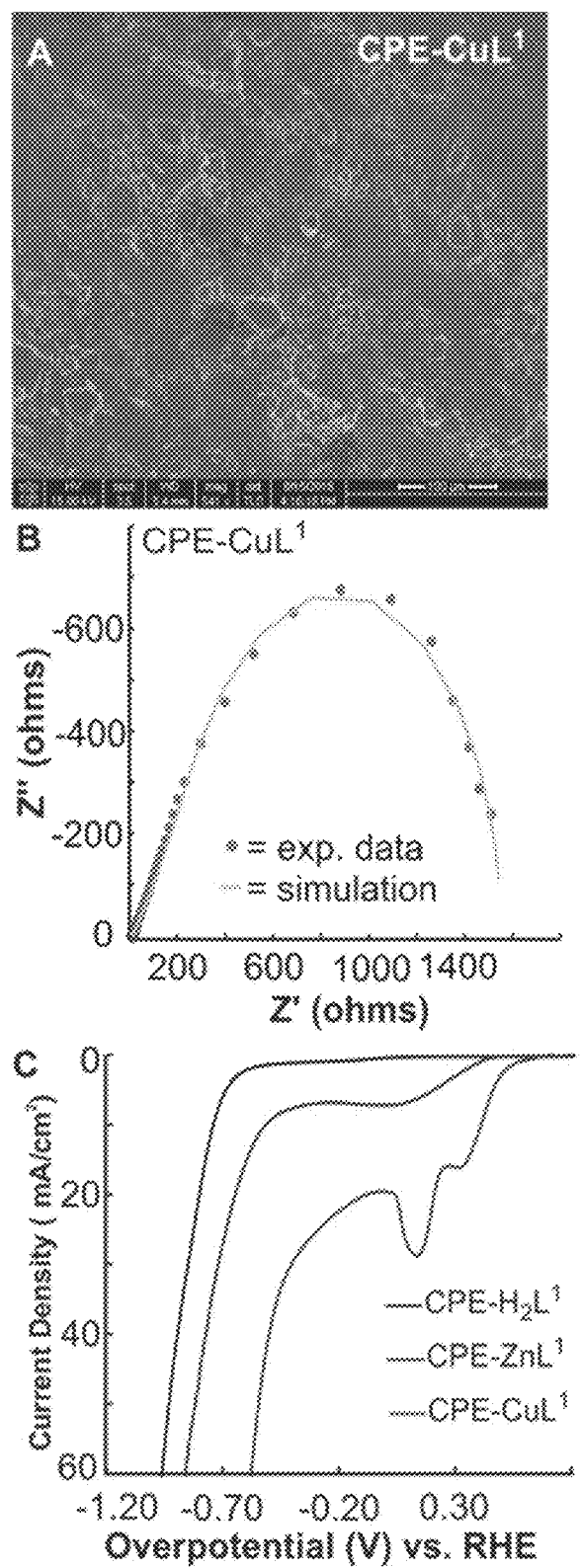
FIG. 66. Carbon Paste Electrode (CPE) analysis—(a) SEM image of CPE-CuL$^1$; (b) Nyquist plot of CPE-CuL$^1$; Polarization curves for modified CPEs.

Polarization curves were recorded for the CPE-CuL$^1$ in 0.5 M H$_2$SO$_4$ solution under ambient conditions, FIG. 66c. The overpotential required to obtain a current density of 60 mA/cm$^2$ is 0.65 V. At lower current densities, the overpotential is below the 0.6 V benchmark for relevant HER catalysts, although the value at the recommended current density of 10 mA/cm$^2$ complicated by a series of events attributed to formation of a catalytically active dinuclear species, as seen in homogenous solution. For CPE-ZnL$^1$ and CPE-H$_2$L$^1$, the overpotential required for 60 mA/cm$^2$ is 0.94 and 1.04 V, respectively.

Initial assessment of the electrode stability of CPE-CuL$^1$ was investigated by repetitive scanning in 0.5 M H$_2$SO$_4$ solution for 500 cycles from 0.0 to −1.7 V at a scan rate of 50 mV/s. The overpotential required for a current density of 100 mA/cm$^2$ increased by only 50 mV. The long term stability of CPE-CuL$^1$ was benchmarked by chronopotentiometry at a fixed catalytic current density of 100 mV/cm$^2$ for 24 hours. The overpotential increased by 97 mV over the first 8 hours and remained constant thereafter indicating good stability over long time electrolysis.

Example Set H: Example Syntheses and Electrochemical Investigations of Amine Derivatives Methods Physical Methods. Elemental analyses were performed by Midwest Microlab, (Indianapolis, Ind., USA). $^1$H and $^{13}$C NMR data were collected on a Varian Inova 500 MHz and Varian 400 MHz NMR Spectrometers in commercial deuterated solvents (Aldrich or Cambridge Isotopes). High-resolution electrospray ionization mass spectrometry in the negative ion mode (−ESI) was performed by the Laboratory for Biological Mass Spectrometry at Texas A&M University. Infrared spectra were recorded on Thermo Nicolet Avatar 360 spectrometer with ATR attachment (4 cm$^{-1}$ resolution). Electronic absorption spectra were recorded with an Agilent 8453 diode array spectrometer with a 1 cm path length quartz cell. All electrochemical measurements were performed using a Gamry Interface potentiostat/galvanostat with a three-electrode cell (glassy carbon working electrode, platinum wire counter electrode, and Ag/Ag ion reference electrode). Reported potentials are scaled vs. a ferrocenium/ ferrocene (Fc$^+$/Fc$^0$) standard (0.00 V), which was determined using ferrocene as an internal standard.

Materials and Methods. All reagents were obtained from commercially available sources and used as received unless otherwise noted. Commercial solvents were additionally dried and purified using an MBraun solvent purification system unless otherwise noted. The compounds in this study are air and moisture stable as solids and were handled on the benchtop with no additional required protection from the atmosphere.

Synthesis. All reactions were performed open to air and under ambient conditions unless otherwise indicated. The N,N'-(dimethylethylenediaminothiosemicarbazanato)-4-(methylthiosemi-carbazanato)butane-2,3-diimine=ATSM/ DM and N,N'-bis(dimethylethylenediaminothiosemi-carbazanato)butane-2,3-diimine=ATSDM ligands were synthesized according to modified literature methods (XIE et al., "Exploiting Copper Redox for $^{19}$F Magnetic Resonance-Based Detection of Cellular Hypoxia" J. Am. Chem. Soc. (2016) Vol. 138, pp. 2937-2940.)

SCHEME H1

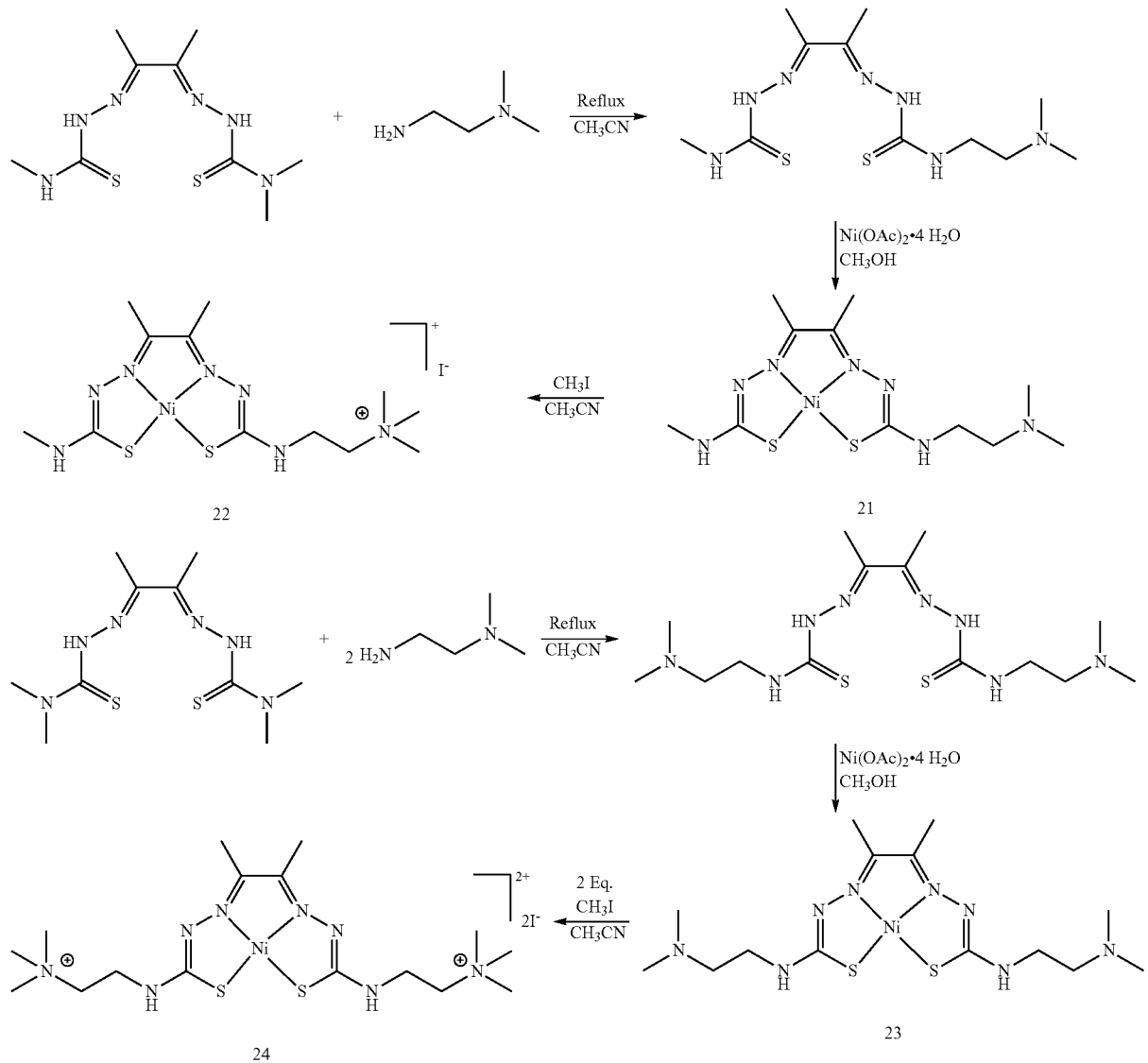

Some syntheses were performed according to Scheme H1.

ATSM/DMEDA: To a suspension of ATSM/DM (0.5 g, 1.8 mmol) in MeCN (50 mL) was added N,N-dimethylethylene diamine (0.440 mL, 4.0 mmol). Formed yellow solution was refluxed overnight. A white precipitate, which formed upon cooling to room temperature, was filtered and dried under vacuum. Yield=0.445 g (78%). $^1$H NMR (500 MHz, d$_6$-DMSO) of ATSM/DMEDA: 10.2 (bs, 2H, —NH—N=C—), 8.33 (q, 2H J$_{HH}$=4 Hz, 7.5 Hz, —NH—C=S), 3.58 (q, 2H, J$_{HH}$=7.5 Hz, 8.3 Hz, —CH$_2$NH—), 3.00 (t, J$_{HH}$=4 Hz, 3H, NH—CH$_3$, 2.43 (t, 2H, J$_{HH}$=8.3 Hz, —CH$_2$N(CH$_3$)$_3$, 2.18 (s, 3H, —CH$_3$), 2.16 (s, 6H, —N(CH$_3$)$_2$), 2.14 (s, 3H, —CH$_3$). $^{13}$C NMR (100 MHz, d$_6$-DMSO): δ/ppm 178.8 (C=S), 178.0 (C=S), 148.4 (C=N), 148.0 (C=N), 57.5 (—CH$_2$NH—), 45.5 (N(CH$_3$)$_2$), 41.9 (—CH$_2$N(CH$_3$)$_2$, 31.6 (CH$_3$NH—), 12.2 (—CH$_3$) 11.8 (—CH$_3$). FT-IR, cm$^{-1}$: 3364 (w, N—H), 3208 (br, m, N—H), 2954 (w), 2817 (w), 2785 (w), 1486 (vs, C=N), 1291 (s, thioamide), 947 (m), 660 (m).

ATSDMEDA: To a suspension of ATSDM (0.5 g, 1.73 mmol) in MeCN (50 mL) was added N,N-dimethylethylene diamine (0.630 mL, 5.73 mmol). Formed orange-yellow solution was refluxed overnight. An off-white solid which formed upon cooling to room temperature was filtered and air dried. Yield=0.473 g (73%). $^1$H NMR (500 MHz, d$_6$-DMSO) of ATSDEMDA: δ/ppm 10.33 (bs, 1H, —NH—N=C—), 8.35 (t, 1H, J$_{HH}$=5.4 Hz, NH—C=S), 3.61 (q, J$_{HH}$=5.8 Hz, 6.4 Hz, 2H, —CH$_2$NH—), 2.45 (t, J$_{HH}$=2.5 Hz, 6.4 Hz, 2H, —CH$_2$N(CH$_3$)$_2$, 2.18 (bs, 6H, —N(CH$_3$)$_2$, 2.16 (s, 3H, —CH$_3$). $^{13}$C NMR (125 MHz, d$_6$-DMSO): δ/ppm 178.1 (C=S), 146.1 (C=N), 57.6(—CH$_2$NH—), 45.5 (—N(CH$_3$)$_2$), 41.9 (—CH$_2$N(CH$_3$)$_2$, 11.9 (CH$_3$). FT-IR, cm$^{-1}$: 3337 (w, N—H), 3140 (br, m, N—H), 2974 (w), 2821 (w), 2767 (w), 1479 (vs, C=N), 1246 (s, thioamide), 806 (m), 606 (m).

NiATSM/DMEDA (21): To a solution of ATSM/DMEDA (0.4 g, 1.25 mmol) in MeOH (50 mL) was added Ni(OAc)$_2$. 4 H$_2$O (0.313 g, 1.25 mmol). Formed dark green suspension was heated with stirring for 4 h. The formed dark green solid was filtered and air dried. Yield=0.383 g (82%). X-ray quality single crystals were obtained via layering technique by slow diffusion of $Et_2O$ into a MeCN solution of 21. $^1$H NMR (400 MHz, $d_6$-DMSO) of NiATSM/DMEDA: δ/ppm 7.66 (bs, 1H, NH—C=S), 7.60 (bs, 1H, NH—C=S), 3.28 (q, $J_{HH}$=6.0 Hz, 2H, —CH$_2$NH—), 2.78 (d, $J_{HH}$=4.2 Hz, 3H, —CH$_3$), 2.33 ppm (t, $J_{HH}$=6.7 Hz, 2H, CH$_2$N(CH$_3$)$_2$,) 2.13 (bs, 6H, —N(CH$_3$)$_2$, 1.93-1.92 (bs, 6H, 2 x-CH$_3$). FT-IR, cm$^{-1}$: 3274 (br, m, N—H), 2945 (br, w), 1476 (vs, C=N), 1219 (s, thioamide), 942 (w), 771 (w). UV-vis (CH$_3$CN/MeOH, 1:1): $\lambda_{max}$, nm (ε, M$^{-1}$ cm$^{-1}$)=257 (27,000), 393 (13,000). Anal. Calc. for $C_{11}H_{21}N_7NiS_2$: C, 35.34; H, 5.66; N, 26.24. Found: C, 35.34; H, 5.65; N, 25.99. (-)ESI-MS, m/z calc. for [M-H]$^-$, [$C_{11}H_{21}N_7NiS_2$]-H; 372.07. Found: 371.96.

NiATSM/TMAEDA (22): To a suspension of NiATSM/DMEDA (0.200 g, 0.534 mmol) in MeCN (25 mL) was added methyl iodide (33.3 µL, 0.534 mmol). The resulting dark green suspension was stirred overnight. Formed dark green solid was filtered and air dried. Yield=0.212 g (77%). X-ray quality single crystals were grown using vapor diffusion technique in an H-shaped tube by slow diffusion of $CH_2Cl_2$ into a MeCN/MeOH (1:1) solution of 22. $^1$H NMR (400 MHz, $d_6$-DMSO) of NiATSM/TMAEDA: δ/ppm 7.96 (bs, 1H, NH—C=S), 7.77 (bs, 1H, NH—C=S), 3.61 (bs, 2H, —CH$_2$NH—), 3.42 ppm (t, $J_{HH}$=5.9 Hz, 2H, CH$_2$$^+$N(CH$_3$)$_3$), 3.09 (bs, 9H, —$^+$N(CH$_3$)$_3$), 2.79 (d, $J_{HH}$=3.5 Hz, 3H, —CH$_3$), 1.96 (bs, 6H, 2 x-CH$_3$). FT-IR, cm$^{-1}$: 3218 (br, s, N—H), 2938 (w), 1488 (br, vs, C=N), 1224 (s, thioamide), 964 (m), 922 (m). UV-vis (CH$_3$CN/MeOH, 1:1): $\lambda_{max}$, nm (ε, M$^{-1}$ cm$^{-1}$)=223 (20,000), 256 (24,000), 398 (12,000). Anal. Calc. for $C_{12}H_{24}IN_7NiS_2$: C, 27.93; H, 4.69; N, 19.00. Found: C, 27.96; H, 4.61; N, 18.96. (-) ESI-MS, m/z calc. for [M-H]$^-$, [$C_{12}H_{24}IN_7NiS_2$]-H; 513.99, Found: 513.99.

NiATSDMEDA (23): To a solution of ATSDMEDA (0.400 g, 1.06 mmol) in MeOH (50 mL) was added Ni(acac)$_2$. 2H$_2$O (0.307 g, 1.06 mmol). Formed dark green solution was heated with stirring for 4 h. A dark green precipitate, formed upon concentration of the solution, was filtered and air dried. Yield=0.337 g (74%). X-ray quality single crystals were obtained using layering technique by slow diffusion of $Et_2O$ into a MeCN/MeOH (1:1) solution of 23. $^1$H NMR (500 MHz, $d_6$-DMSO) of NiATSDEMDA: δ/ppm 7.61 (bs, 1H, —NH—C=S), 3.27 (q, $J_{HH}$=6.2 Hz, 2H, —CH$_2$NH—), 2.34 (t, $J_{HH}$=6.8 Hz, 2H, —CH$_2$N(CH$_3$)$_2$, 2.13 (bs, 6H, —N(CH$_3$)$_2$, 1.92 (bs, 3H, —CH$_3$). FT-IR, cm$^{-1}$: 3361 (br, m, N—H), 3189 (br, m, N—H), 2937 (br, m), 2767 (br, s), 1404 (vs, C=N), 1230 (s, thioamide), 934 (br, m), 769 (m). UV-vis (CH$_3$CN/MeOH, 1:1): $\lambda_{max}$, nm (ε, M$^{-1}$ cm$^{-1}$)=256 (20,000), 398 (11,000). Anal. Calc. for $C_{14}H_{30}N_8NiS_2$: C, 38.99; H, 6.54; N, 25.98. Found: C, 38.76; H, 6.40; N, 25.61. (+)ESI-MS spectrum of NiATSDMEDA (23) calc. for [$C_{14}H_{28}N_8NiS_2$]+H: 431.12. Found: 431.1298.

NiATSTMAEDA (24): To a suspension of NiATSM/DMEDA (0.200 g, 0.464 mmol) in acetonitrile (25 mL) was added methyl iodide (57.8 µL, 0.928 mmol). The resulting dark green suspension was stirred overnight. Formed dark green solid was filtered and air dried. Yield=0.205 g (62%). X-ray quality single crystals were grown using vapor diffusion technique in an H-shaped tube by slow diffusion of $Et_2O$ into a MeCN/MeOH (7:3) solution of 24. $^1$H NMR (500 MHz, $d_6$-DMSO) of NiATSTMAEDA: δ/ppm 8.07 (bs, 1H, —NH—C=S), 3.61 (bs, 2H, —CH$_2$NH—), 3.41 (t, $J_{HH}$=6.6 Hz, 2H, —CH$_2$$^+$N(CH$_3$)$_3$, 3.08 (bs, 9H, —$^+$N(CH$_3$)$_3$, 1.97 (bs, 3H, —CH$_3$). FT-IR, cm$^{-1}$: 3280 (br, m, N—H), 1410 (vs, C=N), 1227 (s, thioamide), 914 (br, m). UV-vis (CH$_3$CN/MeOH, 1:1): $\lambda_{max}$, nm (c, M$^{-1}$ cm$^{-1}$)=226 (33,000), 256 (28,000), 392 (13,000). Anal. Calc. for $C_{16}H_{34}I_2N_8NiS_2$. H$_2$O: C, 26.21; H, 4.95; N, 15.28. Found: C, 25.84; H, 4.71; N, 15.04. (-)ESI-MS, m/z calc. for [M-H]$^-$, [$C_{16}H_{34}I_2N_8NiS_2$]-H; 712.98. Found: 712.97.

Results and Discussion—Synthesis

Two $N_2S_2$ diacetyl-2,3-bis-(N4-alkyl-3-thiosemicarbazone) ligands (H$_2$L$^1$ and H$_2$L$^2$) were prepared via transamination of diacetyl-2,3-N4-methyl-3-thiosemicarbazone-N4-dimethyl-3-thiosemicarbazone and diacetyl-2,3-bis-(N4-dimethyl-3-thiosemicarbazone) with N,N-dimethylethylendiamine (Scheme H1). Compound 21 was obtained by synthesis of H$_2$L$^1$ with nickel(II) acetate tetrahydrate. The same synthetic approach attempted for compound 23, resulted in a protonated version. To overcome this problem, nickel(II) acetylacetonate was used instead as a nickel source, which allowed us to isolated the neutral compound 23. Compounds 21 and 23 were further alkylated with methyl iodide to obtain the charged compounds 22 and 24(See Scheme H1).

The UV-Vis spectra of 21-24 recorded in a mixture of acetonitrile/methanol solution display a ligand to metal charge transfer band near 400 nm. All four compounds display more intense ligand to ligand charge transfer bands near 256 MTh Two additional bands are observed in the alkylated species of 22 (223 nm) and 24 (226 nm), which can be attributed to the presence of the iodide counter anions. The infrared spectra of ligands H$_2$L$^1$ and H$_2$L$^2$ display an N—H stretch between 3337 and 3364 cm$^{-1}$ that is lost upon metal complexation.

Results and Discussion—Crystallographic Studies

X-ray quality single crystals of 21-24 were obtained as orange plates using layering or vapor diffusion techniques. All complexes crystallize as discrete, square planar Ni(II) complexes with no solvent molecules in the crystal lattice. Selected bond distances and angles are summarized in Table H1. Crystal data and structure refinement details are listed in Table H2.

TABLE H1

Selected Bond Distances (Å) and Angles (deg) for 21, 22, and 24.

| Bond distance | 21 (cag265ltb) | 22 (cag267lte) | 24 (cag271lta) |
|---|---|---|---|
| Ni1—N1 | 1.854(2) | 1.860(3) | 1.864(2) |
| Ni1—N2 | 1.861(2) | 1.846(3) | 1.869(2) |
| Ni1—S1 | 2.1540(8) | 2.1642(11) | 2.1710(7) |
| Ni1—S2 | 2.1493(8) | 2.1562(12) | 2.1715(7) |
| S1—C5 | 1.766(3) | 1.764(4) | 1.769(3) |
| S2—C10$^a$ | 1.780(3) | — | — |
| S2—C11$^a$ | — | 1.766(4) | 1.778(2) |
| N1—C1 | 1.304(4) | 1.301(5) | 1.314(3) |
| N1—N3 | 1.375(3) | 1.374(4) | 1.388(3) |
| N2—C2 | 1.307(4) | 1.317(5) | 1.312(3) |
| N2—N6 | 1.377(3) | 1.382(4) | 1.387(3) |
| N3—C5 | 1.321(4) | 1.307(5) | 1.324(3) |
| N4—C5 | 1.335(4) | 1.349(5) | 1.362(3) |
| N4—C6 | 1.461(4) | 1.443(6) | 1.461(3) |
| N6—C10$^a$ | 1.317(4) | — | — |
| N6—C11$^a$ | — | 1.324(5) | 1.316(3) |

TABLE H1-continued

Selected Bond Distances (Å) and Angles (deg) for 21, 22, and 24.

| Bond distance | 21 (cag265ltb) | 22 (cag267lte) | 24 (cag271lta) |
|---|---|---|---|
| N7—C10[a] | 1.329(4) | — | — |
| N7—C11[a] | — | 1.332(5) | 1.360(3) |
| N7—C11[a] | 1.453(4) | — | — |
| N7—C12[a] | — | 1.461(5) | 1.465(3) |
| C1—C2 | 1.471(4) | 1.481(6) | 1.483(3) |
| Bond angle | | | |
| N2—Ni1-N1 | 83.87(11) | 83.45(15) | 83.63(9) |
| N2—Ni1—S2 | 87.37(8) | 87.63(11) | 87.24(7) |
| N1—Ni1—S2 | 170.94(8) | 171.07(10) | 170.82(7) |
| N2—Ni1—S1 | 171.18(8) | 170.68(11) | 170.58(7) |
| N1—Ni1—S1 | 87.47(8) | 87.56(10) | 87.56(6) |
| S2—Ni1—S1 | 101.34(3) | 101.37(4) | 101.61(3) |

[a]The C10 in 21 is the same carbon atom as C11 in 22 and 24. The C11 in 21 is the same carbon atom as C12 in 22 and 24.

of 1.854(2), 1.861(2), 2.1540(8), and 2.1493(8) Å, respectively. The C10-S2, N6-N2, and C2-C1 bond distances of 1.780(3), 1.377(3), and 1.471(4) Å, respectively, are typical of single C—S, N—N, and C—C bonds. The shorter N2-C2 and N6-C10 bond distances of 1.307(4) and 1.317(4) Å, respectively, reveal C=N character.

The main core framework in compound 21, ignoring the functional groups of the pendant amines, is rigorously planar with the largest deviation from the best fit plane of all 15 non-hydrogen atoms of ±0.1437 Å for S1 and a standard deviation of ±0.0612 Å. The distance between the calculated least squares planes (mean: 15 atoms) of the two stack molecules is 3.437 Å. It is worth to mention that bond distances and bond angles within the $N_2S_2$ square plane in compound 21 are similar to the parent NiATSM. However, the core framework in compound 21 has a slightly higher deviation from the best fit plane than NiATSM (±0.0698 Å for S1 and a standard deviation of ±0.0255 Å). The observed higher deviation in 21 is due to the bulky dimethylaminoethyl functional group.

TABLE H2

Crystal Data and Structure Refinement for 21-24.

| Identification code | 21 (cag265ltb) | 22 (cag267lte) | 23 (cag273lta) | 24 (cag271lta) |
|---|---|---|---|---|
| Empirical formula | $C_{11}H_{21}N_7NiS_2$ | $C_{12}H_{24}IN_7NiS_2$ | C14 H24.50 N8 N1 S2 | $C_{16}H_{34}I_2N_8NiS_2$ |
| Formula weight | 374.18 | 516.09 | 427.75 | 715.14 |
| Temperature (K) | 102(3) | 101(1) | 102(2) | 101.95(10) |
| Wavelength (Å) | 0.71073 | 0.71073 | 0.71073 | 0.71073 |
| Crystal system | Orthorhombic | Monoclinic | Triclinic | Triclinic |
| Space group | Pbca | C2/c | P1 | P1 |
| Unit cell dimensions | | | | |
| a (Å) | 11.7031(4) | 13.9471(16) | 7.3123(7) | 8.8516(9) |
| b (Å) | 15.8057(5) | 13.9342(16) | 16.3895(14) | 9.5977(12) |
| c (Å) | 17.6173(4) | 20.699(3) | 17.6227(16) | 16.172(2) |
| α (deg) | 90 | 90.00 | 70.154(8) | 85.494(10) |
| β (deg) | 90 | 91.826(10) | 84.378(8) | 78.439(10) |
| γ (deg) | 90 | 90.00 | 89.994(7) | 80.176(10) |
| V (Å$^3$) | 3258.78(17) | 4020.6(8) | 1975.8(3) | 1324.9(3) |
| Z | 8 | 8 | 4 | 2 |
| d$_{calcd}$ (Mg/m$^3$) | 1.525 | 1.705 | 1.438 | 1.793 |
| Absorption coefficient (mm$^{-1}$) | 1.451 | 2.717 | 1.208 | 3.239 |
| F(000) | 1568 | 2064 | 898 | 704 |
| Crystal color, habit | dark orange plate | orange plate | orange plate | green-brown plate |
| Crystal size (mm$^3$) | 0.40 × 0.20 × 0.02 | 0.33 × 0.04 × 0.04 | 0.38 × 0.08 × 0.04 | 0.41 × 0.12 × 0.02 |
| θ range for data collection (deg) | 3.32 to 27.55 | 3.47 to 28.12 | 3.24 to 25.25 | 3.28 to 30.08 |
| Index ranges | −15 ≤ h ≤ 15 | −18 ≤ h ≤ 18 | −8 ≤ h ≤ 8 | −12 ≤ h ≤ 12 |
| | −20 ≤ k ≤ 20 | −18 ≤ k ≤ 18 | −16 ≤ k ≤ 16 | −13 ≤ k ≤ 13 |
| | −22 ≤ l ≤ 22 | −27 ≤ l ≤ 27 | −21 ≤ l ≤ 21 | −22 ≤ l ≤ 22 |
| Reflections collected | 42277 | 25351 | 20780 | 34415 |
| Independent reflections | 3764 [R(int) = 0.0485] | 4904 [R(int) = 0.049] | 7151 [R(int) = 0.1120] | 7776 [R(int) = 0.0455] |
| Completeness to theta max (%) | 99.8 | 99.7 | 99.8 | 99.8 |
| Absorption correction | multi-scan | multi-scan | multi-scan | multi-scan |
| Max. and min transmission | 1.00 and 0.69 | 1.000 and 0.718 | 1.000 and 0.877 | 1.000 and 0.593 |
| Refinement method | full-matrix least-squares on F$^2$ | full-matrix least-squares on F$^2$ | full-matrix least-squares on F$^2$ | full-matrix least-squares on F$^2$ |
| Data/restrains/parameters | 3764/0/253 | 4904/0/233 | 7151/8/465 | 7776/0/308 |
| Goodness of fit on F$^2$ | 1.073 | 1.074 | 1.051 | 1.060 |
| Final R indices [I > 2σ(I)][a,b] | R1 = 0.0441, wR2 = 0.0957 | R1 = 0.0423, wR2 = 0.0970 | R1 = 0.0739, wR2 = 0.1215 | R1 = 0.0281, wR2 = 0.0508 |
| R indices (all data)[a,b] | R1 = 0.0647, wR2 = 0.1051 | R1 = 0.0571, wR2 = 0.1046 | R1 = 0.1335, wR2 = 0.1424 | R1 = 0.0402, wR2 = 0.0551 |
| Largest diff. peak and hole (e · Å$^{-3}$) | 0.639 and −0.352 | 1.621 and −0.439 | 1.253 and −0.773 | 1.692 and −0.903 |

[a]R1 = Σ||Fo| − |F$_c$||/Σ|F$_o$|. [b]wR2 = {Σ[w(F$_o^2$ − F$_c^2$)$^2$]/Σ[w(F$_o^2$)$^2$]}$^{1/2}$, where w = q/σ$^2$(F$_o^2$) + (qp)$^2$ + bp. GOF = S = {Σ[w(F$_o^2$ − F$_c^2$)$^2$]/(n − p)}$^{1/2}$, where n is the number of reflections and p is the number of parameters refined.

Figure 67:
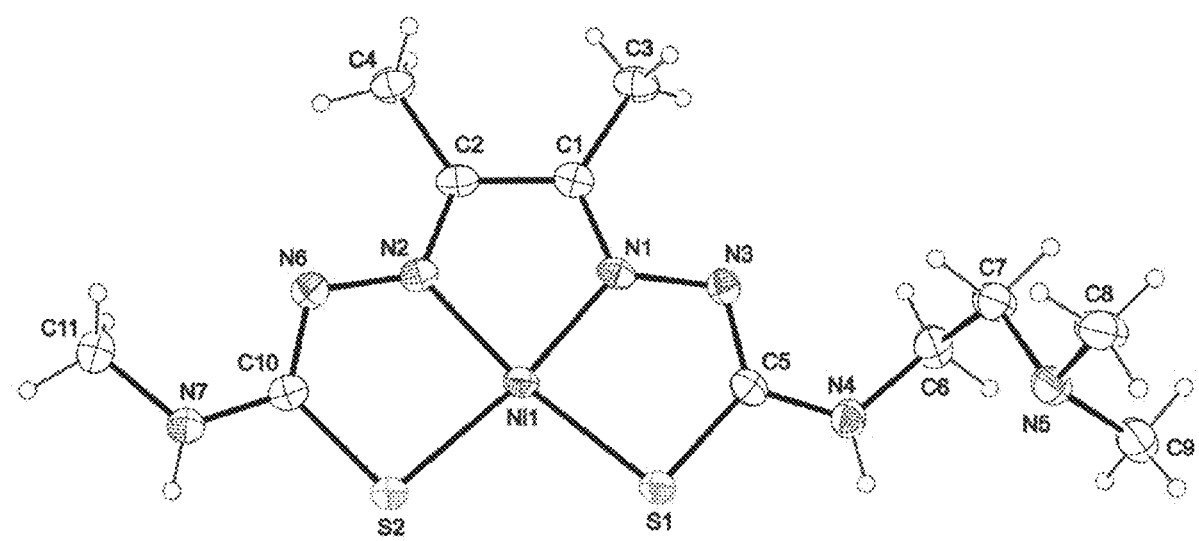
FIG. 67. ORTEP view (50% probability) of compound 21—showing atom labeling for all non-hydrogen atoms in the asymmetric unit.
Figure 68:
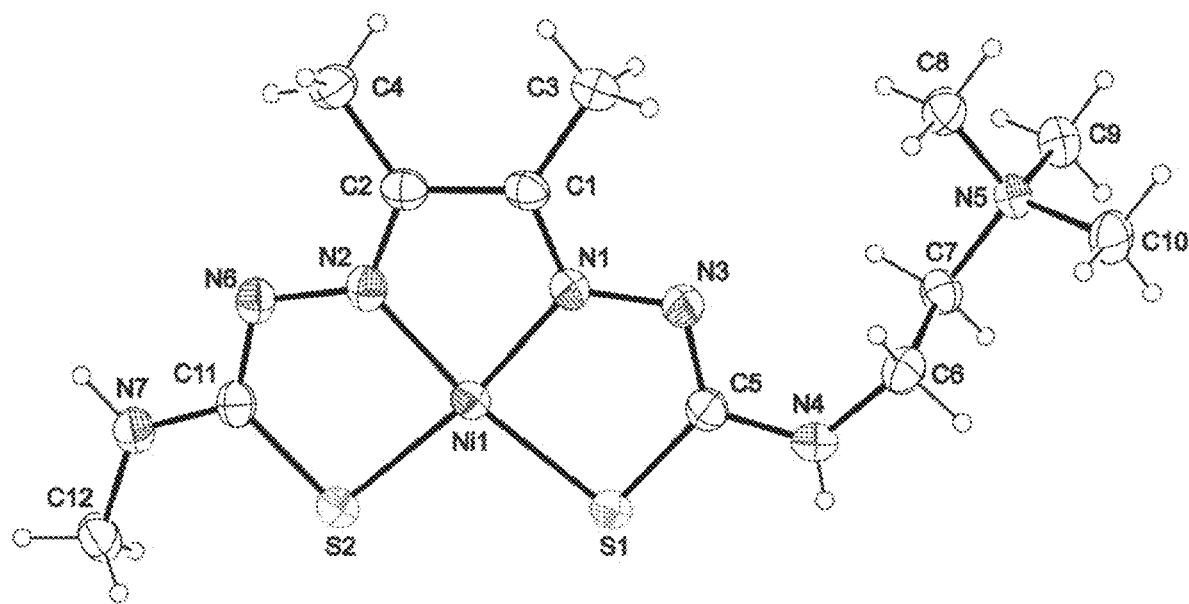
FIG. 68. ORTEP view (50% probability) depicting the cation of compound 22—showing atom labeling for all non-hydrogen atoms in the asymmetric unit. The counter anion iodide is omitted for clarity.

Single crystals of 21 were obtained from a slow diffusion of Et$_2$O into a MeCN solution of 21 as orange plates in the orthorhombic space group Pbca. The asymmetric unit of 21 consists of one equivalent of NiATSM/DMEDA, FIG. 67. The Ni of 21 occupies an N$_2$S$_2$ square plane provided by the N,N'-(dimethylethylenediaminothiosemi-carbazanato)-4-(methylthiosemicarbazanato)-butane-2,3-diimine ligand with Ni—N1, Ni—N2, Ni—S1, and Ni—S2 bond distances X-ray quality single crystals of 22 were isolated from an H-shaped tube by slow diffusion of CH$_2$Cl$_2$ into a MeCN/MeOH solution of 22 as orange plates in the monoclinic space group C2/c. The asymmetric unit of 22 consists of one equivalent of NiATSM/TMAEDA, FIG. 68. Like in compound 21, the Ni of 22 occupies an N$_2$S$_2$ square plane provided by the N,N'-(trimethyl-ethyleneammoniumthiosemicarbazanato)-4-(methylthiosemicarbazanato)butane-2, 3-diimine ligand. The Ni—N1 and Ni—N2 bond distances of 1.860(3) and 1.846(3) Å, respectively, in 22 are the same as those observed in 21. While the Ni—S1 and Ni—S2 bond distances of 2.1642(11) and 2.1562(12) Å, respectively, in 22 are slightly longer than those observed in 21 (Table H1).

Figure 69:
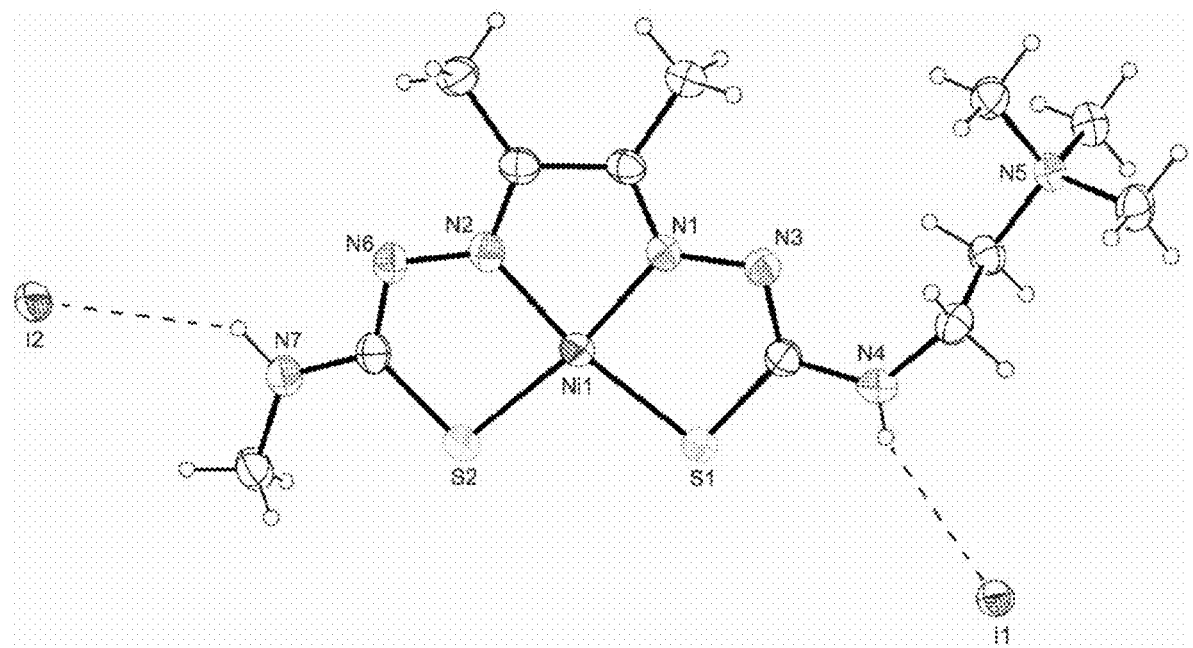
FIG. 69. ORTEP view (50% probability) of compound 22—showing atom labeling for all non-hydrogen atoms in the asymmetric unit.

The observed longer Ni—S bonds in 22 are due to the iodide counter ion interacting with pendant NH resulting in elongation of the Ni—S bonds (FIG. 69). In addition, the Ni—S2 bond distance is longer than Ni—S1 due to the electron withdrawing trimethylammonium functional group. The main core framework in complex 22, ignoring the functional groups of the pendant amines, is rigorously planar with the largest deviation from the best fit plane of all 15 non-hydrogen atoms of ±0.0749 Å for S1 and a standard deviation of ±0.0253 Å, which is nearly the same as in NiATSM. The distance between the calculated least squares planes (mean: 15 atoms) of the two stack molecules is 3.472 Å.

Figure 70:
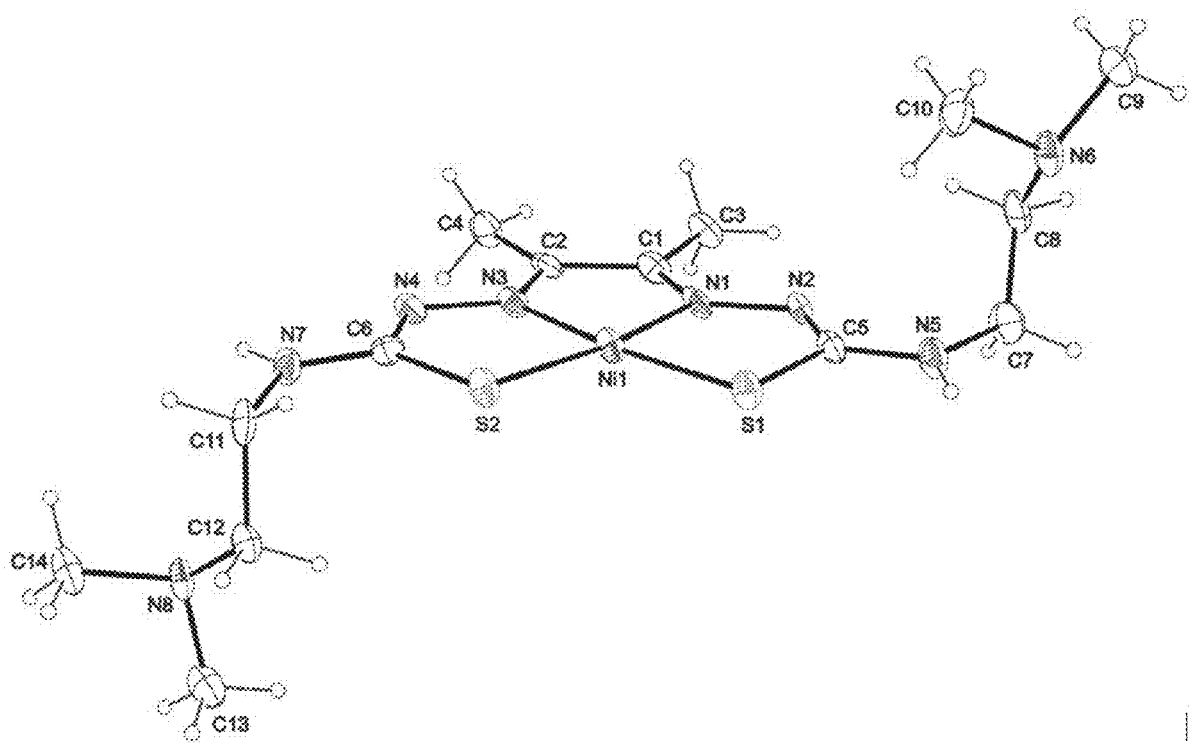
FIG. 70. ORTEP view (50% probability) of compound 23—showing atom labeling for all non-hydrogen atoms in the asymmetric unit.
Figure 71:
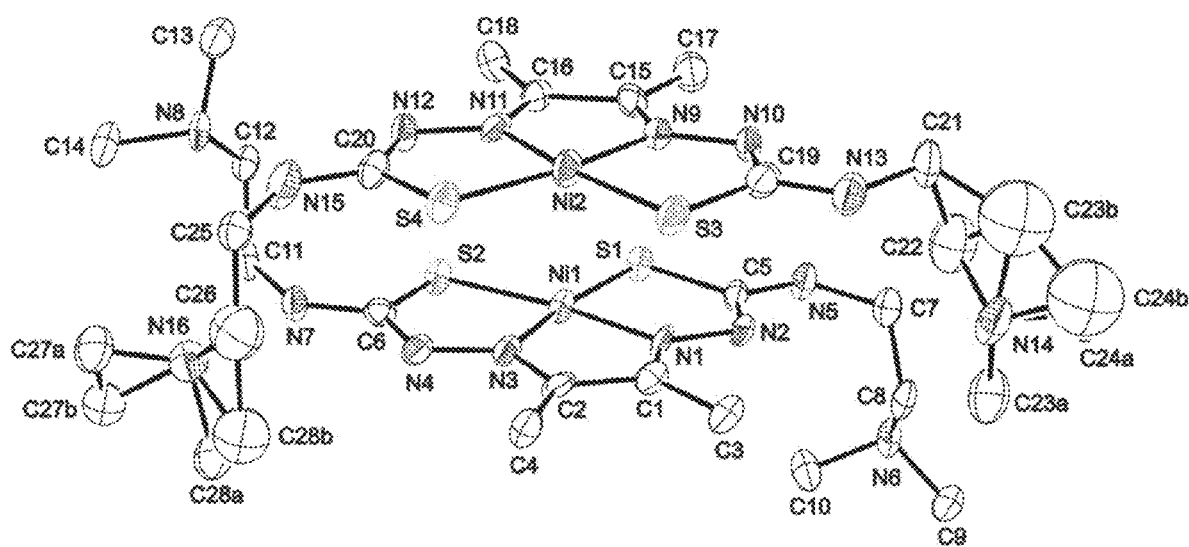
FIG. 71. ORTEP view (50% probability) of compound 23—showing atom labeling for all non-hydrogen atoms in the asymmetric unit. All hydrogen atoms are omitted for clarity.

Compound 23 crystallizes as orange plates from slow diffusion of $Et_2O$ into a MeCN/MeOH solution of 23 in the triclinic space group P-1. The Ni of 23 occupies an $N_2S_2$ square plane provided by the N,N'-bis(dimethylethylenediaminothiosemicarbazanato)butane-2,3-diimine ligand. The asymmetric unit of 23 consists of two, crystallographically distinct equivalents of NiATSDMEDA. Notably, the terminal dimethyl amino groups in the Ni1 molecule are oriented in the opposite way from the main $N_2S_2$ square plane, FIG. 70. While in the second Ni2 molecule they are oriented in the same direction, FIG. 71. The terminal dimethyl amino functional groups in the Ni2 molecule were found to be disordered. Modeled disorder did not help to significantly improve the crystal data quality. Therefore, bond distances and angles for compound 23 will not be discussed in details due to high standard deviation errors.

Figure 72:
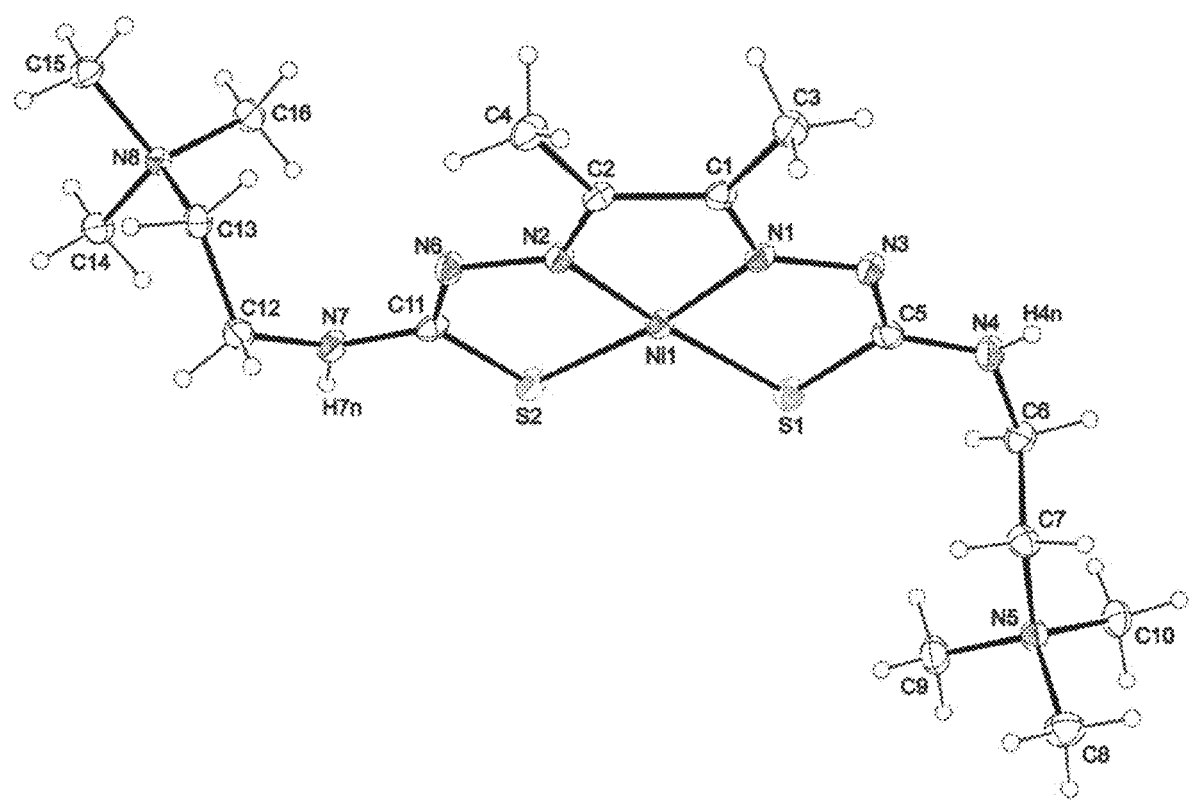
FIG. 72. ORTEP view (50% probability) depicting the cation of compound 24—showing atom labeling for all non-hydrogen atoms in the asymmetric unit. The two counter anion iodides are omitted for clarity.
Figure 73:
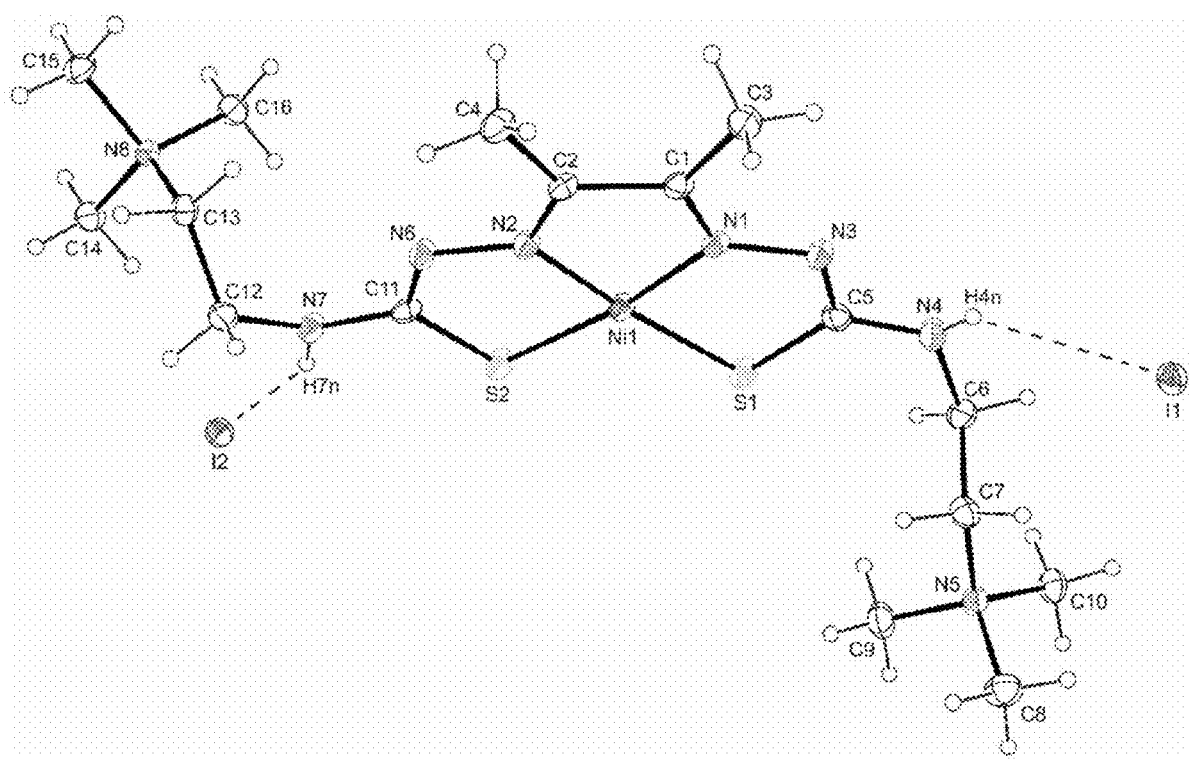
FIG. 73. ORTEP view (50% probability) of compound 24—showing atom labeling for all non-hydrogen atoms in the asymmetric unit.

Green-brown plate crystals of 24 in the triclinic space group P-1 were obtained using vapor diffusion technique in an H-shaped tube by slow diffusion of $Et_2O$ into a MeCN/MeOH solution of 24. The asymmetric unit of 24 consists of one equivalent of NiATSTMAEDA, FIG. 72. The Ni of 24 occupies an $N_2S_2$ square plane provided by the N,N'-bis(trimethylethylene-ammoniumthiosemicarbazanato)butane-2,3-diimine ligand. The Ni—N1 and Ni—N2 bond distances of 1.864(2) and 1.869(2) Å, respectively, in 24 are the same as those observed in 21 and 22. Nevertheless, the Ni—S1 and Ni—S2 bond distances of 2.1710(7) and 2.1715(7) Å, respectively, in 24 are longer than those observed in 21 and 22 (Table H1). The observed longer Ni—S bonds in 24 are due to the iodide counter ions interacting with the pendant NH and the symmetrical electron withdrawing trimethylammonium functional group resulting in elongation of the Ni—S bonds (FIG. 73). The main core framework in compound 24, ignoring the functional groups of the pendant amines, is rigorously planar with the largest deviation from the best fit plane of all 15 non-hydrogen atoms of ±0.0701 Å for S2 and a standard deviation of ±0.0375 Å, which is nearly the same as in 22.

The N2-Ni1-N1, N2-Ni1-S2, N1-Ni1-S1, and S2-Ni1-S1 bond angles in 21, 22, and 24 are the same (Table H1). The sum of the four bond angles around the Ni center in 21, 22, and 24 are 360.05(8), 360.01(10), and 360.04(6)°, respectively.

In the solid state crystal packing of 24, molecules are stacking into an ABAB arrangement along the b axis. The distance between the calculated least squares planes (mean: 15 atoms) of the two stack molecules is 3.485 Å.

Figure 74:
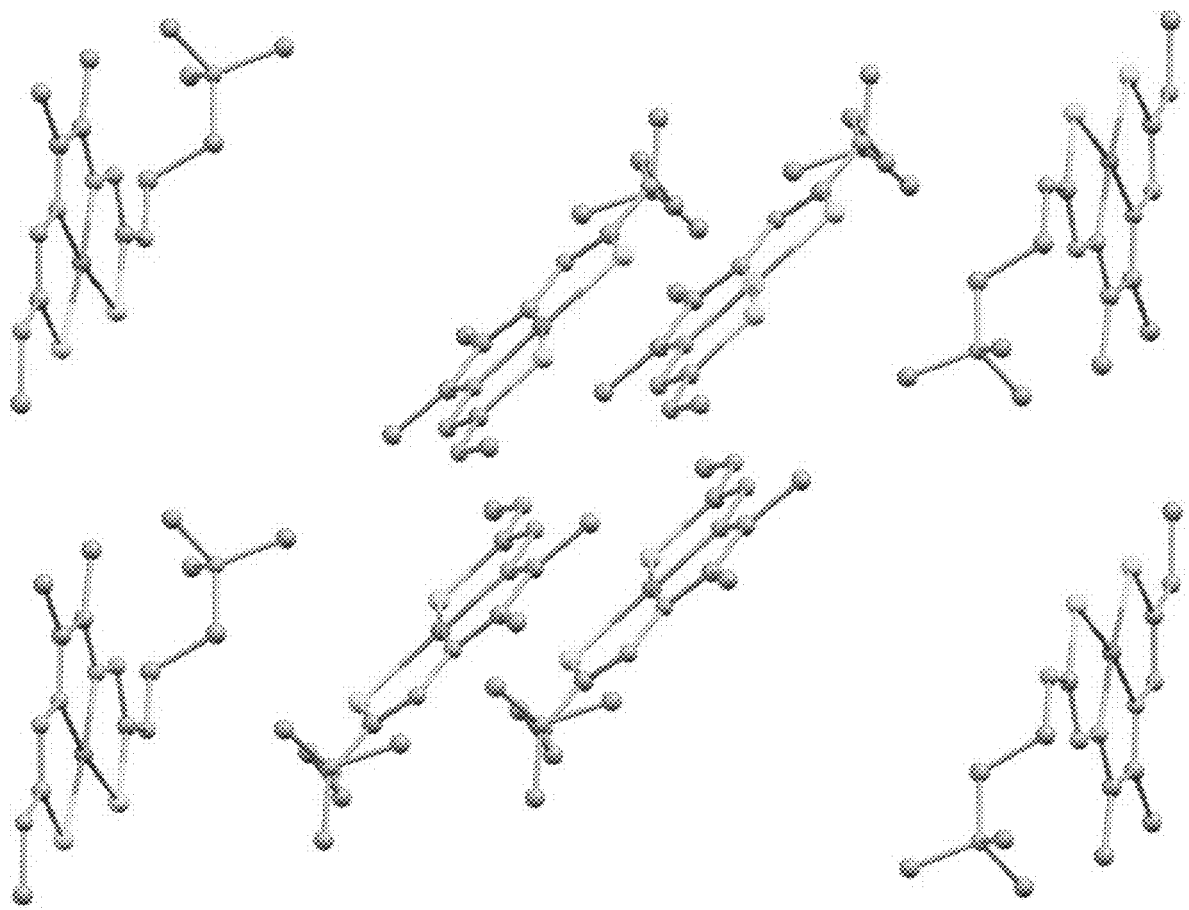
FIG. 74. The unit cell (C2/c) of the cation of compound 22—iodide counter ion and hydrogens atoms are omitted for clarity.
Figure 75:
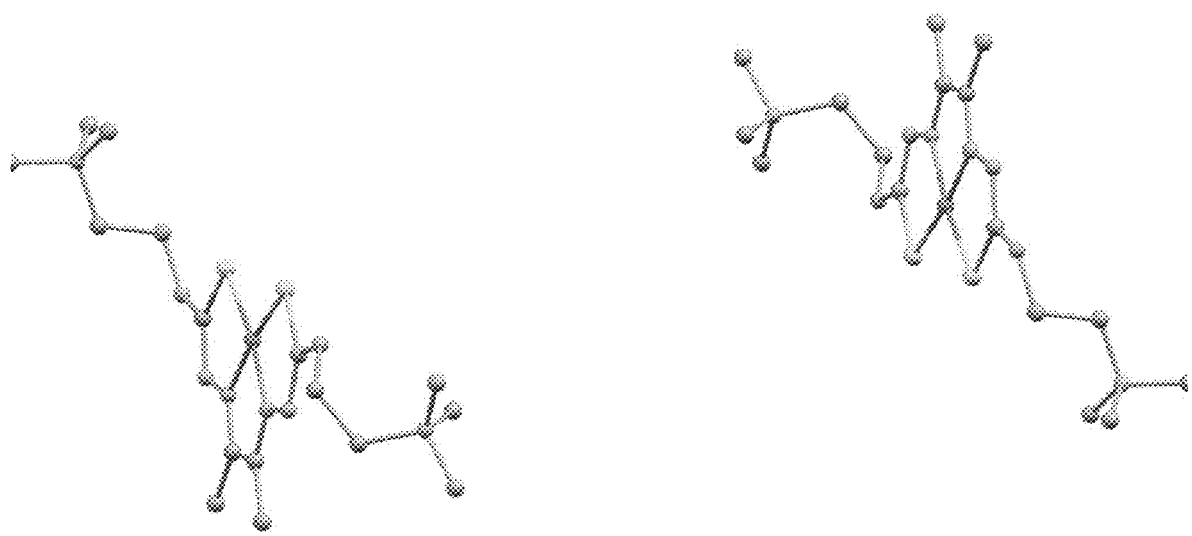
FIG. 75. The unit cell (P-1) of the cation of compound 24—iodide counter ions and hydrogens atoms are omitted for clarity.

FIG. 74 illustrates the unit cell (C2/c) of the cation of compound 22; iodide counter ion and hydrogens atoms are omitted for clarity. FIG. 75 illustrates the unit cell (P-1) of the cation of compound 24; iodide counter ions and hydrogens atoms are omitted for clarity.

Results and Discussion—Electrochemical Studies

Figure 76:
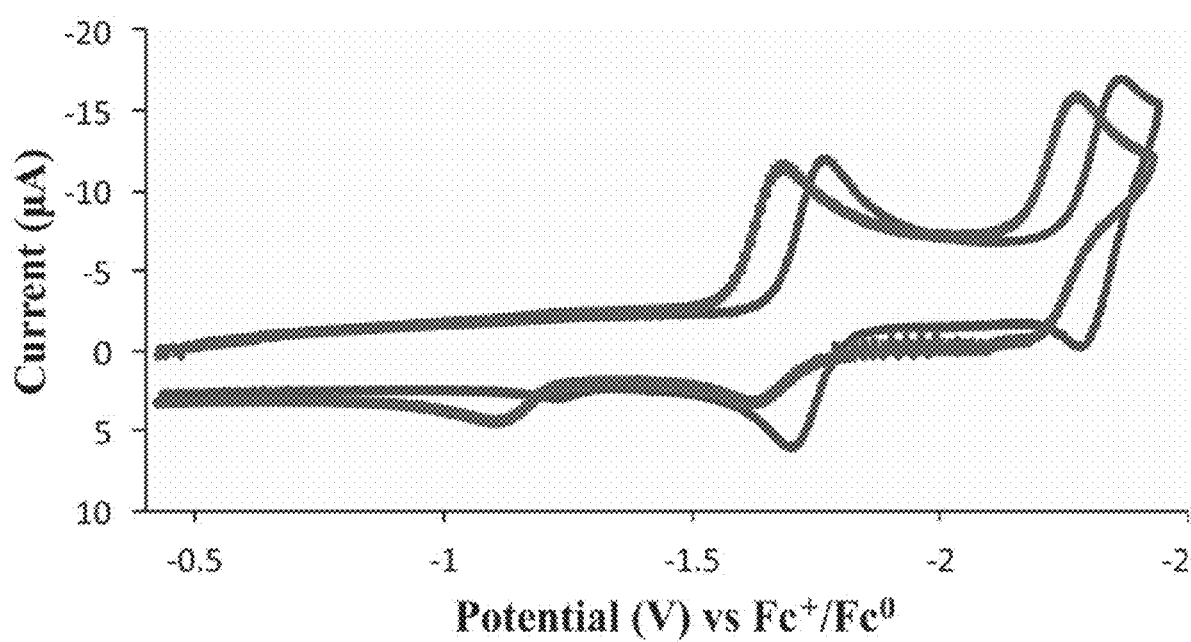
FIG. 76. Cyclic voltammetry for compounds 21 (blue) and 22 (red)—in the absence of substrate.
Figure 77:
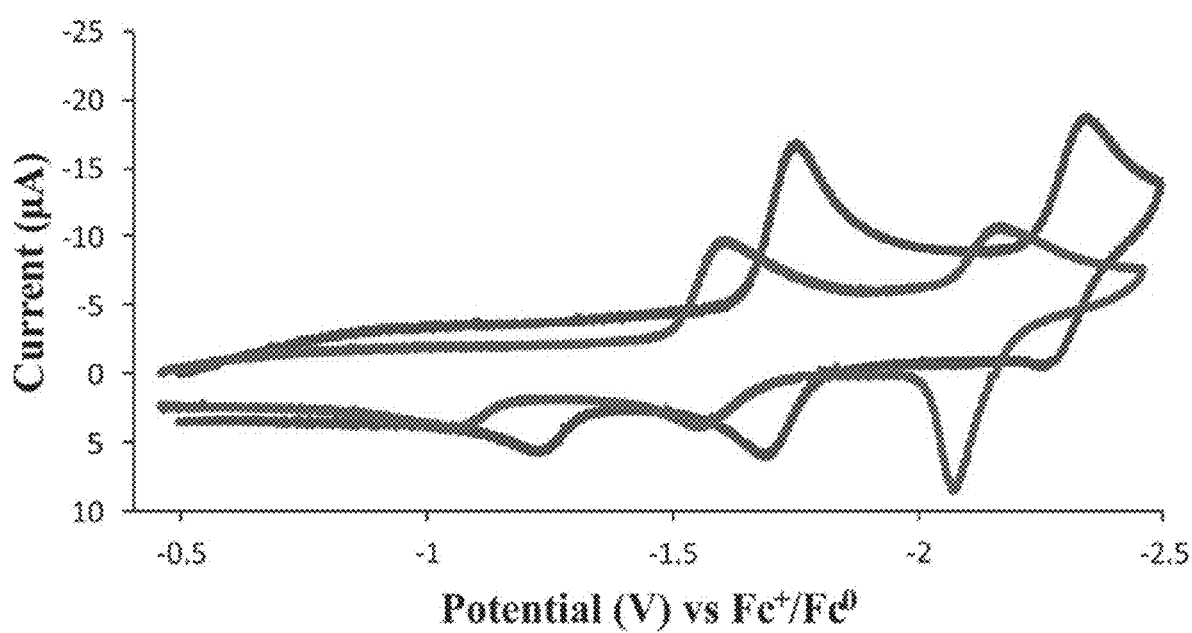
FIG. 77. Cyclic voltammetry for compounds 23 (blue) and 24 (red)—in the absence of substrate.
Figure 78:
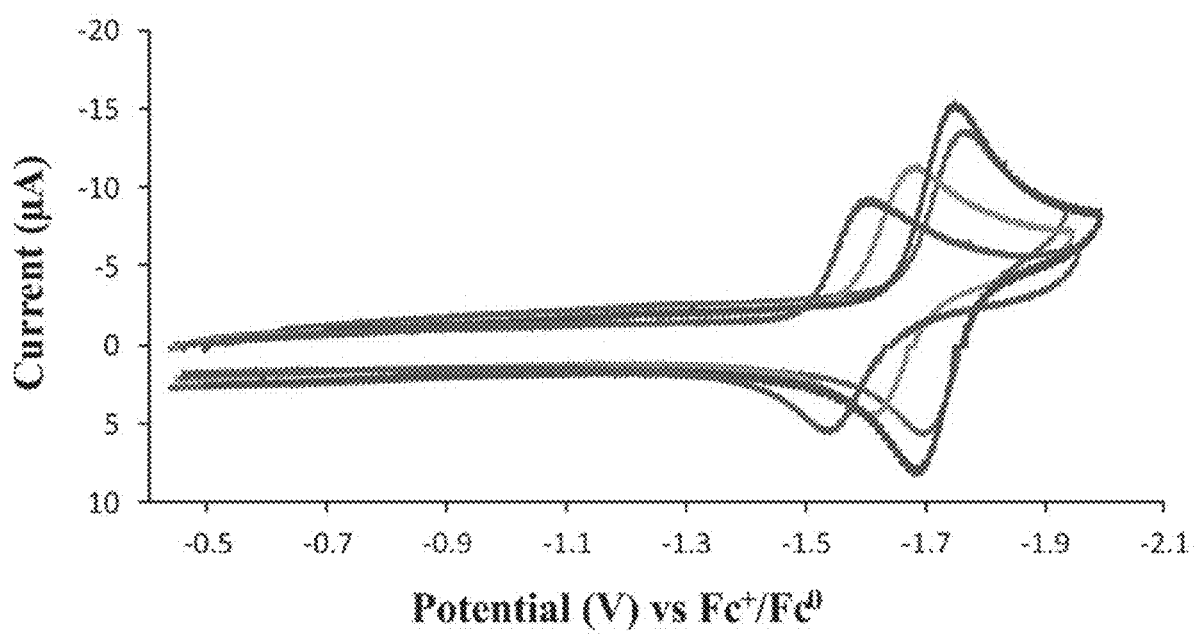
FIG. 78. CV of the first ligand centered reduction/oxidation event Ni(II)L/Ni(II)L⁻ in 21-24 (21—green; 22—orange; 23—blue; 24—red).

The cyclic voltammograms of 21-24 were recorded in acetonitrile with tetrabuytlammonium hexafluorophosphate as a supporting electrolyte. The CV of 21-24 display two quasi-reversible events in the cathodic region from 0 to −2 V vs $Fc^+/Fc^0$ (FIGS. 76 and 77). In addition, all four complexes display an irreversible oxidation event between −1 and −1.3 V, which is only observed after scanning through the second reduction event (FIG. 78). The first event for 21 and 23, $E_{1/2}$=−1.73 and −1.72 V, respectively, is assigned to ligand centered reduction/oxidation, Ni(II)L/Ni(II)L$^-$. The second event for 21 and 23 at −2.32 and −2.31 V, respectively, is assigned as metal-centered $Ni^{II/I}$ couple. The CV of 21 and 23 in MeCN display similar quasi-reversible ligand-centered and metal-centered events as in the reported NiATSM at −1.73 and −2.31 V, respectively. However, the CV of alkylated compounds 22 and 24 display a significant shift, for both electrochemical events, in the anodic direction (FIGS. 76 and 77). Thus, the ligand-centered and metal-centered events in 22 are shifted by −80 and −90 mV, respectively, comparing to the non-alkylated compound 21 (Table H3). While in compound 24, both events are shifted by −140 and −170 mV, respectively, comparing to the non-alkylated compound 23. Therefore, as we anticipated, the double alkylation vs mono alkylation results in a doubling of the electrochemical shifts to a lower potential.

TABLE H3[a]

| Compound | NiL/NiL$^-$ $E_{1/2}$ (V) | $Ni^{II/I}$ $E_{1/2}$ (V) |
|---|---|---|
| 21 | −1.73 (−80 mV) | −2.32 (−90 mV) |
| 22 | −1.65 (−80 mV) | −2.23 (−90 mV) |
| 23 | −1.72 (−140 mV) | −2.31 (−170 mV) |
| 24 | −1.58 (−140 mV) | −2.14 (−170 mV) |

[a]Data recorded on 0.3 mM of 21-24 in 0.1M $Bu_4NPF_6$ $CH_3CN$ solution at a scan rate of 200 mV/s with potentials vs. $Fc^+/Fc^0$.

Results and Discussion—Electrocatalytic Hydrogen Evolution Studies

Figure 79:
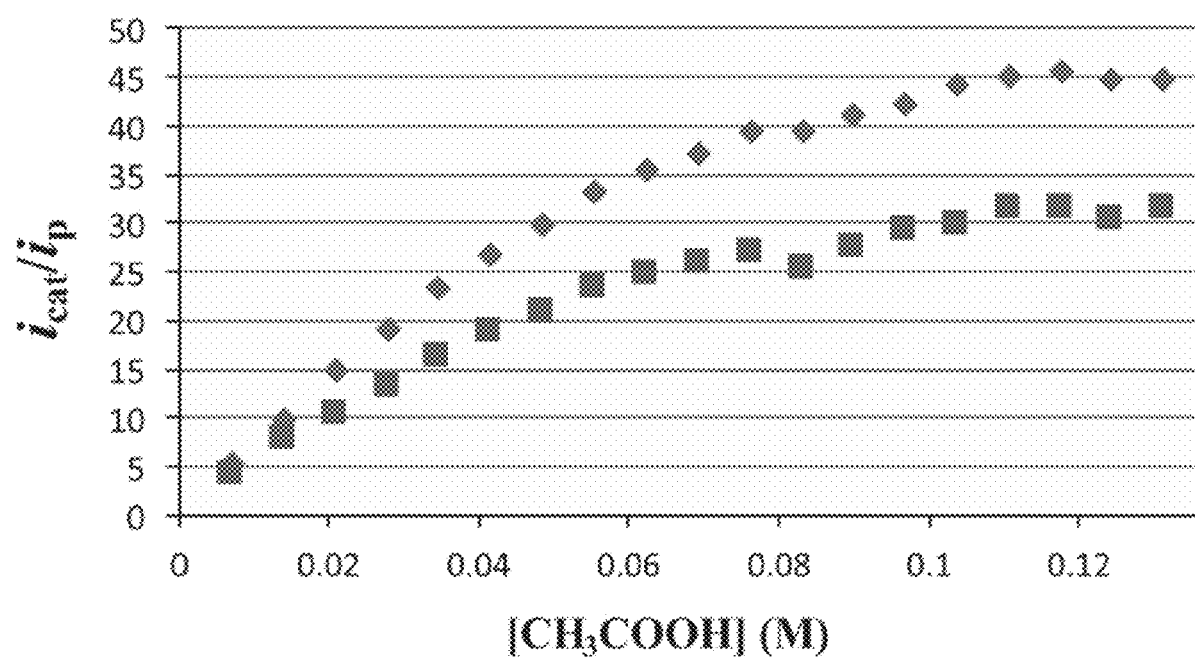
FIG. 79. The $i_{cat}/i_p$ vs [CH$_3$COOH] plots for compounds 21 (blue-diamonds) and 22 (red-squares)—at the scan rate of 200 mV/s.
Figure 80:
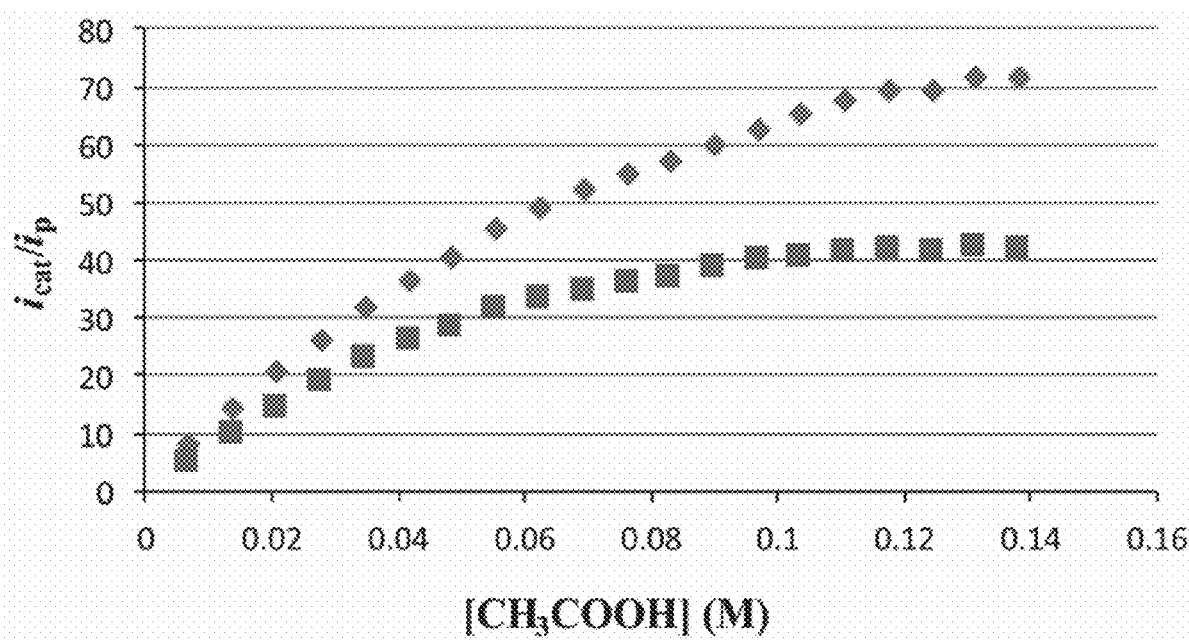
FIG. 80. The $i_{cat}/i_p$ vs [CH$_3$COOH] plots for compounds 23 (blue-diamonds) and 24 (red-squares)—at the scan rate of 200 mV/s.

The performance of 21-24 as electrocatalysts for the hydrogen evolution reaction was evaluated in MeCN using as a proton source glacial acetic acid. The catalytic to peak current ratio ($i_{cat}/i_p$) increase linearly with the increase of the acid concentration. The value of $i_{cat}/i_p$ saturates when the concentration of $CH_3COOH$ reaches 100 mM (FIGS. 79 and 80).

The turnover frequencies (TOF) for 21-24 were determined using foot-of-the-wave analysis (FOWA) (COSTENTIN et al., "Turnover Numbers, Turnover Frequencies, and Overpotential in Molecular Catalysis of Electrochemical Reactions. Cyclic Voltammetry and Preparative-Scale Electrolysis" J. Am. Chem. Soc. (2012) Vol. 134, pp. 11235-11242). Thus, it was found that non-alkylated compounds 21 and 23 have a higher TOF of 2858 and 6296 s$^{-1}$, respectively, than the alkylated compounds 22 and 24 with a TOF of 1524 and 2416 s$^{-1}$, respectively. The same trend was observed for the overpotentials of 21-24 equal to 0.59, 0.66, 0.56, and 0.67 V, respectively. See Table H4. Compound 23 appears to be the most efficient catalyst due to the doubly equivalent basic tertiary amines on the pendant arms.

TABLE H4

| Compound | TOF (s$^{-1}$) | η (V vs Fc$^+$/Fc$^0$) |
|---|---|---|
| 21 | 2858 | 0.59 |
| 22 | 1524 | 0.66 |
| 23 | 6296 | 0.56 |
| 24 | 2416 | 0.67 |

Conclusions—Example Set H

It was demonstrated through electrochemical experiments that compounds 22 and 24 with the point-charges on the ligand framework shows a more anodic onset potential compared to non-alkylated parent compounds 21 and 23.

Cyclic voltammetry studies were performed on compounds 21-24 with addition of glacial acetic acid to see if the compounds are catalytically active. Compounds 21-24 were found to be effective catalysts for the hydrogen evolution reaction (HER).

Additional Embodiments

A1. A compound selected from a compound of Formula (I),

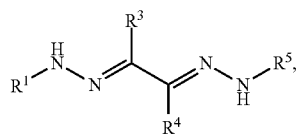

and salts, optical isomers, geometric isomers, salts of isomers, and derivatives thereof, wherein
—$R^1$ is

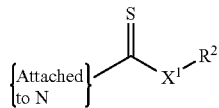

or is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—CO$_2$H), nitro (—NO$_2$), cyano (—CN), ethynyl (—CCH), sulfo (—SO$_3$H), methyl, or ethyl;
—$X^1$ is bivalent —(NH)—, —O—, —(CH$_2$)—, or —S—, which —(NH)— or —(CH$_2$)— can optionally be substituted with one or more (e.g., 0, 1, or 2) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—CO$_2$H), nitro (—NO$_2$), cyano (—CN), ethynyl (—CCH), sulfo (—SO$_3$H), methyl, or ethyl;
—$R^2$ is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—CO$_2$H), nitro (—NO$_2$), cyano (—CN), ethynyl (—CCH), sulfo (—SO$_3$H), methyl, or ethyl;
—$R^3$ is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—CO$_2$H), nitro (—NO$_2$), cyano (—CN), ethynyl (—CCH), sulfo (—SO$_3$H), methyl, or ethyl;
—$R^4$ is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—CO$_2$H), nitro (—NO$_2$), cyano (—CN), ethynyl (—CCH), sulfo (—SO$_3$H), methyl, or ethyl;
—$R^5$ is

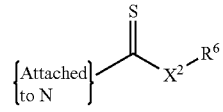

or is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl, heteroaryl (e.g., pyridinyl and 1-methyl imidazolyl), C$_1$-C$_7$ alkyl (e.g., C$_1$, C$_2$, C$_3$, C$_4$, C$_5$, C$_6$, or C$_7$ alkyl), C$_2$-C$_7$ alkenyl (e.g., C$_2$, C$_3$, C$_4$, C$_5$, C$_6$, or C$_7$ alkenyl), C$_2$-C$_7$ alkynyl (e.g., C$_2$, C$_3$, C$_4$, C$_5$, C$_6$, or C$_7$ alkynyl), or C$_1$-C$_6$ alkoxy (C$_1$, C$_2$, C$_3$, C$_4$, C$_5$, or C$_6$ alkoxy), which aryl (e.g., benzene or pyrene), cycloalkyl, heterocyclyl, heteroaryl (e.g., pyridinyl and 1-methyl imidazolyl), C$_1$-C$_7$ alkyl, C$_2$-C$_7$ alkenyl, C$_2$-C$_7$ alkynyl, or C$_1$-C$_6$ alkoxy can optionally be substituted with one or more (e.g., 0, 1, 2, 3, 4, 5, or 6) of halogen (e.g., F, Cl, Br, or I), hydroxy (—OH), C$_1$-C$_5$ alkyl (e.g., C$_1$, C$_2$, C$_3$, C$_4$, or C$_5$ alkyl), C$_1$-C$_4$ alkoxy (C$_1$, C$_2$, C$_3$, or C$_4$ alkoxy), methanoly (—COH), carboxy (—CO$_2$H), nitro (—NO$_2$), cyano (—CN), ethynyl (—CCH), sulfo (—SO$_3$H), methyl, or ethyl;

—X$^2$ is bivalent —(NH)—, —O—, —(CH$_2$)—, or —S—, which —(NH)— or —(CH$_2$)— can optionally be substituted with one or more (e.g., 0, 1, or 2) of halogen (e.g., F, Cl, Br, or I), hydroxy (—OH), C$_1$-C$_5$ alkyl (e.g., C$_1$, C$_2$, C$_3$, C$_4$, or C$_5$ alkyl), C$_1$-C$_4$ alkoxy (C$_1$, C$_2$, C$_3$, or C$_4$ alkoxy), methanoly (—COH), carboxy (—CO$_2$H), nitro (—NO$_2$), cyano (—CN), ethynyl (—CCH), sulfo (—SO$_3$H), methyl, or ethyl; and —R$^6$ is a monovalent H, methanoly (—COH), carboxy (—CO$_2$H), nitro (—NO$_2$), sulfo (—SO$_3$H), halogen (e.g., F, Cl, Br, or I), aryl (e.g., benzene or pyrene), cycloalkyl, heterocyclyl, heteroaryl (e.g., pyridinyl and 1-methyl imidazolyl), C$_1$-C$_7$ alkyl (e.g., C$_1$, C$_2$, C$_3$, C$_4$, C$_5$, C$_6$, or C$_7$ alkyl), C$_2$-C$_7$ alkenyl (e.g., C$_2$, C$_3$, C$_4$, C$_5$, C$_6$, or C$_7$ alkenyl), C$_2$-C$_7$ alkynyl (e.g., C$_2$, C$_3$, C$_4$, C$_5$, C$_6$, or C$_7$ alkynyl), or C$_1$-C$_6$ alkoxy (C$_1$, C$_2$, C$_3$, C$_4$, C$_5$, or C$_6$ alkoxy), which aryl (e.g., benzene or pyrene), cycloalkyl, heterocyclyl, heteroaryl (e.g., pyridinyl and 1-methyl imidazolyl), C$_1$-C$_7$ alkyl, C$_2$-C$_7$ alkenyl, C$_2$-C$_7$ alkynyl, or C$_1$-C$_6$ alkoxy can optionally be substituted with one or more (e.g., 0, 1, 2, 3, 4, 5, or 6) of halogen (e.g., F, Cl, Br, or I), hydroxy (—OH), C$_1$-C$_5$ alkyl (e.g., C$_1$, C$_2$, C$_3$, C$_4$, or C$_5$ alkyl), C$_1$-C$_4$ alkoxy (C$_1$, C$_2$, C$_3$, or C$_4$ alkoxy), methanoly (—COH), carboxy (—CO$_2$H), nitro (—NO$_2$), cyano (—CN), ethynyl (—CCH), sulfo (—SO$_3$H), methyl, or ethyl.

A2. The compound of embodiment A1, wherein (a) R$^3$ is the same as R$^4$;

(b) R$^3$ is the same as R$^4$ and R$^1$ is the same as R$^5$;

(c) R$^3$ is the same as R$^4$, X$^1$ is —(NH)—, X$^2$ is —(NH)—, and R$^2$ is the same as R$^6$;

(d) R$^3$ is the same as R$^4$, R$^3$ is methyl, R$^1$ is the same as R$^5$, R$^1$ is

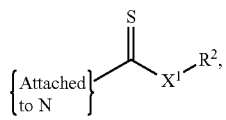

X$^1$ is —(NH)—, and R$^2$ is —CH$_3$;

(e) R$^3$ is the same as R$^4$, R$^3$ is methyl, R$^1$ is the same as R$^5$, R$^1$ is

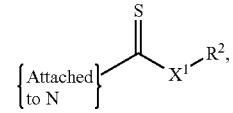

X$^1$ is —(NH)—, and R$^2$ is —C$_5$H$_6$;

(f) R$^3$ is the same as R$^4$, R$^3$ is methyl, R$^1$ is the same as R$^5$, R$^1$ is

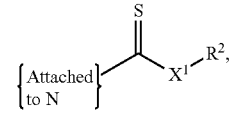

X$^1$ is —(NH)—, and R$^2$ is —CH$_2$F$_3$;

(g) R$^3$ is the same as R$^4$, R$^3$ is methyl, R$^1$ is the same as R$^5$, R$^1$ is

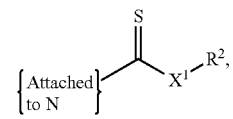

X$^1$ is —(NCH$_3$)—, and R$^2$ is —CH$_3$;

(h) R$^3$ is the same as R$^4$, R$^3$ is methyl, R$^1$ is the same as R$^5$, R$^1$ is

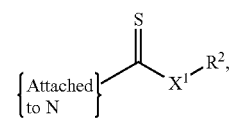

X$^1$ is —O—, and R$^2$ is —CH$_3$;

(i) R$^3$ is the same as R$^4$ and R$^3$ is methyl;

(j) R$^3$ is the same as R$^4$ and R$^3$ is ethyl;

(k) R$^3$ is methyl and R$^4$ is phenyl;

(l) R$^1$ is

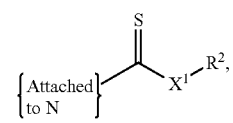

X$^1$ is —(NH)—, R$^2$ is —CH$_3$, R$^5$ is

$X^2$ is —(N—CH(CH$_3$)$_2$)—, and R$^6$ is —CH(CH$_3$)$_2$;
(m) R$^1$ is

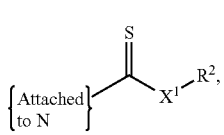

X$^1$ is —(NH)—, R$^2$ is —CH$_3$, R$^5$ is

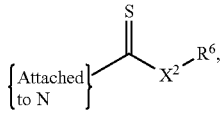

X$^2$ is —(NH)—, and R$^6$ is —C$_5$H$_6$;
(n) R$^1$ is

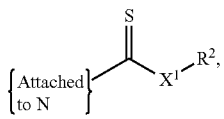

X$^1$ is —(NH)—, R$^2$ is —CH$_3$, R$^5$ is

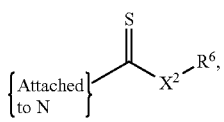

X$^2$ is —(NH)—, and R$^6$ is —CH$_2$CF$_3$;
(o) R$^1$ is

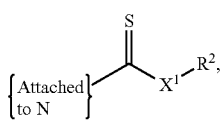

X$^1$ is —(NH)—, R$^2$ is —CH$_3$, R$^5$ is

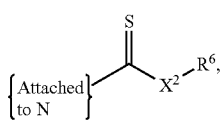

X$^2$ is —O—, and R$^6$ is —CH$_3$;
(p) R$^1$ is

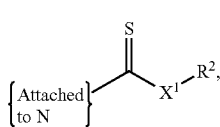

X$^1$ is —(NH)—, R$^2$ is —CH$_3$, R$^5$ is

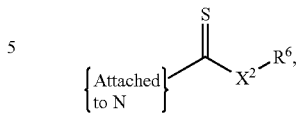

X$^2$ is —O—, and R$^6$ is —CH$_2$CH$_3$;
(q) (1) the limitations of (l) and (2) the limitations of (i), (j), or (k);
(r) (1) the limitations of (m) and (2) the limitations of (i), (j), or (k);
(s) (1) the limitations of (n) and (2) the limitations of (i), (j), or (k);
(t) (1) the limitations of (o) and (2) the limitations of (i), (j), or (k); or
(u) (1) the limitations of (p) and (2) the limitations of (i), (j), or (k).

A3. The compound of embodiment A1 or embodiment A2, wherein Formula (I) further comprises a solvent molecule coordinated with Formula (I).

A4. The compound of any of embodiments A1 to A3, wherein Formula (I) further comprises a solvent molecule coordinated with Formula (I) and the solvent molecule is selected from water, methanol, ethanol, propanol, acetonitrile, dimethylformamide, and acetone.

A5. The compound of any of embodiments A1 to A4, wherein the compound is

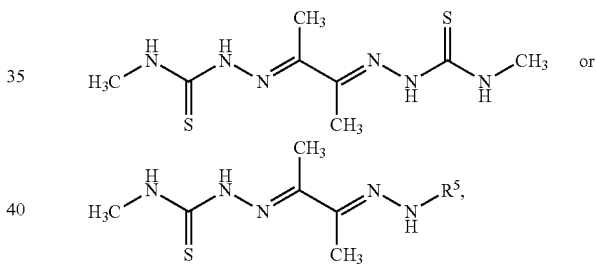

where R$^5$ is pyridinyl, 1-methyl-imidazolyl, an N-containing heterocyclyl, or an N-containing heteroaryl.

A6. The compound of any of embodiments A1 to A5, wherein (a) X$^1$ is not —(NH)—, (b) R$^2$ is not methoxyphenyl or p-methoxyphenyl, or (c) both (a) and (b).

A7. The compound of any of embodiments A1 to A6, wherein (a) X$^2$ is not —(NH)—, (b) R$^6$ is not methoxyphenyl or p-methoxyphenyl, or (c) both (a) and (b).

A8. The compound of any of embodiments A1 to A7, wherein (a) R$^3$ is not methyl, (b) R$^4$ is not methyl, or (c) both (a) and (b).

A9. The compound of any of embodiments A1 to A8, wherein the compound is not

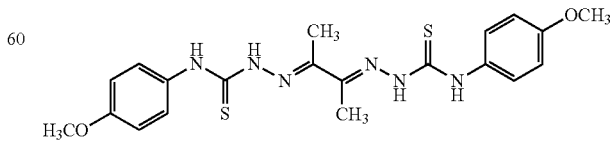

A10. The compound of any of embodiments A1 to A9, wherein the compound is part of a homogenous solution, a homogenous aqueous solution, a heterogeneous solution, a heterogeneous aqueous solution, or a glassy carbon electrode.

A11. A homogenous solution, a homogenous aqueous solution, a heterogeneous solution, or a heterogeneous aqueous solution, each comprising the compound of any of embodiments A1 to A9.

A12. A glassy carbon electrode, a carbon paste (e.g., embedded with one or more of polynuclear catalysts, coordinated polymers, or metal-organic frameworks), covalent modified carbon (e.g., graphene), or non-covalent modified carbon (e.g., graphene), each comprising or reacted with the compound of any of embodiments A1 to A9.

A13. The carbon paste of embodiment A12, wherein the carbon paste comprises an extended structure motif (e.g., motif I, motif II, or motif III of the scheme shown in FIG. 81).

Scheme 11. Synthesis of extended structure motifs (M=Zn, Cu)

B1. A compound selected from Formula (II),

M.L (II) and salts, optical isomers, geometric isomers, salts of isomers, and derivatives thereof, wherein -M is Ni, Pd, Pt, Cu, Ag, Au, Zn, Cd, Hg, Co, Rh, Ti, V, Cr, Mn, or Fe (e.g., M is $Cu^+$, Cut, $Zn^+$, $Co^+$, $Ni^+$, $Cd^+$, $Mn^+$, $Ru^+$, or $Fe^+$; or M is $Cu^+$, Cut, $Zn^+$, $Co^+$, $Ni^+$, $Cd^+$, $Mn^+$, $Ru^+$, or $Fe^+$; or M is $Cu^+$, $Zn^+$, $Ni^+$, $Co^+$, $Cd^{2+}$, $Mn^{2+}$, or $Fe^{2+}$; or M is $Cu^{2+}$, $Zn^{2+}$, $Ni^{2+}$, or $Co^{2+}$; or M is $Cu^{2+}$, $Zn^{2+}$, or $Ni^{2+}$; or M is $Cu^{2+}$, $Zn^{2+}$, or $Co^{2+}$; or M is $Cu^{2+}$ or $Zn^{2+}$) and -L is selected from a thiosemicarbazone or a compound of Formula (I) of embodiments A1-A9.

B2. The compound of embodiment B1 wherein Formula (II) is a compound of Formula (II-A)

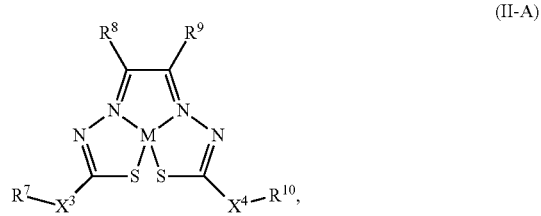

(II-A)

wherein

—$R^7$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$X^3$ is bivalent —(NH)—, —(N—CH($CH_3$)$_2$)—, —(N—$CH_2CH_3$)—, —(N—$CH_3$)—, or —O—, which —(NH)—, —(N—CH($CH_3$)$_2$)—, —(N—$CH_2CH_3$)—, or —(N—$CH_3$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl, or, which —(N—CH($CH_3$)$_2$)—, —(N—$CH_2CH_3$)—, or —(N—$CH_3$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

—$R^8$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$R^9$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl;

—$X^4$ is bivalent —(NH)—, —(N—CH($CH_3$)$_2$)—, —(N—$CH_2CH_3$)—, —(N—$CH_3$)—, or —O—, which —(NH)—, —(N—CH($CH_3$)$_2$)—, —(N—$CH_2CH_3$)—, or —(N—$CH_3$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl, or, which —(N—CH($CH_3$)$_2$)—, —(N—$CH_2CH_3$)—, or —(N—$CH_3$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

—$R^{10}$ is a monovalent H, methanoly (—COH), carboxy (—$CO_2H$), nitro (—$NO_2$), sulfo (—$SO_3H$), halogen (e.g., F, Cl, Br, or I), aryl (e.g., benzene or pyrene), cycloalkyl, heterocyclyl, heteroaryl (e.g., pyridinyl and 1-methyl imidazolyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which aryl (e.g., benzene or pyrene), cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2H$), nitro (—$NO_2$), cyano (—CN), ethynyl (—CCH), sulfo (—$SO_3H$), methyl, or ethyl; and -M is Ni, Pd, Pt, Cu, Ag, Au, Zn, Cd, Hg, Co, Rh, Ti, V, Cr, Mn, or Fe; or M is $Cu^{2+}$, Cut, $Zn^{2+}$, $Co^{2+}$, $Ni^{2+}$, $Cd^{2+}$, $Mn^{2+}$, $Ru^{2+}$, or $Fe^{2+}$; or M is $Cu^{2+}$, Cut, $Zn^{2+}$, $Co^{2+}$, $Cd^{2+}$, $Mn^{2+}$, $Ru^{2+}$, or $Fe^{2+}$; or M is $Cu^{2+}$, $Zn^{2+}$, $Co^{2+}$, $Cd^{2+}$, $Mn^{2+}$, or $Fe^{2+}$; or M is $Cu^{2+}$, $Zn^{2+}$, $Ni^{2+}$, or $Co^{2+}$; or M is $Cu^{2+}$, $Zn^{2+}$, or $Ni^{2+}$; or M is $Cu^{2+}$, $Zn^{2+}$, or $Co^{2+}$; or M is $Cu^{2+}$ or $Zn^{2+}$.

B3. The compound of embodiment B1 or embodiment B2, wherein
(a) $R^3$ is the same as $R^4$;
(b) $R^3$ is the same as $R^4$ and $R^1$ is the same as $R^5$;
(c) $R^3$ is the same as $R^4$, $X^1$ is —(NH)—, $X^2$ is —(NH)—, and $R^2$ is the same as $R^6$;
(d) $R^3$ is the same as $R^4$, $R^3$ is methyl, $R^1$ is the same as $R^5$, $R^1$ is

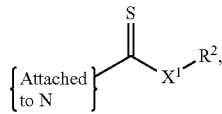

$X^1$ is —(NH)—, and $R^2$ is —$CH_3$;
(e) $R^3$ is the same as $R^4$, $R^3$ is methyl, $R^1$ is the same as $R^5$, $R^1$ is

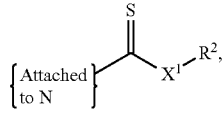

$X^1$ is —(NH)—, and $R^2$ is —$C_5H_6$;
(f) $R^3$ is the same as $R^4$, $R^3$ is methyl, $R^1$ is the same as $R^5$, $R^1$ is

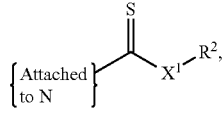

$X^1$ is —(NH)—, and $R^2$ is —$CH_2F_3$;
(g) $R^3$ is the same as $R^4$, $R^3$ is methyl, $R^1$ is the same as $R^5$, $R^1$ is

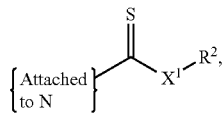

$X^1$ is —($NCH_3$)—, and $R^2$ is —$CH_3$;
(h) $R^3$ is the same as $R^4$, $R^3$ is methyl, $R^1$ is the same as $R^5$, $R^1$ is

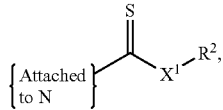

$X^1$ is —O—, and $R^2$ is —$CH_3$;
(i) $R^3$ is the same as $R^4$ and $R^3$ is methyl;
(j) $R^3$ is the same as $R^4$ and $R^3$ is ethyl;
(k) $R^3$ is methyl and $R^4$ is phenyl;
(l) $R^1$ is

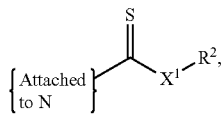

$X^1$ is —(NH)—, $R^2$ is —$CH_3$, $R^5$ is

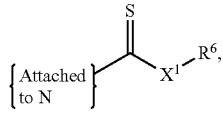

$X^2$ is —(N—$CH(CH_3)_2$)—, and $R^6$ is —$CH(CH_3)_2$;
(m) $R^1$ is

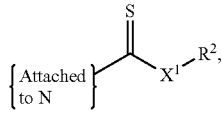

$X^1$ is —(NH)—, $R^2$ is —$CH_3$, $R^5$ is

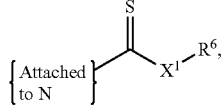

$X^2$ is —(NH)—, and $R^6$ is —$C_5H_6$;
(n) $R^1$ is

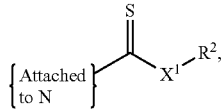

$X^1$ is —(NH)—, $R^2$ is —$CH_3$, $R^5$ is

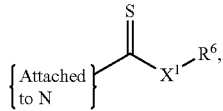

$X^2$ is —(NH)—, and $R^6$ is —CH$_2$CF$_3$;
(o) $R^1$ is

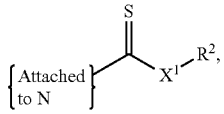

$X^1$ is —(NH)—, $R^2$ is —CH$_3$, $R^5$ is

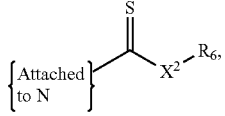

$X^2$ is —O—, and $R^6$ is —CH$_3$;
(p) $R^1$ is

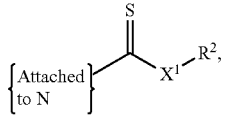

$X^1$ is —(NH)—, $R^2$ is —CH$_3$, $R^5$ is

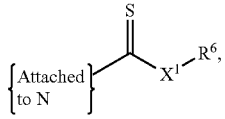

$X^2$ is —O—, and $R^6$ is —CH$_2$CH$_3$;
(q) (1) the limitations of (l) and (2) the limitations of (i), (j), or (k);
(r) (1) the limitations of (m) and (2) the limitations of (i), (j), or (k);
(s) (1) the limitations of (n) and (2) the limitations of (i), (j), or (k);
(t) (1) the limitations of (o) and (2) the limitations of (i), (j), or (k); or
(u) (1) the limitations of (p) and (2) the limitations of (i), (j), or (k).

B4. The compound of any of embodiments B1 to B3, wherein
(a) $R^8$ is the same as $R^9$;
(b) $R^8$ is the same as $R^9$ and $X^3$—$R^7$ is the same as $X^4$—$R^{10}$;
(c) $R^8$ is the same as $R^9$, $X^3$ is —(NH)—, $X^4$ is —(NH)—, and $R^7$ is the same as $R^{10}$;
(d) $R^8$ is the same as $R^9$, $R^8$ is methyl, $X^3$—$R^7$ is the same as $X^4$—$R^{10}$, $X^3$ is —(NH)—, and $R^7$ is —CH$_3$;
(e) $R^8$ is the same as $R^9$, $R^8$ is methyl, $X^3$—$R^7$ is the same as $X^4$—$R^{10}$, $X^3$ is —(NH)—, and $R^7$ is C$_5$H$_6$;
(f) $R^8$ is the same as $R^9$, $R^8$ is methyl, $X^3$—$R^7$ is the same as $X^4$—$R^{10}$, $X^3$ is —(NH)—, and $R^7$ is —CH$_2$F$_3$;
(g) $R^8$ is the same as $R^9$, $R^8$ is methyl, $X^3$—$R^7$ is the same as $X^4$—$R^{10}$, $X^3$ is —(NCH$_3$)—, and $R^7$ is —CH$_3$;
(h) $R^8$ is the same as $R^9$, $R^8$ is methyl, $X^3$—$R^7$ is the same as $X^4$—$R^{10}$, $X^3$ is —O—, and $R^7$ is —CH$_3$;
(i) $R^8$ is the same as $R^9$ and $R^8$ is methyl;
(j) $R^8$ is the same as $R^9$ and $R^8$ is ethyl;
(k) $R^8$ is methyl and $R^9$ is phenyl;
(l) $X^3$ is —(NH)—, $R^7$ is —CH$_3$, $X^4$ is —(N—CH(CH$_3$)$_2$)—, and $R^{10}$ is —CH(CH$_3$)$_2$;
(m) $X^3$ is —(NH)—, $R^7$ is —CH$_3$, $X^4$ is —(NH)—, and $R^{10}$ is —C$_5$H$_6$;
(n) $X^3$ is —(NH)—, $R^7$ is —CH$_3$, $X^4$ is —(NH)—, and $R^{10}$ is —CH$_2$CF$_3$;
(o) $X^3$ is —(NH)—, $R^7$ is —CH$_3$, $X^4$ is —O—, and $R^{10}$ is —CH$_3$;
(p) $X^3$ is —(NH)—, $R^7$ is —CH$_3$, $X^4$ is —O—, and $R^{10}$ is —CH$_2$CH$_3$;
(q) (1) the limitations of (l) and (2) the limitations of (i), (j), or (k);
(r) (1) the limitations of (m) and (2) the limitations of (i), (j), or (k);
(s) (1) the limitations of (n) and (2) the limitations of (i), (j), or (k);
(t) (1) the limitations of (o) and (2) the limitations of (i), (j), or (k); or
(u) (1) the limitations of (p) and (2) the limitations of (i), (j), or (k).

B5. The compound of any of embodiments B1 to B4, wherein the M is Zn$^{2+}$, Co$^{2+}$, Ni$^{2+}$, or Cu$^{2+}$ (e.g., M is Zn$^{2+}$, Co$^{2+}$, or Cu$^{2+}$).

B6. The compound of any of embodiments B1 to B5, wherein Formula (II) further comprises a solvent molecule coordinated with Formula (II).

B7. The compound of any of embodiments B1 to B6, wherein Formula (II) further comprises a solvent molecule coordinated with Formula (II) and the solvent molecule is selected from water, ethanol, propanol, acetonitrile, dimethylformamide, and acetone.

B8. The compound of any of embodiments B1 to B7, wherein the compound is

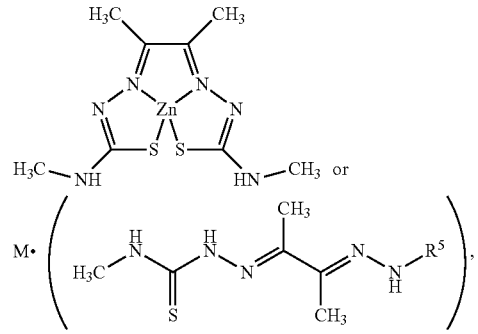

where M is Zn, Co, Ni, or Cu (e.g., M is Zn, Co, or Cu; or M is Zn, Ni, or Cu; or M is Zn or Cu) and $R^5$ is pyridinyl, 1-methyl-imidazolyl, an N-containing heterocyclyl, or an N-containing heteroaryl.

B9. The compound of any of embodiments B1 to B8, wherein (a) $X^1$ is not —(NH)—, (b) $R^2$ is not methoxyphenyl or p-methoxyphenyl, or (c) both (a) and (b).

B10. The compound of any of embodiments B1 to B9, wherein (a) $X^2$ is not —(NH)—, (b) $R^6$ is not methoxyphenyl or p-methoxyphenyl, or (c) both (a) and (b).

B11. The compound of any of embodiments B1 to B10, wherein (a) $R^3$ is not methyl, (b) $R^4$ is not methyl, or (c) both (a) and (b).

B12. The compound of any of embodiments B1 to B11, wherein (a) $X^3$ is not —(NH)—, (b) $R^7$ is not methoxyphenyl or p-methoxyphenyl, or (c) both (a) and (b).

B13. The compound of any of embodiments B1 to B12, wherein (a) $X^4$ is not —(NH)—, (b) $R^{10}$ is not methoxyphenyl or p-methoxyphenyl, or (c) both (a) and (b).

B14. The compound of any of embodiments B1 to B13, wherein (a) $R^8$ is not methyl, (b) $R^9$ is not methyl, or (c) both (a) and (b).

B15. The compound of any of embodiments B1 to B14, wherein the compound is not

B16. The compound of any of embodiments B1 to B15, wherein the compound is part of a homogenous solution, a homogenous aqueous solution, a heterogeneous solution, or a heterogeneous aqueous solution.

B17. A homogenous solution, a homogenous aqueous solution, a heterogeneous solution, or a heterogeneous aqueous solution, each comprising the compound of any of embodiments B1 to B16.

B18. A glassy carbon electrode, a carbon paste (e.g., embedded with one or more of polynuclear catalysts, coordinated polymers, or metal-organic frameworks), covalent modified carbon (e.g., graphene), or non-covalent modified carbon (e.g., graphene), each comprising or reacted with the compound of any of embodiments B1 to B17.

B19. The carbon paste of embodiment B18, wherein the carbon paste comprises an extended structure motif (e.g., motif I, motif II, or motif III of the scheme shown in FIG. 81).

C1. A catalyst (e.g., an electrocatalyst) comprising a composition comprising a compound of Formula (I) (e.g., embodiments A1-A13), a compound of Formula (II) (e.g., embodiments B1-B19), or both.

D1. An anode comprising a composition comprising a compound of Formula (I) (e.g., embodiments A1-A13), a compound of Formula (II) (e.g., embodiments B1-B19), or both.

E1. A cathode comprising a composition comprising a compound of Formula (I) (e.g., embodiments A1-A13), a compound of Formula (II) (e.g., embodiments B1-B19), or both.

F1. An electrochemical cell comprising a composition comprising a compound of Formula (I) (e.g., embodiments A1-A13), a compound of Formula (II) (e.g., embodiments B1-B19), or both.

F2. The electrochemical cell of embodiment F1, wherein the cathode of the electrochemical cell comprises the composition.

G1. A fuel cell comprising a composition comprising a compound of Formula (I) (e.g., embodiments A1-A13), a compound of Formula (II) (e.g., embodiments B1-B19), or both.

G2. The fuel cell of embodiment G1, wherein the anode of the fuel cell comprises the first composition.

H1. A method for producing H2 comprising contacting, in an electrochemical cell, a first composition comprising a compound of Formula (I) (e.g., embodiments A1-A13), a compound of Formula (II) (e.g., embodiments B1-B19), or both with a second composition comprising water.

H2. The method of embodiment H1, wherein the cathode of the electrochemical cell comprises the first composition.

H3. The method of H1 or H2, wherein the TOF is from about 20 $s^{-1}$ to about 100,000 $s^{-1}$, about 100 $s^{-1}$ to about 100,000 $s^{-1}$, from about 500 $s^{-1}$ to about 100,000 $s^{-1}$, from about 500 $s^{-1}$ to about 50,000 $s^{-1}$, from about 500 $s^{-1}$ to about 20,000 $s^{-1}$, about 20 $s^{-1}$, about 100 $s^{-1}$, about 500 $s^{-1}$, about 1000 $s^{-1}$, about 5000 $s^{-1}$, about 10000 $s^{-1}$, about 12000 $s^{-1}$, about 16000 $s^{-1}$, about 20000 $s^{-1}$, about 50000 $s^{-1}$, or about 100,000 $s^{-1}$.

H4. A method for oxidizing an aldehyde or an alcohol comprising contacting, in an electrochemical cell, a composition comprising a compound of Formula (I) (e.g., embodiments A1-A13), a compound of Formula (II) (e.g., embodiments B1-B19), or both.

H5. The method of any of H1-H4, wherein the overpotential is greater than about 0 V, not less than about 0.1 V, not more than about 0.1 V, not more than 0.5 V, not more than 1 V, not more than 10 V, not more than 100 V, from about 0 V to about 2000 V, from about 0 V to about 1000 V, from about 0 V to about 750 V, from about 0 V to about 300 V, from about 0 V to about 350 V, from about 0 V to about 200 V, from about 0 V to about 100 V, from about 0 V to about 20 V, from about 0 V to about 10 V, from about 0 V to about 5 V, from about 0 V to about 2 V, from about 0 V to about 1 V, from about 0.1 V to about 2000 V, from about 0.1 V to about 1000 V, from about 0.1 V to about 750 V, from about 0.1 V to about 300 V, from about 0.1 V to about 350 V, from about 0.1 V to about 200 V, from about 0.1 V to about 100 V, from about 0.1 V to about 20 V, from about 0.1 V to about 10 V, from about 0.1 V to about 5 V, from about 0.1 V to about 2 V, from about 0.1 V to about 1 V, about 0.1 V, about 0.5 V, about 1 V, about 5 V, about 10 V, about 100 V, about 250 V, about 350 V, about 400 V, about 500 V, or about 1000 V.

I1. A method for producing electricity comprising contacting, in a fuel cell, a first composition comprising a compound of Formula (I) (e.g., embodiments A1-A13), a compound of Formula (II) (e.g., embodiments B1-B19), or both with a second composition comprising H2.

I2. The method of embodiment I1, wherein the anode of the fuel cell comprises the first composition.

I3. The method of I1 or I2, wherein the TOF is from about 1 $s^{-1}$ to about 1000 $s^{-1}$, from about 5 $s^{-1}$ to about 1000 $s^{-1}$, from about 5 $s^{-1}$ to about 500 $s^{-1}$, from about 5 $s^{-1}$ to about 200 $s^{-1}$, about 1 $s^{-1}$, about 5 $s^{-1}$, about 10 $s^{-1}$, about 32 $s^{-1}$, about 50 $s^{-1}$, about 76 $s^{-1}$, about 100 $s^{-1}$, about 120 $s^{-1}$, about 200 $s^{-1}$, about 300 $s^{-1}$, about 500 $s^{-1}$, or about 1000 $s^{-1}$.

I4. The method of any of I1-I3, wherein the overpotential is greater than about 0 V, not less than about 0.1 V, not more than about 0.1 V, not more than 0.5 V, not more than 1 V, not more than 10 V, not more than 100 V, from about 0 V to about 2000 V, from about 0 V to about 1000 V, from about 0 V to about 750 V, from about 0 V to about 300 V, from about 0 V to about 350 V, from about 0 V to about 200 V, from about 0 V to about 100 V, from about 0 V to about 20 V, from about 0 V to about 10 V, from about 0 V to about 5 V, from about 0 V to about 2 V, from about 0 V to about 1 V, from about 0.1 V to about 2000 V, from about 0.1 V to about 1000 V, from about 0.1 V to about 750 V, from about 0.1 V to about 300 V, from about 0.1 V to about 350 V, from about 0.1 V to about 200 V, from about 0.1 V to about 100 V, from about 0.1 V to about 20 V, from about 0.1 V to about 10 V, from about 0.1 V to about 5 V, from about 0.1 V to about 2 V, from about 0.1 V to about 1 V, about 0.1 V, about 0.5 V, about 1 V, about 5 V, about 10 V, about 100 V, about 250 V, about 350 V, about 400 V, about 500 V, or about 1000 V.

J1. A method for preparing a compound of Formula (I) (e.g., embodiments A1-A13) comprising any suitable method.

J2. The method of J1, wherein the compound of Formula (I) is prepared comprising (a) reacting a compound of Formula (III)

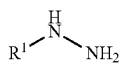
(III)

with a compound of Formula (IV)

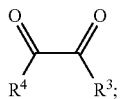
(IV)

(b) reacting a compound of Formula (V)

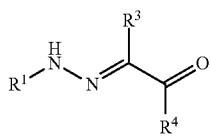
(V)

with a compound of Formula (VI)

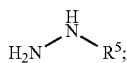
(VI)

and (c) recovering the compound of Formula (I), wherein $R^1$, $R^3$, $R^4$, and $R^5$ are defined as in embodiments A1-A13.

K1. A method for preparing a compound of Formula (II) (e.g., embodiments B1-B19) comprising any suitable method.

K2. The method of K1, wherein the compound of Formula (II) is prepared comprising (a) reacting a compound of Formula (I) (e.g., embodiments A1-A13) with M; and (b) recovering the compound of Formula (II), wherein M is defined as in embodiments B1-B19.

L1. A method for preparing a catalyst (e.g., an electrocatalyst) comprising a composition comprising a compound of Formula (I) (e.g., embodiments A1-A13), a compound of Formula (II) (e.g., embodiments B1-B19), or both, comprising any suitable method.

M1. A method for preparing an anode comprising a composition comprising a compound of Formula (I) (e.g., embodiments A1-A13), a compound of Formula (II) (e.g., embodiments B1-B19), or both, comprising any suitable method.

N1. A method for preparing a cathode comprising a composition comprising a compound of Formula (I) (e.g., embodiments A1-A13), a compound of Formula (II) (e.g., embodiments B1-B19), or both, comprising any suitable method.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties or functions sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

The invention claimed is:

1. A catalyst comprising a composition comprising a compound selected from Formula (I),

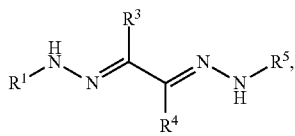
(I)

and
salts, optical isomers, geometric isomers, salts of isomers, and derivatives thereof, wherein
$R^1$ is

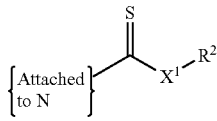

or is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$X^1$ is bivalent —(NH)—, —O—, —($CH_2$)—, or —S—, which —(NH)— or —($CH_2$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$R^2$ is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, amine (—$NH_2$), —$NR_aR_b$, —$N^{(+)}R_aR_bR_c$, methanoly (—COH), carboxy (—$CO_2H$), nitro (—$NO_2$), cyano (—CN), ethynyl (—CCH), sulfo (—$SO_3H$), methyl, or ethyl;

$R^3$ is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$R^4$ is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$R^5$ is

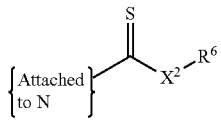

or is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$X^2$ is bivalent —(NH)—, —O—, —($CH_2$)—, or —S—, which —(NH)— or —($CH_2$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$R^6$ is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, amine (—$NH_2$), —$NR_aR_b$, —$N^{(+)}R_aR_bR_c$, methanoly (—COH), carboxy (—$CO_2H$), nitro (—$NO_2$), cyano (—CN), ethynyl (—CCH), sulfo (—$SO_3H$), methyl, or ethyl;

$R_a$, $R_b$, and $R_c$ are each independently selected from $C_1$-$C_5$ alkyl; and the compound is not

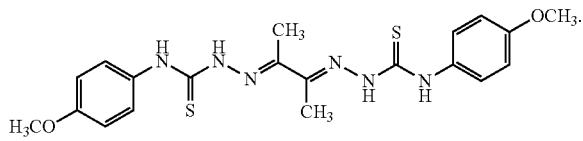 [SMILES: COc1ccc(NC(=S)N/N=C(C)/C(C)=N/NC(=S)Nc2ccc(OC)cc2)cc1]

2. The catalyst of claim 1, wherein
(a) $R^3$ is the same as $R^4$;
(b) $R^3$ is the same as $R^4$ and $R^1$ is the same as $R^5$;
(c) $R^3$ is the same as $R^4$, $X^1$ is —(NH)—, $X^2$ is —(NH)—, and $R^2$ is the same as $R^6$;

(d) $R^3$ is the same as $R^4$, $R^3$ is methyl, $R^1$ is the same as $R^5$, $R^1$ is

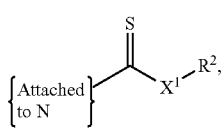

$X^1$ is —(NH)—, and $R^2$ is —$CH_3$;

(e) $R^3$ is the same as $R^4$, $R^3$ is methyl, $R^1$ is the same as $R^5$, $R^1$ is

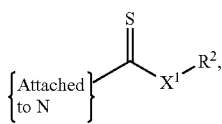

$X^1$ is —(NH)—, and $R^2$ is —$C_5H_6$;

(f) $R^3$ is the same as $R^4$, $R^3$ is methyl, $R^1$ is the same as $R^5$, $R^1$ is

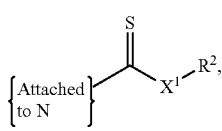

$X^1$ is —(NH)—, and $R^2$ is —$CH_2F_3$;

(g) $R^3$ is the same as $R^4$, $R^3$ is methyl, $R^1$ is the same as $R^5$, $R^1$ is

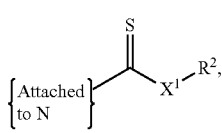

$X^1$ is —($NCH_3$)—, and $R^2$ is —$CH_3$;

(h) $R^3$ is the same as $R^4$, $R^3$ is methyl, $R^1$ is the same as $R^5$, $R^1$ is

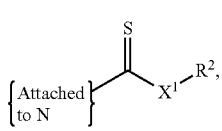

$X^1$ is —O—, and $R^2$ is —$CH_3$;
(i) $R^3$ is the same as $R^4$ and $R^3$ is methyl;
(j) $R^3$ is the same as $R^4$ and $R^3$ is ethyl;
(k) $R^3$ is methyl and $R^4$ is phenyl;
(l) $R^1$ is

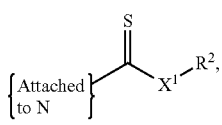

$X^1$ is —(NH)—, $R^2$ is —$CH_3$, $R^5$ is

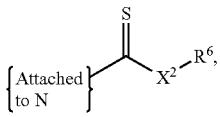

$X^2$ is —(N—$CH(CH_3)_2$)—, and $R^6$ is —$CH(CH_3)_2$;
(m) $R^1$ is

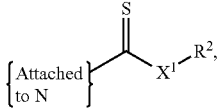

$X^1$ is —(NH)—, $R^2$ is —$CH_3$, $R^5$ is

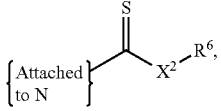

$X^2$ is —(NH)—, and $R^6$ is —$C_5H_6$;
(n) $R^1$ is

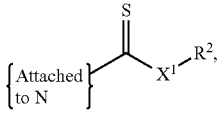

$X^1$ is —(NH)—, $R^2$ is —$CH_3$, $R^5$ is

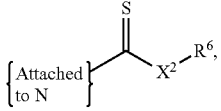

$X^2$ is —(NH)—, and $R^6$ is —$CH_2CF_3$;
(o) $R^1$ is

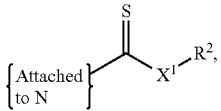

$X^1$ is —(NH)—, $R^2$ is —$CH_3$, $R^5$ is

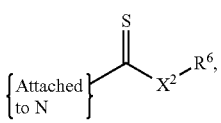

$X^2$ is —O—, and $R^6$ is —CH$_3$;
(p) $R^1$ is

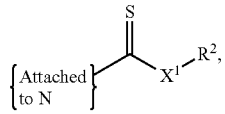

$X^1$ is —(NH)—, $R^2$ is —CH$_3$, $R^5$ is

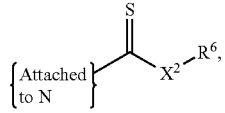

$X^2$ is —O—, and $R^6$ is —CH$_2$CH$_3$;
(q) (1) the limitations of (l) and (2) the limitations of (i), (j), or (k);
(r) (1) the limitations of (m) and (2) the limitations of (i), (j), or (k);
(s) (1) the limitations of (n) and (2) the limitations of (i), (j), or (k);
(t) (1) the limitations of (o) and (2) the limitations of (i), (j), or (k); or
(u) (1) the limitations of (p) and (2) the limitations of (i), (j), or (k).

3. The catalyst of claim 1, wherein Formula (I) further comprises a solvent molecule coordinated with Formula (I).

4. The catalyst of claim 1, wherein one or both of $R^2$ or $R^6$ is (a) $C_1$-$C_7$ alkyl substituted with —$NR_aR_b$, (b) $C_1$-$C_7$ alkyl substituted with —$N^{(+)}R_aR_bR_c$, (c) substituted or unsubstituted benzo crown ether, (d) phenyl substituted with a carboxy, (e) substituted or unsubstituted pyrrolyl, (f) substituted or unsubstituted pyridyl, or (g) substituted or unsubstituted imidazolyl.

5. The catalyst of claim 1, wherein the compound is

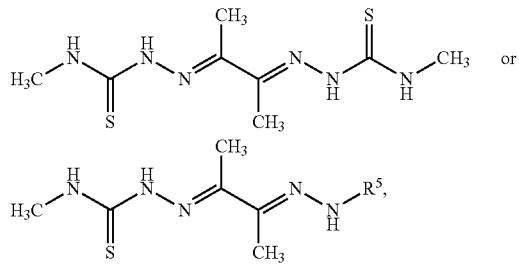

where $R^5$ is pyridinyl, 1-methyl-imidazolyl, an N-containing heterocyclyl, or an N-containing heteroaryl.

6. The catalyst of claim 1, wherein (a) $X^1$ is not —(NH)—, (b) $R^2$ is not methoxyphenyl or p-methoxyphenyl, or (c) both (a) and (b).

7. The catalyst of claim 1, wherein (a) $X^2$ is not —(NH)—, (b) $R^6$ is not methoxyphenyl or p-methoxyphenyl, or (c) both (a) and (b).

8. The catalyst of claim 1, wherein (a) $R^3$ is not methyl, (b) $R^4$ is not methyl, or (c) both (a) and (b).

9. A catalyst comprising a composition comprising a compound selected from Formula (II),
M.L (II) and salts, optical isomers, geometric isomers, salts of isomers, and derivatives thereof, wherein M is Ni, Pd, Pt, Cu, Ag, Au, Zn, Cd, Hg, Co, Rh, Ti, V, Cr, Mn, or Fe;
L is a compound of Formula (I) according to claim 1, and
the compound is not

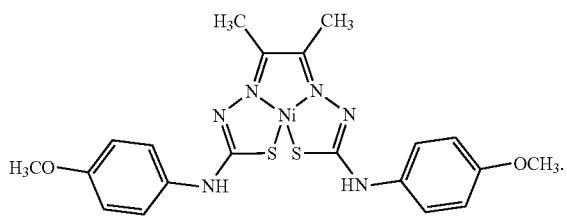

10. The catalyst of claim 9, wherein Formula (II) is a compound of Formula (II-A)

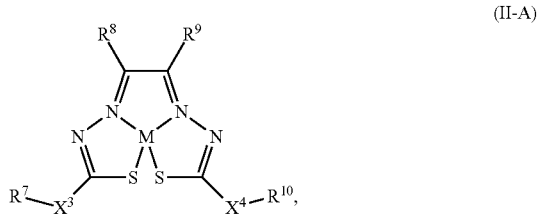

wherein
$R^7$ is a monovalent H, methanoly (—COH), carboxy (—CO$_2$H), nitro (—NO$_2$), sulfo (—SO$_3$H), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, amine (—NH$_2$), —$NR_aR_b$, —$N^{(+)}R_aR_bR_c$, methanoly (—COH), carboxy (—CO$_2$H), nitro (—NO$_2$), cyano (—CN), ethynyl (—CCH), sulfo (—SO$_3$H), methyl, or ethyl;
$X^3$ is bivalent —(NH)—, —(N—CH(CH$_3$)$_2$)—, —(N—CH$_2$CH$_3$)—, —(N—CH$_3$)—, or —O—, which —(NH)—, —(N—CH(CH$_3$)$_2$)—, —(N—CH$_2$CH$_3$)—, or —(N—CH$_3$)— can optionally be substituted with one or more of halogen, hydroxy (—OH), $C_1$-$C_5$ alkyl, $C_1$-$C_4$ alkoxy, methanoly (—COH), carboxy (—CO$_2$H), nitro (—NO$_2$), cyano (—CN), ethynyl (—CCH), sulfo (—SO$_3$H), methyl, or ethyl;
$R^8$ is a monovalent H, methanoly (—COH), carboxy (—CO$_2$H), nitro (—NO$_2$), sulfo (—SO$_3$H), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, methanoly (—COH), carboxy (—CO$_2$H), nitro (—NO$_2$), cyano (—CN), ethynyl (—CCH), sulfo (—SO$_3$H), methyl, or ethyl;
$R^9$ is a monovalent H, methanoly (—COH), carboxy (—CO$_2$H), nitro (—NO$_2$), sulfo (—SO$_3$H), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$X^4$ is bivalent —(NH)—, —(N—CH($CH_3$)$_2$)—, —(N—$CH_2CH_3$)—, —(N—$CH_3$)—, or —O—, which —(NH)—, —(N—CH($CH_3$)$_2$)—, —(N—$CH_2CH_3$)—, or —(N—$CH_3$)— can optionally be substituted with one or more of halogen, hydroxy (—OH), $C_1$-$C_5$ alkyl, $C_1$-$C_4$ alkoxy, methanoly (—COH), carboxy (—$CO_2H$), nitro (—$NO_2$), cyano (—CN), ethynyl (—CCH), sulfo (—$SO_3H$), methyl, or ethyl;

$R^{10}$ is a monovalent H, methanoly (—COH), carboxy (—$CO_2H$), nitro (—$NO_2$), sulfo (—$SO_3H$), halogen, aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy, which aryl, cycloalkyl, heterocyclyl, heteroaryl, $C_1$-$C_7$ alkyl, $C_2$-$C_7$ alkenyl, $C_2$-$C_7$ alkynyl, or $C_1$-$C_6$ alkoxy can optionally be substituted with one or more of halogen, hydroxy (—OH), $C_1$-$C_5$ alkyl, $C_1$-$C_4$ alkoxy, amine (—$NH_2$), —$NR_aR_b$, —$N^{(+)}R_aR_bR_c$, methanoly (—COH), carboxy (—$CO_2H$), nitro (—$NO_2$), cyano (—CN), ethynyl (—CCH), sulfo (—$SO_3H$), methyl, or ethyl;

$R_a$, $R_b$, and $R_c$ are each independently selected from $C_1$-$C_5$ alkyl; and M is Ni, Pd, Pt, Cu, Ag, Au, Zn, Cd, Hg, Co, Rh, Ti, V, Cr, Mn, or Fe.

11. The catalyst of claim 9, wherein
(a) $R^8$ is the same as $R^9$;
(b) $R^8$ is the same as $R^9$ and $X^3$—$R^7$ is the same as $X^4$—$R^{10}$;
(c) $R^8$ is the same as $R^9$, $X^3$ is —(NH)—, $X^4$ is —(NH)—, and $R^7$ is the same as $R^{10}$;
(d) $R^8$ is the same as $R^9$, $R^8$ is methyl, $X^3$—$R^7$ is the same as $X^4$—$R^{10}$, $X^3$ is —(NH)—, and $R^7$ is —$CH_3$;
(e) $R^8$ is the same as $R^9$, $R^8$ is methyl, $X^3$—$R^7$ is the same as $X^4$—$R^{10}$, $X^3$ is —(NH)—, and $R^7$ is —$C_5H_6$;
(f) $R^8$ is the same as $R^9$, $R^8$ is methyl, $X^3$—$R^7$ is the same as $X^4$—$R^{10}$, $X^3$ is —(NH)—, and $R^7$ is —$CH_2F_3$;
(g) $R^8$ is the same as $R^9$, $R^8$ is methyl, $X^3$—$R^7$ is the same as $X^4$—$R^{10}$, $X^3$ is —(NCH$_3$)—, and $R^7$ is —$CH_3$;
(h) $R^8$ is the same as $R^9$, $R^8$ is methyl, $X^3$—$R^7$ is the same as $X^4$—$R^{10}$, $X^3$ is —O—, and $R^7$ is —$CH_3$;
(i) $R^8$ is the same as $R^9$ and $R^8$ is methyl;
(j) $R^8$ is the same as $R^9$ and $R^8$ is ethyl;
(k) $R^8$ is methyl and $R^9$ is phenyl;
(l) $X^3$ is —(NH)—, $R^7$ is —$CH_3$, $X^4$ is —(N—CH(CH$_3$)$_2$)—, and $R^{10}$ is —CH(CH$_3$)$_2$;
(m) $X^3$ is —(NH)—, $R^7$ is —$CH_3$, $X^4$ is —(NH)—, and $R^{10}$ is —$C_5H_6$;
(n) $X^3$ is —(NH)—, $R^7$ is —$CH_3$, $X^4$ is —(NH)—, and $R^{10}$ is —$CH_2CF_3$;
(o) $X^3$ is —(NH)—, $R^7$ is —$CH_3$, $X^4$ is —O—, and $R^{10}$ is —$CH_3$;
(p) $X^3$ is —(NH)—, $R^7$ is —$CH_3$, $X^4$ is —O—, and $R^{10}$ is —$CH_2CH_3$;
(q) (1) the limitations of (l) and (2) the limitations of (i), (j), or (k);
(r) (1) the limitations of (m) and (2) the limitations of (i), (j), or (k);
(s) (1) the limitations of (n) and (2) the limitations of (i), (j), or (k);
(t) (1) the limitations of (o) and (2) the limitations of (i), (j), or (k); or
(u) (1) the limitations of (p) and (2) the limitations of (i), (j), or (k).

12. The catalyst of claim 9, wherein the M is $Zn^{2+}$, $Co^{2+}$, $Ni^{2+}$, or $Cu^{2+}$.

13. The catalyst of claim 9, wherein Formula (II) further comprises a solvent molecule coordinated with Formula (II).

14. The catalyst of claim 9, wherein one or both of $R^7$ or $R^{10}$ is (a) $C_1$-$C_7$ alkyl substituted with —$NR_aR_b$, (b) $C_1$-$C_7$ alkyl substituted with —$N^{(+)}R_aR_bR_c$, (c) substituted or unsubstituted benzo crown ether, (d) phenyl substituted with a carboxy, (e) substituted or unsubstituted pyrrolyl, (f) substituted or unsubstituted pyridyl, or (g) substituted or unsubstituted imidazolyl.

15. The catalyst of claim 9, wherein the compound is

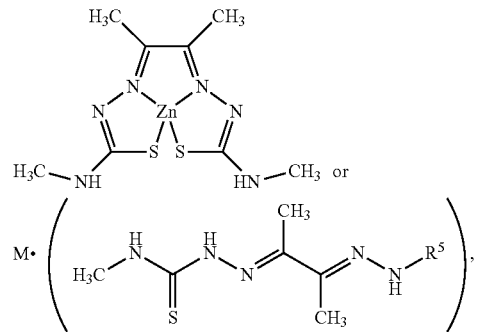

where M is Zn, Co, Ni, or Cu and $R^5$ is pyridinyl, 1-methylimidazolyl, an N-containing heterocyclyl, or an N-containing heteroaryl.

16. The catalyst of claim 9, wherein (a) $X^3$ is not —(NH)—, (b) $R^7$ is not methoxyphenyl or p-methoxyphenyl, or (c) both (a) and (b).

17. The catalyst of claim 9, wherein (a) $X^4$ is not —(NH)—, (b) $R^{10}$ is not methoxyphenyl or p-methoxyphenyl, or (c) both (a) and (b).

18. The catalyst of claim 9, wherein (a) $R^8$ is not methyl, (b) $R^9$ is not methyl, or (c) both (a) and (b).

19. The catalyst of claim 9, wherein the catalyst is an electrocatalyst.

20. An electrochemical cell comprising a composition comprising the catalyst of claim 9.

21. The electrochemical cell of claim 20, wherein the cathode of the electrochemical cell comprises the composition.

22. A method for producing $H_2$ comprising contacting, in an electrochemical cell, a first composition comprising the catalyst of claim 9, with a second composition comprising water.

23. The method of claim 22, wherein the cathode of the electrochemical cell comprises the first composition.

24. The catalyst of claim 1, wherein the catalyst is an electrocatalyst.

25. An electrochemical cell comprising a composition comprising the catalyst of claim 1.

26. The electrochemical cell of claim 25, wherein the cathode of the electrochemical cell comprises the composition.

27. A method for producing $H_2$ comprising contacting, in an electrochemical cell, a first composition comprising the catalyst of claim 1, with a second composition comprising water.

28. The method of claim 27, wherein the cathode of the electrochemical cell comprises the first composition.

29. The method of claim 27, wherein the TOF of $H_2$ production is from about 20 $s^{-1}$ to about 100,000 $s^{-1}$, about 100 $s^{-1}$ to about 100,000 $s^{-1}$, from about 500 $s^{-1}$ to about 100,000 $s^{-1}$, from about 500 $s^{-1}$ to about 50,000 $s^{-1}$, from about 500 $s^{-1}$ to about 20,000 $s^{-1}$, about 20 $s^{-1}$, about 100 $s^{-1}$, about 500 $s^{-1}$, about 1000 $s^{-1}$, about 5000 $s^{-1}$, about 10000 $s^{-1}$, about 12000 $s^{-1}$, about 16000 $s^{-1}$, about 20000 $s^{-1}$, about 50000 $s^{-1}$, or about 100,000 $s^{-1}$.

* * * * *